(12) United States Patent
Robertson et al.

(10) Patent No.: US 12,716,845 B2
(45) **Date of Patent: *Aug. 25, 2026**

(54) METHODS OF DISEASE DETECTION AND CHARACTERIZATION USING COMPUTATIONAL ANALYSIS OF URINE RAMAN SPECTRA

(71) Applicant: Virginia Tech Intellectual Properties, Inc., Blacksburg, VA (US)

(72) Inventors: John L. Robertson, Floyd, VA (US); Ryan Senger, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 400 days.

This patent is subject to a terminal disclaimer.

(21) Appl. No.: 17/146,301

(22) Filed: Jan. 11, 2021

(65) Prior Publication Data

US 2021/0215610 A1 Jul. 15, 2021

Related U.S. Application Data

(60) Provisional application No. 62/993,908, filed on Mar. 24, 2020, provisional application No. 62/983,045,
(Continued)

(51) Int. Cl.
*G01N 21/65* (2006.01)
*G01N 33/493* (2006.01)
(Continued)

(52) U.S. Cl.
CPC ........... *G01N 21/65* (2013.01); *G01N 33/493* (2013.01); *G16B 40/30* (2019.02); *G16H 10/40* (2018.01);
(Continued)

(58) Field of Classification Search
CPC ................. G01N 21/65; G01N 33/493; G01N 2201/129; G16H 10/40; G16B 40/30
See application file for complete search history.

(56) References Cited

U.S. PATENT DOCUMENTS 3,598,727 A 8/1971 Willock
4,172,033 A 10/1979 Willock
(Continued)

FOREIGN PATENT DOCUMENTS

EP 1637586 A2 3/2006
WO 2007011571 A2 1/2007
(Continued)

OTHER PUBLICATIONS

Fisher, A. K. (2018). Raman Chemometrics and Application to Enzyme Kinetics and Urinalysis [Doctoral dissertation, Virginia Tech]. Semantic Scholar. 142 p. <URL: www.semanticscholar.org/paper/Raman-Chemometrics-and-Application-to-Enzyme-and-Fisher/0d9773853f5ece82993ea928e97ef212ae023941> (Year: 2018).*
(Continued)

*Primary Examiner* — G. Steven Vanni
*Assistant Examiner* — Meredith Abbott Vassell
(74) *Attorney, Agent, or Firm* — New River Valley IP Law, P.C.; Michele L. Mayberry; Ashley M. Gates

(57) ABSTRACT

Disease detection and characterization using computational analysis of Raman spectra is used to detect disease-specific multi-molecular patterns "spectral fingerprint" associated with specific diseases, cellular physiologic derangements, or altered metabolism from systemic reactions to disease. Comparison of the Raman spectral fingerprint of urine from subjects with specific diseases and those not (healthy persons) provides the means to identify key disease-associated changes in urine molecular composition. Methods include applying baseline correction to spectra of a desired wav-
(Continued)

enumber range e.g., with the Goldindec algorithm, or with ISREA and StaBAL; vector or specific band normalization; and one or more of principal component analysis (PCA); discriminant analysis of principal components (DAPC); principal least squares (PLS) regression, machine learning with neural networks (NN); identification of wavenumber loadings; calculation of total canonical distance (TCD); total spectral distance (TSD), total principal component distance (TPD); ANOVA; pairwise comparisons; and performing leave-one-out or multi-fold cross-validation analysis of chemometric models (DAPC, PLS, NN) to report predictive capabilities in terms of accuracy, sensitivity (true-positives), and specificity (true-negatives), positive predictive value (PPV) and negative predictive value (NPV).

14 Claims, 62 Drawing Sheets

Related U.S. Application Data filed on Feb. 28, 2020, provisional application No. 62/958,993, filed on Jan. 9, 2020, provisional application No. 62/958,983, filed on Jan. 9, 2020.

(51) Int. Cl.

*G06F 16/38* (2019.01)
*G16B 40/30* (2019.01)
*G16H 10/40* (2018.01)

(52) U.S. Cl.

CPC ........ *G01N 2201/129* (2013.01); *G06F 16/38* (2019.01)

(56) References Cited

U.S. PATENT DOCUMENTS 4,267,040 A 5/1981 Schal
4,769,134 A 9/1988 Allan et al.
5,112,127 A 5/1992 Carrabba et al.
5,507,723 A 4/1996 Keshaviah
5,534,997 A 7/1996 Schrader
5,553,616 A 9/1996 Ham et al.
5,786,893 A 7/1998 Fink et al.
6,100,975 A 8/2000 Smith et al.
6,151,522 A 11/2000 Alfano et al.
6,284,131 B1 9/2001 Hogard et al.
6,632,680 B1 10/2003 Deslauriers et al.
7,326,576 B2 2/2008 Womble et al.
7,505,128 B2 3/2009 Zribi et al.
7,524,671 B2 4/2009 Clarke et al.
7,651,851 B2 1/2010 Clarke et al.
8,125,623 B2 2/2012 Munger et al.
8,133,194 B2 3/2012 Szamosfalvi et al.
8,638,431 B2 1/2014 Ashok et al.
8,699,020 B1 4/2014 Zhou et al.
8,945,936 B2 2/2015 Ash et al.
8,953,159 B2 2/2015 Cunningham et al.
9,089,126 B2 7/2015 Faulkner et al.
9,215,985 B2 12/2015 Gross et al.
9,267,845 B2 2/2016 Ichijyo et al.
9,550,020 B2 1/2017 Kelly et al.
9,713,666 B2 7/2017 Pudil et al.
11,324,869 B2 5/2022 Robertson et al.
11,674,903 B2 6/2023 Robertson et al.
11,959,858 B2 4/2024 Robertson et al.
2006/0281068 A1 12/2006 Maier et al.
2007/0109535 A1 5/2007 Maier et al.
2008/0015487 A1 1/2008 Szamosfalvi et al.
2008/0097272 A1 4/2008 Daniel et al.
2008/0158544 A1 7/2008 Womble et al.
2010/0070197 A1 3/2010 Wang et al.
2010/0165324 A1 7/2010 Womble et al.
2012/0008130 A9 1/2012 Munger et al.
2012/0099102 A1 4/2012 Bello
2012/0276549 A1 11/2012 Cunningham et al.
2013/0056418 A1 3/2013 Kopperschmidt et al.
2014/0052386 A1 2/2014 Guenther et al.
2014/0098359 A1 4/2014 Gross et al.
2016/0252459 A1 9/2016 Bell et al.
2017/0045455 A1 2/2017 Robertson et al.
2021/0270742 A1 9/2021 Senger et al.
2021/0389251 A1 12/2021 Robertson et al.
2022/0040390 A1 2/2022 Robertson et al.
2023/0147592 A1 5/2023 Robertson et al.
2023/0243752 A1 8/2023 Robertson et al.

FOREIGN PATENT DOCUMENTS

WO 2012140022 A1 10/2012
WO 2015164620 A1 10/2015
WO 2016004322 A2 1/2016
WO 2020176663 A1 9/2020

OTHER PUBLICATIONS

Del Mistro et al., (2015). Analytical and Bioanalytical Chemistry, 407, 3271-3275. (Year: 2015).*

Bispo et al., (2013). Journal of biomedical optics, 18(8), p. 087004-087004. (Year: 2013).*

Xu and Du, (Jul. 27-Aug. 1, 2019). ISREA:A Novel Approach for Raman Spectrum Baseline Correction and Its Application on Real Data [abstract]. JSM 2019, Denver, CO. [Retrieved online Jun. 2, 2023] <URL: https://ww2.amstat.org/meetings/jsm/2019/onlineprogram/AbstractDetails.cfm?abstractid=304883> (Year: 2019).*

Fisher et al., (2018). The Rametrix™ Lite Toolbox v1.0 for MATLAB®. Journal of Raman Spectroscopy, 49(5), 885-896. (Year: 2018).*

Liu et al., ((2015). Goldindec: a novel algorithm for Raman spectrum baseline correction. Applied spectroscopy, 69(7), 834-842).*

Xu et al., (2021). ISREA: an efficient peak-preserving baseline correction algorithm for Raman spectra. Applied Spectroscopy, 75(1), 34-45.*

Schena, F.P., 2011. Management of patients with chronic kidney disease. Internal and emergency medicine, 6, pp. 77-83. (Year: 2011).*

Bonifacio, A., Cervo, S. and Sergo, V., 2015. Label-free surface-enhanced Raman spectroscopy of biofluids: fundamental aspects and diagnostic applications. Analytical and bioanalytical chemistry, 407, pp. 8265-8277. (Year: 2015).*

Webster, A.C., Nagler, E.V., Morton, R.L. and Masson, P., 2017. Chronic kidney disease. The lancet, 389(10075), pp. 1238-1252. (Year: 2017).*

Van Rhijn, B.W., Van der Poel, H.G. and van Der Kwast, T.H., 2005. Urine markers for bladder cancer surveillance: a systematic review. European urology, 47(6), pp. 736-748. (Year: 2005).*

Canetta, E., et al., 2011. Modulated Raman spectroscopy for enhanced identification of bladder tumor cells in urine samples. Journal of biomedical optics, 16(3), pp. 037002/1-037002/7 (7 pages). (Year: 2011).*

Movasaghi, Z., Rehman, S. and Rehman, I.U., 2007. Raman spectroscopy of biological tissues. Applied Spectroscopy Reviews, 42(5), pp. 493-541. (Year: 2007).*

Hassler, L. et al., "Evidence for and against direct kidney infection by SARS-CoV-2 in patients with COVID-19", CJASN 2021; 16, 1755-1765, 2021.

Hirsch, J. S. et al., "Acute kidney injury in patients hospitalized with COVID-19", Kidney Int. 2020; 98: 209-218.

Huttanus, H. et al. "Raman Chemometric Urinalysis (Rametrix™) as a screen for bladder cancer," PLoS One. 2020; 15(8): e0237070. Published online Aug. 21, 2020.

Hyde, F.W. et al., "Detection of antigens in urine of mice and humans infected with Borrelia burgdorferi, etiologic agent of Lyme disease," J Clin Microbiol 27, 58-61 (1989).

Jha, V. et al., "Chronic kidney disease: global dimension and perspectives", The Lancet, 2013, 382(9888), 260-272.

(56) References Cited

OTHER PUBLICATIONS

Kerr, L.T. et al., Methodologies for bladder cancer detection with Raman based urine cytology. Analytical Methods, 2016;8: 4991-5000, Abstract only.
Lafuente, B. et al.,"The power of databases: the RRUFF project". In: T. Armbruster, R.M. Danisi, editors. Highlights in Mineralogical Crystallography. W. De Gruyter, Berlin, Germany, 2015, 32 pages.
Lee, S. et al., "Improving Clearance for Renal Replacement Therapy", Kidney 360 Publish Ahead of Print, published May 12, 2021, 32 pages.
Lo, P.A. et al., Automatic Raman spectroscopic urine crystal identification system using fluorescent image-guided 2D scanning platform with Fe3O4 crystal violet nanoclusters. J Raman Spectrosc 2018;50(1)34-50, Abstract only.
Magni, R. et al., "Application of Nanotrap technology for high sensitivity measurement of urinary outer surface protein A carboxyl terminus domain in early stage Lyme borreliosis," J Transl Med (2015) 13: 346, 22 pages.
Meyer, T. W. et al., "Dialysis Cannot be Dosed", Semin Dial. 2011; 24(5): 471-479, 19 pages.
Minka "A statistical learning/pattern recognition glossary." Retrieved Jun. 29, 2005: 2008. Available online http://alumni.media.mit.edu/~tpminka/statlearn/glossary/glossary.htm., accessed Jul. 1, 2020 (Year: 2005).
Mohamed, M. M. et al., "Acute kidney injury associated with coronavirus disease 2019 in urban New Orleans", Kidney360 2020; 1: 614-622, 19 pages.
Moledina, D. G. et al., "The association of COVID-19 with acute kidney injury independent of severity of illness: A multicenter cohort study", Am. J. Kidney Dis. 2021; 77: 490-499.e1, 12 pages.
Movasaghi, Z. et al., Raman Spectroscopy of Biological Tissues. Appl Spectrosc Rev. 2007;42: 493-541.
Murugan, R. and Kellum, J. A., "Acute kidney injury: what's the prognosis?" Nat. Rev. Nephrol. 2011; 7(4): 209-217.
Ng, J. H. et al., "Pathophysiology and pathology of acute kidney injury in patients with COVID-19", Adv. Chronic Kidney Dis. 2020; 27: 365-376.
Pegalajar-Jurado, A. et al., (2018) "Identification of urine metabolites as biomarkers of early Lyme Disease," Nature Scientific Reports 8:12204, 12 pages.
Pei, G. et al., "Renal involvement and early prognosis in patients with COVID-19 pneumonia", J. Am. Soc. Nephrol. 2020; 31: 1157-1165.
Rauter, C. et al., "Critical evaluation of urine-based PCR assay for diagnosis of Lyme borreliosis," Clin Diagn Lab Immunol 12: 910-917 (2005).
Richardson, S. et al., "Presenting characteristics, comorbidities, and outcomes among 5700 patients hospitalized with COVID-19 in the New York City area", JAMA 2020; 323: 2052-2059.
Robertson, J. L. et al. (2022), "Alterations in the molecular composition of COVID-19 patient urine, detected using Raman spectroscopic/computational analysis", Plos One 17(7): e0270914, 16 pages.
Senger, R.S. and Robertson, J.L. "The RametrixTM PRO Toolbox v1.0 for MATLAB®". PeerJ. 2020. 8: e8179.
Senger, R.S. and Scherr, D., "Resolving complex phenotypes with Raman spectroscopy and chemometrics", Curr. Opin. Biotechnol. 2020; 66:277-282, 16 pages.
Senger, R.S. et al. "Spectral characteristics of urine from patients with end-stage kidney disease analyzed using Raman Chemometric Urinalysis (Rametrix)". PLoS One. 2020. 15(1): e0227281).
Senger, R.S. et al. "Spectral characteristics of urine specimens from healthy human volunteers analyzed using Raman chemometric urinalysis (Rametrix)". PLoS One. 2019. 14(9): e0222115.
Shapiro, A. et al., Raman molecular imaging: a novel spectroscopic technique for diagnosis of bladder cancer in urine specimens. Eur Urol. 2011;59: 106-112.
Sharma, P. et al., "COVID-19-associated kidney injury: A case series of kidney biopsy findings", J. Am. Soc. Nephrol. 2020; 31: 1948-1958.
Shen, Y. et al., "Raman imaging of small biomolecules", Annu. Rev. Biophys. 2019; 48:347-369.
Shinzawa, H. et al., "Multivariate data analysis for Raman spectroscopic imaging" Journal of Raman Spectroscopy, 2009, 40:1720-1725.
Stemcell Technologies, "Loading the RoboSepTM-S Carousel and Starting a Run", 2017, https://www.youtube.com/watch?v=uhMR_xheVik.
Su, H. et al., "Renal histopathological analysis of 26 postmortem findings of patients with COVID-19 in China", Kidney Int. 2020; 98: 219-227.
Thermo Fisher Scientific, "DXR SmartRaman Spectrometer", 2017, 8 pages.
Turi, K. N. et al., "A review of metabolomics approaches and their application in identifying casual pathways of childhood asthma", J. Allergy Clin. Immunol. 2018; 141(4):1191-1201, 48 pages.
Ward, R. A. et al., "Dialysate Flow Rate and Delivered Kt/Vurea for Dialyzers with Enhanced Dialysate Flow Distribution", Clin J Am Soc Nephrol 6: 2235-2239, Sep. 2011.
Xu, Y. et al., "Sparse logistic regression on functional data", Stat. Interface, vol. 0 (2021) 1, 9 pages.
Yang, Y.T. et al., Off-Resonance SERS Nanoprobe-Targeted Screen of Biomarkers for Antigens Recognition of Bladder Normal and Aggressive Cancer Cells. Analytical Chemistry 2019;91(13): 8213-8220.
Zu, T.N.K. et al., Assessment of ex vivo Perfused Liver Health by Raman Spectroscopy. J Raman Spectrosc. 2015; 46: 551-558, Abstract only.
Zu, T.N.K. et al., Near-Real-Time Analysis of the Phenotypic Responses of *Escherichia coli* to 1-Butanol Exposure Using Raman Spectroscopy. J Bacteriol. 2014; 196: 3983-3991.
(Robertson, John L. et al.) Co-pending U.S. Appl. No. 15/305,940, filed Oct. 21, 2016, Specification, Claims, and Figures.
(Robertson, John L. et al.) Co-pending U.S. Appl. No. 17/345,735, filed Jun. 11, 2021, Specification, Claims, and Figures.
(Robertson, John L. et al.) Co-pending U.S. Appl. No. 17/434,294, filed Aug. 26, 2021, Specification, Claims, and Figures.
(Robertson, John L. et al.) Co-Pending U.S. Appl. No. 17/982,019, filed Nov. 7, 2022, Specification, Drawings, and Claims.
(Senger, R. et al.) Co-Pending U.S. Appl. No. 17/188,737, filed Mar. 1, 2021, Specification, Drawings, and Claims.
AcuTech Scientific Inc., "The World Highest Reproducible Raman Spectrometer: AcuScan 1500 Manual(2:22)", 2014, https://youtu.be/43iwhIGSZOA?si=dqAIVKAUv1xQ3cVm.
Athamneh, A.I.M. and Senger R.S. Peptide-Guided Surface-Enhanced Raman Scattering Probes for Localized Cell Composition Analysis. Appl Env Microbiol. 2012;78: 7805-7808.
Athamneh, A.I.M. et al., Phenotypic Profiling of Antibiotic Response Signatures in *Escherichia coli* Using Raman Spectroscopy. Antimicrob Agents Chemother. 2014;58: 1302-1314.
Balan et al. "Vibrational spectroscopy fingerprinting in medicine: from molecular to clinical practice." Materials 12.18 (2019): 2884, 40 pages.
Batlle, D. et al. "Acute Kidney Injury in COVID-19: Emerging Evidence of a Distinct Pathophysiology", J. Am. Soc. Nephrol. 2020; 31: 1380-1383.
Beattie, J. Renwick et al. "Prediction of Adipose Tissue Composition Using Raman Spectroscopy: Average Properties and Individual Fatty Acids", 2006, 8 pages.
Bird, B. et al., Cytology by Infrared Micro-Spectroscopy: Automatic Distinction of Cell Types in Urinary Cytology. Vib Spectrosc. 2008;48: 101-106, 15 pages.
Bouatra, S. et al. The Human Urine Metabolome. Plos One. 2013;8: e73076, 25 pages.
Canetta, E. et al., Modulated Raman spectroscopy for enhanced identification of bladder tumor cells in urine samples. J Biomed Opt. 2011;16(3): 037002, 8 pages.
Castelli, F. A. et al., "Metabolomics for personalized medicine: the input of analytical chemistry from biomarker discovery to point-of-care tests", Anal. Bioanal. Chem. 414, 759-789 (2022).
Chen, Y. T. et al., "Mortality rate of acute kidney injury in SARS, MERS, and COVID-19 infection: A systematic review and meta-analysis", Crit. Care 2020; 24: 439, 4 pages.

(56) References Cited

OTHER PUBLICATIONS

Chen, Z. and Kim, J. "Urinary proteomics and metabolomics studies to monitor bladder health and urological diseases", BMC Urol. 2016; 16 (Mar. 22): 11, 13 pages.
Cheng, S. et al., "Potential impact and study considerations of metabolomics in cardiovascular health and disease: A scientific statement from the American Heart Association", Circ. Cardiobasc. Genet. 2017; 10(2): e000032, 13 pages.
Cheng, Y. et al., "Kidney disease is associated with in-hospital death of patients with COVID-19", Kidney Int. 2020; 97: 829-838.
Chiu, Y.C. et al., Enhanced Raman sensitivity and magnetic separation for urolithiasis detection using phosphonic acid-terminated Fe3O4 nanoclusters. J. Mater. Chem. B 2015(3):4282-4290.
Co-pending U.S. Appl. No. 15/305,940, Applicant-Initiated Interview Summary dated Mar. 28, 2022, 3 pages.
Co-pending U.S. Appl. No. 15/305,940, Applicant-Initiated Interview Summary, dated Jan. 18, 2023, 4 pages.
Co-pending U.S. Appl. No. 15/305,940, Final Office Action dated Dec. 1, 2021, 27 pages.
Co-pending U.S. Appl. No. 15/305,940, Final Office Action dated Dec. 22, 2022, 18 pages.
Co-pending U.S. Appl. No. 15/305,940, Final Office Action dated Jul. 13, 2020, 22 pages.
Co-pending U.S. Appl. No. 15/305,940, Non-Final Office Action dated Jun. 2, 2022, 37 pages.
Co-pending U.S. Appl. No. 15/305,940, Non-Final Office Action dated May 7, 2021, 24 pages.
Co-pending U.S. Appl. No. 15/305,940, Non-Final Office Action dated Nov. 1, 2019, 16 pages.
Co-pending U.S. Appl. No. 15/305,940, Notice of Allowance dated Feb. 1, 2023, 7 pages.
Co-pending U.S. Appl. No. 15/305,940, Response After Final Office Action, dated Jan. 13, 2023, 6 pages.
Co-pending U.S. Appl. No. 15/305,940, Response to Dec. 1, 2021 Final Office Action, dated Feb. 25, 2022, 17 pages.
Co-pending U.S. Appl. No. 15/305,940, Response to Jul. 13, 2020 Final Office Action, filed Oct. 13, 2020, 11 pages.
Co-pending U.S. Appl. No. 15/305,940, Response to Jun. 2, 2022 Non-Final Office Action, dated Dec. 2, 2022, 31 pages.
Co-pending U.S. Appl. No. 15/305,940, Response to Mar. 27, 2019 Restriction Requirement, filed Sep. 27, 2019, 9 pages.
Co-pending U.S. Appl. No. 15/305,940, Response to May 7, 2021 Non-Final Office Action, filed Sep. 7, 2021, 14 pages.
Co-pending U.S. Appl. No. 15/305,940, Response to Nov. 1, 2019 Non-Final Office Action, filed May 1, 2020, 13 pages.
Co-pending U.S. Appl. No. 15/305,940, Restriction Requirement dated Mar. 27, 2019, 9 pages.
Co-pending U.S. Appl. No. 15/305,940, Rule 132 Affidavit dated Dec. 2, 2022, 23 pages.
Co-pending U.S. Appl. No. 17/345,735, Non-Final Office Action dated Jun. 14, 2023, 15 pages.
Co-pending U.S. Appl. No. 17/345,735, Notice of Allowance dated Dec. 1, 2023, 7 pages.
Co-pending U.S. Appl. No. 17/345,735, Response to Jun. 14, 2023 Non-Final Office Action, dated Nov. 14, 2023, 8 pages.
Co-pending U.S. Appl. No. 17/434,294, Notice of Allowance dated Dec. 29, 2021, 11 pages.
Co-pending International Application No. PCT/US20/19964, International Search Report and Written Opinion dated May 22, 2020, 7 pages.
Dator, R. et al., "Metabolomics profiles of smokers from two ethnic groups with differing lung cancer risk", Chem. Res. Toxicol. 2020; 33(8):2087-2098.
Daugirdas, John T. et al. "Improved equation for estimating single-pool Kt/V at higher dialysis frequencies", Nephrol Dial Transplant (2013) 28: 2156-2160.
Daugirdas, John T. et al. "Surface-Area-Normalized Kt/V: A Method of Rescaling Dialysis Dose to Body Surface Area-Implications for Different-Size Patients by Gender", Semin Dial. 2008; 21(5): 415-421, 17 pages.
Emwas, A. H. et al., "Standardizing the experimental conditions for using urine in NMR-based metabolomic studies with a particular focus on diagnostic studies: a review", Metabolomics 2015; 11(4): 872-894.
Fisher, M. et al., "AKI in hospitalized patients with and without COVID-19: A comparison study", J. Am. Soc. Nephrol. 2020; 31: 2145-2157.
Gautam, R. et al. "Review of multidimensional data processing approaches for Raman and infrared spectroscopy". EPJ Techn. Instrum. 2015. 2(1): 8, 38 pages.
Gowda, G. A. et al., "Metabolomics-based methods for early disease diagnostics", Expert Rev. Mol. Diagn. 2008; 8(5):617-633, 28 pages.
(Robertson, John L. et al) Co-pending International Application No. PCT/US20/19964, filed Feb. 26, 2020, Specification, Claims, Figures.
(Robertson, John L. et al.) Co-pending U.S. Appl. No. 18/122,180, filed Mar. 16, 2023, Specification, Claims, and Figures.
(Robertson, John L. et al.) Co-Pending International Application No. PCT/US2015/027323, filed Apr. 23, 2015 and published as WO2015164620 on Oct. 29, 2015, Specification, Claims, Figures.
Afseth, N.K. and Kohler, A. "Extended multiplicative signal correction in vibrational spectroscopy, a tutorial" Chemometrics and Intelligent Laboratory Systems. 2012. 117: 92-99. 10.1016/j.chemolab.2012.03.004, Abstract only.
Beattie, J.R. and McGarvey, J.J. "Estimation of signal backgrounds on multivariate loadings improves model generation in face of complex variation in backgrounds and constituents". J of Raman Spectrosc. 2013. 44(2): 329-338. 10.1002/jrs.4178, Abstract only.
Boelens, H.F.M & Eilers, P.H.C., Baseline correction with asymmetric least squares smoothing, Leiden University Medical Centre report (2005).
Cai, T.T. et al. "Enhanced Chemical Classification of Raman Images Using Multiresolution Wavelet Transformation". Appl. Spectrosc. 2001. 55(9): 1124-1130.
Cai, Y. et al. "Baseline correction for Raman spectra using penalized spline smoothing based on vector transformation". Anal. Methods. 2018. 10(28): 3525-3533, Abstract only.
Candeloro, P. et al. "Raman database of amino acids solutions: A critical study of extended multiplicative signal correction". Analyst. 2013. 138(24): 7331-7340).
Carswell, W. et al., "Raman Spectroscopy as a non-cytological detection and quantification urinalysis method for microhematuria in human urine", Appl. Spectro. 2022. 76(3): 1-11.
Celia-May, D. et al. Theoretical principles of Raman spectroscopy. Phys. Sci. Rev.:2019; 19:4.
Centers for Disease Control and Prevention, National Chronic Kidney Disease Factsheet, 2014, 4 pages.
Chen, D. et al. "Adaptive wavelet transform suppresses background and noise for quantitative analysis by Raman spectrometry". Anal. Bioanal. Chem. 2011. 400(2): 625-634, Abstract Only.
Collins, AJ et al., "Death, hospitalization, and economic associations among incident hemodialysis patients with hematocrit values of 36 to 39%," J Am Soc Nephrol 12(11):2465-73, 2001.
Co-pending U.S. Appl. No. 18/122,180, Non-Final Office Action dated May 24, 2024, 20 pages.
Co-pending international Application No. PCT/US2015/027323 International Search Report and Written Opinion dated Sep. 8, 2015, 11 pages.
Das, R.S. and Agrawal, Y.K. "Raman spectroscopy: Recent advancements, techniques and applications". Vib. Spectrosc. 2011. 57(2): 163-176, Abstract only.
Depciuch, J. et al. "Application of Raman Spectroscopy and Infrared Spectroscopy in the Identification of Breast Cancer". Appl. Spectrosc. 2016. 70(2): 251-263.
Dobre, M, Meyer, TW, Hostetter, TH, "Searching for uremic toxins," Clin J Am Soc Nephrol 8: 322-327, 2013.
Duranton, F et al., "Normal and pathological concentrations of uremic toxins," J Am Soc Nephrol 23: 1258-1270, 2012.
Eilers, P.H.C. "A perfect smoother". Anal. Chem. 2003. 75(14): 3631-3636, Abstract only.

(56) References Cited

OTHER PUBLICATIONS

Eknoyan, G. et al., "Effects of dialysis dose and membrane flux in maintenance hemodialysis," New Engl Journ Med 347: 2010-2019, 2002.
He, S. et al. "Baseline correction for Raman spectra using an improved asymmetric least squares method". Anal. Methods. The Royal Society of Chemistry, 2014. 6(12): 4402-4407.
Ito, S, Yoshida, M, "Review: Protein-bound uremic toxins: new culprits of cardiovascular events in chronic kidney disease patients," Toxins 6: 665-678, 2014; doi:10.3390/toxins6020665.
Kim, Jaejin et al., "Feasibility Study for the Monitoring of Urea in Dialysate Solution using Raman Spectroscopy", Bull. Korean Chem. Soc. 2011, vol. 32, No. 3 805-808.
Layman-Amato, R. et al., "Water treatment for hemodialysis: an update", Nephrology Nursing J., 2013, 40(5), 383-404, 465.
Levey, AS et al., "Controlling the epidemic of cardiovascular disease in chronic renal disease: What do we need to learn? Where do we go from here?," Amer J Kid Disease 32: 853-906, 1998.
Li, J. et al. "Wavelet transform based on the optimal wavelet pairs for tunable diode laser absorption spectroscopy signal processing". Appl. Spectrosc. 2015. 69(4): 496-506.
Liabeuf, S, Drukke, TB, Massay, ZA, "Protein-bound uremic toxins: new insight from clinical studies," Toxins 3: 911-919, 2011.
Lieber, C.A. and Mahadevan-Jansen, A. "Automated Method for Subtraction of Fluorescence from Biological Raman Spectra". Appl. Spectrosc. 2003. 57: 1363-1367, Abstract only.
Liland, K. et al. "Model-based pre-processing in Raman spectroscopy of biological samples". J. Raman Spectrosc. 2016. 47(6): 643-650.
Liland, K. et al. "Optimal Choice of Baseline Correction for Multivariate Calibration of Spectra" Appl. Spectrosc. 2010, 64: 1007-1016.
Mahadevan-Jansen, A. and Richards-Kortum, R.R. "Raman spectroscopy for the detection of cancers and precancers". J. Biomed. Opt. 1996. 1(1): 31-70.
Martens, H. and Stark, E. "Extended multiplicative signal correction and spectral interference subtraction: new preprocessing methods for near infrared spectroscopy." J. Pharm. Biomed. Anal. 1991. 9 8: 625-635, Abstract only.
Mazet, V. et al. "Background removal from spectra by designing and minimising a non-quadratic cost function". Chemom. Intell. Lab. Syst. 2005. 76(2): 121-133.
Meyer, TW, Hostetter, TH, "Uremia", New Engl J Med 357: 1316-1325, 2007.
Mosier-Boss, P.A. et al. "Fluorescence rejection in Raman spectroscopy by shifted-spectra, edge detection, and FFT filtering techniques". Appl. Spectrosc. 1995. 49: 630-638.
Peng, J. et al. "Asymmetric least squares for multiple spectra baseline correction". Anal. Chim. Acta. 2010. 683(1): 63-68.
Scholtes-Timmerman, M. et al. "A novel approach to correct variations in Raman spectra due to photo-bleachable cellular components". Analyst. 2009. 134(2): 387-393.
Schulze, G. et al. "Investigation of selected baseline removal techniques as candidates for automated implementation". Appl. Spectrosc. 2005. 59(5): 545-574.
Senger, R.S., Kavuru, V., Sullivan, M., Gouldin, A., Lundgren, S., Merrifield, K. (2019), Spectral characteristics of urine specimens from healthy human volunteers analyzed using Raman chemometric urinalysis (Rametrix). PLoS One 14(9): e0222115.
Senger, R.S., Sullivan, M., Gouldin, A., Lundgren, S., Merrifield, K., Steen, C., Spectral characteristics of urine from patients with end-stage kidney disease analyzed using Raman Chemometric Urinalysis (Rametrix) PLoS One 15(1): e0227281, 2020.
Shusterman, V. et al. "Enhancing the precision of ECG baseline correction: selective filtering and removal of residual error". Comput. Biomed. Res. 2000. 33(2): 144-160, Abstract only.
Stellman, C.M. et al. "Multivariate Raman Imaging of Simulated and Real World Glass-Reinforced Composites". Appl. Spectrosc. 1996. 50: 552-557, Abstract only.
Talari, A. et al. Raman spectroscopy of biological tissues. Appl. Spectrosc. Rev. 2015; 50(1): 46-111.
Vanholder, R, et al., European Uremic Toxin Work Group (EUTox), "Review on uremic toxins: classification, concentration, and interindividual variability," Kidney Int. May 2003;63(5):1934-43, 2003.
Wang, N. et al. "Recent advances in spontaneous Raman spectroscopic imaging: Instrumentation and applications" Current Medicinal Chemistry, vol. 27, No. 36, 2020, pp. 6188-6207(20), Available online Jul. 26, 2019, Abstract only.
Zhang, D. and Ben-Amotz, D. "Enhanced Chemical Classification of Raman Images in the Presence of Strong Fluorescence Interference". Appl. Spectrosc. OSA, 2000, 54(9): 1379-1383, Abstract only.
Zhao, J. et al. "Automated autofluorescence background subtraction algorithm for biomedical Raman spectroscopy". Appl. Spectrosc. 2007. 61(11): 1225-1232, Abstract only.
Cai, Y. et al. "Baseline correction for Raman spectra using penalized spline smoothing based on vector transformation". Anal. Methods. 2018. 10(28): 3525-3533.
Co-Pending U.S. Appl. No. 17/188,737, Non-Final Office Action dated Mar. 24, 2025, 32 pages.
Co-Pending U.S. Appl. No. 17/188,737, Response to Dec. 23, 2024 Restriction Requirement, dated Feb. 15, 2025, 2 pages.
Co-Pending U.S. Appl. No. 17/188,737, Restriction Requirement dated Dec. 23, 2024, 7 pages.
Co-pending U.S. Appl. No. 18/122,180, Corrected Notice of Allowance dated May 23, 2025, 5 pages.
Co-pending U.S. Appl. No. 18/122,180, Examiner Interview Summary dated Sep. 19, 2024, 7 pages.
Co-pending U.S. Appl. No. 18/122,180, Final Office Action dated Oct. 29, 2024, 16 pages.
Co-pending U.S. Appl. No. 18/122,180, Notice of Allowance dated May 12, 2025, 7 pages.
Co-pending U.S. Appl. No. 18/122,180, Response to May 24, 2024 Non-Final Office Action, dated Sep. 24, 2024, 7 pages.
Co-pending U.S. Appl. No. 18/122,180, Response to Oct. 29, 2024 Final Office Action, dated Jan. 29, 2025, 7 pages.
Jensen, P. S. et al., "Online monitoring of urea concentration in dialysate with dual-beam Fourier-transform near-infrared spectroscopy", Journal of Biomedical Optics 9(3), 553-557 (May/Jun. 2004).
Collins et al., "The State of Chronic Kidney Disease, ESRD, and Morbidity and Mortality in the First Year of Dialysis," 2009, Clin. J. Am. Soc. Nephrol., 4, p. S5-S11.
Co-Pending U.S. Appl. No. 17/188,737, Final Office Action dated Oct. 29, 2025, 37 pages.
Co-Pending U.S. Appl. No. 17/188,737, Response to Mar. 24, 2025 Non-Final Office Action dated Sep. 24, 2025, 35 pages.

* cited by examiner

METHODS OF DISEASE DETECTION AND CHARACTERIZATION USING COMPUTATIONAL ANALYSIS OF URINE RAMAN SPECTRA

CROSS-REFERENCE TO RELATED APPLICATIONS

This application relies on the disclosure of and claims priority to and the benefit of the filing date of U.S. Provisional Application Nos. 62/958,983 and 62/958,993, filed Jan. 9, 2020, 62/993,908, filed Mar. 24, 2020, and 62/983,045, filed Feb. 28, 2020, each of which is hereby incorporated by reference herein in its entirety.

BACKGROUND OF THE INVENTION

Field of the Invention

The present invention relates to the field of disease detection and characterization. More particularly, the present invention relates to methods of detecting or characterizing disease using computational analysis of urine Raman spectra.

SUMMARY OF THE INVENTION

All diseases alter normal physiology and homeostasis. These alterations can occur at the molecular, subcellular, cellular, tissue, organ, organ system and organism levels, frequently manifesting in alterations in multiple locations (molecular->organism). Common alterations include changes in metabolism, coordinated physiologic functions (maintenance of blood pressure, for example), and molecular/cellular/tissue structure and integrity. The degree (amount) of alteration, duration of alteration (seconds to years), and response/defense mechanisms determine the severity and outcomes of disease.

Changes in metabolism or activation of systemic response/defense mechanisms can be reflected in the production and molecular composition of urine. Here are three examples: 1) the presence of infection in the urinary tract will change the pH, viscosity, concentration, and molecular composition of urine; 2) the presence and growth of neoplasms in the kidney will alter the number of functional physiologic units (nephrons), may incite inflammatory responses to tumor tissue and dead/dying renal tissue, and may compromise the integrity of the renal circulation. It would be common to find degenerate normal and tumor cells, excessive proteins, inflammatory cells and their mediator byproducts, products of tumor cell metabolism, blood, and proteins in urine; and 3) diabetes mellitus is a metabolic/vascular disease caused by an insufficiency of insulin effects. Persons with diabetes mellitus frequently have excessive amounts of filtered glucose and protein in urine, a reflection of altered (compromised) kidney function and myriad systemic metabolic derangements and altered gut microbiome.

Raman spectra collected from analysis of urine specimens permits analysis of the molecular composition of the urine by detection of variances in chemical bond energetics/configuration. These variances are indicative of common chemical bonds associated with specific molecules, such as urea, creatinine, other metabolic byproducts, and toxins. See Saatkamp, et. al, *Journal of Biomedical Optics* 21 (3), 037001 (March 2016). Urine contains thousands of molecules reflective of whole-body physiology and metabolism. These are all represented as bands occurring at different Raman shifts in a Raman spectrum of urine. The molecular composition of urine changes constantly as a reflection of metabolism and is altered in disease states, and changes in the types and amounts of molecules. This is referred to as the "spectral fingerprint" of a particular disease, individual, or even response to therapy.

Rametrix™ analysis of urine Raman spectra has been used to detect disease-specific multi-molecular patterns associated with specific diseases, cellular physiologic derangements (proteinuria) or altered metabolism from systemic reactions to disease. These multi-molecular patterns can consist of hundreds of molecules that can alter the thousands of bands appearing in a Raman spectrum. These result in a Raman "spectral fingerprint" of a particular disease, individual, or response to therapy. In the broad perspective, Rametrix™ is able to relate the Raman spectral fingerprint of urine to its actual molecular fingerprint in order to derive information about patient health. Comparison of the Raman spectral fingerprint of urine from healthy persons and those with specific diseases provides the means to identify key disease-associated changes in urine molecular composition.

Differentiating diseases is possible by examining all or some of the following factors: 1) type and amount of protein in the urine, 2) the decrement in GFR, 3) the presence of absence of blood (heme) and inflammatory cells/debris, 4) unique molecular signatures regions indicative of urea, creatinine, peptidoglycan, phosphatidylinositol, fatty acids and lipids, phosopholipids, cholesterol, glycogen, carotenoids, collagen, carbohydrates, nitrates and phosphates, uremic toxins (guanidine and indoxyl sulfate), and nucleic acids (DNA and RNA), 5) changes in metabolism indicated by protein metabolism and breakdown products (including the amount and types of amino acids), 6) spectral signature Raman bands that differ from those in urine of healthy individuals, and/or 7) the actual number of Principal Components needed to differentiate disease groups. Such disease-associated abnormalities are detectable in urine and can be associated with one or more diseases. An outline of the disease-associated factors that are applicable to various diseases is provided in Table 1.

TABLE 1

Disease-Associated Abnormalities Detectable with Rametrix ™ Molecular Urinalysis

| Bladder cancer (all types, grades, and stages) | | | | | | | | | |
|---|---|---|---|---|---|---|---|---|---|
| | 1 | 2 | 3 | 4 | 5 | 6 | 7 | 8 | 9 |
| Metric | | X | | X | | | X | X | X |

Cancer of the genitourinary tract frequently disrupts tissue integrity and vasculature, leading to bleeding, cellular and connective tissue disruptionm, and the release of TABLE 1-continued Disease-Associated Abnormalities
Detectable with Rametrix ™ Molecular Urinalysis both tissue degradation products and molecules associated with tumor growth and metabolism.

Acute cystitis
(all types, grades, stages, and etiologies, including infectious and non-infectious etiologies)

| | 1 | 2 | 3 | 4 | 5 | 6 | 7 | 8 | 9 |
|---|---|---|---|---|---|---|---|---|---|
| Metric | | X | | | | X | X | | X |

Inflammatory conditions affecting any tissue can result in tissue disruption, including cellular and connective tissue degradation, loss of normal tissue/organ integrity, disruption of normal function, and release of physiological and inflammatory mediators locally or in urine.

Chronic cystitis (all types, grades, stages, and etiologies, including infectious and non-infectious etiologies)

| | 1 | 2 | 3 | 4 | 5 | 6 | 7 | 8 | 9 |
|---|---|---|---|---|---|---|---|---|---|
| Metric | | X | | | | X | X | | X |

Inflammatory conditions affecting any tissue can result in tissue disruption, including cellular and connective tissue degradation, loss of normal tissue/organ integrity, disruption of normal function, and release of physiological and inflammatory mediators locally or in urine.

Schistosomiasis

| | 1 | 2 | 3 | 4 | 5 | 6 | 7 | 8 | 9 |
|---|---|---|---|---|---|---|---|---|---|
| Metric | | X | X | | X | X | | | X |

Inflammatory conditions affecting any tissue can result in tissue disruption, including cellular and connective tissue degradation, loss of normal tissue/organ integrity, disruption of normal function, and release of physiological and inflammatory mediators locally or in urine.

Kidney cancer
(all types, grades and stages)

| | 1 | 2 | 3 | 4 | 5 | 6 | 7 | 8 | 9 |
|---|---|---|---|---|---|---|---|---|---|
| Metric | | X | X | X | | X | | X | |

Cancer of the genitourinary tract frequently disrupts tissue integrity and vasculature, leading to bleeding, cellular and connective tissue disruption, and the release of both tissue degradation products and molecules associated with tumor growth and metabolism.

Prostate cancer
(all types, grades, and stages)

| | 1 | 2 | 3 | 4 | 5 | 6 | 7 | 8 | 9 |
|---|---|---|---|---|---|---|---|---|---|
| Metric | | X | X | X | | X | | X | |

Cancer of the genitourinary tract frequently disrupts tissue integrity and vasculature, leading to bleeding, cellular and connective tissue disruption, and the release of both tissue degradation products and molecules associated with tumor growth and metabolism.

Prostatitis
(acute and chronic)

| | 1 | 2 | 3 | 4 | 5 | 6 | 7 | 8 | 9 |
|---|---|---|---|---|---|---|---|---|---|
| Metric | | X | X | X | | X | | | X |

Inflammatory conditions affecting any tissue can result in tissue disruption, including cellular and connective tissue degradation, loss of normal tissue/organ integrity, disruption of normal function, and release of physiological and inflammatory mediators locally or in urine.

Cervical cancer
(all types, grades, and stages)

| | 1 | 2 | 3 | 4 | 5 | 6 | 7 | 8 | 9 |
|---|---|---|---|---|---|---|---|---|---|
| Metric | | | X | X | | | | X | |

Cancer of the genitourinary tract frequently disrupts tissue integrity and vasculature, leading to bleeding, cellular and connective tissue disruption, and the release of both TABLE 1-continued

| Disease-Associated Abnormalities Detectable with Rametrix ™ Molecular Urinalysis | | | | | | | | | |
|---|---|---|---|---|---|---|---|---|---|
| tissue degradation products and molecules associated with tumor growth and metabolism. | | | | | | | | | |
| **Uterine cancer (all types, grades, and stages)** | | | | | | | | | |
| | 1 | 2 | 3 | 4 | 5 | 6 | 7 | 8 | 9 |
| Metric | | | X | X | | | | X | |
| Cancer of the genitourinary tract frequently disrupts tissue integrity and vasculature, leading to bleeding, cellular and connective tissue disruption, and the release of both tissue degradation products and molecules associated with tumor growth and metabolism. | | | | | | | | | |
| **Ovarian cancer (all types, grades, and stages)** | | | | | | | | | |
| | 1 | 2 | 3 | 4 | 5 | 6 | 7 | 8 | 9 |
| Metric | | | X | X | | | | X | |
| Cancer of the genitourinary tract frequently disrupts tissue integrity and vasculature, leading to bleeding, cellular and connective tissue disruption, and the release of both tissue degradation products and molecules associated with tumor growth and metabolism. | | | | | | | | | |
| **Cancer of the adrenal gland (all types, grades, and stages)** | | | | | | | | | |
| | 1 | 2 | 3 | 4 | 5 | 6 | 7 | 8 | 9 |
| Metric | X | | | | X | | X | X | X |
| Cancer frequently disrupts tissue integrity and vasculature, cellular and connective tissue disruption, and the release of both tissue degradation products and molecules associated with tumor growth and metabolism. | | | | | | | | | |
| **Cushing's disease and Cushing's syndrome** | | | | | | | | | |
| | 1 | 2 | 3 | 4 | 5 | 6 | 7 | 8 | 9 |
| Metric | X | | | | X | | X | X | X |
| Cancer frequently disrupts tissue integrity and vasculature, cellular and connective tissue disruption, and the release of both tissue degradation products and molecules associated with tumor growth and metabolism. Tumors of the hypothalamus, pituitary gland, and adrenal glands can release hormone-like products (paraneoplastic effects) that have systemic consequences. | | | | | | | | | |
| **Multiple myeloma with Bence-Jones proteinuria (all stages and grades)** | | | | | | | | | |
| | 1 | 2 | 3 | 4 | 5 | 6 | 7 | 8 | 9 |
| Metric | X | | X | X | X | X | X | X | |
| Cancer frequently disrupts tissue integrity and vasculature, cellular and connective tissue disruption, and the release of both tissue degradation products and molecules associated with tumor growth and metabolism. Tumors of the bone marrow, such as multiple myeloma can release hormone-like products (paraneoplastic effects) that have systemic consequences. | | | | | | | | | |
| **Acute kidney injury (all types and etiologies)** | | | | | | | | | |
| | 1 | 2 | 3 | 4 | 5 | 6 | 7 | 8 | 9 |
| Metric | X | X | X | X | X | X | X | | X |
| Inflammatory, hypoperfusion and toxicant exposures conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| **Acute kidney failure (all types and etiologies)** | | | | | | | | | |
| | 1 | 2 | 3 | 4 | 5 | 6 | 7 | 8 | 9 |
| Metric | X | X | X | X | X | X | X | | X |
| Inflammatory, hypoperfusion and toxicant exposures conditions affecting any tissue | | | | | | | | | |

TABLE 1-continued

| Disease-Associated Abnormalities Detectable with Rametrix ™ Molecular Urinalysis | | | | | | | | | |
|---|---|---|---|---|---|---|---|---|---|
| can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Chronic kidney failure (all types, stages, and etiologies) | | | | | | | | | |
| | 1 | 2 | 3 | 4 | 5 | 6 | 7 | 8 | 9 |
| Metric | X | | X | X | X | X | X | | X |
| Inflammatory, hypoperfusion and toxicant exposures conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Acute glomerulonephritis (all types and etiologies) | | | | | | | | | |
| | 1 | 2 | 3 | 4 | 5 | 6 | 7 | 8 | 9 |
| Metric | X | X | X | X | X | X | X | | X |
| Inflammatory conditions affecting any tissue can result in tissue disruption, including cellular, vascular, and connective tissue degradation, loss of normal tissue/organ integrity, disruption of normal function, and release of physiological products/metabolites, and inflammatory mediators locally or in urine. | | | | | | | | | |
| Chronic glomerulonephritis (all types and etiologies) | | | | | | | | | |
| | 1 | 2 | 3 | 4 | 5 | 6 | 7 | 8 | 9 |
| Metric | X | X | X | X | X | X | X | | X |
| Inflammatory conditions affecting any tissue can result in tissue disruption, including cellular, vascular, and connective tissue degradation, loss of normal tissue/organ integrity, disruption of normal function, and release of physiological products/metabolites, and inflammatory mediators locally or in urine. | | | | | | | | | |
| Focal and diffuse segmental glomerulosclerosis (all stages, grades, and etiologies, including hypertension) | | | | | | | | | |
| | 1 | 2 | 3 | 4 | 5 | 6 | 7 | 8 | 9 |
| Metric | X | | X | X | X | X | X | | X |
| Inflammatory conditions affecting any tissue can result in tissue disruption, including cellular, vascular, and connective tissue degradation, loss of normal tissue/organ integrity, scarring, disruption of normal function, and release of physiological products/metabolites, and inflammatory mediators locally or in urine. | | | | | | | | | |
| Membranous nephropathy (all types, stages, and etiologies) | | | | | | | | | |
| | 1 | 2 | 3 | 4 | 5 | 6 | 7 | 8 | 9 |
| Metric | X | | X | X | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Membranoproliferative glomerulonephritis (all stages, grades, and etiologies, including systemic lupus erythematosus) | | | | | | | | | |
| | 1 | 2 | 3 | 4 | 5 | 6 | 7 | 8 | 9 |
| Metric | X | | X | X | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |

TABLE 1-continued

| Disease-Associated Abnormalities Detectable with Rametrix ™ Molecular Urinalysis | | | | | | | | | |
|---|---|---|---|---|---|---|---|---|---|
| Hemolytic uremic syndrome | | | | | | | | | |
| | 1 | 2 | 3 | 4 | 5 | 6 | 7 | 8 | 9 |
| Metric | X | X | X | X | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| IgA nephropathy (all stages, grades, and etiologies) | | | | | | | | | |
| | 1 | 2 | 3 | 4 | 5 | 6 | 7 | 8 | 9 |
| Metric | X | X | X | X | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Minimal change nephropathy (all stages, grades, and etiologies) | | | | | | | | | |
| | 1 | 2 | 3 | 4 | 5 | 6 | 7 | 8 | 9 |
| Metric | X | | X | | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Congenital nephropathy (all stages, grades, and etiologies) | | | | | | | | | |
| | 1 | 2 | 3 | 4 | 5 | 6 | 7 | 8 | 9 |
| Metric | X | | X | | | | | | X |
| Congenital conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Diabetic nephropathy | | | | | | | | | |
| | 1 | 2 | 3 | 4 | 5 | 6 | 7 | 8 | 9 |
| Metric | X | | X | X | X | X | X | | X |
| Complex metabolic conditions affecting any tissue can result in tissue disruption, including cellular, vascular, and connective tissue degradation, loss of normal tissue/organ integrity, disruption of normal function, compensatory pathologic remodeling, and release of physiological products/metabolites, and metabolic mediators locally or in urine. | | | | | | | | | |
| Protein-losing nephropathy and nephrotic syndrome (all stages, grades, and etiologies) | | | | | | | | | |
| | 1 | 2 | 3 | 4 | 5 | 6 | 7 | 8 | 9 |
| Metric | X | | X | | X | X | X | | X |
| Inflammatory, hypoperfusion and toxicant exposures conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. In this syndrome, excessive amounts of physiologically-important proteins are lost in urine. | | | | | | | | | |
| Acute pyelonephritis (all stages, grades, and etiologies) | | | | | | | | | |
| | 1 | 2 | 3 | 4 | 5 | 6 | 7 | 8 | 9 |
| Metric | X | X | X | X | X | X | X | | X |

TABLE 1-continued

| Disease-Associated Abnormalities Detectable with Rametrix ™ Molecular Urinalysis | | | | | | | | | |
|---|---|---|---|---|---|---|---|---|---|
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Chronic pyelonephritis (all stages, grades, and etiologies) | | | | | | | | | |
| | 1 | 2 | 3 | 4 | 5 | 6 | 7 | 8 | 9 |
| Metric | X | X | X | X | X | X | X | | X |
| Inflammatory conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Lyme disease (all stages and clinical presentations) | | | | | | | | | |
| | 1 | 2 | 3 | 4 | 5 | 6 | 7 | 8 | 9 |
| Metric | X | | | | | | X | | X |
| Inflammatory/infectious conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Atypical borreliosis | | | | | | | | | |
| | 1 | 2 | 3 | 4 | 5 | 6 | 7 | 8 | 9 |
| Metric | X | | | | | | X | | X |
| Inflammatory/infectious conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Myalgic Encephalomyelitis/Chronic Fatigue Syndrome (ME/CFS) (all stages, grades, and etiologies) | | | | | | | | | |
| | 1 | 2 | 3 | 4 | 5 | 6 | 7 | 8 | 9 |
| Metric | | | | | | | X | | X |
| Inflammatory/infectious conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Systemic mold allergy/toxicity | | | | | | | | | |
| | 1 | 2 | 3 | 4 | 5 | 6 | 7 | 8 | 9 |
| Metric | | | | | | | X | | X |
| Allergic and conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |
| Hemobartonellosis | | | | | | | | | |
| | 1 | 2 | 3 | 4 | 5 | 6 | 7 | 8 | 9 |
| Metric | | X | | | | | X | | X |
| Inflammatory/infectious conditions affecting any tissue can result in tissue disruption, including cellular, vascular, and connective tissue degradation, loss of normal tissue/organ integrity, disruption of normal function, compensatory pathologic remodeling, and release of physiological products/metabolites, and inflammatory mediators locally or in urine. | | | | | | | | | |

TABLE 1-continued

| Disease-Associated Abnormalities Detectable with Rametrix ™ Molecular Urinalysis | | | | | | | | | |
|---|---|---|---|---|---|---|---|---|---|
| SARS-COV-1 (Severe Acute Respiratory Syndrome Coronavirus Disease) | | | | | | | | | |
| | 1 | 2 | 3 | 4 | 5 | 6 | 7 | 8 | 9 |
| Metric | | | | | X | X | X | | X |
| Given the results with Lyme, atypical borreliosis, and *Hemobartonella* (all infectious diseases, but with distinct 'molecular fingerprints') and mold allergy (a systemic inflammatory disease) the inventors hypothesize COVID19 and related viruses will also produce 'systemic inflammatory reaction/metabolic change' fingerprints. | | | | | | | | | |
| SARS-COV-2 (COVID-19 Disease) | | | | | | | | | |
| | 1 | 2 | 3 | 4 | 5 | 5 | 7 | 8 | 9 |
| Metric | | | | | X | X | X | | X |
| Given the results with Lyme, atypical borreliosis, and *Hemobartonella* (all infectious diseases, but with distinct 'molecular fingerprints') and mold allergy (a systemic inflammatory disease) the inventors hypothesize COVID19 and related viruses will also produce 'systemic inflammatory reaction/metabolic change' fingerprints. | | | | | | | | | |
| MERS-COV-2 (Middle Eastern Respiratory Syndrome Disease) | | | | | | | | | |
| | 1 | 2 | 3 | 4 | 5 | 6 | 7 | 8 | 9 |
| Metric | | | | | X | X | X | | X |
| Given the results with Lyme, atypical borreliosis, and *Hemobartonella* (all infectious diseases, but with distinct 'molecular fingerprints') and mold allergy (a systemic inflammatory disease) the inventors hypothesize COVID19 and related viruses will also produce 'systemic inflammatory reaction/metabolic change' fingerprints. | | | | | | | | | |

Key:
1-Alterations in type and amount of nitrogenous waste products
2-Alterations in type and amount of hemoglobin-associated molecules
3-Alterations in type and amount of collagen-associated molecules
4-Alterations in type and amount of nucleic acid (DNA/RNA)-associated molecules
5-Alterations in type and amount of excreted/filtered normal and abnormal metabolites
6-Alterations in type and amount of plasma proteins/protein-associated molecules including albumin, globulins, complement, and coagulation proteins
7-Alterations in amount and molecular diversity of Raman-detectable molecules
8-Tumor growth-associated molecules (including metabolic, secreted, and cell degradation-associated molecules)
9-Disease-specific biomarker clusters Methods of the invention include obtaining from urine a Raman "spectral fingerprint" of a particular disease, individual, or response to therapy and comparing that to the Raman "spectral fingerprint" of urine from healthy persons and those with specific diseases to identify/characterize disease. Embodiments of the invention include classifying a sample or specimen, such as from a subject, according to whether the subject has a particular state, condition and/or disease (which terms may be used interchangeably throughout this specification and claims), wherein the classifying can include whether the sample, specimen or subject is positive or negative for a specified feature; whether the sample, specimen or subject has or does not have a specified disease; whether the sample, specimen or subject has or does not have a specified condition; whether the sample, specimen or subject is in a particular state of being (such as ethnicity, age, or other identifying characteristic, etc.); or the sex of the subject, such as whether the sample, specimen or subject is male or female; or having a particular disease state or severity (such as stage of cancer); disease duration; or age or sex of the subject/patient. Particular methods include truncating Raman spectra to a desired wavenumber range; applying baseline correction e.g., with the Goldindec algorithm, or with ISREA and/or StaBAL; vector or specific band normalization; principal component analysis (PCA); discriminant analysis of principal components (DAPC); principal least squares (PLS) regression, machine learning with or without neural networks (NN); identification of wavenumber loadings; calculation of total canonical distance (TCD); total spectral distance (TSD), total principal component distance (TPD); ANOVA; pairwise comparisons; and performing leave-one-out or multi-fold cross-validation analysis of chemometric models (DAPC, PLS, NN) to report predictive capabilities in terms of accuracy, sensitivity (true-positives), and specificity (true-negatives), positive predictive value (PPV) and negative predictive value (NPV). Any one or more of these methods/functions/applications/analyses can be used alone or in any combination with one another. Such methods and combinations of these techniques and various examples are described in more detail below.

BRIEF DESCRIPTION OF THE DRAWINGS

The accompanying drawings illustrate certain aspects of implementations of the present disclosure, and should not be construed as limiting. Together with the written description the drawings serve to explain certain principles of the disclosure.

DETAILED DESCRIPTION OF VARIOUS EMBODIMENTS OF THE INVENTION

Figure 1:
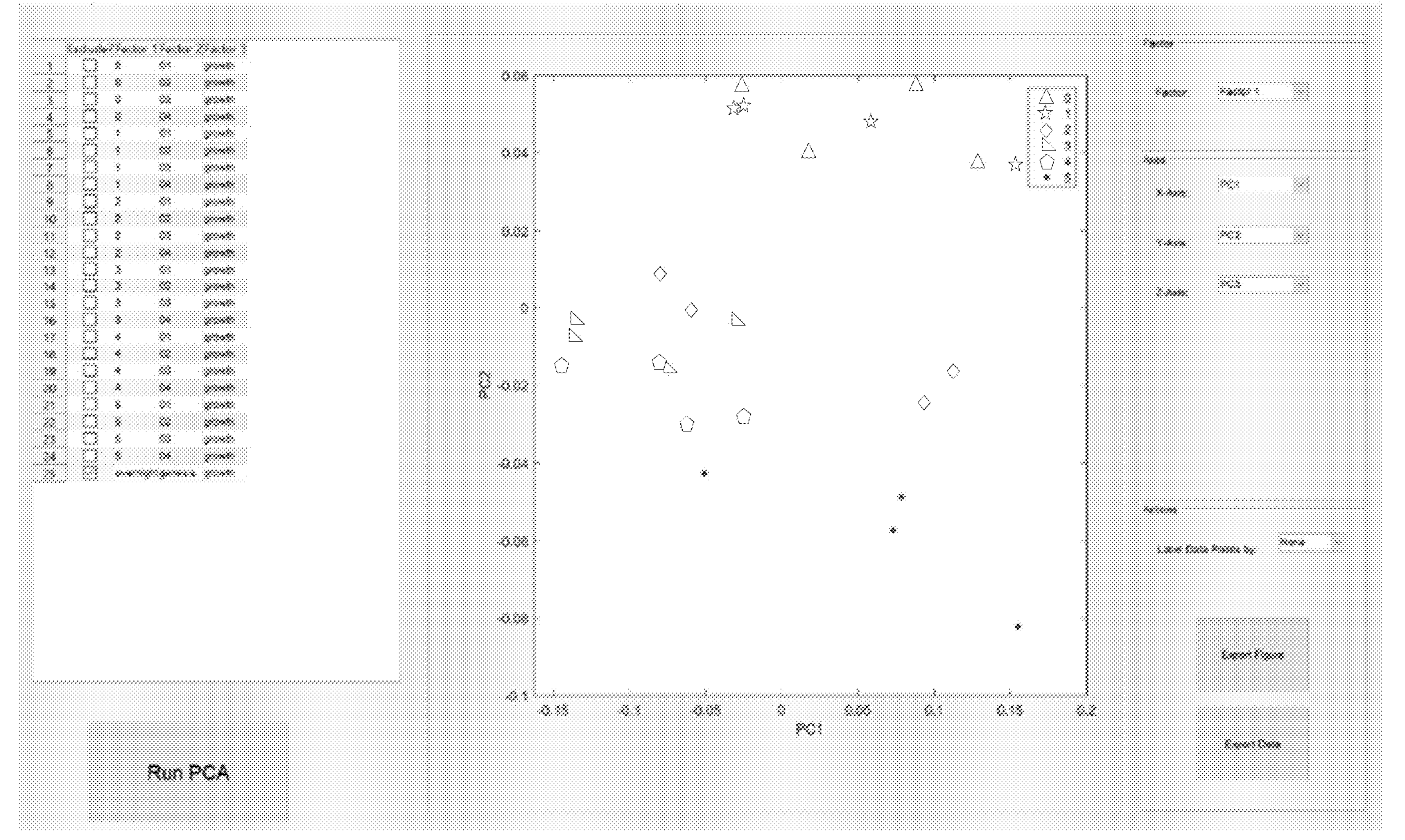
FIG. 1 is a schematic of the principal component analysis (PCA) module.

Embodiments of the invention provide various disease detection and characterization methods using computational analysis of Raman spectra. These methods are used to detect disease-specific multi-molecular patterns associated with specific diseases. The multi-molecular patterns result in a Raman "spectral fingerprint," that can be compared with that of urine from healthy persons or those with specific diseases. Specific methods include: a) optionally truncating spectra to a desired wavenumber range; 2) applying baseline correction e.g., with the Goldindec algorithm, or with ISREA and StaBAL; 3) vector or specific band normalization; 4) principal component analysis (PCA); 5) discriminant analysis of principal components (DAPC); 6) identification of wavenumber loadings for PCA and DAPC; 7) calculation of total canonical distance (TCD); and 8) performing leave-one-out analysis of chemometric DAPC models to report predictive capabilities in terms of accuracy, sensitivity (true-positives), and specificity (true-negatives).

These methods of the invention can be used in detecting or characterizing any one or more of the following diseases: Bladder cancer (all types, grades, and stages); Acute cystitis (all types, grades, stages, and etiologies, including infectious and non-infectious etiologies); Chronic cystitis (all types, grades, stages, and etiologies, including infectious and non-infectious etiologies); Schistosomiasis; Kidney cancer (all types, grades and stages); Prostate cancer (all types, grades, and stages); Prostatitis (acute and chronic); Cervical cancer (all types, grades, and stages); Uterine cancer (all types, grades, and stages); Ovarian cancer (all types, grades, and stages); Cancer of the adrenal gland (all types, grades, and stages); Cushing's disease and Cushing's syndrome; Multiple myeloma with Bence-Jones proteinuria (all stages and grades); Acute kidney injury (all types and etiologies); Acute kidney failure (all types and etiologies); Chronic kidney failure (all types, stages, and etiologies); Acute glomerulonephritis (all types and etiologies); Chronic glomerulonephritis (all types and etiologies); Focal and diffuse segmental glomerulosclerosis (all stages, grades, and etiologies, including hypertension); Membranous nephropathy (all stages, grades, and etiologies); Membranoproliferative glomerulonephritis (all stages, grades, and etiologies, including systemic lupus erythematosus); Hemolytic uremic syndrome; IgA nephropathy (all stages, grades, and etiologies); Minimal change nephropathy (all stages, grades, and etiologies); Congenital nephropathy (all stages, grades, and etiologies); Diabetic nephropathy; Protein-losing nephropathy and nephrotic syndrome (all stages, grades, and etiologies); Acute pyelonephritis (all stages, grades, and etiologies); Chronic pyelonephritis (all stages, grade, and etiologies); Lyme disease (all stages and clinical presentations); Atypical borreliosis; Myalgic Encephalomyelitis/Chronic Fatigue Syndrome (ME/CFS) (all types, stages, and etiologies); Systemic mold allergy/toxicity; Hemobartonellosis; SARS-COV-1 (Severe Acute Respiratory Syndrome Coronavirus Disease); SARS-COV-2 (COVID-19 Disease); and MERS-COV-2 (Middle Eastern Respiratory Syndrome Disease).

Embodiments of the invention include various Aspects. The Aspects can be used alone or in combination with any other Aspect. Embodiments of the invention also include combining any feature of any Aspect with any feature of any other Aspect.

Aspect 1 is a method of identifying a condition of a subject, comprising:

obtaining Raman spectra from a urine sample from a subject;

comparing the Raman spectra of the urine sample to a selected model;

wherein the selected model is constructed from various Raman spectra of urine from individuals having and not having a specified condition, and by:

applying baseline correction to a range of wavenumbers of the various Raman spectra to obtain baseline corrected Raman spectra;

performing normalization of the baseline corrected Raman spectra to obtain normalized Raman spectra;

performing principal component analysis (PCA) of the normalized Raman spectra to identify principal components (PCs) of the urine from the individuals having and not having the specified condition;

performing one or more analysis, such as discriminant analysis of principal components (DAPC), Partial Least Squares (PLS), machine learning, and/or neural networks (NN), to obtain one or more chemometric models based on one or more of the PCs and for the DAPC analysis, comprising canonicals equal in number to the PCs;

for the DAPC analysis, determining a fractional contribution of each wavenumber to each canonical of one or more of the DAPC models to determine which wavenumbers give rise to separations seen in a plot of two or more of the canonicals;

and testing one or more of the chemometric models, such as the DAPC models, using a leave-one-out or multi-fold cross-validation technique to select one of the chemometric models as the selected model having a desired level of accuracy, sensitivity, specificity, positive predictive value, and/or negative predictive value;

wherein the comparing of the Raman spectra of the urine sample to the selected model comprises identifying whether the urine sample is classified according to the selected model as being urine either from a subject who has or does not have the specified condition.

Aspect 2 is the method of Aspect 1, further comprising:

identifying statistically significant spectral differences between the urine from the individuals having the specified condition and the urine from individuals not having the specified condition by performing one or more of total canonical distance (TCD), total principal component distance (TPD), or total spectral distance (TSD).

Aspect 3 is the method of Aspect 1 or 2, wherein the selected model is one where: if the testing is based on the leave-one-out analysis, the leave-one-out analysis provides leave-one-out accuracy, sensitivity and/or specificity that exceeds random chance accuracy, sensitivity, and/or specificity; and/or if the testing is based on multi-fold cross-validation, the testing reveals a favorable positive predictive value and/or negative predictive value, and/or the testing provides a positive predictive value (PPV) and/or negative predictive value (NPV) that exceed(s) random chance PPV and/or NPV, and/or the testing provides an accuracy, sensitivity and/or specificity that exceeds random chance accuracy, sensitivity, and/or specificity.

Aspect 4 is a method of identifying a condition of a subject, comprising:

obtaining Raman spectra from a urine sample from a subject;

comparing the Raman spectra of the urine sample to a selected model;

wherein the selected model is constructed from:

one or more multivariate analysis techniques applied to various Raman spectra of urine from individuals having and not having a specified condition;

wherein one or more of the multivariate analysis techniques involves identifying statistically significant spectral differences between the urine from the individuals having the specified condition and those not having the specified condition by performing total principal component distance (TPD) and/or total spectral distance (TSD) analysis; and wherein the comparing comprises identifying whether the urine sample is classified according to the selected model as being urine either from a subject who has or does not have the specified condition.

Aspect 5 is the method of Aspect 4, wherein:

one or more of the multivariate analysis techniques comprises performing one or more analysis, such as discriminant analysis of principal components (DAPC), Partial Least Squares (PLS), machine learning, and/or neural networks (NN), to obtain one or more chemometric models;

and further comprising testing one or more of the chemometric models, such as the DAPC models, using a leave-one-out or multi-fold cross-validation technique to select one of the chemometric models as the selected model having a desired level of accuracy, sensitivity, specificity, positive predictive value, and/or negative predictive value.

Aspect 6 is a method of identifying a condition of a subject, comprising:

obtaining Raman spectra from a urine sample from a subject;

comparing the Raman spectra of the urine sample to a selected model;

wherein the selected model is constructed from various Raman spectra of urine from individuals having and not having a specified condition, and by:

applying baseline correction to a range of wavenumbers of the various Raman spectra to obtain baseline corrected Raman spectra;

performing normalization of the baseline corrected Raman spectra to obtain normalized Raman spectra;

performing principal component analysis (PCA) of the normalized Raman spectra to identify principal components (PCs) of the urine from the individuals having and not having the specified condition;

performing one or more analysis, such as discriminant analysis of principal components (DAPC), Partial Least Squares (PLS), machine learning, and/or neural networks (NN), to obtain one or more chemometric models based on one or more of the PCs and for the DAPC analysis, comprising canonicals equal in number to the PCs;

for the DAPC analysis, determining a fractional contribution of each wavenumber to each canonical of one or more of the DAPC models to determine which wavenumbers give rise to separations seen in a plot of two or more of the canonicals;

and identifying statistically significant spectral differences between the urine from the individuals having the specified condition and the urine from individuals not having the specified condition by performing total principal component distance (TPD) and/or total spectral distance (TSD);

wherein the comparing of the Raman spectra of the urine sample to the selected model comprises identifying whether the urine sample is classified according to the selected model as being urine either from a subject who has or does not have the specified condition.

Aspect 7 is the method of Aspect 6, further comprising testing one or more of the chemometric models, such as the DAPC models, using a leave-one-out or multi-fold cross-validation technique to select one of the chemometric models as the selected model having a desired level of accuracy, sensitivity, specificity, positive predictive value, and/or negative predictive value.

Aspect 8 is the method of any of aspects 1-7, wherein the selected condition is any one or more of Bladder cancer (all types, grades, and stages); Acute cystitis (all types, grades, stages, and etiologies, including infectious and non-infectious etiologies); Chronic cystitis (all types, grades, stages, and etiologies, including infectious and non-infectious etiologies); Schistosomiasis; Kidney cancer (all types, grades and stages); Prostate cancer (all types, grades, and stages); Prostatitis (acute and chronic); Cervical cancer (all types, grades, and stages); Uterine cancer (all types, grades, and stages); Ovarian cancer (all types, grades, and stages); Cancer of the adrenal gland (all types, grades, and stages); Cushing's disease and Cushing's syndrome; Multiple myeloma with Bence-Jones proteinuria (all stages and grades); Acute kidney injury (all types and etiologies); Acute kidney failure (all types and etiologies); Chronic kidney failure (all types, stages, and etiologies); Acute glomerulonephritis (all types and etiologies); Chronic glomerulonephritis (all types and etiologies); Focal and diffuse segmental glomerulosclerosis (all stages, grades, and etiologies, including hypertension); Membranous nephropathy (all stages, grades, and etiologies); Membranoproliferative glomerulonephritis (all stages, grades, and etiologies, including systemic lupus erythematosus); Hemolytic uremic syndrome; IgA nephropathy (all stages, grades, and etiologies); Minimal change nephropathy (all stages, grades, and etiologies); Congenital nephropathy (all stages, grades, and etiologies); Diabetic nephropathy; Protein-losing nephropathy and nephrotic syndrome (all stages, grades, and etiologies); Acute pyelonephritis (all stages, grades, and etiologies); Chronic pyelonephritis (all stages, grade, and etiologies); Lyme disease (all stages and clinical presentations); Atypical borreliosis; Myalgic Encephalomyelitis/Chronic Fatigue Syndrome (ME/CFS) (all types, stages, and etiologies); Systemic mold allergy/toxicity; Hemobartonellosis; SARS-COV-1 (Severe Acute Respiratory Syndrome Coronavirus Disease); SARS-COV-2 (COVID-19 Disease); and MERS-COV-2 (Middle Eastern Respiratory Syndrome Disease).

Aspect 9 is the method of any of Aspects 1-8, wherein the baseline correction is performed using the Goldindec algorithm, ISREA and/or StaBAL.

Aspect 10 is the method of any of Aspects 1-9, wherein the PCs used for one or more of the chemometric models comprise one or more PCs of the urine from the individuals having the specified condition.

Aspect 11 is the method of any of Aspects 1-10, wherein the PCs used for one or more of the chemometric models are selected based on a total number of PCs and/or based on type.

Aspect 12 is the method of any of Aspects 1-11, wherein the selected model is one comprising an accuracy of at least about 90-100%, a sensitivity of at least about 90-100%, and/or a specificity of at least about 85-100%.

Aspect 13 is the method of any of Aspects 1-12 wherein the selected model is one comprising an accuracy of at least about 99-100%, sensitivity 99-100%, specificity 95-100%.

Aspect 14 is the method of any of Aspects 1-13, wherein the selected model is one comprising an accuracy of about 100%, a sensitivity of about 100%, and/or a specificity of about 100%.

Aspect 15 is the method of any of Aspects 1-12, wherein the selected model is one where the DAPC model is based on 2-50 PCs, 30-40 PCs, or 35-38 PCs.

Aspect 16 is the method of any of Aspects 1-15, wherein the selected model is one where the DAPC model is based on 2-50 PCs and the selected model is one comprising an accuracy of at least about 90-100%, a sensitivity of at least about 90-100%, and/or a specificity of at least about 85-100%.

Aspect 17 is the method of any of Aspects 1-16, wherein the selected model is one where the DAPC model is based on 30-40 PCs and the selected model is one comprising an accuracy of at least about 99-100%, a sensitivity of at least about 99-100%, and/or a specificity of at least about 95-100%.

Aspect 18 is the method of any of Aspects 1-17, wherein the selected model is a DAPC model based on 35-38 PCs and exhibiting an accuracy of 100%, a sensitivity of 100%, and/or a specificity of 100%.

Aspect 19 is the method of any of Aspects 1-18, wherein the sensitivity represents true positives and/or the specificity represents true negatives.

Aspect 20 is the method of any of Aspects 1-19, wherein the true positives represent urine from the individuals having the specified condition.

Aspect 21 is the method of any of Aspects 1-20, wherein the true negatives represent urine from the individuals not having the specified condition.

Aspect 22 is the method of any of Aspects 1-21, further comprising truncating the range of wavenumbers to a desired wavenumber range.

Aspect 23 is the method of any of Aspects 1-22, wherein if the TCD is calculated, the TCD is calculated using a standard distance formula across all canonical values between a reference group and an experimental group, such as the urine from the individuals having the specified condition or from the individuals not having the specified condition.

Aspect 24 is the method of any of Aspects 1-23, wherein if the TSD is calculated:

the TSD is calculated for one or more (or every) Raman shift of the range of wavenumbers (or the desired wavenumber range);

the TSD is a sum of a distance between a spectrum of a first urine and a corresponding spectrum of a reference standard (such as Surine);

wherein the first urine is the urine from the individuals having the specified condition or from the individuals not having the specified condition; and the sum is performed over selected Raman shifts (or all Raman shifts), such as all Raman shifts within 600-1,800 $cm^{-1}$.

Aspect 25 is the method of any of Aspects 1-24, wherein four principal components (PCs) are selected as the top four PCs, and the TPD is calculated as a sum of a distance between the top four principal components of urine, from the individuals having the specified condition or from the individuals not having the specified condition, and a reference standard (such as Surine).

Aspect 26 is the method of Aspect 25, wherein the top four PCs are selected such that each surpasses a 0.3% contribution of a principal component contribution, or is more than 0.1% contribution for PCA, or is more than 0.4% contribution for DAPC.

Aspect 27 is the method of Aspect 25 or 26, wherein the top four PCs are selected such that together the top four PCs represent over 85%, over 90%, over 91%, over 92%, over 93%, over 94%, over 95%, over 96%, over 97%, over 98%, over 99%, over 99.5%, over 99.9% of the dataset variance.

Aspect 28 is the method of any of Aspects 1-27, where if leave-one-out is performed, the leave-one-out technique is performed in a manner such that:

one spectrum is left out and treated as an unknown;

the PCA and DAPC analyses are performed using the remaining spectra;

classification (by positive or negative, and/or disease or no disease, and/or condition or no condition, and/or male or female, and/or having a particular disease state or severity or stage of cancer, and/or disease duration, and/or age, and/or sex of patient) of the unknown is predicted by one or more of the DAPC models;

parts (a)-(c) are repeated for other or each spectrum in a dataset; and the predictions are evaluated as correct or incorrect and evaluation metrics are calculated based thereon.

Aspect 29 is the method of any of Aspects 1-28, wherein a cross-validation technique, such as the leave-one-out technique, is performed such that every specimen in the dataset is evaluated as an unknown.

Aspect 30 is the method of any of Aspects 1-29, wherein the identifying of whether the urine sample is classified as being (a) from a subject who has the specified condition or (b) from a subject who does not have the specified condition is performed in a manner such that it is determined that the spectra of the urine sample fits closer mathematically to one or the other statistically significant groups (a) or (b).

Aspect 31 is the method of any of Aspects 1-30, wherein the specified condition is whether the subject is male or female.

Aspect 32 is the method of Aspect 31, wherein the selected model has an accuracy of about 70% in determining whether the subject is male or female.

Aspect 33 is the method of any of Aspects 1-32, wherein the various Raman spectra are collected in a range spanning the 200-2000 $cm^{-1}$ wavenumber range, such as over a Raman shift range of 250-1950 $cm^{-1.}$ Aspect 34 is the method of any of Aspects 1-33, wherein if baseline correction is performed, the baseline correction is applied to a truncated range of wavenumbers in the range of 400-1800 $cm^{-1}$, such as in the range of 600-1800 $cm^{-1.}$ Aspect 35 is the method of any of Aspects 1-34, wherein if normalization is performed, the normalization is performed using vector or specific wavenumber band normalization.

Aspect 36 is the method of any of Aspects 1-35, wherein if PCA is performed, the performing of the PCA comprises transforming intensity values of the normalized Raman spectra intensities into principal component scores.

Aspect 37 is the method of Aspect 36, further comprising using the principal component scores to calculate a fractional contribution of each wavenumber to each principal component to obtain a % contribution.

Aspect 38 is the method of Aspect 37, further comprising evaluating which wavenumbers were of greatest importance to each principal component.

Aspect 39 is the method of any of Aspects 1-38, wherein if DAPC is performed, the DAPC is performed to obtain one or more DAPC models based on a number of PCs that is up to one less than a total number of PCs calculated, such as from 1-100 selected PCs.

Aspect 40 is the method of any of Aspects 1-39, wherein if DAPC is performed, the DAPC is performed using 90% to less than 100% of the PCs calculated.

Aspect 41 is the method of any of Aspects 1-40, wherein if DAPC is performed, one or more of the DAPC models represents from 90% to 99.9% of the dataset variance.

Aspect 42 is the method of any of Aspects 1-41, wherein if TCD is performed, one or more, and preferably all canonicals are used to calculate the distances of each group from a reference group.

Aspect 43 is the method of any of Aspects 1-42, wherein distinguishing features of variability in Raman spectra of urine and the wavenumbers that give rise to the separations indicating a difference between having and not having chronic kidney disease is one or more or all of the urea band in the range of about 1,000 to 1,005 $cm^{-1}$, such as at 1,002 $cm^{-1,\ 1,003}$ $cm^{-1}$, uric acid at 981 $cm^{-1}$, creatinine at 680 $cm^{-1}$, collagen at 870 $cm^{-1}$, glucose at 1,071 $cm^{-1;\ 1,117}$ $cm^{-1}$; and/or others, for example, when the Raman spectra are collected using a 785 nm laser.

Aspect 44 is the method of any of Aspects 1-42, wherein distinguishing features of variability in Raman spectra of urine and the wavenumbers that give rise to the separations indicating a difference between having and not having bladder cancer (BCA) occur at, for example, one or more or all of phosphatidylinositol (576 $cm^{-1}$), nucleic acids (721, 827, and 1340 $cm^{-1}$), protein (particularly collagen) (817, 981, 1065, 1127, and 1340 $cm^{-1}$), and aromatic amino acids (827 and $10^{04}$ $cm^{-1}$), cholesterol and fatty acids (702 and 1297 $cm^{-1}$), monosaccharides (846 $cm^{-1}$), glycogen (1048 $cm^{-1}$), and/or carotenoids (1417 and 1518 $cm^{-1}$), for example, when the Raman spectra are collected using a 785 nm laser.

Aspect 45 is the method of any of Aspects 1-42, wherein distinguishing features of variability in Raman spectra of urine and the wavenumbers that give rise to the separations indicating a difference between having and not having hematuria occur at, for example, one or more or all of 1,050-1,250 $cm^{-1}$ (lipids, carbohydrates, phosphate stretching, and C—N stretching of amides and proteins (among others); 1,590-1,750 $cm^{-1}$ (protein assignments, namely to aromatic amino acids); and/or 669, 750, 752, 999, 1,122, 1,210, 1,444, 1,543, 1,579, 1,617 $cm^{-1}$ (heme and red blood cells), for example, when the Raman spectra are collected using a 785 nm laser.

Aspect 46 is the method of any of Aspects 1-42, wherein distinguishing features of variability in Raman spectra of urine and the wavenumbers that give rise to the separations indicating a difference between having and not having Lyme disease occur at, for example, one or more or all of the 1,000 to 1,005 $cm^{-1}$ bands, such as at the 1,002 $cm^{-1}$ and/or 1,003 $cm^{-1}$ bands (representative of urea); around 900 $cm^{-1}$ and from 1,200-1,400 $cm^{-1}$ (all commonly associated with tryptophan and protein, including collagen); 620 $cm^{-1}$ (related to aromatics); 880 $cm^{-1}$ (tryptophan); 1,360 $cm^{-1}$ (tryptophan); 642 $cm^{-1,\ 665}$ $cm^{-1}$ (related to tyrosine); 880 $cm^{-1}$ (tryptophan); 1,211 $cm^{-1}$ (tyrosine and phenylalanine); and/or 1,364 $cm^{-1}$ (tryptophan), for example, when the Raman spectra are collected using a 785 nm laser.

Aspect 47 is the method of any of Aspects 1-42, wherein distinguishing features of variability in Raman spectra of urine and the wavenumbers that give rise to the separations indicating a difference between having and not having ME/CFS occur at, for example, one or more or all of the 1,000 to 1,005 $cm^{-1}$ bands, such as at the 1,002 $cm^{-1}$ and/or 1,003 $cm^{-1}$ bands (representative of urea); around 900 $cm^{-1}$ and from 1,200-1,400 $cm^{-1}$ (all commonly associated with tryptophan and protein, including collagen), for example, when the Raman spectra are collected using a 785 nm laser.

Aspect 48 is a method of quantifying eGFR and/or proteinuria comprising:

- obtaining Raman spectra from a urine sample from a subject;
- baselining and transforming the spectra with ISREA and/or StaBAL;
- analyzing the baseline and transformed spectra by principal component analysis (PCA), discriminant analysis of principal components (DAPC), partial least squares (PLS), and artificial neural networks (NN) to detect the presence of disease;
- wherein eGFR and/or proteinuria are quantified by analyzing peak height and/or area under the curve of one or more peaks of interest.

Aspect 49 is the method of Aspect 48, wherein if StaBAL is used, the StaBAL is used to optimize nodes so a particular disease becomes visible in transformed spectra by emphasizing one of more of the peaks of interest and/or minimizing other peak(s).

Aspect 50 is the method of Aspect 48 or 49, wherein key wavenumber clusters are selected based on interpretation of known pathologic features of a specified condition that may affect the types of molecules expected, such as selecting a set of key wavenumbers associated with a patient that is positive for hypertension and diabetes (HT/DM+) or selecting a set of key wavenumbers associated with a patient that is negative (HT/DM−).

These embodiments and a detailed description of these methods is provided below, as well as examples of how to apply the methods in the context of various diseases. One of skill in the art would know that the methods and specific combinations of the analyses performed can be combined in different combinations and used with any of the diseases/conditions specified herein, as well as with any other disease/condition that would be expected to be detected by these means.

Section I

Computational Analysis of Raman Spectra-Chronic Kidney Disease

To contribute to the growing interest in using Raman spectroscopy to analyze biological samples and provide chemometric analysis, the inventors have developed and applied a Raman Chemometrics (Rametrix™) Toolbox and Raman spectral correction/baselining methods for use with MATLAB®. The LITE version of the Rametrix™ Toolbox provides a graphical user interface for application of the following to Raman spectra: baseline correction with the Goldindec algorithm, vector or specific band normalization, principal component analysis (PCA), discriminant analysis of principal components (DAPC), identification of wavenumber loadings for PCA and DAPC, and calculation of total canonical distance (TCD). Raman spectroscopy and analysis with the Rametrix™ LITE Toolbox was applied to generate calibration curves, monitor enzymatic reactions, and track *E. coli* culture growth. (See Fisher, AK, Carswell, WF, Athamaneh, AIM, Sullivan, MC, Robertson, J L, Bevan, DR, Senger, R S, "The Rametrix™ LITE Toolbox v1.0 for MATLAB®," J Raman Spectro 49 (5): 885-896, 2018 ("Fisher, A, et. al. (2018)").

Results were quantitatively consistent with traditional methods of analysis. Additionally, the ability to distinguish urine specimens from healthy individuals and from patients receiving treatment for chronic kidney disease through peritoneal dialysis and intermittent hemodialysis was demonstrated using PCA and DAPC of Raman spectra, suggesting future applications to detect or monitor progression of the disease.

Raman spectroscopy is now used widely to monitor diverse biological applications, from contrasting lipids, nucleic acids, and collagen content of healthy versus cancer cells to identifying the chemical components of seeds, nuts, and oils. Raman spectra of biological samples are often comprised of many uncharacterized components in low and variable concentrations. Organic chemicals often have bands appearing at multiple wavenumbers, which can overlap with and enhance the intensity of those from other components. Interference from fluorescence by analyte or sample impurities can impose a large background, and wavenumber bands may drift depending on the instrument and environment. For these reasons, assigning specific chemicals or molecular attributes to distinct wavenumber regions can be cumbersome, and such approaches have largely been supplemented by chemometric ones.

Chemometric approaches for interpreting complex biological spectra, such as the least-squares regression-based technique biochemical component analysis and the more generally-applicable technique of principal component analysis (PCA), allow comparative analysis of preprocessed spectra. PCA can be applied readily to any group of spectra, with or without prior knowledge of sample groups or classifications, and provides a visual representation of major similarities and differences among samples through clustering. PCA can be limited in its application to Raman spectra by its inability to provide assessment of groups or the relationships among groups of spectra.

Applying multivariate analysis of variance (MANOVA) to principal components arising from PCA is a more recent technique originally used to provide a faster and more robust alternative to Bayesian clustering algorithms when analyzing large datasets given by modern DNA sequencing technologies. Discriminant analysis of original variables focuses on between-group variability while neglecting within-group variation. Furthermore, the number of variables interpreted by MANOVA must be less than the number of samples given. In both Raman spectroscopy and sequencing data, MANOVA of Raman intensities at different wavenumbers or allele frequencies would require thousands of samples. Analyzing instead the principal components of the original variables discards any prior correlations and vastly reduces the number of variables provided to MANOVA while remaining information-rich.

Discriminant Analysis of Principal Components (DAPC) can be applied to a set of data classified into a priori groups based on experimental "factors" to provide a visual interpretation of the relationships among those groups. DAPC has been used successfully to interpret seasonal influenza hemagglutinin sequencing data, providing an obvious visual demonstration of a sudden change in allele frequency between seasons. It also has been used with Raman spectroscopy to characterize the phenotypic responses of *E. coli* colonies exposed to various alcohol toxins. Unlike PCA alone, DAPC can interpret and use minor variances among data to arrange a priori groups into logical patterns, allowing correlation with independent variables.

When several principal components are used in DAPC, an equal number of "canonicals" (dimensions of DAPC) are formed. Dataset clustering in DAPC is often visualized using a 2 or 3-dimensional plot, which is only representative of the first 2 or 3 canonicals. However, several more canonicals may exist and contain valuable information related to the separation of groups in the dataset. To capture all this multidimensional information into a single value for quantitative analysis, the inventors developed the concept of Total Canonical Distance (TCD). The TCD is calculated using a standard distance formula across all canonical values between a reference group and an experimental group. The TCD calculation is shown in Eq. 1, where j is the total number of canonicals generated from DAPC, $C_i$ is the value of the $i^{th}$ canonical, and the subscripts ref and exp refer to reference and experimental groups, respectively.

$$TCD = \sum_{i=1}^{j} \left(\sqrt{C_{ref,i} - C_{exp,i}}\right)^2 \quad \text{Eq. 1}$$

Application of these tools to Raman spectra from biological systems allows both qualitative and quantitative analysis of system dynamics, comparable to traditional methods of analysis, such as UV/vis spectroscopy and enzymatic assays. The inventors conducted the following experiments, arranged in order of increasing complexity, to demonstrate the methodology: (i) the construction of a calibration curve for 2-nitrophenol, (ii) determination of glucose concentrations by enzymatic assay, (iii) the construction of a calibration curve for bovine serum albumin (BSA) through monitoring a Bradford assay reaction, and (iv) periodic monitoring of *E. coli* culture growth. Finally, the Rametrix™ LITE Toolbox was applied to Raman spectra of urine specimens from healthy individuals and patients being treated with peritoneal dialysis for chronic kidney disease (CKD). Analysis of urine samples by Raman and spectral processing with the Rametrix™ LITE Toolbox allowed a fast, non-invasive analysis that revealed critical molecular differences in the urine composition of healthy individuals and CKD patients. These studies demonstrate the wide variety of uses for Raman spectroscopy and chemometric analysis using the Rametrix™ LITE Toolbox.

Rametrix™ LITE Toolbox. Users of the Rametrix™ LITE Toolbox apply the platform for viewing (and overlaying) Raman spectra as well as performing the preprocessing steps of baselining and normalization. The user can select one or multiple spectra and view raw, raw accompanied by baseline, baselined, or normalized spectra in the viewing pane. The user can also specify if one or multiple spectra should be excluded from further analysis due to the presence of cosmic irradiation spikes or excessive noise. The user has the option of truncating spectra to any desired wavenumber range and applying baselining using the Goldindec algorithm, selected for its tolerance of high peaks and high peak ratios. The baseline polynomial order, the estimated peak ratio, and the smoothing window size can be specified as parameters for the Goldindec algorithm. Spectral normalization can be performed relative to a specified Raman band (chosen wavenumber) or by vector normalization according to Eq. 2, where y is the Raman intensity at each wavenumber in the truncated range, p is the range of wavenumbers in each spectrum, and y' is the vector normalized intensity at each wavenumber in the truncated range.

$$y' = \frac{y}{\sqrt{\sum_{j=1}^{p} y_j^2}} \quad \text{Eq. 2}$$

All collected raw Raman spectra were truncated to the biological fingerprint range of 600-1800 $cm^{-1}$. The spectra were baselined by correcting for fluorescence and background drift with a smoothing window size of 5. The polynomial order and peak ratio were adjusted for each experiment and are recorded in Table 2.

TABLE 2

Goldindec algorithm parameters and input parameters for DAPC in each experiment

| Experiment | Baseline Polynomial Order | Estimated Peak Ratio | Dataset Variability Explained by PCs |
|---|---|---|---|
| 2-Nitrophenol Calibration Curve | 5 | 0.35 | 93.9% |
| Glucose Assay | 6 | 0.4 | 99.2% |
| BSA Concentration Curve | 5 | 0.5 | 95.4% |
| *E. coli* Growth | 3 | 0.5 | 95.2% |
| Rametrix ™ Urinalysis | 9 | 0.6 | 98.1% |

PCA Module: Principal Component Analysis (PCA)

The PCA module allows the user to perform PCA on the dataset, generating one less principal component than the number of spectra provided, and view principal component scores (spectra plotted along principal component axes) in 2 or 3-dimensions. The user is also given the option to assign data labels on the resulting plot, so outliers can be identified easily. Axes can be adjusted to correspond to different principal components. PCA is performed in the Rametrix™ LITE Toolbox using the "pca" function from the Statistics and Machine Learning Toolbox™ in MATLAB®.

PC Contributions Module: Wavenumber Contribution to Principal Components. The PC Contributions module allows the user to identify the total contribution of each principal component to the total dataset variance as well as the influence of each wavenumber to that principal component. Results for several principal components can be visualized simultaneously in a viewing pane, and these results can be used to identify specific Raman bands (that may correspond with specific molecules) give rise to variance in the dataset. Specifically, these results reveal which bands lead to separations in PCA clustering. These bands can be linked to individual molecules through the use of Raman spectral reference libraries.

In general, principal components are linear combinations of Raman intensities at all wavenumbers of all spectra loaded in the Explore module. The fractional contribution, w, of each wavenumber to each principal component is calculated by Eq. 3, where z is the loading for each wavenumber (as calculated for a specific principal component by the "pca" function in MATLAB®), and p is the range of wavenumbers in each spectrum.

$$w = \frac{z^2}{\sum_{j=1}^{p} z_j^2} \quad \text{Eq. 3}$$

This calculation can be carried out separately for every wavenumber and/or principal component. It provides a graphical interpretation of how each wavenumber intensity contributes to the variance in the dataset, accounted for by each principal component.

DAPC Module: Discriminant Analysis of Principal Components (DAPC)

The DAPC module allows the user to perform DAPC with respect to any dataset "factor" specified. The user also has the option to perform DAPC using either a specified number of principal components or the required number of principal components to represent a specified variability (% total) of the dataset. The user can view results on a 2 or 3-dimensional canonical plot and assign specific canonicals to axes. The formation of data clusters on the canonical plot is indicative of similarity (to be shown in Results). The DAPC analysis is performed using the "manova1" function from the MATLAB® Statistics and Machine Learning Toolbox™ with principal component scores from the PCA module.

Canonical Contributions Module: Wavenumber Contributions to Canonicals. Similar to the PC Contributions module, the Canonical Contributions module applies Eq. 3 to DAPC results to determine which wavenumbers give rise to separations seen in the canonical plot(s). Specifically, the fractional contribution of each principal component to each canonical is calculated (Eq. 3) and multiplied by the original matrix of wavenumber contributions for principal components. The resulting matrix contains the fractional contribution of each wavenumber to each canonical. This analysis helps determine which wavenumber(s) drive the cluster separations in DAPC. These wavenumber(s) can then be attributed to specific molecules though the use of spectral libraries, such as the following reference for biological tissues. This module allows the user to check that the intended molecule(s) are giving rise to cluster separations in DAPC; otherwise, the chemistry of the system may be changing in in an unanticipated way. When the mechanisms involved are unknown, the Canonical Contributions module can be used to discover how a system is changing.

TCD Module: Total Canonical Distance. TCD is applied in the TCD module of the Rametrix™ LITE Toolbox to further quantify DAPC results. A reference factor (e.g., an analytical standard of known molecular composition) is selected, and the distance across all canonicals used in DAPC is calculated between that reference and every other factor group. The correlation between the TCD and independent variable values is then calculated, as well as a linear least-squares equation of a fitted line through the data.

Implementation. The Goldindec baseline algorithm parameters and the number of principal components used for DAPC analysis are given in Table 2 (above). Each application of DAPC was provided with "factor" labeling of each spectrum based on the experimental design.

Instrumentation. All Raman spectra were collected using an Agiltron (Woburn, MA) PeakSeeker™ PRO-785 Raman spectrometer utilizing a 100 mW, 785 nm laser with spot size 0.1-0.2 mm. Spectra spanned the 200-2000 $cm^{-1}$ wavenumber range with resolution of 8 $cm^{-1}$. An integration time of 15 s was used on all samples, which were prepared for Raman measurement in 2 mL screw thread glass autosampler vials with 10 mm screw thread caps (ThermoFisher; Waltham, MA).

All spectrophotometric measurements were taken with a Spectronic Genesis 10 Bio spectrophotometer (ThermoFisher). Samples were prepared for spectrophotometric measurement in Plastibrand 1.5 mL disposable cuvettes 12.5×12.5×45 mm (ThermoFisher).

Calibration Curves

2-Nitrophenol. 2-Nitrophenol (Sigma-Aldrich; St. Louis, MO) was prepared in DI water to final concentrations of 20 mM, 10 mM, 5 mM, 1000 μM, 500 μM, and 100 μM. Two 1 mL samples of the 20 mM concentration and four 1 mL samples of all other concentrations were measured with the spectrophotometer at 420 nm and with the Raman spectrometer, using DI water used for spectrophotometer blank. The 20 mM concentrations were out of absorbance range of the spectrophotometer. A dark subtract was performed before each round of Raman measurements to remove noise caused by charge-accumulation on the CCD detector.

Glucose Assay. Three samples each of 0, 4, 8, 12, and 16 μL of 1 mg/mL glucose in 200 μL of 1% benzoic acid standard were mixed with 400 μL of Sigma Glucose (GO) assay reagent (Sigma-Aldrich) containing glucose oxidase and peroxidase. The samples were incubated in a 37° C. water bath for 30 minutes before 400 μL of 12 N sulfuric acid was added to each sample to quench the enzymatic reaction. Samples were measured by Raman spectroscopy and by the spectrophotometer at 340 nm. The 0 mg/mL samples contained the assay reagent and were used as the spectrophotometer blank and a dark subtract before rounds of Raman measurements to remove noise from charge-accumulation on the CCD detector.

Protein Content. Three samples each of 0, 50, 100, 250, 500, 750, and 1000 μg/mL purified Bovine Serum Albumin (BSA) (New England Biolabs; Ipswich, MA) were prepared in DI water and measured with Raman spectroscopy after dark subtract using a DI water blank. The samples, except for the 50 μg/ml sample (out of range concentration), were then evaluated by traditional Bradford assay using Coomassie Plus™ Protein Assay Reagent (ThermoFisher) with spectrophotometric measurement at 595 nm. The 0 μg/mL BSA sample served as the spectrophotometer blank.

Bacterial Growth. Chemically competent *E. coli* 10-B cells (New England Biolabs) were grown in 2 mL lysogeny broth overnight at 37° C. and 200 RPM. Four 2.5 mL samples were made with 250 L of the culture and 9.75 mL of fresh lysogeny broth. A 1 mL aliquot of each sample was measured with the Raman spectrometer and an Eppendorf BioPhotometer plus for $OD_{600}$ immediately after introduction of fresh media and every hour thereafter for 5 hours, while incubating the cultures at 37° C. and with low-speed centrifugation at 200 RPM in between measurements.

Rametrix™ Urinalysis. Urine specimens were collected from 20 healthy volunteers on the Virginia Tech campus and 31 patients undergoing peritoneal dialysis treatment for management of chronic kidney disease from Fresenius Kidney Care Crystal Springs (Roanoke, VA). Specimens were frozen and stored at −30° C. for no longer than 4 weeks prior to analysis. Specimens were thawed and warmed to 37° C., transferred to glass sample vials, and scanned by Raman with a 100 mW 785 nm laser with a 10 s integration time. Each sample was scanned 10 times.

The Rametrix™ LITE Toolbox for MATLAB® was developed for streamlined applications of Goldindec algorithm baselining, normalization, PCA, DAPC, and TCD to sets of Raman spectra. The toolbox is organized into the following seven tabs. (i) Start: loading and saving files, (ii) Explore: exploring and preprocessing spectra, (iii) PCA: performing PCA on spectra, (iv) PC Contributions: examining wavenumber contributions to principal components, (v) DAPC: performing DAPC, (vi) Canonical Contributions: examining wavenumber contributions to canonicals, and (vii) TCD: calculating TCD between experimental groups and a reference group. A full examination of the functionalities provided by the Rametrix™ LITE Toolbox and recommendations for sample collection and preprocessing are as follows:

Start Module. The Start module, contains four buttons for loading Raman spectra in different file formats and three buttons for saving program output in various formats. All load buttons, except for the Load RDA button, will request a folder location containing all spectra for analysis in the indicated file format. The spectra will be internally labeled by factors given in the file names, with individual factors separated by underscores. All spectra must have the same number of factors.

The Load .SPC button will read .SPC files, a standard file format for many spectroscopic instruments. The Load .TXT button can read plain text files containing the wavenumbers and the intensities in two columns with only whitespace separating the values. The .CSV file format should be used for comma separated values with each row containing a wavenumber followed by its associated intensity, separated by a comma. The .RDA file format is unique to the RDA Toolbox and when loaded will restore a saved session in the Toolbox.

The Save RDA button will preserve the settings of an Rametrix™ LITE Toolbox work session to be recalled later. The Save .CSV button will save multiple comma-separated value files prefixed by what preprocessing manipulation was performed on the spectrum contained in each file. When in a PC operating system, the Save Excel Summary button will create a Microsoft Excel® formatted file with separate work sheets for the information given by each Rametrix™ LITE Toolbox module (located in tabs). In a Mac operating system, the Save Excel Summary button will instead request a folder location in which to save multiple .csv files that will contain the information from each Rametrix™ LITE Toolbox module. Writing the summary will take several moments on most systems.

Explore Module. Once the spectra have been loaded, the table on the left of the Explore module tab will populate with each column in the table containing the sequential factors that were separated by underscores in each spectrum file name. The first column in the table contains checkboxes that, when enabled, will cause the associated spectrum to be disregarded in the PCA and DAPC module calculations. Selecting a spectrum or multiple spectra in the table will display their data in the figure window in the center of the screen, modified by the option selected in the popup menu along the bottom of the screen.

Directly beneath the spectra table is the Average Spectra button. Activating it will initialize the calculation to average the raw intensities of each set of spectra of n factors when the first n-1 factors match. It will then delete the last column in the table, which is recommended to contain replicate number of a sample scan. If any spectra are enabled for exclusion, the Average Spectra functionality will delete them before performing its calculation.

Along the bottom of the tab are text fields in which to enter the desired wavenumber range for analysis followed by text fields describing the desired inputs to the Goldindec algorithm, the baseline polynomial order, and estimated peak ratio. If baselining calculations are unable to coalesce within 30 iterations, the algorithm is forced to continue on to the next spectrum. Baseline shape for every spectrum should be reviewed before proceeding with analysis. Window size for smooth, a MATLAB® function to smooth spectra, can be specified via the fifth text field.

A popup menu enables selection of the desired display option for spectra selected in the table, and will apply the selected operation to all loaded spectra. The first option, 'None', will only apply truncation to the loaded spectra. The second option, 'Show Baseline', is primarily used to preview the effects of the Goldindec algorithm on the truncated spectra. The third option will display the selected baselined spectra, and the fourth and fifth options will apply the selected normalization method to the baselined spectra. Vector normalization is defined in Eq. 1 (above).

Wavenumber normalization divides each Raman intensity in the truncated range of a spectrum by the baselined intensity in the same spectrum at the standard peak specified by the user in the remaining text field. The selected standard peak must be inside the truncation range.

The Export Figure button will export the current RDA Explore tab graph into a MATLAB® figure window for ease of customization, analysis, and saving the figure in different file formats.

PCA Module. The principal component analysis (PCA) module, shown in FIG. 1, displays the same table of spectra and factors as the Explore tab and will dynamically update as spectra are selected for exclusion or inclusion in any following calculations. The Run PCA button will perform principal component analysis on all spectra, except on those that have been designated for exclusion, using the 'pca' MATLAB® function. An input (n×p) data matrix of Raman intensities from each spectrum n by wavenumber p will be orthogonally transformed by the 'pca' function.

The input matrix will be comprised of the intensities adjusted by user specifications in the Explore tab popup menu. If the 'None' option is selected, then only the raw spectra in the truncation range will undergo PCA. The 'Show Baseline' and 'Baselined Only' options will provide the 'pca' function with the baselined wavenumber intensities within the truncation range. The 'Baselined and Vector Normalized' and the 'Baselined and Wavenumber Normalized' options will provide the latest normalized spectra within the truncation range to the 'pca' function.

The total number of principal components will be one less than the number of spectra provided or equal to the number of wavenumbers provided in the spectra, whichever value is lower. Projecting the Raman intensities onto the principal components transforms the intensity values into principal component scores and allows each spectrum to be graphed as a single data point along the principal components.

The figure in the center of the PCA module will default to an X—Y-Z coordinate system where each axis is one of the first three principal components calculated by the Run PCA button functionality. On the right of the PCA module, a specific factor position can be selected. This will not affect any calculations done by the Run PCA button, but will determine the initial data point color, legend, and potential labeling in the generated figure. The Run PCA button must be activated again for any change to the data point color or figure legend by the factor selection to take effect. Each axis can be adjusted to display the PCA Scores for a different principal component using the X, Y, and Z-axis popup menus, and the figure itself can be rotated for a better view. The last popup menu on the right of the tab allows the user to select among three different options for labeling data points: unlabeled, by row in the table on the left of the tab, or by the subcategory of the currently selected factor. The generated figure can also be exported to MATLAB® as before in the Explore module. Finally, the Export Data button will direct the user to save a .CSV file containing a matrix of PCA scores.

PC Contributions Module. After the Run PCA button in the PCA module is activated, the MATLAB® 'pca' function output is used to calculate the fractional contribution of each wavenumber to each principal component. The 'pca' function assigns coefficients to each wavenumber for every principal component, and the fractional contribution of the variability of each wavenumber in the supplied spectra to each principal component can therefore be calculated and displayed. The Rametrix™ LITE Toolbox calculates the fractional contribution of each wavenumber to each principal component according to Eq. 2 (above).

Figure 2:
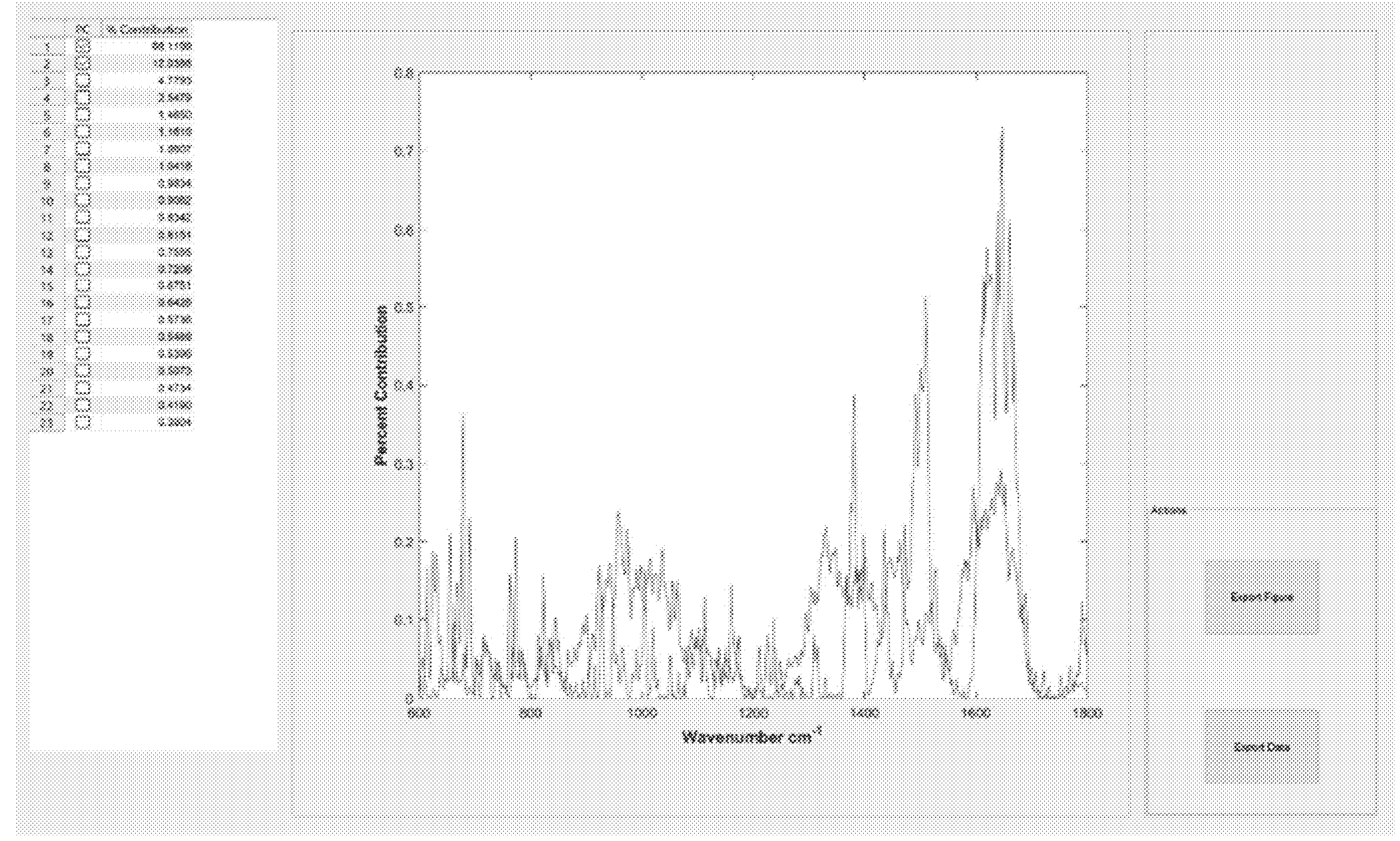
FIG. 2 is a schematic of the PC contributions module.

This calculation is carried out separately for every wavenumber and principal component (PC). The table on the left of the PC Contributions module is shown in FIG. 2.

This table lists every principal component. Enabling the checkbox next to each principal component will graph it in the figure in the center of the display. The user can then evaluate which wavenumbers were of greatest importance to each principal component. Additionally, the % contribution of each principal component to the total system variability is displayed in the second column of the table.

Figure 3:
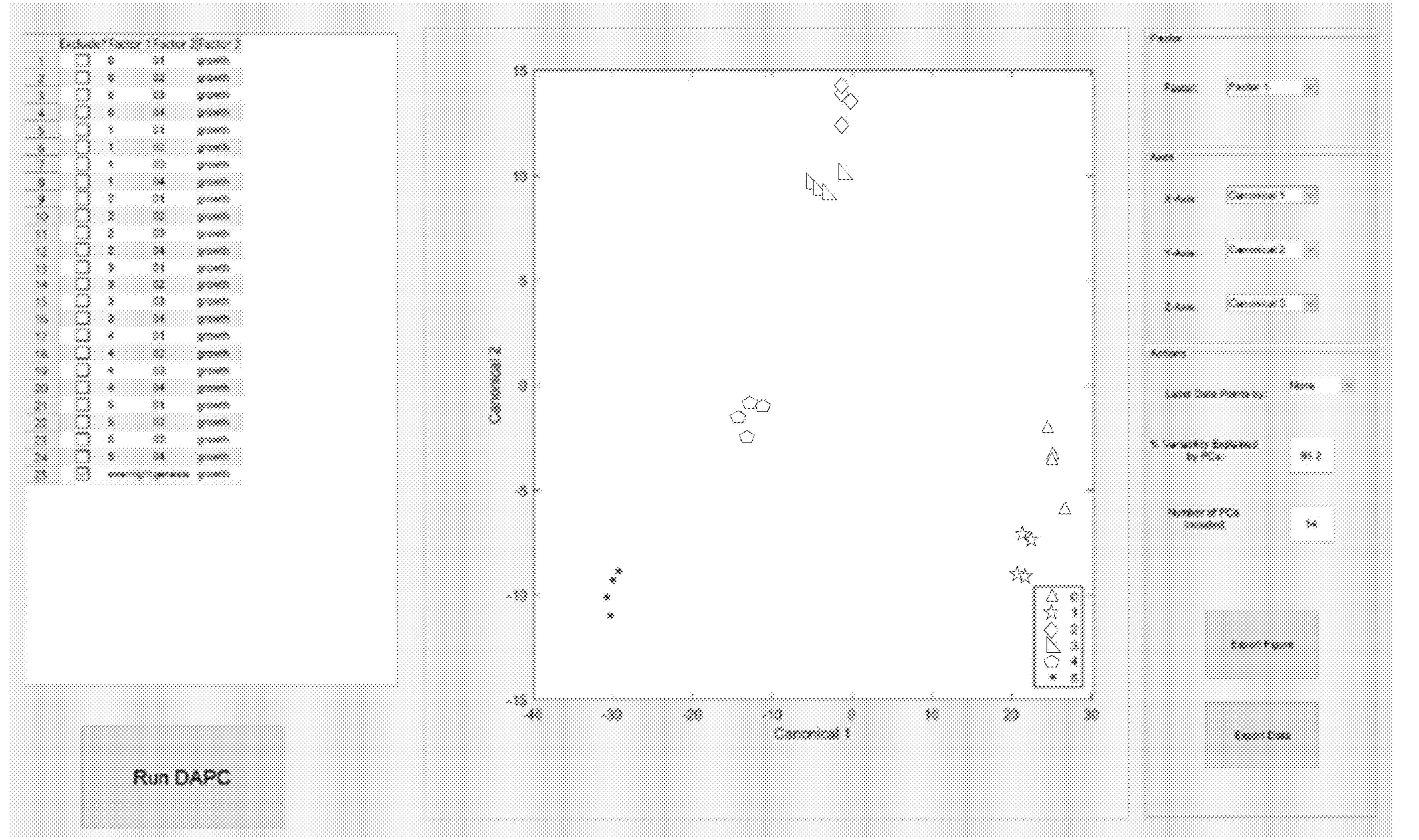
FIG. 3 is a schematic of the discriminant analysis of principal components (DAPC) module.

DAPC Module. The discriminant analysis of principal components (DAPC) module is shown in FIG. 3.

The DAPC Module shares the same table on the left as the Explore and PCA modules and dynamically updates the spectra designated for exclusion. Before activating the Run DAPC button, the user must select the factor with which to define the spectrum groups in the popup menu in the upper right-hand corner of the display. The Rametrix™ LITE Toolbox uses the MATLAB® function 'manova1' to perform discriminant analysis utilizing the user-supplied factor labeling of spectra as a priori groups and the % Variability Explained by PCs text field or the Number of PCs Included text field to decide how many PC Scores to pass to the function. Editing the value in either field will update the value in the other.

After adjusting settings and activating the Run DAPC button, the figure in the center of the tab will display the first three canonicals calculated by the 'manova1' function as the X, Y, and Z axes of the graph. The user can then manipulate the display in the same manner as in the PCA module; adjusting axes, labeling data points, rotating the figure, exporting the figure, and exporting the data.

Figure 4:
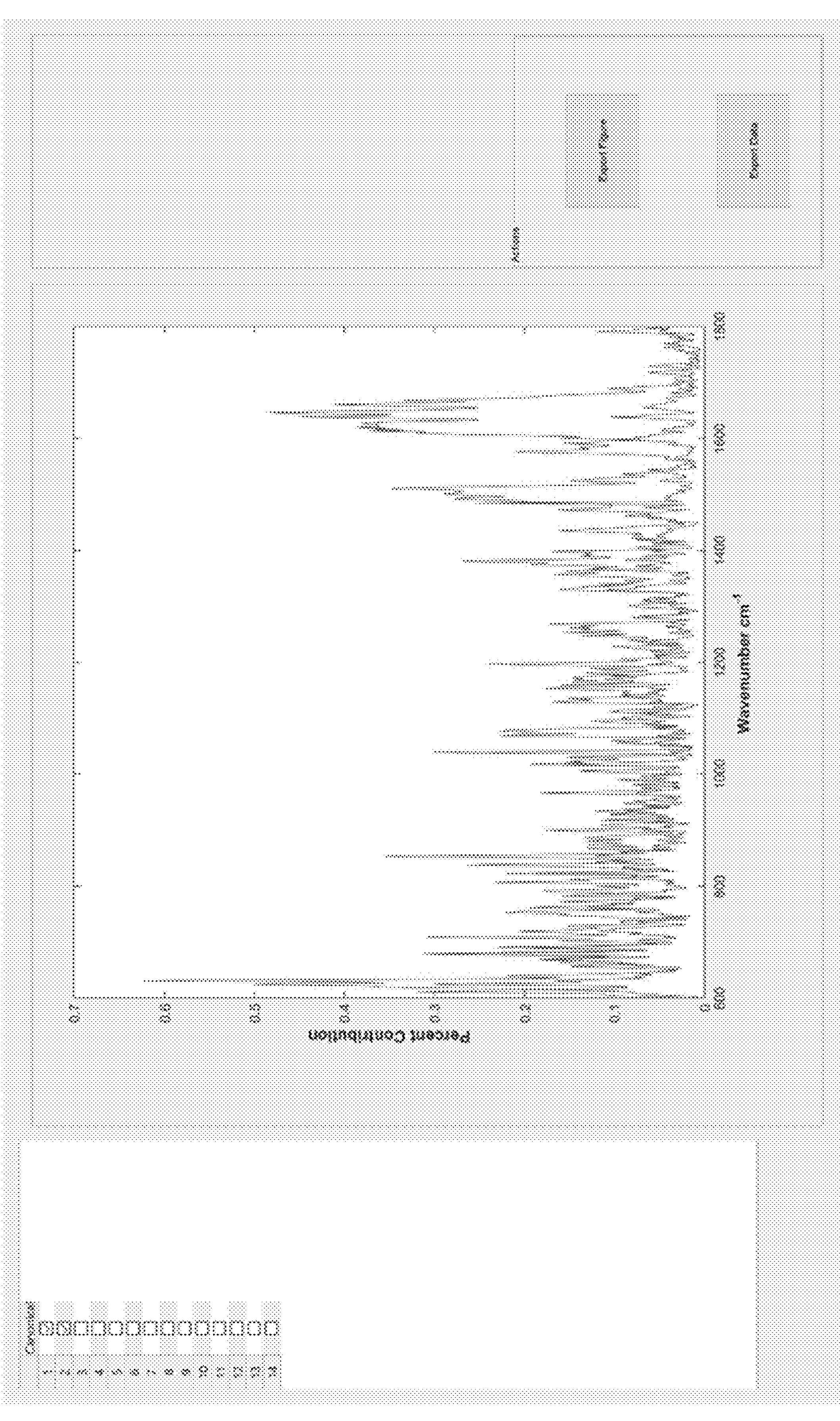
FIG. 4 is a schematic of the canonical contributions module.

Canonical Contributions Module. Like the PC Contributions module, the Canonical Contributions module (FIG. 4) calculates the wavenumber contribution to each canonical after the Run DAPC button is activated.

The Rametrix™ LITE Toolbox uses Eq. 2 (above), this time with z representing the loading of each principal component given to the Run DAPC functionality. After the fractional contribution of each principal component is calculated, the Rametrix™ LITE Toolbox multiples the matrix of wavenumber fractional contributions by principal components stored from the Run PCA functionality with the newly made matrix of principal component fractional contributions by canonicals. The resulting matrix of wavenumber loadings by canonicals is used to populate the data for the table in the Canonical Contributions module, which can be operated in the same manner as the table in the PC Contributions module.

Figure 5:
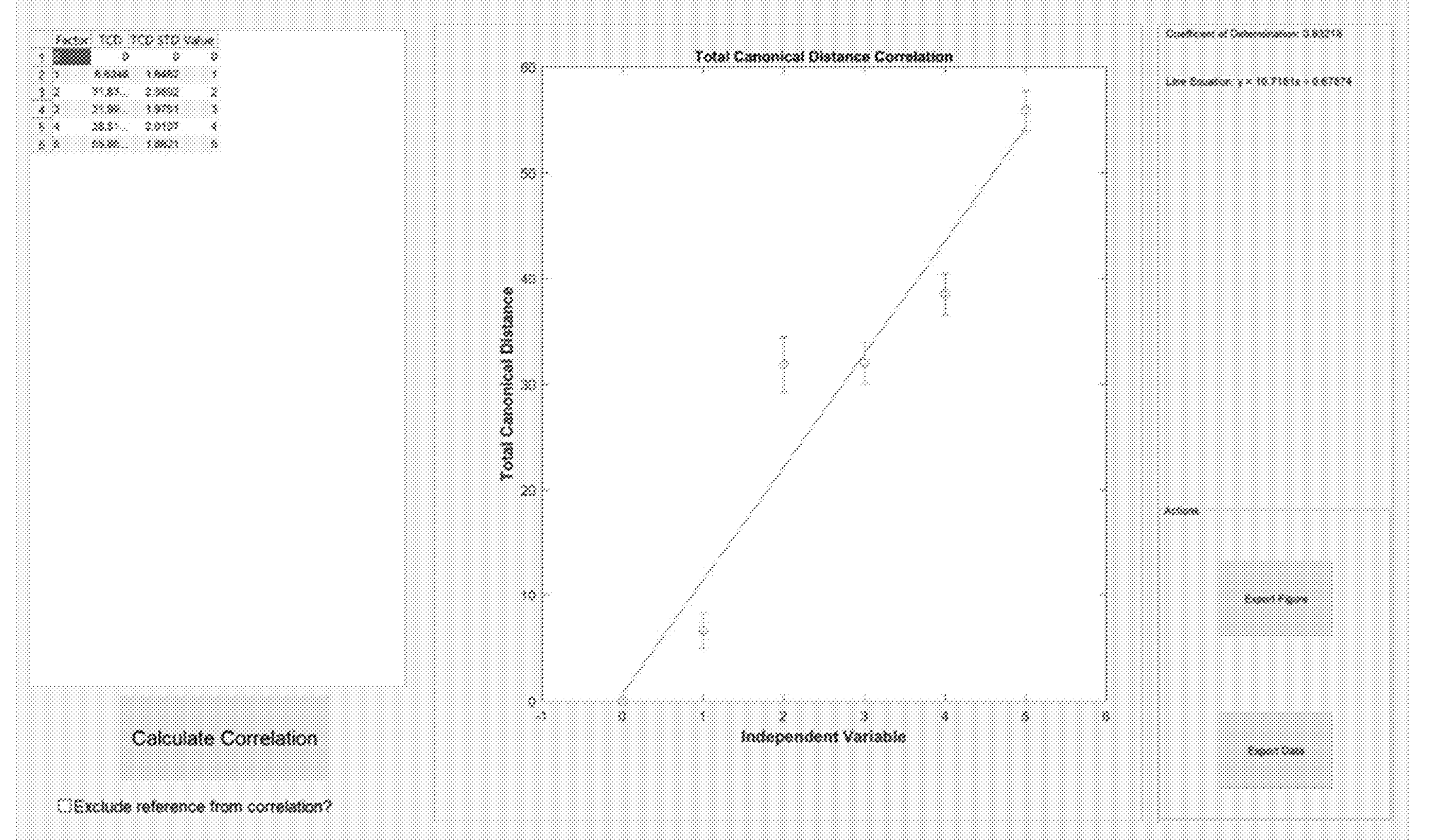
FIG. 5 is a schematic of the total canonical distances (TCD) module.
Figures 6A, 6B:
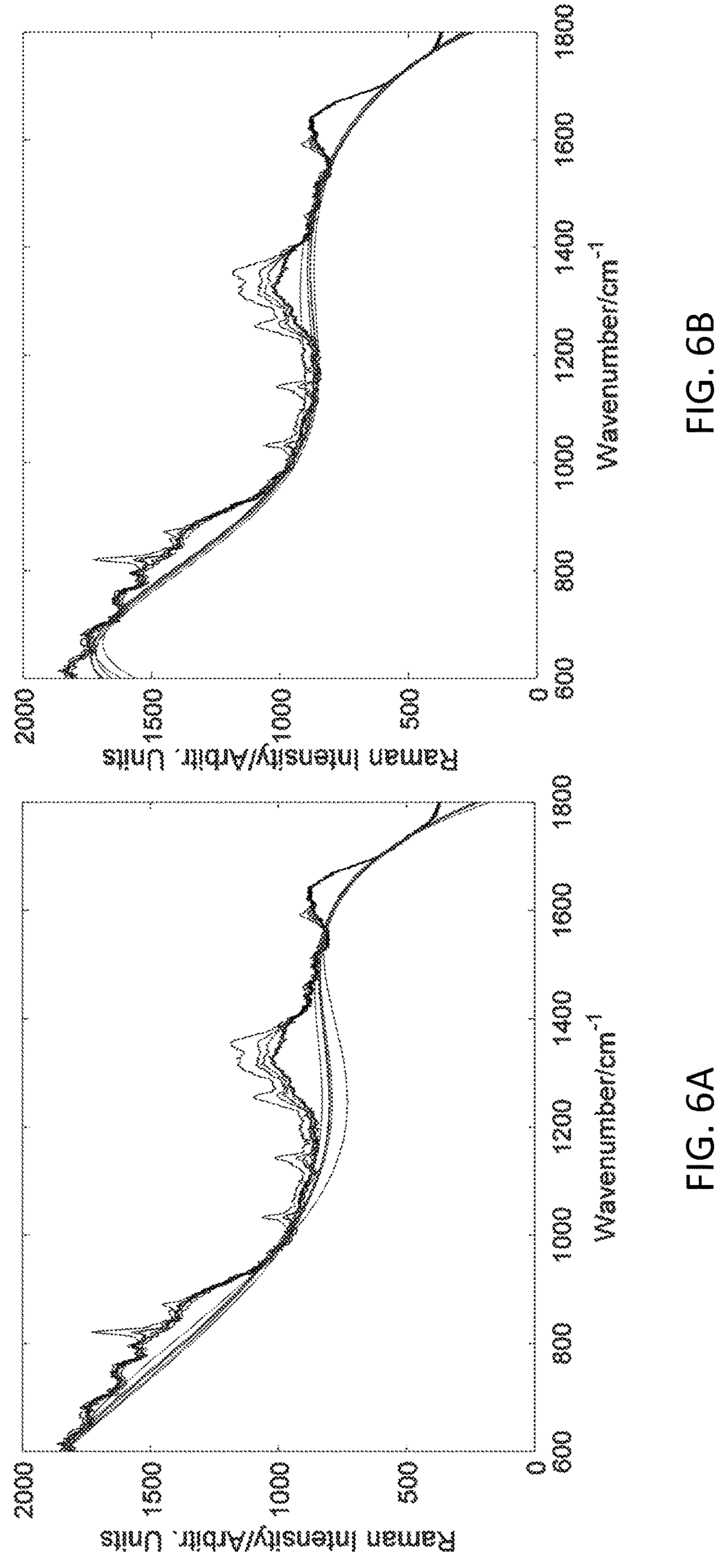
FIGS. 6A-D are graphs showing a baseline estimation example using the 2-nitrophenol concentration curve data, averaged. The best baseline polynomial order and estimated peak ratio for the data are 5 and 0.3. At first the default estimated peak ratio of 0.5 is used while the baseline polynomial order is adjusted to first A) 4 and then B) 6. Then the correct baseline polynomial order of C) 5 is applied, and D) the estimated peak ratio is adjusted to 0.3.
Figures 6C, 6D:
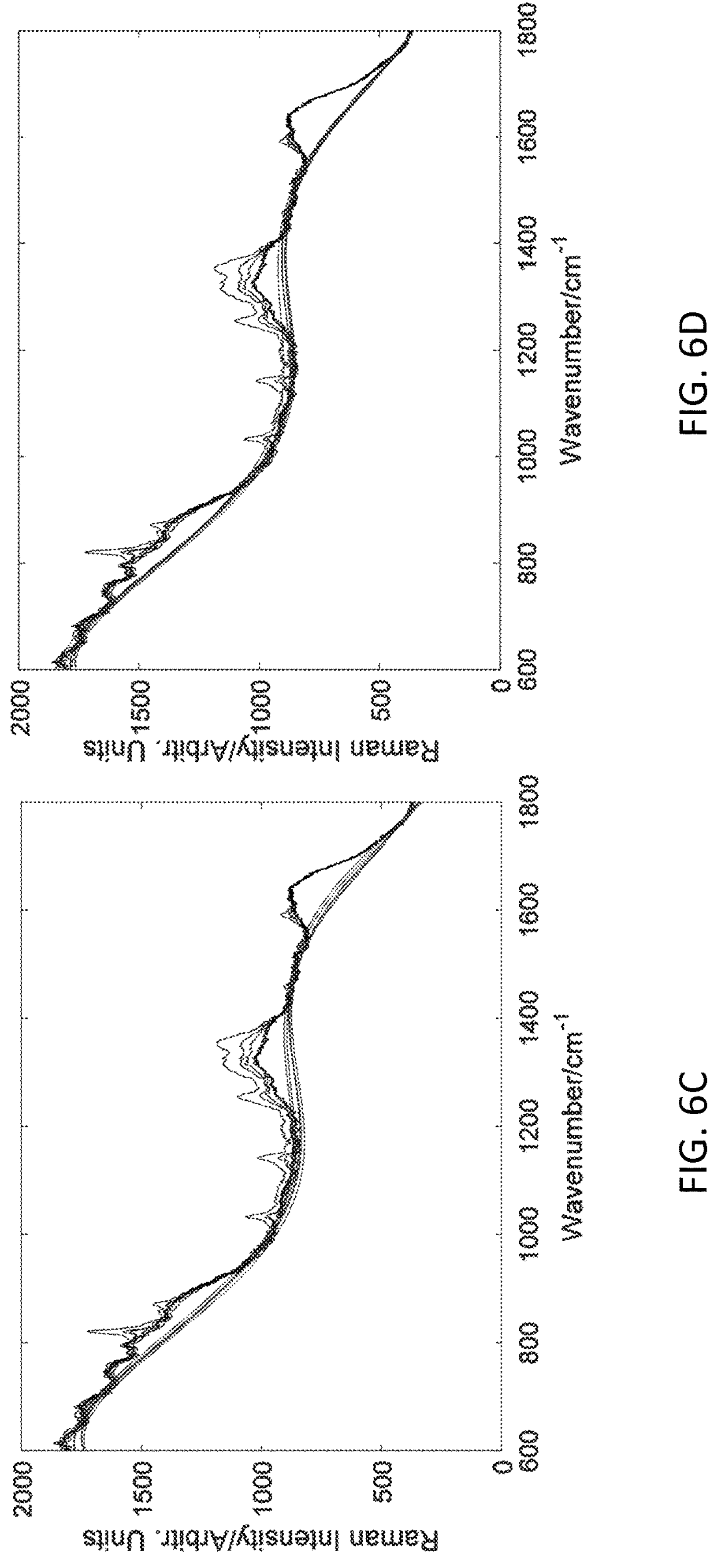

TCD Module. The total canonical distances (TCD) module is shown in FIG. 5.

The TCD Module provides a quantitative interpretation for the output of the DAPC module. All canonicals, not just those shown in the viewing pane in the DAPC module, are used to calculate the distances of each group from a reference group. The table on the left of the tab lists the groups, provided by the factor selected by the user in the latest DAPC calculation, in its leftmost column. Selecting one of those groups will designate it as the reference group and the total canonical distance calculation will be performed, populating the next two columns in the table. The final column in the table is editable, and the user may input independent variable values for each group into the cells in that column.

Once all cells in the table have been filled, the user can click on the Calculate Correlation button. The 'polyfit' and 'polyval' MATLAB® functions will use the independent variable values entered by the user and the total canonical distances calculated by selecting a reference group to calculate the linear fit between the data. The resulting line will be displayed along with the data points in the viewing pane in the center of the tab. The R2 value and equation of the line will be displayed in the upper right-hand corner of the tab. The user has the option of excluding the reference group from the correlation calculation by enabling the checkbox below the Calculate Correlation button.

As in all previous tabs, the Export Figure button will open the figure in the viewing pane for editing by MATLAB®, and the Export Data button will provide enable saving the tab analysis data as a .CSV file.

Recommendations for Data Collection and Analysis.

Sample Collection. The most reliable data analysis will come from a small number of scans each of a large range of samples. Multiple scans of the same sample can either be used to compile an average spectrum of the sample, or be carried through analysis to DAPC. Sample size can be anywhere from only a dozen to several hundred or thousands of spectra. If the baselining calculations are taking too long, averaging of spectra is encouraged.

Spectrum names should contain multiple factors separated by underscores. Each factor represents a subcategory in a category denoted by the position of the factor in the spectrum file name. The first factors in every spectrum can be evaluated in DAPC together as a priori groups, as with the second factors in every spectrum, and so on. Every spectrum loaded in to the Rametrix™ LITE Toolbox must have the same number of factors in their file names. Factors should be selected based on the type of data analysis desired, bearing in mind that the arrangement of the groups calculated by DAPC can provide insight into the relationships between those groups.

Evaluation of scatter plots of Raman spectra provided by PCA and DAPC must be based on a solid understanding of the mathematical techniques to avoid erroneous interpretation. Raman spectra that are too similar to one another cannot be reliably interpreted via PCA. DAPC uses PCs as uncorrelated variables of lesser number than samples taken while still retaining as much information as possible, but providing too much information results in overfitting group assignments, reducing the within-group variation to 0 and obfuscating potentially important inter-group relationships. Providing only one Raman spectrum per group category does not allow reliable interpretation via DAPC. For the best data, repeated trials are recommended where spectra come from different samples within the same category, as opposed to multiple Raman spectra of the same sample. As with all analytical techniques, increased sample size increases data resolution.

Selection of Goldindec Parameters. The algorithm used for baselining spectra requires two inputs specified by the user: baseline polynomial order and estimated peak ratio. The baseline polynomial order will modify the overall shape of the baseline. Look for the baseline for each spectrum in the 'Show Baseline' option in the Explore Tab to match the overall shape of the suspected background noise. Increase the baseline polynomial order if the baseline fails to follow the curve of one or more of the large, low peaks of background. The Goldindec algorithm will not attempt to follow the curve of tall peaks that are representative of sample features. Decrease the baseline polynomial order if the baseline has more peaks than the shape of the background.

The estimated peak ratio should be a value from 0.1 to 0.9, estimated in 0.1 increments. The Goldindec algorithm is robust enough to attain high accuracy when within 10% of the correct peak ratio. After overall baseline shape is attained as closely as possible with the baseline polynomial order, the estimated peak ratio should be increased if the baseline is too high, and decreased if the baseline is too low. Ultimately, the baseline should directly overlay the suspected background.

Selection of these parameters is best attained through trial and error via the use of the 'Show Baseline' option in the Explore module along the bottom of the screen. FIGS. 6A-D display an example of baseline estimation and honing. FIGS. 6A-D show a baseline estimation example using the 2-nitrophenol concentration curve data, averaged. The best baseline polynomial order and estimated peak ratio for the data are 5 and 0.3. At first the default estimated peak ratio of 0.5 is used while the baseline polynomial order is adjusted to first (FIG. 6A) 4 and then (FIG. 6B) 6. Then the correct baseline polynomial order of (FIG. 6C) 5 is applied, and (FIG. 6D) the estimated peak ratio is adjusted to 0.3.

Visualizing Multiple Spectra in the Explore Module. The Explore module allows the visualization of a single or multiple spectra, as shown in FIGS. 6A-D. Multiple spectra can be highlighted individually using the +control/command buttons in PC/Mac and selecting individual entries in the Explore module list of loaded spectra on the left. Or, a range of spectra can be selected using the +shift button and selecting the spectra at the ends of the range to view. The inventors noticed that selecting multiple spectra through hold-click (i.e., drag and drop) selecting does not work properly in MATLAB® at this time.

Applying Different Baseline Settings to Spectra Sets to be Evaluated Together. To avoid cluttering the interface of the Explore module, only one set of baseline options can be applied to any set of loaded spectra. To be able to evaluate spectra in PCA and DAPC that have been corrected to different baselines, a work-around is suggested.

Load the sets of spectra in separate batches and apply to each the desired baseline options. Use the Export Data button to save each set of the baselined (and normalized) spectra to .CSV files in a chosen folder. Once all preprocessing has been completed, load the baselined (and normalized) spectra into the RDA Toolbox together and keep the popup menu in the Explore module set to 'None' when performing PCA and DAPC. It is not possible to normalize spectra without first applying baseline calculations in the Rametrix™ LITE Toolbox, so if normalization is desired it is recommended to be carried out before saving the .CSV files.

The Effect of Variability Inclusion on DAPC Analysis. PCA provides at least n-1 principal components that each describe a portion of the total system variability. The first principal component will account for the greatest possible variances in a linear arrangement of the wavenumber intensities, and each subsequence principal component will represent consecutively less system variability.

Figures 7A, 7B:
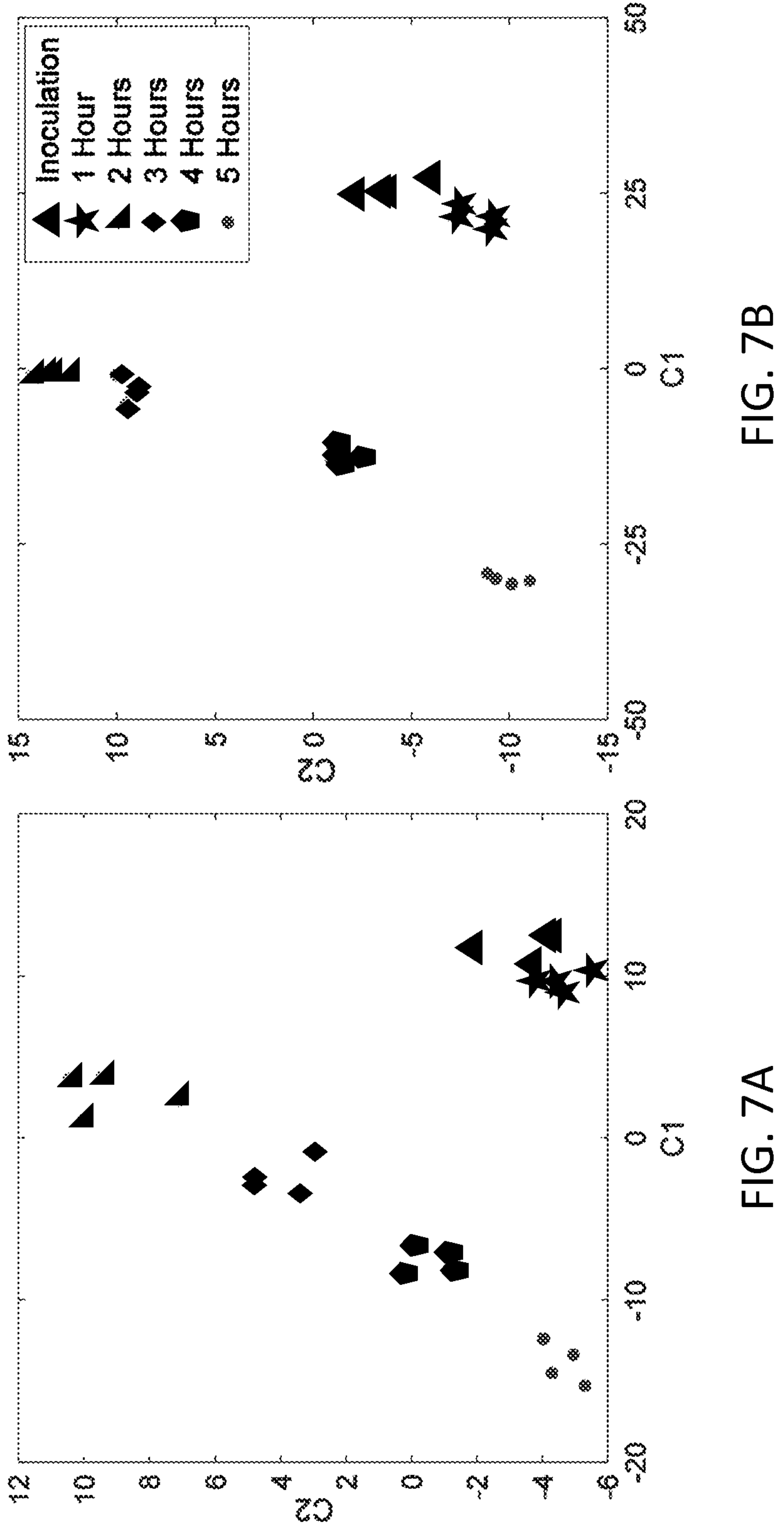
FIGS. 7A-C are graphs of *E. coli* 10-B culture growth from inoculation to 5-hour incubation in 37° C. at 200 RPM interpreted via DAPC using A) 90%, B) 95%, and C) 98% of the total system variability.
Figure 7C:
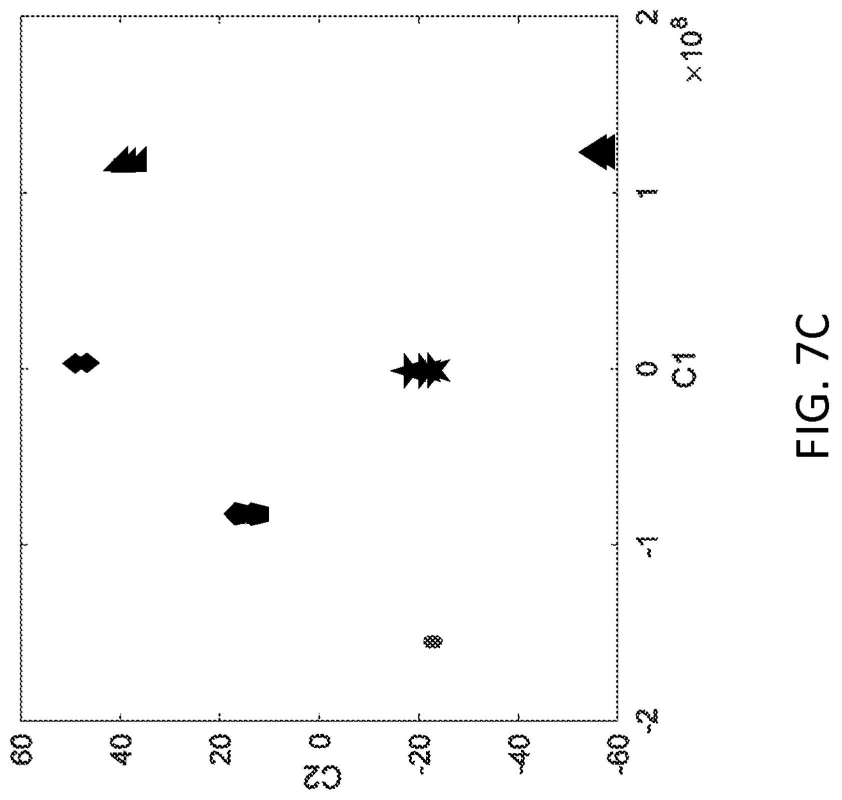

The number of principal components used in the DAPC calculations must account for less than 100% of the total system variability, and thusly the maximum number of principal components that can be used is one less than the total number calculated. However, too many principal components can perfectly discriminate (overfit) sampled individuals, eliminating any within-group variation to an unrealistic degree, demonstrated in FIGS. 7A-C. Note how the scale of the axes grows more dramatic, and how the within-group variability diminishes as more system variability is provided to the DAPC calculation. There is currently no consensus on the best amount of total system variability to consider in DAPC analysis. The default of 90% is only meant to provide a useful starting point. In embodiments, the number of principal components used in the DAPC model can range for example from 75% up to 100%, of from 80% up to 100%, or from 85% to 99%, or from 90% up to 100%, or 91%, 92%, 93%, 94%, 95%, 96%, 97%, 98%, or any percentage from 50% up to 100%, or any range within these percentages.

Experimental Implementations. Modules of the Rametrix™ LITE Toolbox (including PCA, DAPC, and TCD) were applied to Raman spectra collected from common wet-lab experiments designed to demonstrate the versatility and applicability of the approach. Results were compared with traditional methods of analysis for determining chemical concentration, protein content, and cellular density in liquid culture. A final experiment, referred to as Rametrix™ urinalysis, demonstrates that Raman spectroscopy with analysis by PCA can be used to detect differences in urine samples from healthy individuals and patients with chronic kidney disease.

2-Nitrophenol Calibration Curve

Figures 8A, 8B:
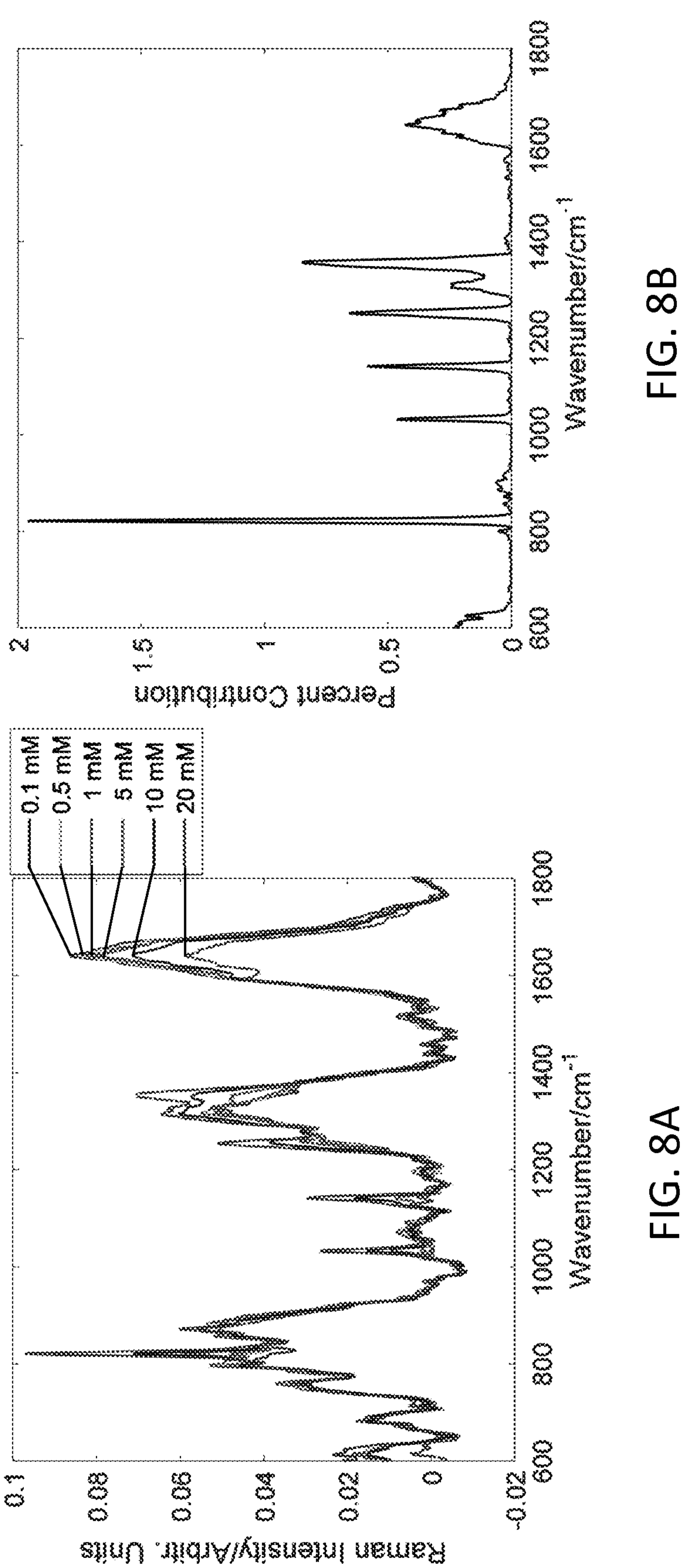
FIGS. 8A-D are graphs of 2-Nitrophenol calibration curves by absorbance and Raman spectroscopy: A) Averaged Raman spectra, baselined with the Goldindec algorithm and vector normalized; B) Wavenumber loadings for the first principal component; C) DAPC of Raman spectra; and D) TCD of each factor group plotted against each sample absorbance at 420 nm.
Figures 8C, 8D:
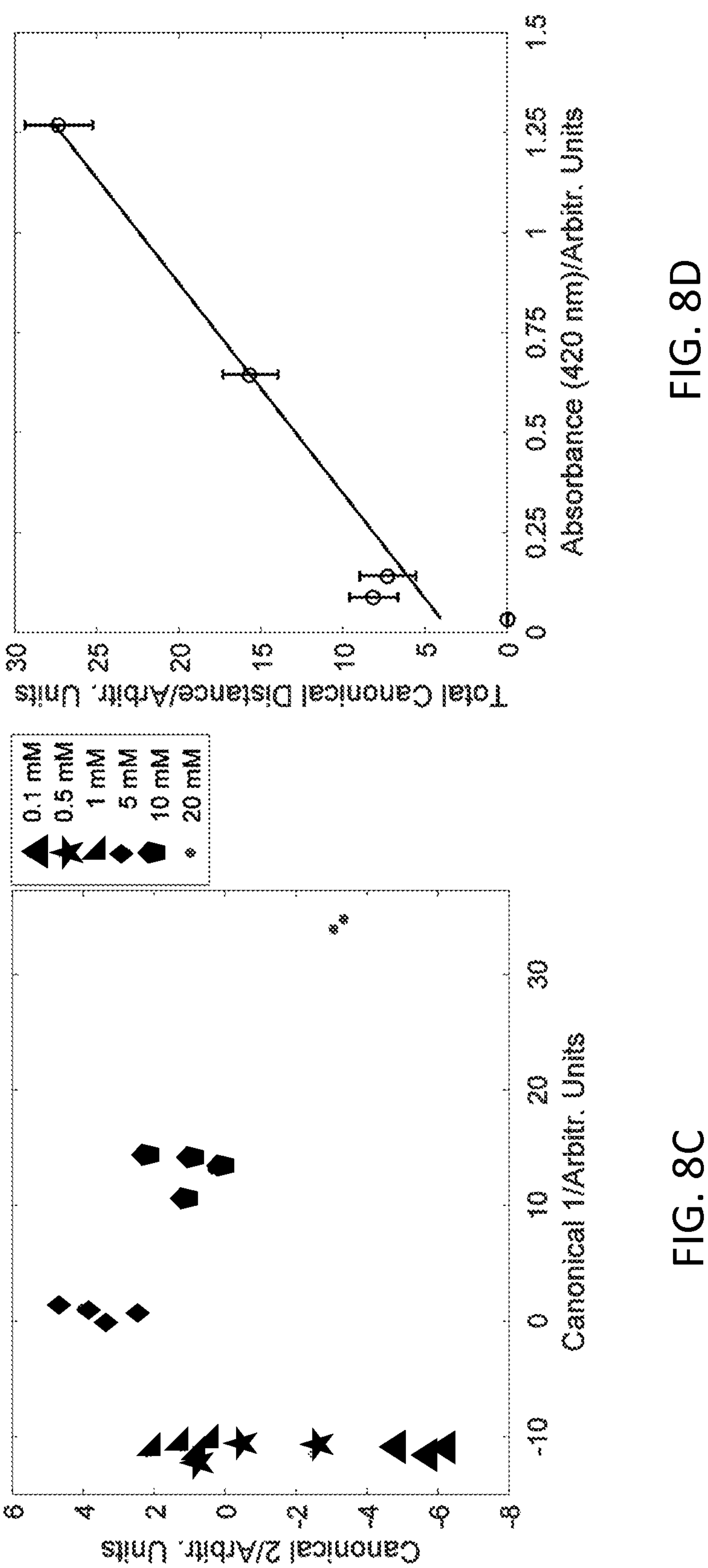

To demonstrate the applicability of the Rametrix™ LITE Toolbox in MATLAB®, a simple 2-nitrophenol calibration curve was generated using (i) Raman measurements with PCA, DAPC, and TCD and (ii) traditional spectroscopy using absorbance measurements at 420 nm. Four of the analysis methodologies included in the Rametrix™ LITE Toolbox are demonstrated in FIGS. 8A-D: (i) baselining and normalization of raw Raman spectra (FIG. 8A), (ii) PC wavenumber loadings (FIG. 8B), (iii) DAPC (FIG. 8C), and TCD (FIG. 8D). PCA results were also generated but are not shown in FIGS. 8A-D. With PCA, samples aligned along principal component 1 (PC1) in order of ascending concentration. The PC1 accounted for 79.2% of the dataset variance, and PC2 accounted for 5.2%. PCA of Raman spectra was able to also incorporate measurements of 20 mM of 2-nitrophenol, which was beyond the scope of the spectrophotometer. To verify that the largest source of variability in the first principal component was the differing concentrations of 2-nitrophenol, the wavenumber loadings were evaluated by the PC Contribution module (FIG. 8B) and compared to the expected wavenumber bands for 2-nitrophenol. The wavenumbers that contributed most to the first principal component were 821, 1032, 1142, 1254 $cm^{-1}$, and the 1285-1375 $cm^{-1}$ range. The 821 $cm^{-1}$ band is commonly indicative of $NO_2$ in-plane angle bending, and the remaining bands indicate CC, CO, and NO stretching, all of which are characteristic of 2-nitrophenol structure. DAPC results (FIG. 8C) provide less within-sample variability than observed with PCA (not shown) and align in order of ascending concentration along canonical 1. Here, the calibration along canonical 1 is non-linear, and considerable influence of canonical 2 is observed at low concentrations. To quantify the sample concentration differences using DAPC, the TCD was calculated and plotted against spectrophotometric absorbance data (FIG. 8D). A correlation coefficient (R2) value of 0.94 was calculated (excluding the 20 mM samples), indicating high correlation between TCD of Raman spectra and spectrophotometric absorbance. See Table 3. Such methods can be similarly applied to analysis of urine and discernment of "spectral fingerprints" indicating normality or abnormality.

TABLE 3

TCD values, TCD standard deviations, and absorbance (420 nm) values for 2-Nitrophenol calibration curves

| Factor | TCD | TCD St. Dev. | Absorbance (420 nm) |
|---|---|---|---|
| 0.1 mM | 0 | 0 | 0.0330 |
| 0.5 mM | 7.09 | 1.56 | 0.0870 |
| 1 mM | 7.00 | 2.07 | 0.141 |
| 5 mM | 14.5 | 1.66 | 0.644 |
| 10 mM | 25.5 | 1.96 | 1.27 |

Enzymatic Assay for Glucose

Figures 9A, 9B:
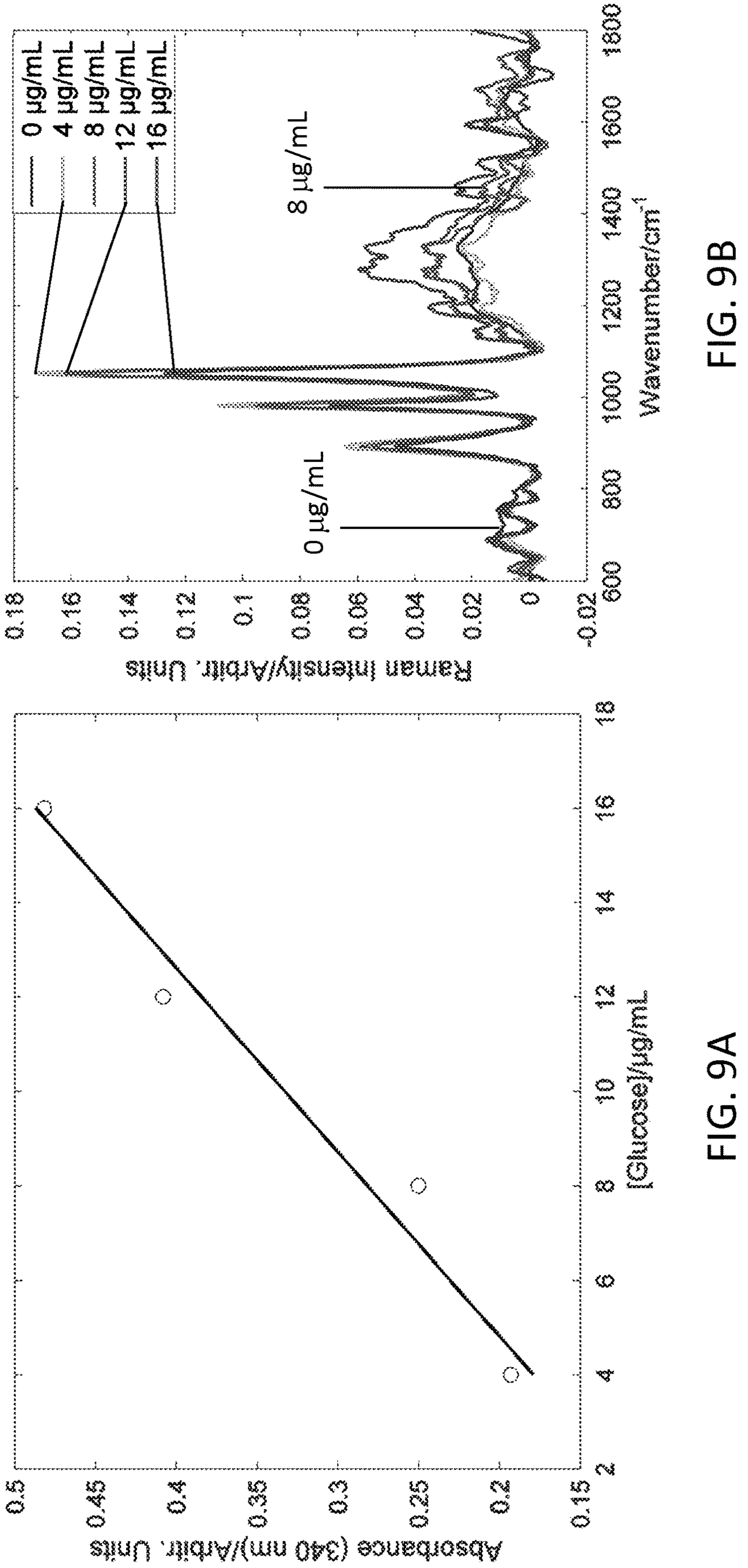
FIGS. 9A-D are graphs showing a Glucose assay measured by absorbance and Raman spectroscopy: A) Averaged glucose absorbances at 340 nm; B) Averaged Raman spectra, baselined with Goldindec algorithm and vector normalized; C) PCA of Raman spectra; and D) DAPC of Raman spectra.
Figure 9D:
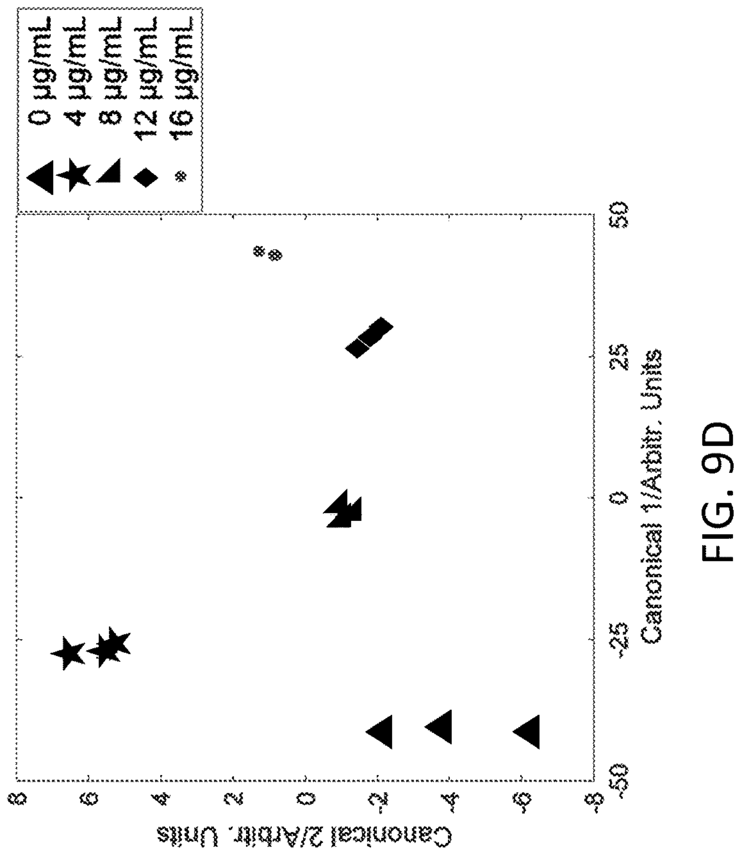
Figure 9C:
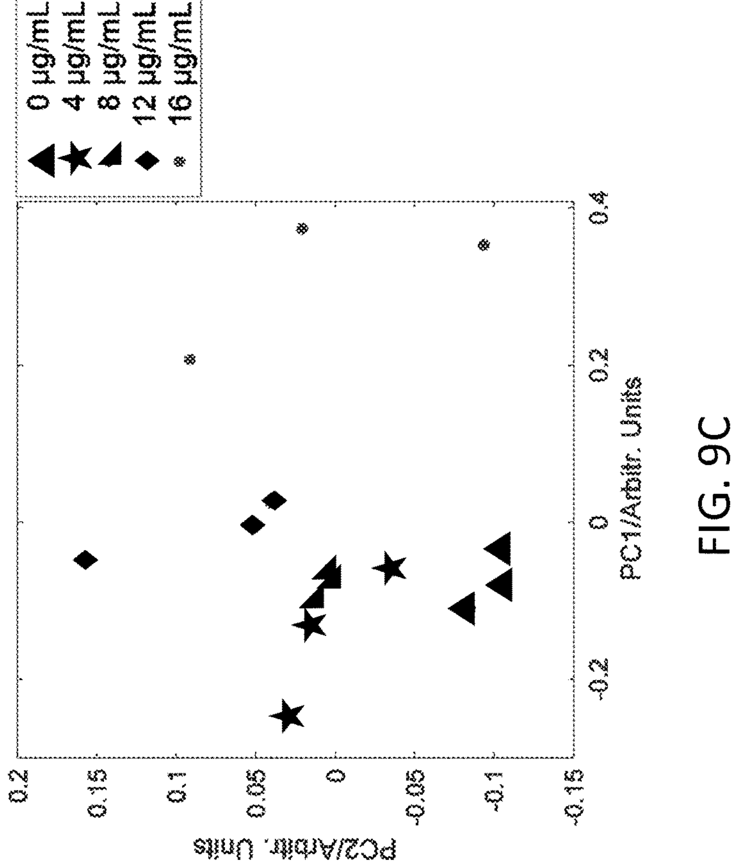

Next, an enzyme-based commercial glucose assay was run, and results were obtained by traditional absorbance measurements at 340 nm and Raman spectroscopy. This implementation is more complex than the previous example because enzymatic reactions were involved to measure glucose concentrations. The calibration curve based on absorbance (340 nm) is given in FIG. 9A, and an R2 value of 0.97 was obtained between glucose concentration and absorbance at 340 nm. PCA and DAPC results of the Raman approach are given in FIG. 9C and FIG. 9D. Data clusters were arranged in ascending order along principal components 1 and 2 and canonical 1. The multivariate analysis technique employed by DAPC transformed the loosely grouped PCA scores of the data into linearly-arranged cohesive units, with little variance in canonical 2 compared to the overall range of canonical 1. Application of DAPC to Raman spectra allows recovery of logical progression from least to greatest concentration, which is not observable in any single peak location in the complex baselined and vector normalized Raman spectra shown in FIG. 9D. Calculating the TCD (not shown) between DAPC groups and correlating with absorbance produced an R2 value of 0.99 (excluding the 0 μg/mL samples). Data are in Table 4. Such methods can be similarly applied to analysis of urine and discernment of "spectral fingerprints" indicating normality or abnormality.

TABLE 4

TCD values, TCD standard deviations, and absorbance (340 nm) values for the enzymatic assay for glucose

| Factor | TCD | TCD St. Dev. | Absorbance (340 nm) |
|---|---|---|---|
| 4 μg/mL | 0 | 0 | 0.193 |
| 8 μg/mL | 17.7 | 1.21 | 0.250 |
| 12 μg/mL | 46.0 | 1.31 | 0.408 |
| 16 μg/mL | 61.9 | 1.30 | 0.482 |

Protein Concentration

Figures 10A, 10B:
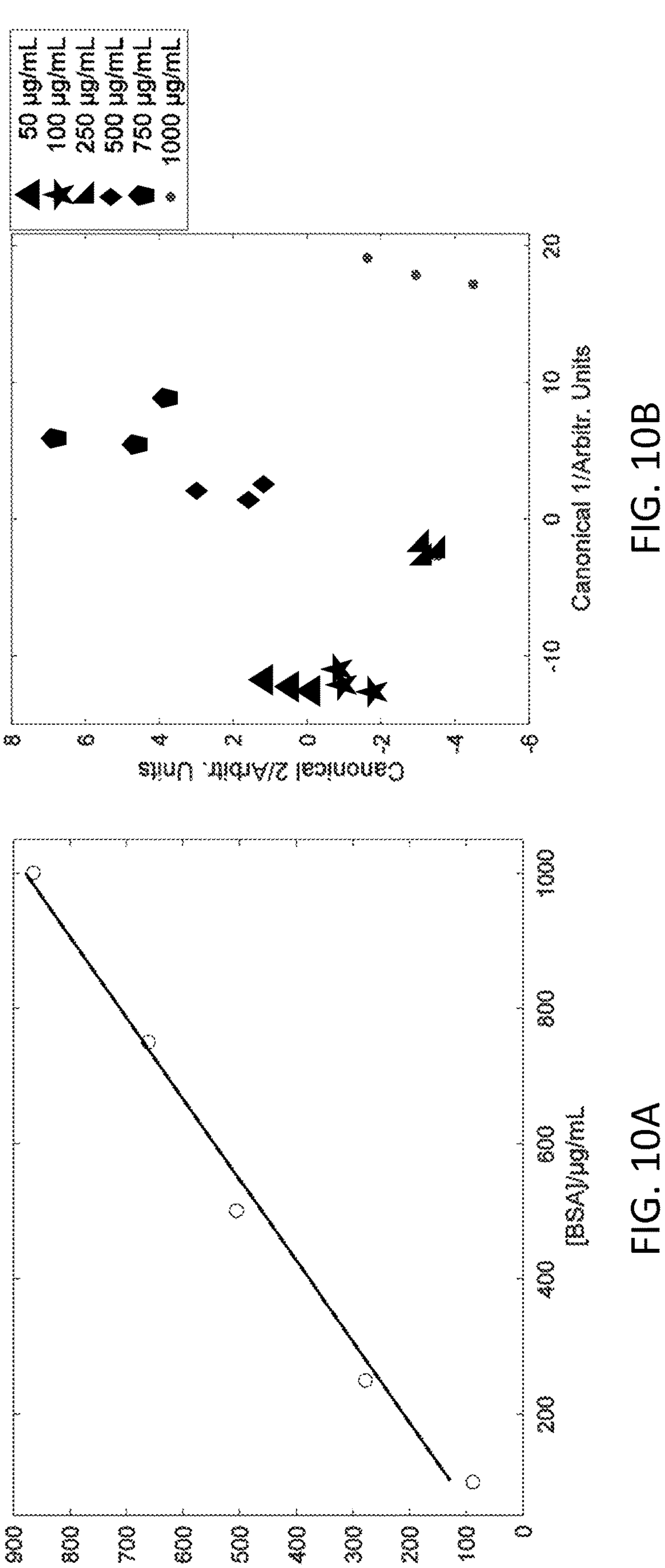
FIGS. 10A-D are graphs of a Bradford assay of BSA measured by absorbance and Raman spectroscopy: A) Averaged BSA with Bradford reagent absorbance measurements at 595 nm with standard deviations; B) DAPC of Raman spectra; C) Wavenumber loadings of first canonical; and D) Total canonical distances of each factor group plotted against each sample absorbance at 595 nm.
Figures 10C, 10D:
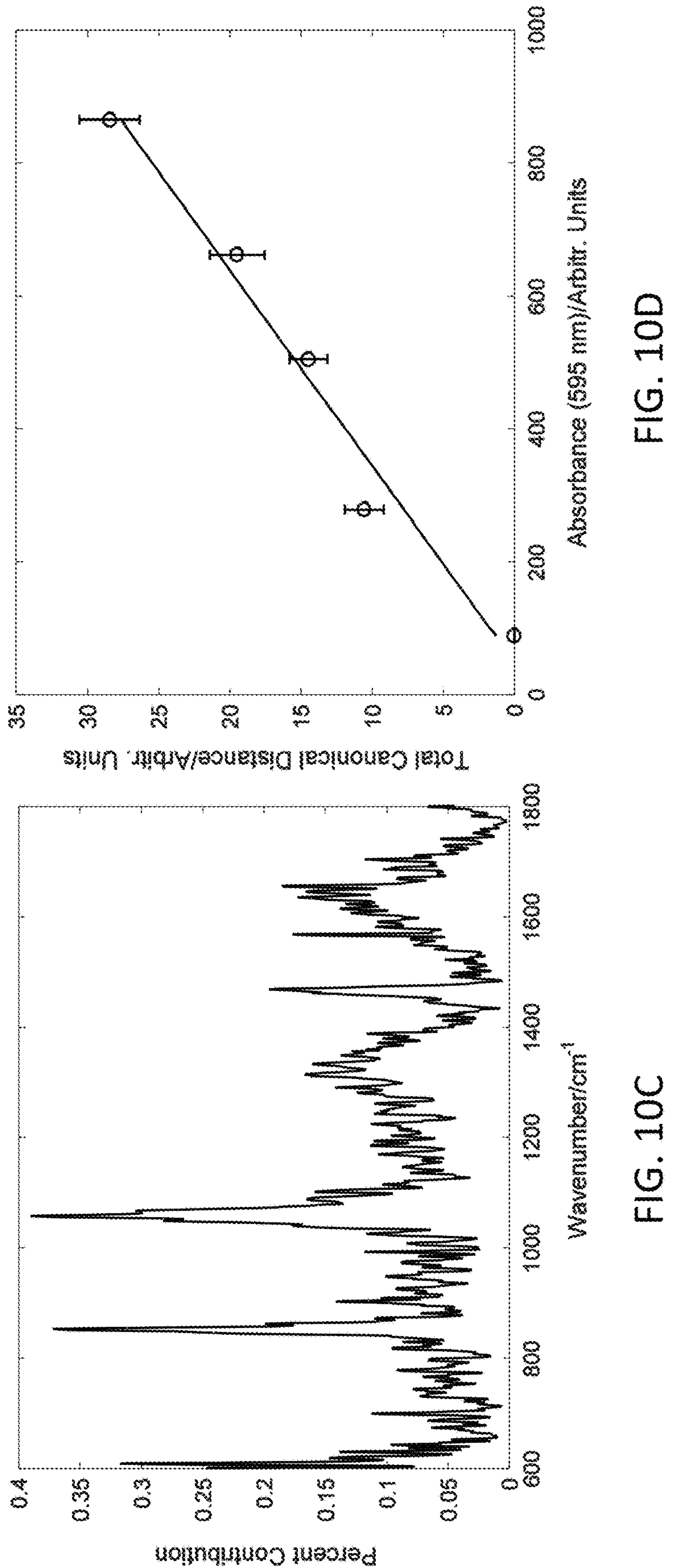

Calibration curves for bovine serum albumin (BSA) were obtained by (i) standard Bradford assays with absorbance measurements at 595 nm and (ii) through Raman spectroscopic analysis and calculation of the TCD. The purpose was to demonstrate that the Raman methodology can distinguish differing concentrations of large, chemically complex molecules (i.e., proteins) as well as it does for small molecules (e.g., 2-nitrophenol). The calibration curve resulting from the standard Bradford assay and absorbance measurements at 595 nm is shown in FIG. 10A. This analysis produced an R2 of 0.99 between concentration and absorbance. DAPC results of the Raman spectra taken before addition of Bradford reagent are shown in FIG. 10B. The wavenumber loadings for the first canonical are given in FIG. 10C and show four prominent bands around 600, 850, 1060, and 1470 $cm^{-1}$. These are most likely representative of disulfide bonds, tyrosine, C—N bonds, and $CH_2$ and $CH_3$ angle bending, all of which are common features of proteins, including BSA. TCD results were plotted against average absorbance of samples treated with Bradford reagent in FIG. 10D. This analysis revealed a correlation R2 value of 0.97 (excluding the 50 μg/mL samples). The raw TCD and absorbance data are given in Table 5. Such methods can be similarly applied to analysis of urine and discernment of "spectral fingerprints" indicating normality or abnormality.

TABLE 5

TCD values, TCD standard deviation, and absorbance (595 nm) values for the BSA calibration curve

| Factor | TCD | TCD St. Dev. | Absorbance (595 nm) |
|---|---|---|---|
| 100 μg/mL | 0 | 0 | 88 |
| 250 μg/mL | 10.6 | 1.37 | 278 |
| 500 μg/mL | 14.5 | 1.34 | 505 |
| 750 μg/mL | 19.5 | 1.95 | 661 |
| 1000 μg/mL | 28.5 | 2.11 | 865 |

Monitoring Microbial Culture Growth

Figures 11A, 11B:
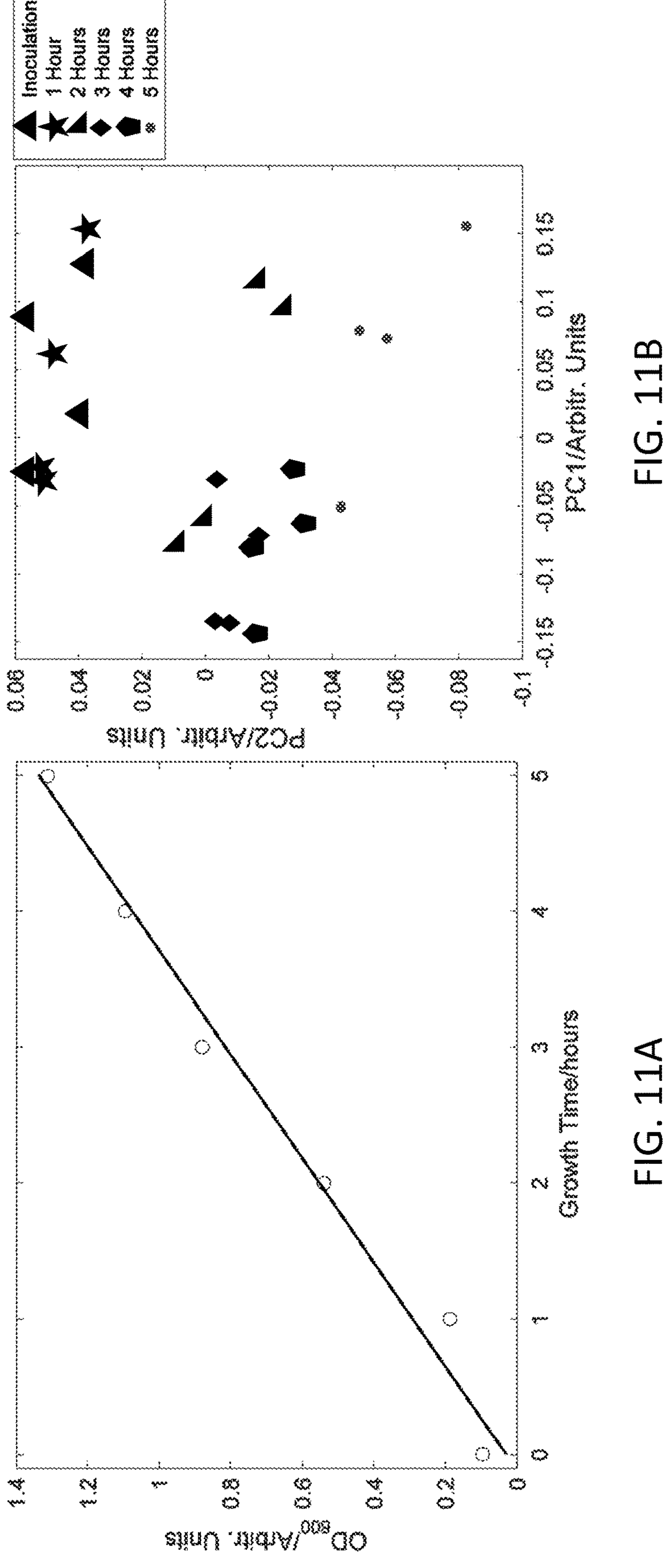
FIGS. 11A-D are graphs of *E. coli* liquid culture growth over time measured by $OD_{600}$ and Raman spectroscopy: A) Averaged $OD_{600}$ with standard deviations; B) PCA of Raman spectra; C) DAPC of Raman spectra; and D) Total canonical distances of each factor group plotted against each sample $OD_{600}$.
Figures 11C, 11D:
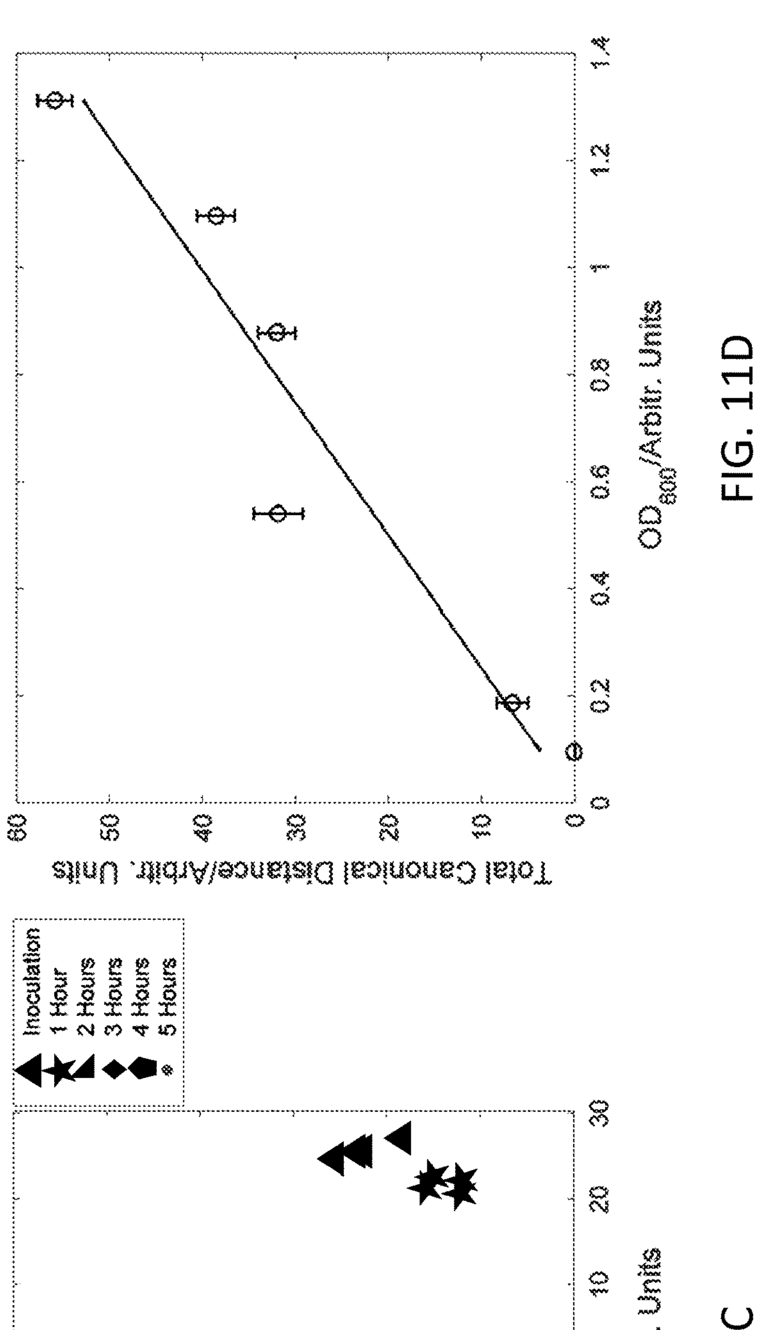

Another biological application to test the robustness of the Raman methodology and Rametrix™ LITE Toolbox was monitoring *E. coli* liquid culture growth over time with both $OD_{600}$ and Raman spectroscopy. A typical growth curve was observed in the *E. coli* samples over the first five hours of incubation following inoculation when measured by $OD_{600}$ (FIG. 11A). PCA of Raman spectra (FIG. 11B) demonstrated that the spectra are extremely variable and difficult to categorize before applying DAPC (FIG. 11C), whereupon logical progression by time was observed, decreasing along canonical 1. A large gap along canonical 2 between the first and second hour of growth may be representative of the shift from lag to exponential growth phases. TCD results were plotted against $OD_{600}$ in FIG. 11D and an R2 value of 0.92 was obtained for the correlation. The TCD and absorbance values are given in Table 6. Such methods can be similarly applied to analysis of urine and discernment of "spectral fingerprints" indicating normality or abnormality.

TABLE 6

TCD values, TCD standard deviation, and $OD_{600}$ values for *E. coli* culture growth

| Factor | TCD | TCD St. Dev. | $OD_{600}$ |
|---|---|---|---|
| Inoculation | 0 | 0 | 0.095 |
| 1 Hour | 6.6 | 1.65 | 0.187 |
| 2 Hours | 31.8 | 2.59 | 0.540 |
| 3 Hours | 32.0 | 1.98 | 0.878 |
| 4 Hours | 38.5 | 2.01 | 1.100 |
| 5 Hours | 55.9 | 1.88 | 1.310 |
| Growth Rate ($hour^1$) | 0.39 | | 0.38 |

To determine if the growth rate could still be ascertained by TCD, both TCD and $OD_{600}$ growth curves were normalized and used to calculate the growth rate. These data are also presented in Table 6, and very good agreement was observed whether $OD_{600}$ or TCD was used to calculate growth rate.

Rametrix™ Molecular Urinalysis

Figures 12A, 12B:
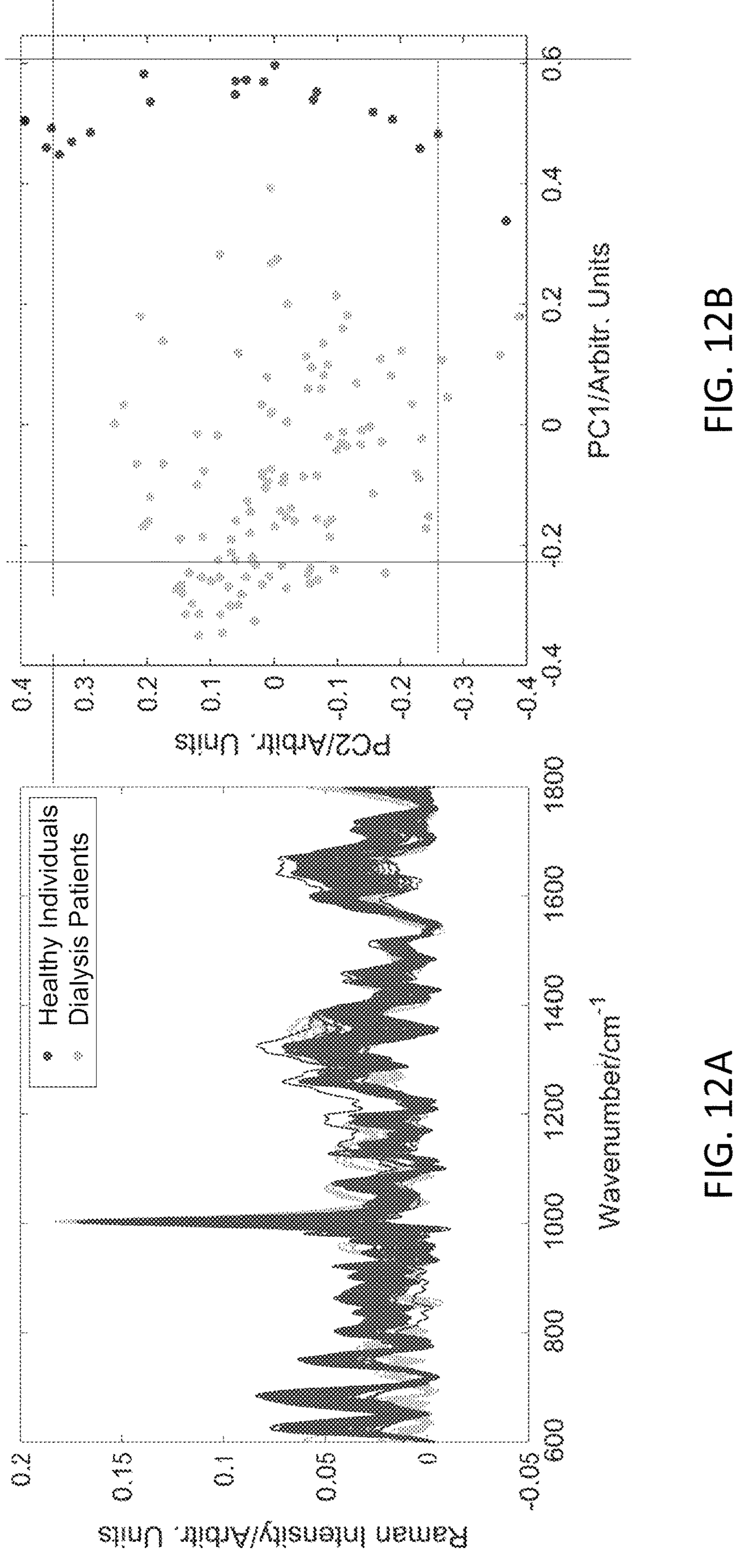
FIGS. 12A-D are graphs of Rametrix™ urinalysis of healthy individuals and dialysis patients: A) Averaged Raman spectra of different time points per individual, baselined with the Goldindec algorithm and vector normalized; B) PCA of Raman spectra; C) DAPC of Raman spectra; and D) Wavenumber loadings of canonical 1.
Figures 12C, 12D:
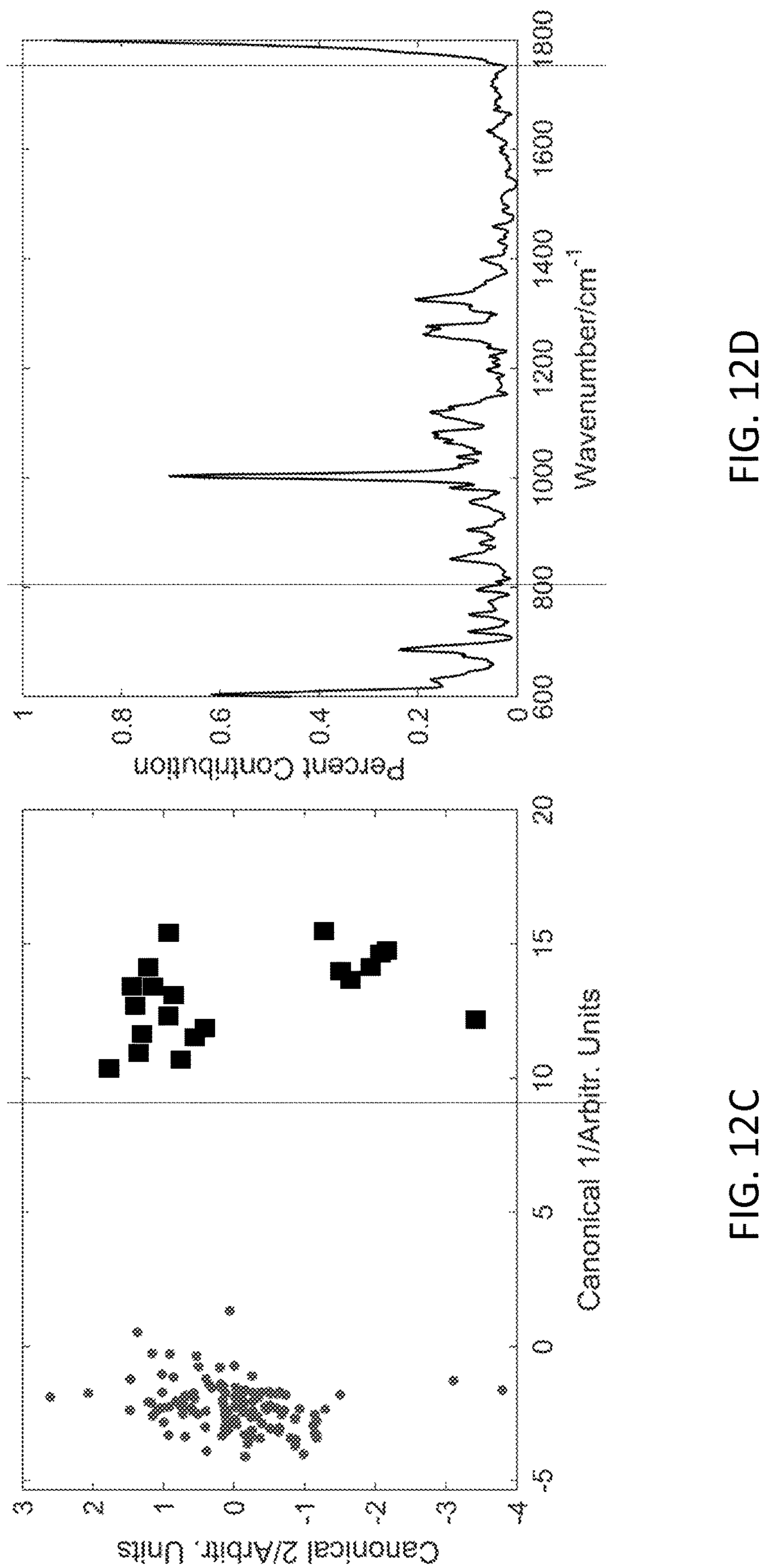
Figures 13A, 13B:
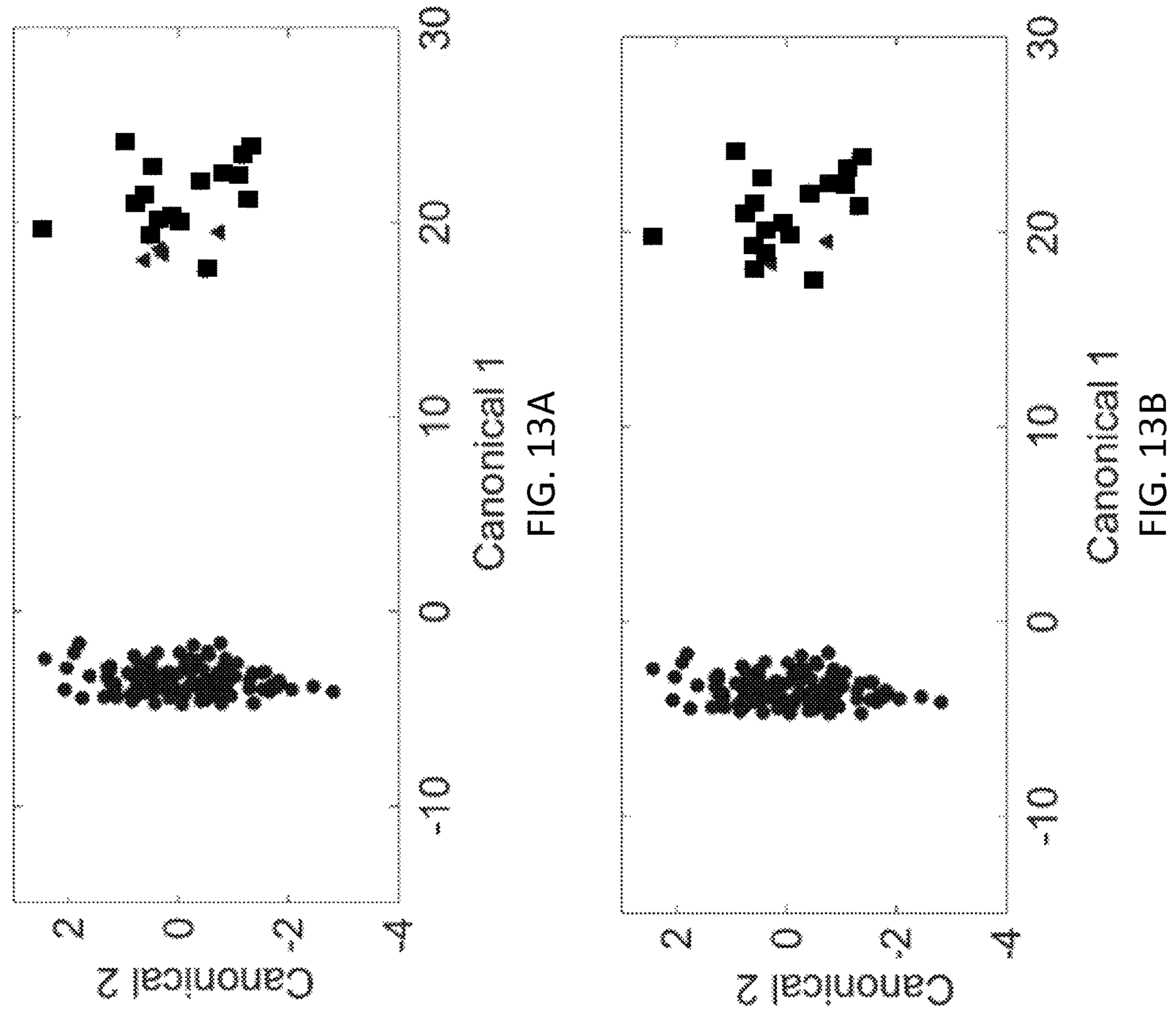
FIGS. 13A-D are graphs showing spectral clustering by DAPC with predicted classifications. DAPC models were built with: A) 1 PC, B) 10 PCs, C) 35 PCs, D) 70 PCs. Data points appearing as circles and squares were classified correctly. Data points appearing as triangles were classified incorrectly.
Figures 13C, 13D:
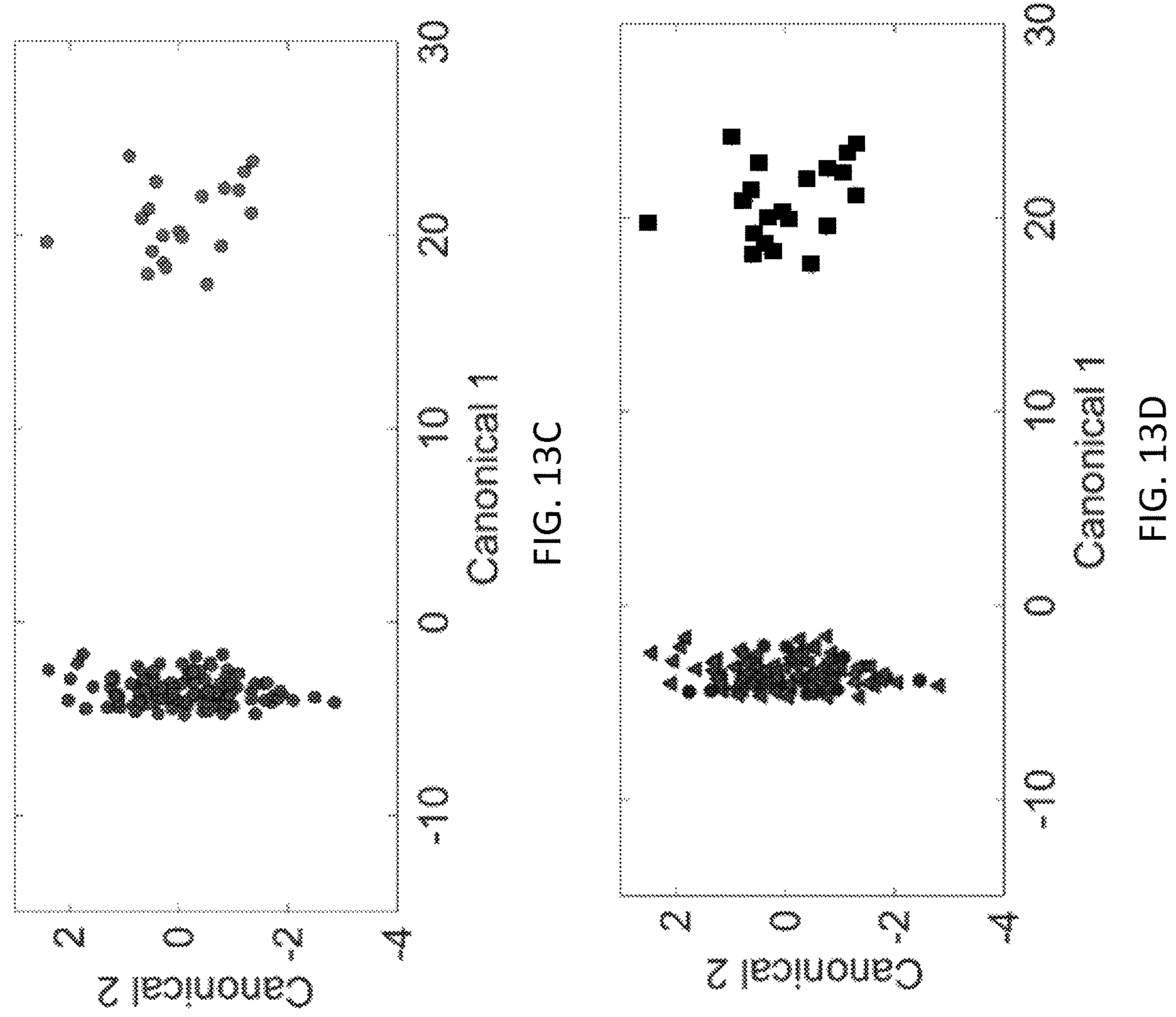

Raman spectroscopy and processing with the Rametrix™ LITE Toolbox in MATLAB® can replicate the qualitative analysis returned by a wide range of standard analytical techniques, but it can also provide qualitative information for complex samples that would otherwise require metabolomics analysis. To demonstrate this capability, urine specimens from healthy individuals and from chronic kidney disease patients undergoing peritoneal dialysis treatments were analyzed by Raman spectroscopy and the spectra processed using the Rametrix™ LITE Toolbox. Spectra were first baselined and normalized (FIG. 12A) and then compared by PCA (FIG. 12B) and DAPC (FIG. 12C). The separation of healthy individuals and chronic kidney disease patients is obvious in PCA (FIG. 12B), without the benefit of defined groups, but this separation became more defined by DAPC (FIG. 12C). Urine represents a particularly complex matrix, with over 2,500 known chemical components, and the Raman spectra are accordingly complex. The greatest distinguishing sources of variability in the spectra between the healthy individuals and chronic kidney disease patients were identified in the wavenumber loadings of canonical 1 from DAPC (FIG. 12D). The urea band at 1003 $cm^{-1}$ is the major distinguishing feature, but the presence of many other bands in the wavenumber loadings indicate there are many more features from which to extract patient health data. These have the potential to be previously unknown biomarkers of disease. Further detailed analysis could be conducted utilizing factors such as disease state, disease severity, disease duration, age and sex of patient providing urine sample, sample collection time, and other sample qualifiers to track disease progression and give valuable insight into overall patient health.

To provide a streamlined computational pipeline for processing Raman spectra and performing multivariate statistical analyses, such as PCA, DAPC, and TCD, the inventors have developed and provide the Rametrix™ LITE Toolbox for MATLAB®. Here, use of the Rametrix™ LITE Toolbox is demonstrated and it is shown how it can provide qualitative (i.e., separation of groups through DAPC) and quantitative analyses (i.e., recreating calibration curves with TCD). The quantitative analysis approach showed good agreement with standard analytical techniques involving spectrophotometric absorbance measurements (see above). While many of the examples given in this document are simple in nature, such as generating calibration and growth curves, the use of TCD to do this is a new concept. It is valuable because a Raman spectrum captures a snapshot of the chemical composition of a sample, which can then be deconvoluted to reveal further information. For example, here it has been shown that Raman spectroscopy and calculation of TCD can generate a reliable growth curve for *E. coli*. Though $OD_{600}$ measurements are easily obtained, additional information is contained in the Raman spectra that can contribute to more robust analysis. It has been shown previously that properties such as membrane fatty acid configuration, membrane fluidity, and amino acids content can be extracted from Raman spectra of *E. coli* cells growing under stressed conditions. Additionally, analysis of *E. coli* cultures by DAPC can distinguish among the *E. coli* phenotypes that arise from exposure to non-lethal doses of alcohols and different classes of antibiotics. Such changes in cellular phenotype arise from genetically-driven stress responses and are accompanied by changes in chemical composition (i.e., metabolomics, lipidomics, etc.). With current technologies, the characterization of these chemical changes requires cell deconstruction and several types of analysis, many involving mass spectrometry. The primary components of the signal can be used along with multivariate statistics to determine the similarities and differences of experimental groups. The observed differences may then be traced back to individual Raman bands, which can be identified using Raman spectral reference libraries. The Rametrix™ LITE Toolbox enables this type of analysis through inclusion of the PC Contributions and Canonical Contributions modules. While this was not demonstrated for the case of *E. coli* culture growth, it was demonstrated for the calibration curves of 2-nitrophenol and BSA. For the case of *E. coli* culture growth, how would one know if observed changes were due to growth, as opposed to changes in pH or byproduct accumulation? The PC and Canonical Contribution modules can answer this question. Notably, bands associated with major biological macromolecules (e.g., protein, fatty acids, nucleic acids, etc.) should dominate the PC and Canonical Contributions modules if observed changes are due to culture growth. Raman bands for these molecules can be found in Raman spectral reference libraries, including this one. This is confirmed here for the case for *E. coli* culture growth.

Along these lines, the Rametrix™ LITE Toolbox can be used to discover why (or how) a system changes when the mechanism(s) are unknown. This was true for the example of chronic kidney disease presented here. Nephrologists have located several useful clinical biomarkers of chronic kidney disease to enable early diagnosis. However, it is likely that additional useful biomarkers and unique combinations of numerous biomarkers exist that could provide additional information to clinicians. One or more of these potential biomarkers may be responsible for the uncharacterized bands in FIG. 12D. Further investigation into these, through the use of Raman spectral reference libraries and/or mass spectrometry, may yield the identity (ies) of novel biomarker(s). This illustrates one way that Raman spectroscopy and the Rametrix™ LITE Toolbox can be used for discovery.

The Rametrix™ LITE Toolbox for MATLAB® provides a user-friendly means of processing spectra and performing multivariate statistical analysis to generate qualitative and quantitative results. Though almost all the replicated analytical techniques used here to demonstrate the application of Raman spectroscopy and the Rametrix™ LITE Toolbox were of a biological nature, the methodologies available in the Rametrix™ LITE Toolbox can be applied to any source of spectra, or nearly any data that can be provided in matrix format. Evaluation with PCA and DAPC distills the complex measurement of the chemical spectrum in a sample into visually digestible scatter plots for analysis, without sacrificing depth of information, and TCD has proven to provide a quantitative element to this analysis.

Section II

Chronic Kidney Disease-Additional Computational Approaches

The Rametrix™ LITE Toolbox v1.0 for MATLAB® The predictive capabilities of existing tools for chemometric analysis of vibrational spectroscopy data, such as the Rametrix™ LITE Toolbox v1.0 for MATLAB®, are evaluated with respect to when "unknown" samples are introduced. Here, the Rametrix™ PRO Toolbox v1.0 is introduced to provide this capability. (Senger, R, Robertson, J, "The Rametrix PRO™ Toolbox V1.0 for MATLAB®," Peer J, 3:35799:2:0,Jan. 6, 2020 ("Senger, R, Robertson, J (2020)").

The Rametrix™ PRO Toolbox v1.0 was constructed for MATLAB® and works with the Rametrix™ LITE Toolbox v1.0. It performs leave-one-out analysis of chemometric DAPC models and reports predictive capabilities in terms of accuracy, sensitivity (true-positives), and specificity (true-negatives).

Rametrix™ PRO, was used to validate Rametrix™ LITE models used to detect chronic kidney disease (CKD) in spectra of urine obtained by Raman spectroscopy. The dataset included Raman spectra of urine from 20 healthy individuals and 31 patients undergoing peritoneal dialysis treatment for CKD. The number of spectral principal components (PCs) used in building the DAPC model impacted the model accuracy, sensitivity, and specificity in leave-one-out analyses. For the dataset in this study, using 35 PCs in the DAPC model resulted in 100% accuracy, sensitivity, and specificity in classifying an unknown Raman spectrum of urine as belonging to either a CKD patient or a healthy volunteer. Models built with fewer or greater number of PCs showed inferior performance, which demonstrated the value of Rametrix™ PRO in evaluating chemometric models constructed with Rametrix™ LITE.

Through advances in instrumentation, vibrational spectroscopy, including Raman spectroscopy, has become rapid, portable, and inexpensive, making it ideal for use in screening assays of biological fluids, chemical solutions, cells, or other materials. The spectrum obtained by Raman spectroscopy is representative of the molecular composition of that sample but can be complex and difficult to deconvolute into its molecular components. This is especially true of biological samples. The differentiation between healthy and urine from patients with chronic kidney disease (CKD) was done by a chemometric analysis of Raman spectra using principal component analysis (PCA) and discriminant analysis of principal components (DAPC) (Fisher, 2018). In a chemometric analysis, Raman spectra are treated as "spectral fingerprints," and multivariate statistical tools discover unique features and similarities among spectra (Shinzawa H, Awa K, Kanematsu W, Ozaki Y. 2009. Multivariate data analysis for Raman spectroscopic imaging. Journal of Raman Spectroscopy 40:1720-1725. DOI: 10.1002/jrs.2525; Gautam R, Vanga S, Ariese F, Umapathy S. 2015. Review of multidimensional data processing approaches for Raman and infrared spectroscopy. *EPJ Techniques and Instrumentation* 2:1-38. DOI: 10.1140/epjti/s40485-015-0018-6)( ). Software packages such as CytoSpec™, Unscrambler™, and others include such tools. The Raman Chemometrics (Rametrix™) LITE Toolbox (Fisher, 2018) was created for MATLAB® to further streamline the creation of Raman-based chemometric screens. It offers tools for Raman spectral processing along with PCA, DAPC, and other tools for spectral comparisons in an easy-to-use graphical interface.

Here, the companion Rametrix™ PRO Toolbox v1.0 for MATLAB® is introduced. In particular, it evaluates DAPC models using a leave-one-out procedure. Metrics are reported regarding the prediction accuracy of the model, including sensitivity (true-positive rate) and specificity (true-negative rate). Rametrix™ PRO was used to evaluate the chemometric DAPC models (Fisher, 2018) that classify Raman spectra of urine as belonging to healthy individuals (i.e., "healthy") or CKD patients (i.e., "unhealthy").

Raman spectra files (in .SPC format) were processed using the Rametrix™ LITE Toolbox in MATLAB r2018a (MathWorks; Natick, MA) as described previously (Fisher, 2018). Briefly, spectra were (i) truncated to include a Raman shift range of 400-1,800 $cm^{-1}$, (ii) baselined using the Goldindec algorithm (Liu J, Sun J, Huang X, Li G, Liu B. 2015. Goldindec: A Novel Algorithm for Raman Spectrum Baseline Correction. *Applied Spectroscopy* 69:834-842. DOI: 10.1366/14-07798 ("Liu, J, et. al. (2015)")) (baseline polynomial order=3; estimated peak ratio=0.5; smoothing window size=5), (iii) vector normalized, and (iv) scan replicates averaged for each patient. PCA and DAPC models were also built using the Rametrix™ LITE Toolbox. Multiple DAPC models were produced by varying the number of principal components (PCs) used in model construction.

The Rametrix™ PRO Toolbox v1.0 was used to perform leave-one-out analysis on all DAPC models. Spectra classification for each left-out spectrum (i.e., "healthy" or "unhealthy") was predicted and compared to the actual classification. The averaged spectrum from each healthy individual or CKD patient was excluded from model construction and predicted in the leave-one-out routine. Thus, the leave-one-out validation was done with respect to individual specimens and individuals, not according to scan replicates. Model accuracy was calculated as the percentage of spectra where classification was predicted correctly. Sensitivity (i.e., the true-positive rate) and specificity (i.e., the true-negative rate) were also calculated and reported as percentages.

Rametrix™ PRO also has the capability to calculate "random chance" values of prediction accuracy, sensitivity, and specificity for any dataset. Such a technique is helpful for datasets with multiple potential classifications with unequal representation. In these cases, the calculated accuracy, sensitivity, and specificity of leave-one-out validation routines are best presented relative to their random chance values.

Specimens collected. Voided urine specimens were collected from 20 healthy human volunteers and 31 patients with CKD Stage 4-5, undergoing peritoneal dialysis therapy. Although the methods outlined throughout this specification are performed on human urine, any source of urine can be used, including from any biological system, animal or mammal, such as dogs, cats, livestock, birds, fowl, or any other veterinary urine sample. Single specimens were collected from the healthy human volunteers (n=20), and multiple time-point specimens were obtained from the CKD patients (n=118). Briefly, specimens were stored at −35° C. prior to analysis. They were thawed and warmed to 37° C. and transferred to 1 mL glass vials (ThermoFisher Scientific; Waltham, MA) for analysis by Raman spectroscopy.

Raman spectroscopy. Spectra were obtained using an Agiltron (Woburn, MA) PeakSeeker™ Raman spectrometer. Scans were obtained from liquid phase samples using a 785 nm laser operated at 100 mW with 10 s integration time. A total of 10 scans were obtained and averaged for each sample.

Results. The leave-one-out analysis results, obtained with the Rametrix™ PRO Toolbox and the urinalysis dataset (i.e., n=20 "healthy" and n=118 "unhealthy" specimens), are given in Table 7.

TABLE 7

Leave-one-out results of the urinalysis dataset using the Rametrix ™ PRO Toolbox.

| Number of PCs in DAPC Model | Dataset Variance Explained by PCs | Model Accuracy | Model Sensitivity | Model Specificity |
|---|---|---|---|---|
| 1 | 47.03% | 97% | 100% | 80% |
| 2 | 78.92% | 99% | 100% | 95% |
| 3 | 89.16% | 99% | 100% | 95% |
| 4 | 93.89% | 99% | 100% | 95% |
| 5 | 95.93% | 99% | 100% | 95% |
| 6 | 97.23% | 99% | 100% | 95% |
| 7 | 97.90% | 99% | 100% | 95% |
| 8 | 98.36% | 99% | 100% | 95% |
| 9 | 98.78% | 99% | 100% | 90% |
| 10 | 99.01% | 99% | 100% | 90% |
| 15 | 99.52% | 99% | 100% | 90% |
| 20 | 99.70% | 98% | 100% | 85% |
| 25 | 99.79% | 99% | 100% | 95% |
| 30 | 99.83% | 99% | 100% | 95% |
| 35 | 99.87% | 100% | 100% | 100% |
| 40 | 99.89% | 99% | 99% | 100% |

TABLE 7-continued

Leave-one-out results of the urinalysis dataset using the Rametrix™ PRO Toolbox.

| Number of PCs in DAPC Model | Dataset Variance Explained by PCs | Model Accuracy | Model Sensitivity | Model Specificity |
|---|---|---|---|---|
| 45 | 99.91% | 95% | 94% | 100% |
| 50 | 99.93% | 92% | 91% | 100% |
| 55 | 99.94% | 83% | 81% | 100% |
| 60 | 99.95% | 72% | 67% | 100% |
| 70 | 99.96% | 29% | 17% | 100% |
| 80 | 99.97% | 22% | 8% | 100% |
| 90 | 99.98% | 1the4% | 0% | 100% |
| 100 | 99.99% | 14% | 0% | 100% |

The analysis was repeated for DAPC models built using different number of PCs. Typically, as the number of PCs is increased in DAPC model-building, the separation of clusters improves. As the number of PCs used to build the DAPC model surpassed 40 (which contained approximately 99.89% of the dataset variance), the prediction accuracy of the model decreased precipitously. For the urinalysis dataset analyzed in this study, DAPC models built with 35-38 PCs returned 100% accuracy, sensitivity, and specificity in leave-one-out analyses. Simpler models (i.e., built from 2-10 PCs) returned 99% accuracy, 100% sensitivity, and 95% specificity for identifying an unknown Raman spectrum of a urine specimen as coming from a "healthy" volunteer or "unhealthy" CKD patient. In embodiments, methods employing 2-50 principal components (PCs) in the DAPC model can be expected to have an accuracy of at least about 90-100%, a sensitivity of at least about 90-100%, and/or a specificity of at least about 85-100%; with 30-40 PCs employed in the DAPC model such methods can be expected to have an accuracy of at least about 99-100%, a sensitivity of at least about 99-100%, and/or a specificity of at least about 95-100%; and with 35-38 PCs employed in the DAPC model such methods can be expected to have an accuracy of about 100%, a sensitivity of about 100%, and a specificity of about 100%. The term "about" in the context of this specification means+10%. These far exceed the random chance accuracy, sensitivity, and specificity values of 50%. These results suggest that Raman spectroscopy and Rametrix™ technology can be used to classify effectively whether an unknown urine specimen is from a healthy individual or a CKD patient.

DAPC model clustering results are shown in FIGS. 13A-D for models built with 2, 10, 35, and 70 PCs, respectively.

PCA results, used to build the DAPC models, were presented previously with Rametrix™ LITE results. In DAPC plots, each data point represents an entire Raman spectrum. Clustering is indicative of spectra recognized as similar for well-functioning models. In FIGS. 13A-D, those samples classified correctly are represented by circles (healthy patients) and squares (unhealthy patients), and those classified incorrectly are represented by triangles (unhealthy CKD patients). The clustering between spectra of healthy and unhealthy specimens is apparent, as are the mis-classifications by DAPC models. This is readily apparent in the model built with 70 PCs (FIG. 13D), where likely model over-fitting resulted in several mis-classifications.

The Rametrix™ PRO Toolbox v1.0 comes with distinct functions that work with the Rametrix™ LITE Toolbox to validate DAPC spectra classification models. It generates a DAPC classification for an "unknown" sample and applies leave-one-out analysis over an entire spectral dataset. This process was used to evaluate DAPC models by blinding one sample to DAPC model building and treating it as an unknown. An additional function of Rametrix™ PRO generates random chance values of accuracy, sensitivity, and specificity, which can be used to put leave-one-out results into better perspective. For example, if accuracy, sensitivity, and specificity values are below expectations but exceed the random chance values, it is likely that more samples are needed to improve model performance. Thus, if random chance values are exceeded, the DAPC model is showing at least some success at classifying samples.

The leave-one-out procedure of Rametrix™ PRO was demonstrated using the urinalysis dataset described above (Fisher, 2018) and described further here. Comparing the predicted and known classifications for all specimens allowed calculation of model accuracy, sensitivity, and specificity. Here, a "positive" result was the presence of CKD, and a "negative" result was the absence of CKD (i.e. healthy). A "true" result occurs when model prediction matches the known classification, and a "false" result occurs when these differ. Thus, the model accuracy is the percentage of true results (both positive and negative) over the entire dataset, where a value of 100% means that predictions for all specimens were correct. The model sensitivity (i.e. true-positive rate) gives the percentage of true results that were predicted correctly. This also means the percentage of urine specimens from CKD patients that were classified with the "unhealthy" label. The model specificity (i.e., true-negative rate) gives the percentage of false results that were predicted correctly. This value also represents the percentage of urine specimens from healthy volunteers classified as "healthy."

Although the dataset size of this study is somewhat small (138 urine specimens), it suggests that Rametrix™ can be used as a screening technology to identify individuals with undiagnosed CKD, at any stage of the disease from Stages 1-5, such as early stage CKD or late- or end-stage CKD, such as Stage 4-5 patients.

The Rametrix™ PRO Toolbox v1.0, enables leave-one-out evaluation of PCA and chemometric DAPC models produced by Rametrix™ LITE. It can also calculate the random chance accuracy, sensitivity, and specificity for any dataset. Raman spectroscopy is fast and inexpensive, and Rametrix™ ensures that Raman spectral signatures of the hundreds of molecular components are used in classifications. The Rametrix™ LITE and PRO Toolboxes can be applied to all studies, above and beyond urine-based studies, involving chemometric data from Raman or other vibrational spectroscopy.

Section III

Spectral Characteristics of Urine Specimens from Healthy Human Volunteers Analyzed Using Raman Chemometric Urinalysis (Rametrix)

Raman chemometric urinalysis (Rametrix™) was used to analyze 235 urine specimens from healthy individuals. (See Senger, R, Kavuru, V, Sullivan, M, Gouldin, A, Lundgren, S, Merrifield, K, Steen, C, Baker, E, Vu, T, Agnor, B, Martinez, G, Coogan, H, Carswell, W, Karageorge, L, Dev, D, Du, P, Sklar, A, Pirkle, J, Orlando, G, Lianos, E, Robertson, J L (2019a) "Spectral characteristics of urine specimens from healthy human volunteers analyzed using Raman Chemometric Urinalysis (Rametrix™)," PLOS One 2019, doi: 10.1371/journal.pone.0222115 ("Senger, R, Kavuru, V, et. al. (2019)")).

The purpose of this study was to establish the "range of normal" for Raman spectra of urine specimens from healthy individuals. Ultimately, spectra falling outside of this range will be correlated with kidney and urinary tract disease. Results showed consistently overlapping Raman spectra of urine specimens with significantly larger variances in Raman shifts, found by PCA, corresponding to urea, creatinine, and glucose concentrations. A 2-way ANOVA test found that age of the urine specimen donor was statistically significant ($p<0.001$) and donor sex (female or male identification) was less so ($p=0.0526$). With DAPC models and blind leave-one-out build/test routines using the Rametrix™ PRO Toolbox (also available through GitHub), an accuracy of 71% (sensitivity=72%; specificity=70%) was obtained when predicting whether a urine specimen from a healthy unknown individual was from a female or male donor. Finally, from female and male donors (n=4) who contributed first morning void urine specimens each day for 30 days, the co-occurrence of menstruation was found statistically insignificant to Rametrix™ results ($p=0.695$). In addition, Rametrix™ PRO was able to link urine specimens with the individual donor with an average of 78% accuracy. Taken together, this study established the range of Raman spectra that could be expected when obtaining urine specimens from healthy individuals and analyzed by Rametrix™ and provides the methodology for linking results with donor characteristics.

Metabolomic analysis of normal human urine has identified over 2,000 separate chemical entities (Bouatra S, Aziat F, Mandal R, Guo AC, Wilson MR, Knox C, et al. The Human Urine Metabolome. PLOS ONE. 2013; 8: e73076. doi: 10.1371/journal.pone.0073076 ("Bouatra, S, et. al. (2013)"). This and other-omics technologies, along with deep sequencing, have been used over the past decade in search of disease biomarkers, particularly for kidney disease. In particular, biomarkers have been sought for chronic kidney disease (CKD) and end-stage kidney disease (ESKD), multifactorial diseases affecting up to 10% of the US population, and acute kidney injury (AKI), a significant cause of morbidity/mortality in hospitalized patients. While a few candidate biomarker molecules for these diseases have been identified (cystatin C, periostin), these are not commonly measured (or readily available) to caregivers in patient care settings. This is due to expense, requirement for advanced technology (such as mass spectrometry), and lack of validation for the broad spectrum of clinical presentations of CKD and AKI.

In an alternative approach, the inventors have invented and extensively validated a Raman spectroscopy-based technology called Raman chemometric urinalysis (Rametrix™) to analyze urine (Senger R, Du P, DeLaTorre Campos D, Carswell W, Webster K, Sullivan M, et al. Assessment of Urine Specimen Storage Conditions using Raman Chemometric Urinalysis (Rametrix™). Submitted to PeerJ. 2019 ("Senger, R, Du, P, et. al. (unpublished)"); Fisher, A, et. al. (2018); Senger, R, Robertson, J (2020). The purpose of this study was to use Rametrix™ to evaluate urine from healthy volunteers, both cross sectionally and longitudinally to establish a baseline or "range of normal" for when Rametrix™ is used to screen for the presence of disease. The hypothesis was that Rametrix™ would be able to identify differences in urine samples from subjects based on age, sex, presence of menstruation, and over a 30-day collection cycle. Specific goals of this study included determining (i) what Raman shifts contribute to dataset variance; (ii) if observed variances can be correlated with age, sex, or a particular individual; (iii) what variations occur over a 30-day urine collection cycle for multiple healthy individuals; and (iv) if menstruation causes significant changes in the Raman spectra of urine.

Two hundred thirty-five (235) urine specimens were collected from 48 (39 females, 9 males) healthy human volunteers. For this study, "healthy" was defined as free of infectious, metabolic, or degenerative disease at the time of sample collection, and with no history/evidence of renal disease (based on laboratory serum creatinine measurements). Urine obtained from a healthy individual was referred to as "normal" urine, and the "range of normal" encompasses the variations in Raman spectra of normal urine. The age range of the population was 18 to 70 years, with 87.5% of the specimens from volunteers aged 19-22 years; the sample population median age was 21 years. Specimens were collected between Jan. 8, 2017 and Jul. 21, 2018. The sample size (235 urine specimens) was determined by the maximum number of healthy volunteers and specimens collected curing the collection period.

A thirty-day (30-day) urine specimen collection from 3 female and 1 male healthy donor volunteers is also included as a subset. First morning voids were collected each day, and repetitive collections were done to determine amount of variance (due to diet, lifestyle, and hydration, primarily) in urine molecular composition from the same individual over 30 days. These collection subsets were also used to determine if normal menstruation had a significant effect on the Raman molecular signature of normal urine, since the presence of blood in urine (hematuria) can be a sign of genitourinary pathology when not associated with menstruation.

Free-catch (voided) urine specimens were collected in sterile 30 mL urine specimen cups, generally at the time of first daily urination following sleep. Following collection, specimens were refrigerated immediately and then stored at −35° C. until analyzed. Unused portions of the specimen were stored at −35° C. for the duration of the study and re-analyzed, as needed.

A synthetic urine analytical standard, Surine™ Urine Negative Control (Dyna-Tek Industries, Lenexa, KS) was obtained and used as a control reagent for sample measurements.

An Agiltron (Woburn, MA) PeakSeeker™ dispersive Raman spectrometer was used for analyses. The system was equipped to analyze bulk liquid samples, and a 785 nm (30 mW) laser excitation for 30 s with spectral resolution of 8 $cm^{-1}$ was used. Urine samples were equilibrated to 25° C., transferred to 1.5 mL glass vials, and placed in the spectrometer. Intensity data was collected over the Raman shift range of 250-1950 $cm^{-1}$, which contains the accepted biological range where distinct signatures of biological molecules appear (Movasaghi Z, Rehman S, Rehman DIU. Raman Spectroscopy of Biological Tissues. Appl Spectrosc Rev. 2007; 42:493-541. doi: 10.1080/05704920701551530 ("Movasaghi, Z, et. al. (2007)"). The inventors have published similar methodology using a Bruker Senterra™ Raman microscope (Athamneh AIM, Senger RS. Peptide-Guided Surface-Enhanced Raman Scattering Probes for Localized Cell Composition Analysis. Appl Env Microbiol. 2012; 78:7805-7808. doi: 10.1128/AEM.02000; Athamneh AIM, Alajlouni RA, Wallace RS, Seleem MN, Senger RS. Phenotypic Profiling of Antibiotic Response Signatures in *Escherichia coli* Using Raman Spectroscopy. Antimicrob Agents Chemother. 2014; 58:1302-1314. doi: 10.1128/AAC.02098; Zu TNK, Athamneh AIM, Collakova E, Robertson J, Hawken T, Aardema C, et al. Assessment of ex vivo Perfused Liver Health by Raman Spectroscopy. J Raman Spectrosc. 2015; 46:551-558. doi: 10.1002/jrs.4688; Zu TNK, Athamneh AIM, Wallace RS, Collakova E, Senger RS. Near-Real-Time Analysis of the Phenotypic Responses of *Escherichia coli* to 1-Butanol Exposure Using Raman Spectroscopy. J Bacteriol. 2014; 196:3983-3991. doi: 10.1128/JB.01590-14, and preliminary data analysis revealed the PeakSeeker™ analysis of liquid urine produced a detailed spectrum with simplified sample handling and analysis requirements. A minimum of 10 individual spectra were acquired per sample prior to data analysis.

Computational methodology. Spectral baselining was done using the Goldindec algorithm (Liu, J, et. al. (2015)), all scan replicates were averaged, and resulting spectra were vector normalized. Rametrix™ computations were applied using the Rametrix™ LITE Toolbox for MATLAB® (Fisher, A, et al. (2018)) and the Rametrix™ PRO Toolbox for MATLAB® (Senger, R, Robertson, J (2020)). MATLAB® r2018a (The MathWorks, Inc.; Natick, MA) with the Statistics and Machine Learning Toolbox was used for all Rametrix™ and statistical calculations.

Figures 14A, 14B:
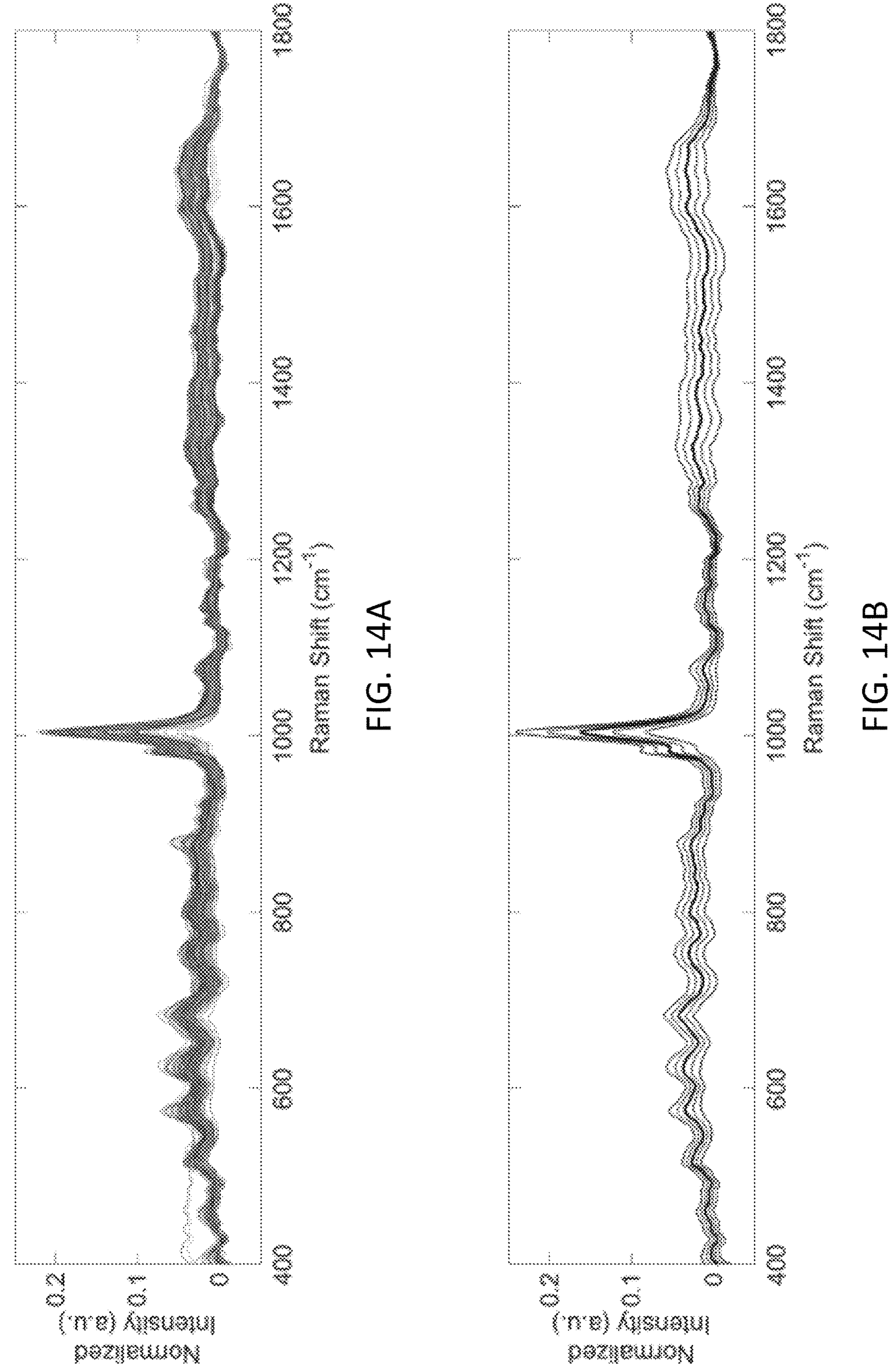
FIGS. 14A-B are graphs showing Raman spectra from 235 urine specimens from healthy individuals. A) Overlaid vector normalized spectra. B) The average urine spectrum with ranges of 1 and 2 standard deviations.

Raman spectra of urine. Raman spectra were obtained from 235 urine specimens of healthy individuals. Overlaid spectra, following baselining, replicate averaging, and vector normalization are shown in FIG. 14A. An overall averaged Raman spectrum of normal urine was derived from these spectra and is shown in FIG. 14B. This includes ranges of plus/minus one and two standard deviations from the average healthy urine spectrum. Evident in FIGS. 14A-B is notable variance in the Raman spectra at specific Raman shifts and ranges. These represent the range of normal for Raman spectra of urine from healthy individuals, and they were investigated further by principal component analysis (PCA) using the Rametrix™ LITE Toolbox for MATLAB®.

Figures 15A, 15B:
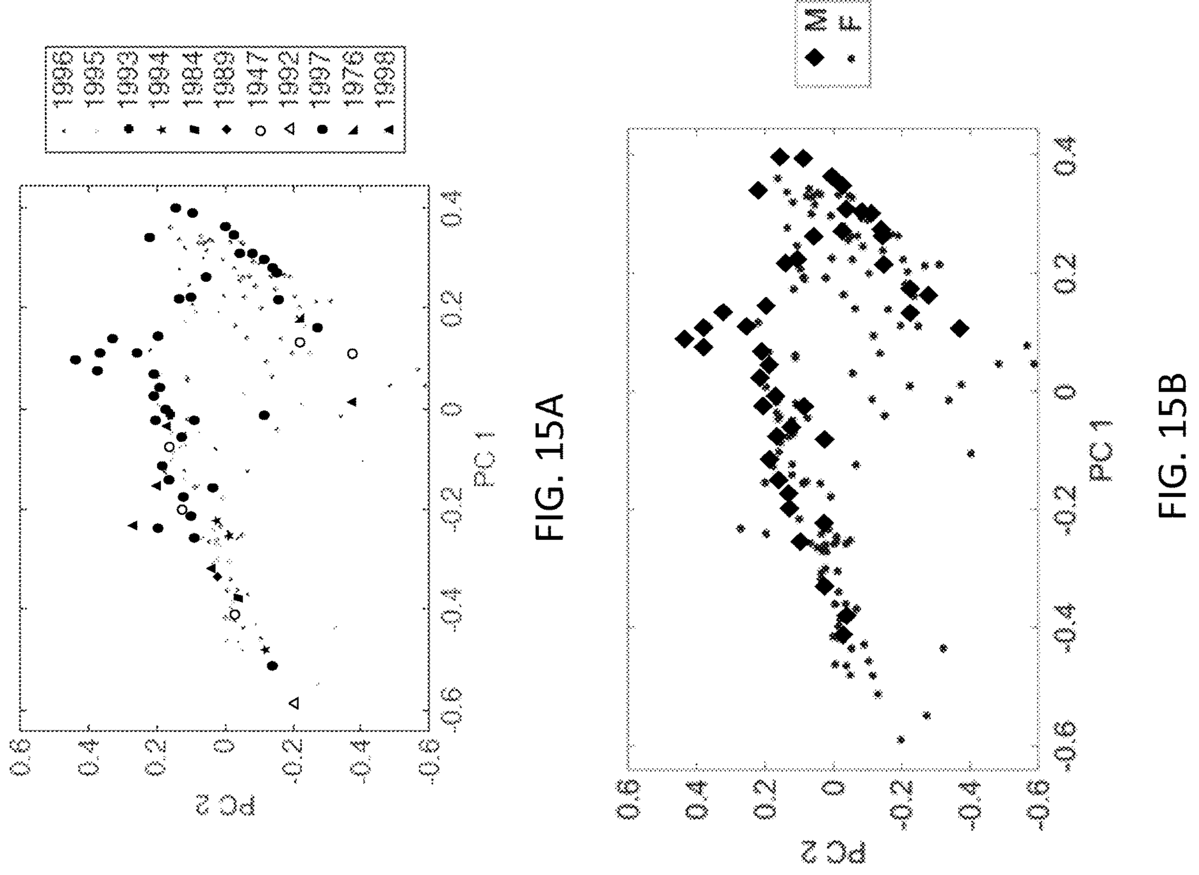
FIGS. 15A-C are graphs showing principal component analysis (PCA) results for Raman spectra of 235 urine specimens from healthy individuals. PCA results based on: A) year individual was born and B) sex of individual. C) Contributions of Raman shift leading to separations among principal components.
Figure 15C:
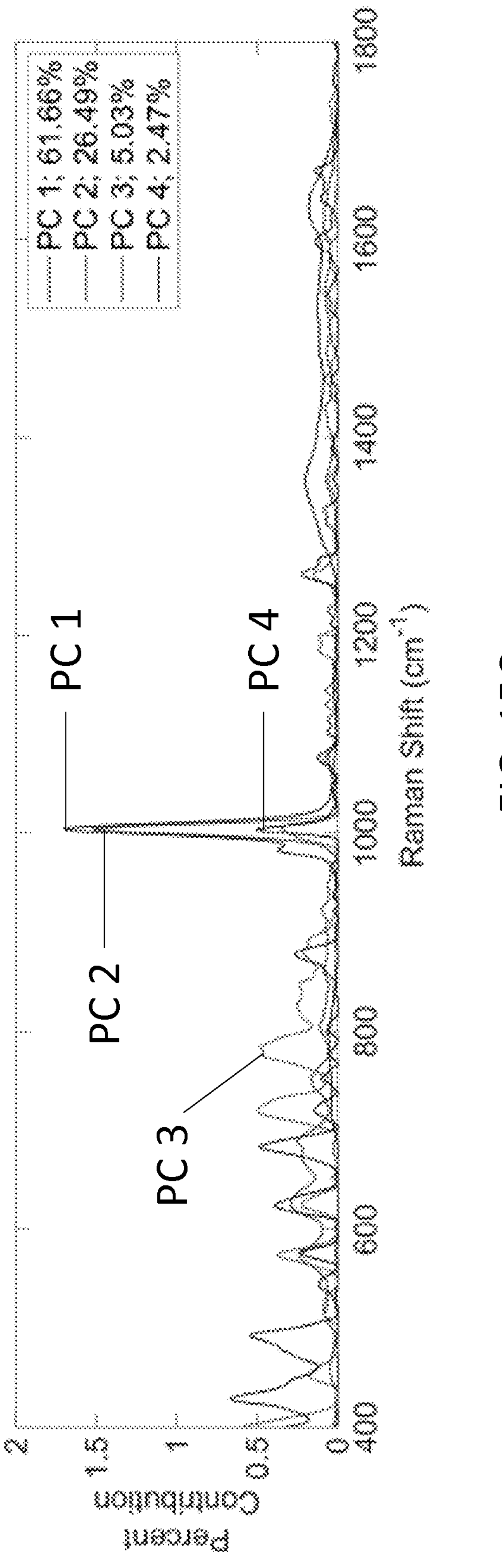

Principal component analysis. PCA results are shown in FIGS. 15A-B and are coded by (A) birth year of the healthy individual and (B) sex (F=female; M=male). Initial inspection revealed no clustering according to birth year or sex, and these were investigated further through statistical analyses and model predictions (discussed later). The Rametrix™ LITE Toolbox for MATLAB® enables identification of Raman shifts leading to the separation of data points in PCA. These are shown for the first four principal components in FIG. 15C. Together, these first four principal components represent 95.7% of the dataset variance. The Raman shift at 1,002 $cm^{-1}$ was the largest contributor to the dataset variance and was represented in multiple principal components (FIG. 15C). In urine, this Raman shift is dominated by urea, suggesting the concentration of urea varies widely for healthy individuals. Other notable molecules identified in this figure are uric acid (981 $cm^{-1}$), creatinine (680 $cm^{-1}$), collagen (870 $cm^{-1}$), and glucose (1,071 $cm^{-1; 1,117}$ $cm^{-1}$; and others). While these examples have been validated by scanning pure standards, research is ongoing to correlate more Raman shifts in FIG. 15C with known urine metabolites.

Figure 16A:
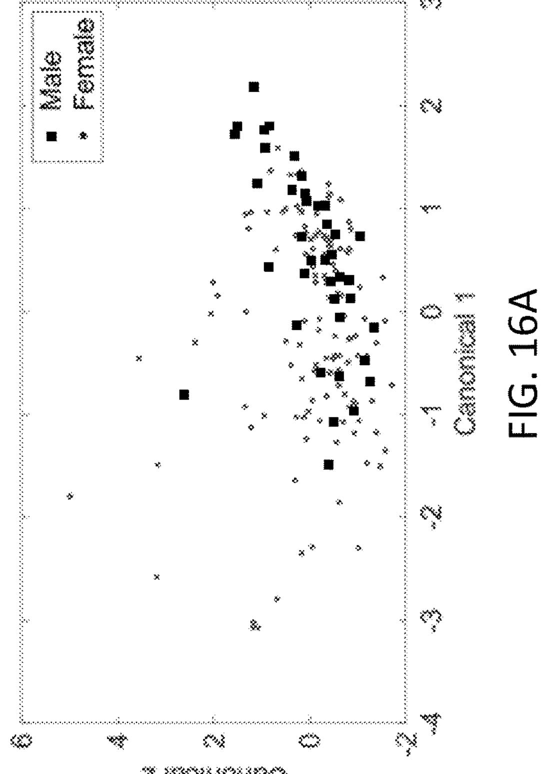
FIGS. 16A-D are graphs showing discriminant analysis of principal components (DAPC) results. DAPC results for models made with the following number of principal components and percentage of dataset variability explained by those principal components: A) 3, 90%; B) 4, 95%; C) 10, 99%; D) 35, 99.9%.
Figure 16B:
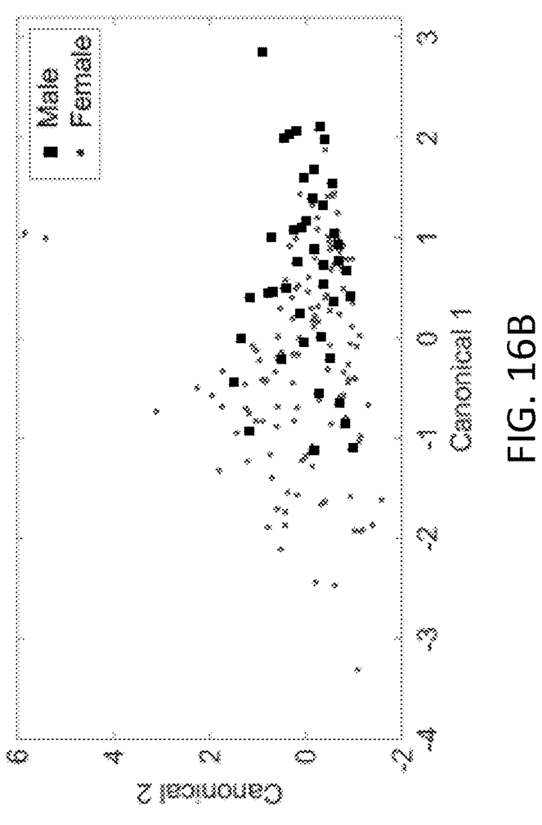
Figures 16C, 16D:
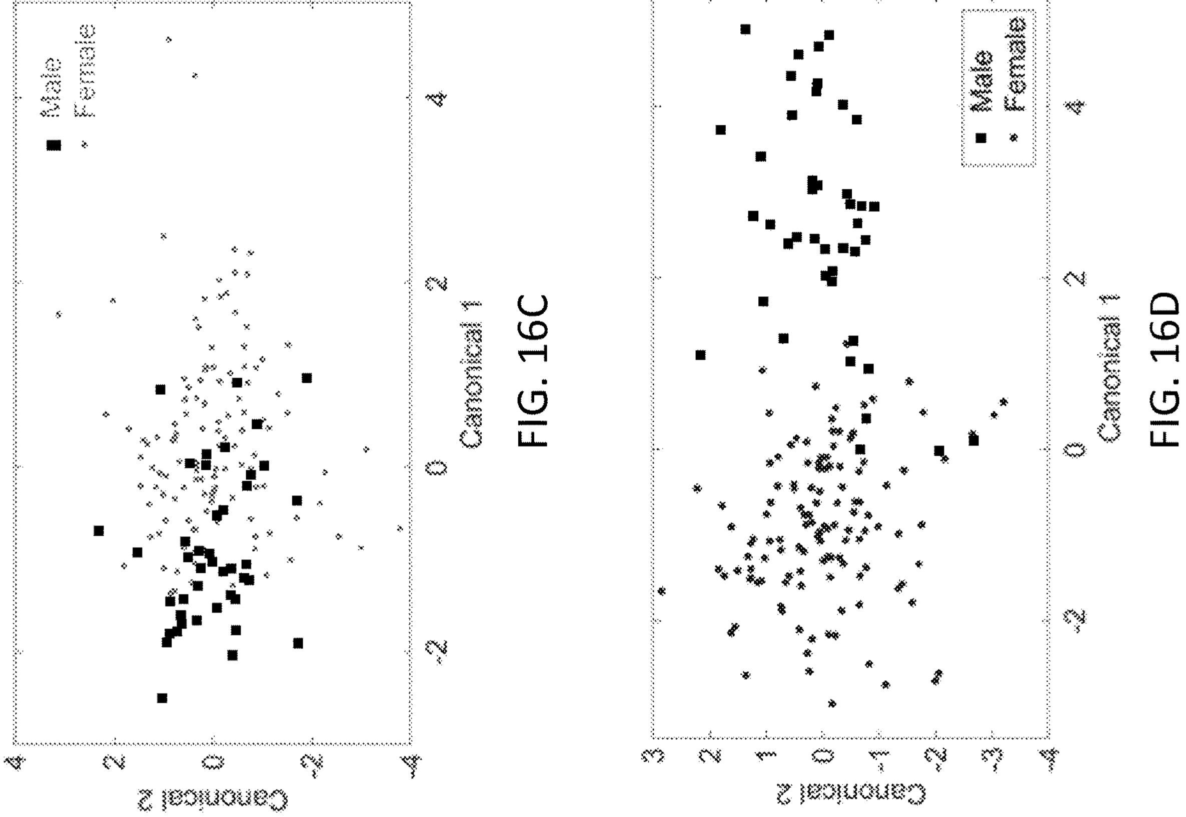

Discriminant analysis of principal components models. The Rametrix™ LITE Toolbox for MATLAB® allows the construction of discriminant analysis of principal components (DAPC) models that can be used to further cluster Raman spectra based on specified attributes. This was applied to the dataset of Raman spectra from healthy individuals to determine whether true differences exist between urine specimens based on sex. The DAPC models were constructed using different numbers of principal components and are shown in FIGS. 16A-D. Increasing the numbers of principal components allowed more of the dataset variance to be included in the DAPC models and led to better clustering and separation between the spectra based on sex. Similar to PCA results, in DAPC models (FIGS. 16A-D), each point represents an entire Raman spectrum, and clustering occurs among spectra with similarities. The DAPC models were constructed to represent 90% of the dataset variance with three principal components (FIG. 16A); 95% of dataset variance with four principal components (FIG. 16B); 99% with ten principal components (FIG. 16C); and 99.9% with thirty-five (35) principal components (FIG. 16D). Visual separation of clusters based on sex was apparent as at least 99% of the dataset variance was included in the DAPC models. Next, it was tested whether these models could predict whether an unknown urine specimen was from a female or male donor.

The Rametrix™ PRO Toolbox for MATLAB® was developed to make predictions of unknown specimens using DAPC models built in the Rametrix™ LITE Toolbox and to evaluate these models using a leave-one-out build/test routine. Here, DAPC models were built using all but one of the data points (i.e., spectra) in the dataset. The classification (i.e., donor sex) of that remaining spectrum was predicted using the DAPC models, and it was recorded whether or not the prediction was correct. This routine was then repeated for every spectrum in the dataset. From there, the accuracy, sensitivity, and specificity of the model predictions were calculated. The model accuracy refers to the percentage of the total number of data points that were predicted correctly. The sensitivity refers to the true positive rate. In this case, it was the percentage of specimens from females that were identified correctly as female. The specificity refers to the true negative rate. In this case, it was the percentage of specimens from males that were identified correctly as male. Results are shown in Table 8. Accuracy ranges from 71-84% were obtained for the four DAPC models tested. However, the DAPC model consisting of 10 principal components (representing 99% of the dataset variance) performed best in terms of accuracy (71%), sensitivity (72%), and specificity (70%). While other models had better accuracy and sensitivity, their specificity values were well below 70%. The DAPC model consisting of 35 principal components (representing 99.9% of the dataset variance) showed signs of overfitting the data (i.e., improved DAPC clustering but reduced accuracy and/or specificity in leave-one-out trials). Together, this means that Rametrix™ can predict whether a urine specimen from a healthy individual belonged to a female or male with about 70% accuracy. This is far better than the 50% probability assigned by chance.

TABLE 8

Rametrix ™ PRO results showing the ability to predict whether an known urine specimen came from a female donor.

| Percent Variability Explained by Principal Components | Number of Principal Components used in DAPC Model | Accuracy* | Sensitivity* | Specificity* |
|---|---|---|---|---|
| 90% | 3 | 77% | 94% | 26% |
| 95% | 4 | 71% | 76% | 56% |
| 99% | 10 | 71% | 72% | 70% |
| 99.9% | 35 | 84% | 100% | 37% |

*Predictions were from a leave-one-out training/testing routine.

Statistical analysis. The entire spectral dataset was analyzed by 2-way ANOVA to determine if the factors "sex" (i.e., female or male) or "birth year" of the specimen donor were statistically significant. To do this, Raman spectra had to be reduced to a single number per spectrum. Previously, the inventors explored three ways of doing this, and determined that calculation of the Total Spectral Distance (TSD) and Total Principal Component Distance (TPD) were most adequate (Senger, R, DeLaTorre, D, et. al. (unpublished)), however, any one or more of TSD, TPD and/or TCD can be used depending on the particular application. The following is a brief explanation of the TPD calculation. PCA reduces a complex Raman spectrum, composed of intensity value for each Raman shift between (400-1800 $cm^{-1}$), to a single number computed from principal components. The principal components are ranked by the amount of dataset variance that they can explain, meaning that Raman spectra encompassing many intensity data points can be represented by only a few principal components. For urine specimens in this dataset, four principal components were found to contain more than 95% of the dataset variance (see FIG. 15C). With a urine specimen reduced to its four principal components, it can be compared with the urine analytical standard Surine™ using its four principal components and the distance formula, as shown in Eq. 4, where $P_{u,i}$ is the $i^{th}$ principal component of a urine specimen, and $P_{control,i}$ is the $i^{th}$ principal component of Surine™ (i.e., the control).

$$TPD = \sum_{i=1}^{4} \sqrt{(P_{u,i} - P_{control,i})^2} \quad (4)$$

2-Way ANOVA results for TPD given factors of sex and birth year (e.g., age) are shown in Table 9.

TABLE 9

2-Way ANOVA results based on TPD calculations.

| Source | Sum of Squares | Degrees of Freedom | Singular? | Mean Squares | F-Statistic | p-Value |
|---|---|---|---|---|---|---|
| Sex (F/M) | 0.0678 | 1 | 1 | 0.0677 | 3.81 | 0.0526 |
| Birth Year | 0.770 | 10 | 1 | 0.0770 | 4.33 | 2.25E−05 |
| Error | 2.86 | 161 | 0 | 0.0178 | n/a | n/a |
| Total | 3.71 | 173 | 0 | n/a | n/a | n/a |

Initially, the interaction of sex and birth year was considered in the 2-way ANOVA, and this was found to be insignificant (p=0.166). Then, 2-way ANOVA was repeated without the interaction term included, and this returned p-values of 0.0526 for sex and <0.001 for birth year. This suggest that significant differences in Raman spectra of urine from healthy individuals change significantly with age and possibly significantly with sex, depending on the confidence level chosen. This correlates with the accuracy, sensitivity, and specificity obtained for predicting whether the urine specimen donor was female or male (Table 8).

30-Day study results. Three healthy females and one male contributed first morning void urine specimens every day for 30 days. The specimens collected during days of menstruation were identified by the female donors.

The TPD was calculated for each urine specimen, and the average, range, and standard deviation values per donor are given in Table 10.

TABLE 10

TPD results for the 30-day study.

| 30-Day Donor | Average TPD* (±1 s.d.) | TPD Range |
|---|---|---|
| Female 1 | 0.301 ± 0.111 | 0.0391-0.516 |
| Female 2 | 0.225 ± 0.151 | 0.00831-0.421 |
| Female 3 | 0.107 ± 0.101 | 0.00843-0.385 |
| Male 1 | 0.257 ± 0.140 | 0.0151-0.492 |

*Average TPD values are given ±1 standard deviation (s.d.).

A 2-way ANOVA test was applied to the 30-day dataset and revealed that the individual donor was statistically significant (p<0.001), but the presence of menstruation was not (p=0.695). The factor interaction term did not apply (p=0.294). Next, pairwise comparisons were applied using Tukey's honestly significant difference test. These revealed that specimens from donor Female 3 were statistically different (all p-values≤0.0022) from those of all other donors. Specimens from all other donors (other than Female 3) were found not statistically different from one another (all p-values>0.059).

Next, Rametrix™ PRO was tested to determine if it can identify a urine specimen collected during menstruation and if it can correlate an unknown urine specimen with the donor. Results are given in Table 11 for DAPC models constructed using 9 PCs (representing 99% of the dataset variability) and 30 PCs (representing 99.9% of the dataset variability). Similar to the Rametrix™ PRO results shown in Table 8, using 99% of the dataset variability provided better results, even though the visual clustering was more distinct when using 99.9% of the dataset variability. Results indicate that specimen collection during menstruation cannot be identified in this dataset using Rametrix™ PRO (10% sensitivity in Table 11).

TABLE 11

Rametrix ™ PRO results for the 30-day study.

| | Accuracy* | Sensitivity* | Specificity* |
|---|---|---|---|
| 99% Variability Explained by Principal Components (9 PCs) | | | |
| Menstruation | 91% | 10% | 98% |
| Female 1 | 75% | 57% | 81% |
| Female 2 | 80% | 58% | 89% |
| Female 3 | 84% | 57% | 92% |
| Male 1 | 74% | 77% | 73% |
| 99.9% Variability Explained by Principal Components (30 PCs) | | | |
| Menstruation | 11% | 100% | 3% |
| Female 1 | 77% | 7% | 100% |
| Female 2 | 74% | 3% | 100% |
| Female 3 | 81% | 23% | 100% |

*Predictions were from a leave-one-out training/testing routine.

This also indicates that menstruation was not responsible for skewing Rametrix™ urine screening results dramatically in this dataset, which is consistent with ANOVA test results. For the four healthy individual donors (3 female, 1 male) in the 30-day study, Rametrix™ PRO was able to correctly correlate an unknown urine specimen with the donor with an average of 78% accuracy (62% sensitivity; 84% specificity). This is well above the random chance probability of 25%. Finally, for each individual donor in the 30-day study, no distinct pattern was observed for how urine specimens changed over the course of the 30 days.

Determining what is normal is critical for identifying what is abnormal. Ultimately, Rametrix™ analysis of urine will be used to screen for the presence of diseases, and the inventors' previously-published proof-of-concept with healthy individuals and ESKD patients (Fisher et al., 2018) supports this notion. However, the variance in Raman spectra of urine specimens from healthy individuals needs to be known for more reliable datasets of Raman spectra of normal urine to be constructed and validated. This study represents a first attempt to obtain this range of normal for use with Rametrix™, a Raman spectroscopy-based technology. Interestingly, in this expanded study (relative to the proof-of-concept) with 235 urine specimens from healthy individuals, different levels of spectral variance were observed at different Raman shifts. PCA with the Rametrix™ LITE Toolbox for MATLAB® helped determine which Raman shifts were most significant in accounting for differences between urine specimens. Many of these correlated with well-characterized urine components, such as urea, creatinine, and glucose, but there are several other bands yet to be identified (FIG. 15C).

Specifically, the inventors found that significant differences ($p<0.001$) in Raman spectra of a urine specimen can be attributed to the age of the donor, even if the donor is in good health. Fewer differences ($p=0.0526$) were observed based on the sex of the donor, and the ability to predict the sex of the donor of an unknown urine specimen was attempted. The accuracy (71%) of predicting donor sex using Rametrix™ PRO, sensitivity (72%), and specificity (70%) were better than random chance (50%). While this result may not yet be relevant clinically, it demonstrates the degree to which differences according to sex are real and discernable. ANOVA results revealed the significance of these factors, and the Rametrix™ PRO results demonstrate the degree of overlap that exists. In addition, donor characteristics, such as age and sex, may play important roles in future Rametrix™ screens that identify the presence of disease. Additionally, the 30-day study subset of urine specimens revealed menstruation did not contribute statistically significant changes to the Rametrix™ spectral signature of urine ($p=0.695$). Also, individuals collected over 30 days showed variations, but it was difficult to establish correlations to diet and lifestyle at this point. Knowing the range of normal variation is also critical should Rametrix™ be used to screen urine specimens for the presence of disease and/or track patient progress in response to treatment. Clearly, more work is needed in relating these variations to diet and lifestyle. Furthermore, repeated collections from an individual may be used to define what is normal for that individual. Rametrix™ PRO was able to correlate an unknown specimen with the donor in the 30-day study with 78% accuracy (62% sensitivity; 84% specificity). This further supports that establishing a range of normal for an individual may hold value when using Rametrix™ to screen for the presence of disease, as each individual may have a slightly different version of normal.

From here, this dataset of Raman spectra of urine specimens from healthy individuals will be used in expanded studies to compare against those obtained from patients with kidney and urinary tract diseases. This approach will ultimately lead to Rametrix™ being used to screen for the presence of diseases and track the progress of treatments.

Section IV

Spectral Characteristics of Urine from Patients with End-Stage Kidney Disease Analyzed Using Raman Chemometric Urinalysis (Rametrix)

Raman Chemometric Urinalysis (Rametrix™) was used to discern differences in Raman spectra from (i) 362 urine specimens from patients receiving peritoneal dialysis (PD) therapy for end-stage kidney disease (ESKD), (ii) 395 spent dialysate specimens from those PD therapies, and (iii) 235 urine specimens from healthy human volunteers. Rametrix™ analysis includes spectral processing (e.g., truncation, baselining, and vector normalization); principal component analysis (PCA); statistical analyses (ANOVA and pairwise comparisons); discriminant analysis of principal components (DAPC); and testing DAPC models using a leave-one-out build/test validation procedure. Results showed distinct and statistically significant differences between the three types of specimens mentioned above. Further, when introducing "unknown" specimens, Rametrix™ was able to identify the type of specimen (as PD patient urine or spent dialysate) with better than 98% accuracy, sensitivity, and specificity. Rametrix™ was able to identify "unknown" urine specimens as from PD patients or healthy human volunteers with better than 96% accuracy (with better than 97% sensitivity and 94% specificity). This demonstrates that an entire Raman spectrum of a urine or spent dialysate specimen can be used to determine its identity or the presence of ESKD by the donor.

Section IV

The chemical composition, physical characteristics, and types/amounts of suspended materials in urine change when kidney (and systemic) disease is present. In this study, Raman Chemometric Urinalysis (Rametrix™) was used to determine if differences in molecular spectra could be detected in the following specimen types: (i) urine from healthy human volunteers, (ii) urine from patients undergoing peritoneal dialysis (PD) therapy for end-stage kidney disease (ESKD) and (iii) spent dialysate from these patients receiving PD therapy. Rametrix™ relies on Raman spectroscopy and a biological region of the spectrum (400-1,800 $cm^{-1}$) that is composed of spectral signatures of the thousands of molecules known to the urine metabolome. Furthermore, Rametrix™ uses off-the-shelf Raman spectrometers, which are becoming more affordable, low-profile, and conducive to clinical laboratory use.

In the past, sophisticated analyses, including mass spectrometry, liquid/gas chromatography, and kinetic nephelometry have been used to detect analytes (i.e., "biomarkers") in urine associated with metabolism or disease. In addition, urine contains byproducts of therapeutics that help clinicians monitor and adjust therapies and can indicate environmental and occupational toxin exposure.

Urine biomarker studies to detect chronic kidney disease have been conducted almost exclusively in research settings. For example, Zurbig and co-workers used capillary electrophoresis, coupled online to electrospray ionization time-of-flight mass spectrometry (CE-MS), to identify polypeptide patterns in human urine. However, proteomic spectral patterns in urine, as biomarkers for kidney disease, have not been accepted widely as diagnostic tools, and proteomic patterns identified in that study could not be translated to specific molecules with physiological and pathophysiological significance. This significantly dampened enthusiasm for proteomic spectral pattern recognition as a tool to diagnose and study genitourinary tract disease.

The presence of albumin (and other proteins) in urine is an accepted indicator of the presence and severity of chronic kidney disease (CKD) and regular monitoring of the urine of patients in early stages of CKD may be quite useful in detecting responses to medical/lifestyle management, as well as detecting progression of disease. Although economical and convenient, dipstick/dry chemistry testing for the presence of protein is unlikely to be either sufficiently sensitive or specific in management of CKD. Abnormalities in the composition of urine sediments (hematuria, pyuria, casts, and other changes) also are considered potential indicators of CKD and may be of greater value than single spot measurements of urine proteins with dipstick assays. Other molecular indicators of CKD, including the presence of complex metabolic by-products collectively termed "uremic solutes," are not measured routinely in serum or urine, either by dipstick/dry chemistry assays or standard laboratory automated urinalysis, but may become important diagnostic biomarkers, since they are important in the pathogenesis/progression of CKD and systemic co-morbidities such as cardiovascular disease. (See Kavuru, V, Vu, T, Karageorge, L, Choudhury, D, Senger, R, Robertson, J, "Dipstick analysis of urine chemistry: benefits and limitations of dry chemistry-based assays," Postgrad Med Published on-line Oct. 19 2019, doi: 10.1080/00325481.2019.1679540, ("Kavuru, V, Vu, T, et. al., 2019"); Kavuru V, et al. (2020) Dipstick analysis of urine chemistry: benefits and limitations of dry chemistry-based assays. *Postgraduate Medicine* 132 (3): 225-233.

For these and other reasons, biomarker and "-omics" technologies are used rarely (or are not readily available) by caregivers in patient care settings. This is due to expense, the daunting requirement for advanced technology (such as mass spectrometry), expertise required for interpretation of results, and a lack of assay validation with large datasets of normal and abnormal specimens. In fact, the complexity of both acute and chronic kidney diseases, and other genitourinary tract pathologies, makes large dataset sampling and validation both unlikely and cost-prohibitive. Rametrix™, on the other hand, provides robust spectral information about the urine metabolome, using instrumentation that is inexpensive. To achieve useful results, minimal technician training is required, and Rametrix™ software automates analysis. This has enabled studies, such as this and others, using very large datasets, to discover spectral differences between normal and abnormal (e.g., diseased, stressed, decayed, chemically treated, etc.) samples.

Previously, the inventors reported the Rametrix™ analysis of 235 urine specimens obtained from consented, healthy, human volunteers (see above for discussion). This work identified common Raman spectral characteristics seen in urine specimens obtained from healthy persons of both sexes and between 18-70 years of age. The inventors focused on determining the variation (or lack thereof) in spectral signatures from several subsets of individuals over 30 days, comparing data from single time-point (first voided sample in the morning) collections. As part of this work, the inventors noted significant effects of sex and age of the donor but negligible effects of menstruation on Raman spectral characteristics.

Here, the inventors describe the results of Rametrix™ analysis of 362 urine specimens collected from patients with ESKD, who had residual renal function and were undergoing PD treatments. The inventors also describe Rametrix™ analysis of 395 specimens of spent dialysate from those patients undergoing PD treatments. These were then compared with the 235 urine specimens from healthy human volunteers using Rametrix™. All collections and data analysis were devoted to testing the hypothesis that "Rametrix™ analysis of urine specimens can discern significant molecular composition differences between (i) PD patient urine and spent dialysate and (ii) PD patient urine and urine from healthy individuals." The study to discern the molecular differences between PD patient urine and spent dialysate was designed to demonstrate the capabilities of Rametrix™ analysis and provide a basis for future studies that look at patient-specific molecules that are removed by PD or the kidneys. The study to discern PD patient urine from urine of healthy individuals was designed to identify new patients who should receive PD therapy and to be able to monitor the progress of those patients receiving PD therapy.

Three groups of specimens were compared in this study: (i) urine from patients undergoing PD therapy for ESKD, (ii) the spent dialysate from those PD therapies, and (iii) urine from healthy human volunteers. Briefly, 235 urine specimens were collected from 48 (39 females, 9 males) healthy human volunteers with no history or evidence of renal disease. Volunteers were also free of infectious or degenerative disease at the time of sample collection. The age range of the healthy volunteer population was 18-70 years; 87.5% of volunteers were of ages 19-22 years, and the median age was 21 years.

For patients undergoing PD therapies, 362 urine specimens were collected from 96 patients, and 395 spent dialysate specimens from 115 patients comprised the dataset. Patients had advanced ESKD and were undergoing PD treatment. Patients ranged in age from 24-90 years old. The mean age was 60 years, and the median age was 63.5 years. Multiple collections (4-8 separate collections) were available from multiple patients, allowing repetitive measurements and correlations over a protracted course of PD therapy (18 months).

Specimens were collected at the time of routine PD adequacy evaluation (generally every 1-3 months) over a period ranging from 18-24 months. For routine adequacy testing, patients collected all urine produced in a 24-hour period and also collected all spent dialysate from multiple cycles of treatment that occurred over 24 hours. These urine samples and spent dialysate collections were brought to the dialysis center, where aliquots of urine and spent dialysate were transferred into sterile specimen cups and then immediately frozen to −15° C. Both urine and spent dialysate specimens were stored at this temperature until analyzed. Urine specimens from healthy human volunteers were stored immediately at −35° C. until analyzed.

The inventors previously determined the suitability of collection and storage conditions in a separate study of urine stability and adhered to the guidelines set forth in that study. Unused portions of urine and spent dialysate specimens were stored at −35° C. for the duration of the study and re-analyzed, as needed.

Analytical standards. Surine™ Urine Negative Control (Dyna-Tek Industries, Lenexa, KS) was used as a control standard for urinalysis. Unused dialysate (obtained from Valley Nephrology Associates; Roanoke, VA) was also used as a reference control in this study.

Raman methodology and measurements. The inventors' experimental methods were used (Senger and Robertson, 2020); (Senger, R, DeLaTorre, D, et. al. (unpublished)). Briefly, an Agiltron PeakSeeker™ dispersive Raman spectrometer (Woburn, MA) was used, and all specimens were Raman scanned as bulk liquid samples in 1.5 mL glass vials at 25° C. using 785 nm (30 mW) laser excitation for 30 s with spectral resolution of 8 $cm^{-1}$. A minimum of 10 scans were collected per specimen and averaged.

Computational methodology. Spectral processing and analyses were performed with the Rametrix™ LITE, Rametrix™ PRO, and Statistics and Machine Learning Toolboxes were used with MATLAB r2018A (The MathWorks, Inc.; Natick, MA). Raman spectra were truncated to 400-1,800 $cm^{-1}$, baseline corrected using the Goldindec algorithm, and vector normalized. Principal component analysis (PCA) and discriminant analysis of principal components (DAPC)

models were constructed using the Rametrix™ LITE Toolbox, and DAPC models were tested by leave-one-out analysis with the Rametrix™ PRO Toolbox. 1-Way ANOVA and pairwise comparisons using Tukey's honestly significant difference (HSD) procedure were performed in MATLAB.

Raman spectroscopy of PD patient urine and spent dialysate.

Figures 17A, 17B:
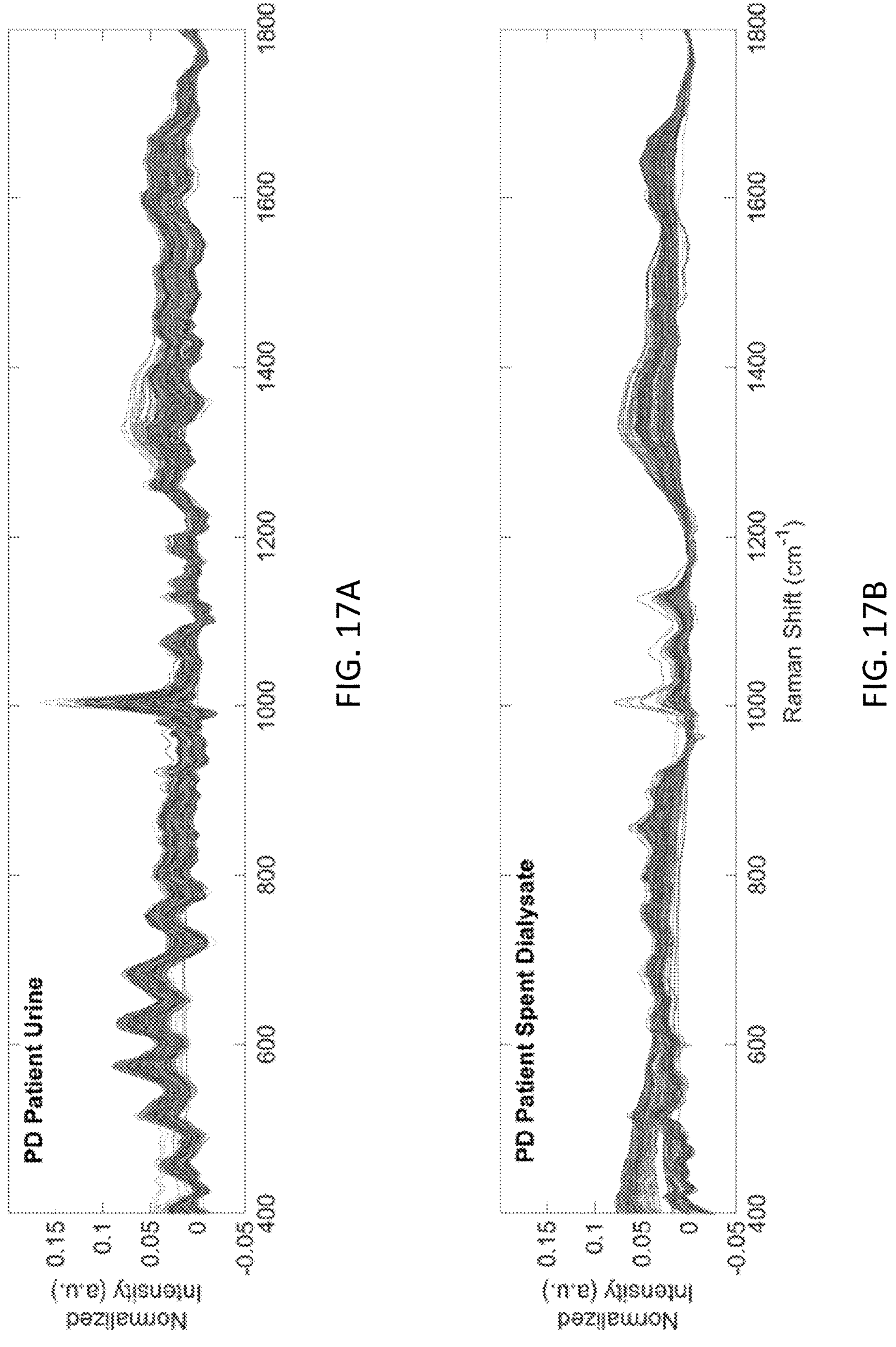
FIGS. 17A-B are graphs showing Raman spectra of PD patient urine and spent dialysate. A) Averaged, baselined, and vector normalized Raman spectra from 362 urine specimens obtained from patients receiving PD therapy for ESKD. B) Averaged, baselined, and vector normalized Raman spectra from 395 spent PD dialysate specimens.

Raman spectra from 362 urine specimens and 395 spent dialysate specimens from PD patients were averaged (per specimen), baseline corrected using the Goldindec algorithm, and vector normalized. These were plotted together in FIG. 17A (PD patient urine) and FIG. 17B (spent dialysate). Raman spectra of the 235 urine specimens from healthy human volunteers were processed similarly and are described above. Apparent in FIGS. 17A-B, there are observable differences between Raman spectra of PD patient urine and spent dialysate. In particular, there are clear differences in the urea (1,002 $cm^{-1}$) content of these specimens. While all specimens seemed to show a basic spectral signature of urine or spent dialysate, there were considerable differences between the individual spectra within these specimen types. These were explored further by PCA and statistical tests to provide quantitative metrics.

Figures 18A, 18B:
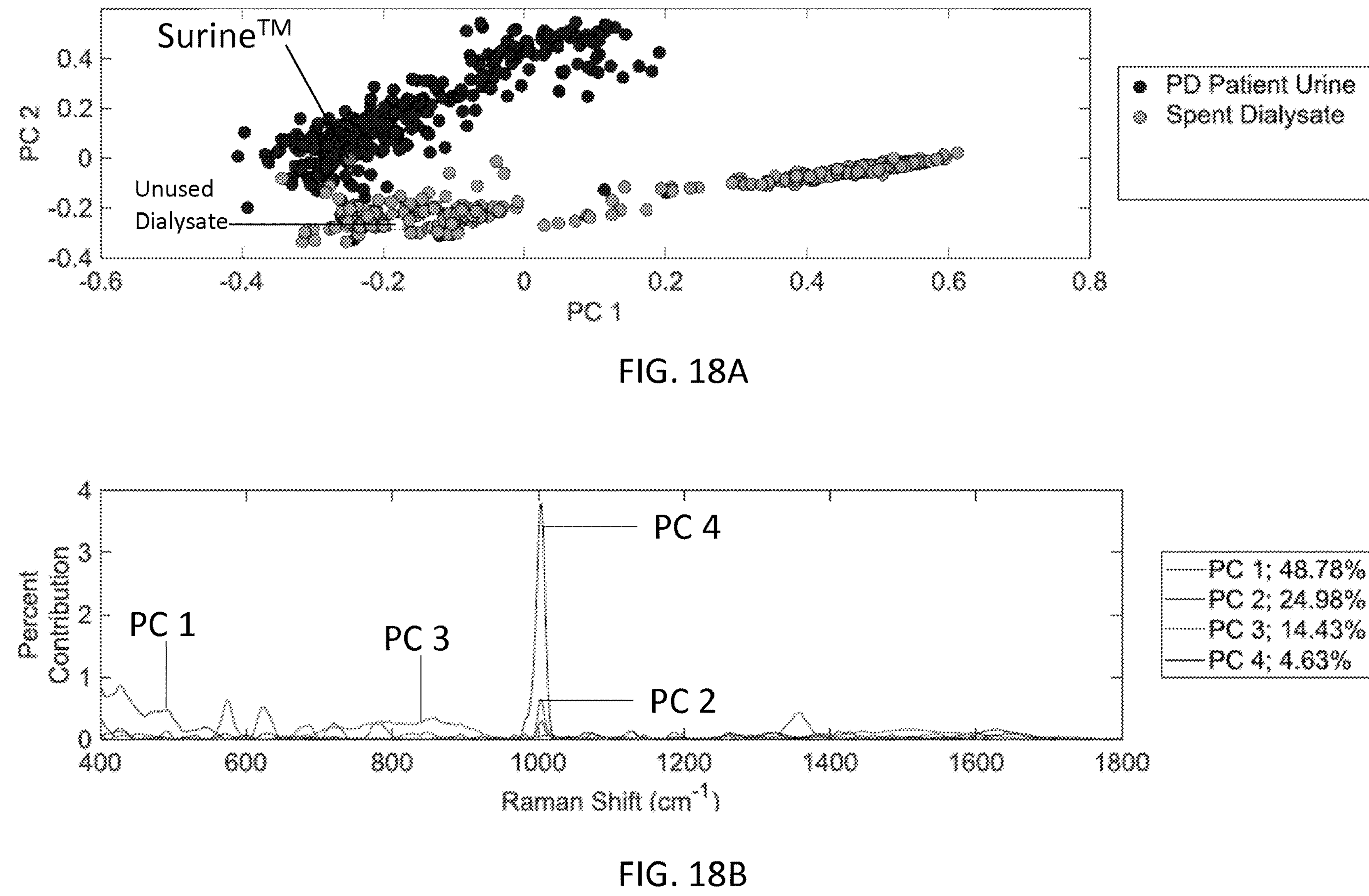
FIGS. 18A-B are graphs showing: A) PCA results for Raman spectra of 362 urine specimens obtained from patients receiving PD therapy for ESKD and 395 spent dialysate specimens and B) contributions of Raman shifts leading to separations among principal components.

Principal component analysis. The PD patient urine specimens were compared against the spent dialysate specimens using PCA in the Rametrix™ LITE Toolbox. The first two principal components are plotted in FIG. 18A. Here, significant separation is observed between the two specimen types (i.e., PD urine and spent dialysate). PCA was applied with two controls: (i) Surine™ as a urinalysis standard and (ii) unused dialysate. Surine™ clustered with the urine specimens, and the unused dialysate clustered with the spent dialysate, showing some similarity between these specimen types. The Rametrix™ LITE Toolbox also identifies Raman shifts that lead to the separation of clusters in PCA. These can be traced back to individual molecules by scanning individual standards, metabolomic knowledge, and spectral libraries. For the PD patient urine and spent dialysate dataset, these Raman shift contributions are shown in FIG. 18B. Contributions from the top four principal components are shown, and together, these represent over 92% of the dataset variance. Again, the Raman shift at 1,002 $cm^{-1}$ was the most dominant, present in all principal components, and is representative of urea in urine and dialysate specimens. Other notable Raman shifts in FIG. 18B include creatinine (680 $cm^{-1}$) and glucose (1,071 $cm^{-1; \ 1,117}$ $cm^{-1}$; others). Research is ongoing to validate more Raman shifts in this and similar plots using Raman scans of standards and metabolomic analysis. The inventors note, however, the chemometric approach of Rametrix™ (described below) allow meaningful results to be obtained without the assignment of analytes to individual Raman bands.

Figures 19A, 19B:
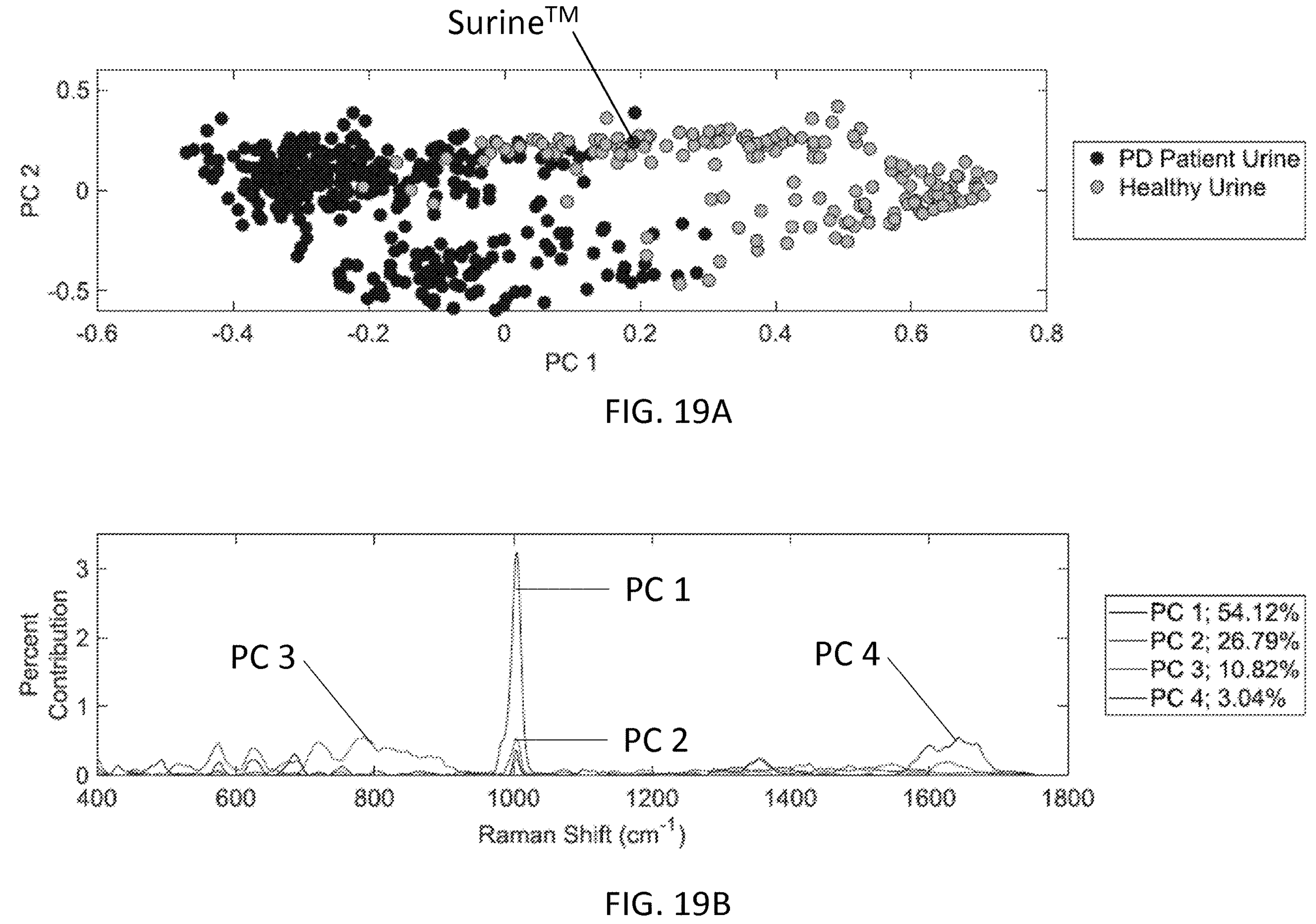
FIGS. 19A-B are graphs showing: A) PCA results for Raman spectra of 362 urine specimens obtained from patients receiving PD therapy for ESKD and 235 urine specimens from healthy individuals and B) contributions of Raman shifts leading to separations among principal components.

The PD patient urine specimens were also compared against the urine specimens from healthy human volunteers by PCA. These results are shown in FIG. 19A and show the separation of clusters between the two specimen types, suggesting significant spectral differences and molecular compositions. This time, the Surine™ analytical control clustered with urine specimens from healthy volunteers, rather than those from PD patients. The spectral differences (i.e., signal intensities at each Raman shift) that lead to the observed separation between urine specimens from PD patients and healthy volunteers in PCA are given in FIG. 19B. The top four principal components represent more than 94% of the dataset variance in this case. Here, urea (1,002 $cm^{-1}$) is dominant in the first principal component (PC 1). Again, creatinine and glucose are apparent in FIG. 19B, and additional Raman shift contributions are present relative to the comparison of PD patient urine and spent dialysate (FIG. 18B).

Statistical analyses. The entire dataset (consisting of Raman scans of healthy human volunteer urine, PD patient's urine, and spent dialysate) was analyzed by one-way (1-way) ANOVA to determine if the type of specimen was statistically significant. To do this, the spectra were each quantified to a single numerical value through calculation of the total principal component distance (TPD). This calculation has been explained and demonstrated previously. Briefly, TPD represents how closely the Raman spectrum of a specimen resembles that of Surine™. To calculate this, the distance formula is applied between the top four principal components of a specimen and those of Surine™. This procedure reduces a data-rich Raman spectrum down to a single numerical value, which allows statistical tests to be applied. In particular, a 1-way ANOVA test of TPD values for all specimen types (i.e., healthy human urine, PD patient urine, or spent dialysate) returned a p-value less than 0.001, which confirmed that the type of specimen was statistically significant. Results of pairwise comparison tests with Tukey's HSD procedure are shown in Table 12. Statistical significance ($p<0.001$) was obtained when comparing (i) PD patient urine with spent dialysate, (ii) PD patient urine with healthy human volunteer urine, and (iii) PD patient spent dialysate with healthy human volunteer urine. Results confirm these types of specimens are all different from one another. Other pairwise comparisons did not return statistical significance likely because only single controls (Surine™ and unused dialysate) were included in the dataset.

TABLE 12

Pairwise comparisons using Tukey's HSD procedure.

| Specimen 1 | Specimen 2 | p-Value |
|---|---|---|
| Spent PD Dialysate | PD Patient Urine | <0.001 |
| Spent PD Dialysate | Unused Dialysate | 0.906 |
| Spent PD Dialysate | Healthy Urine | <0.001 |
| Spent PD Dialysate | Surine ™ | 0.0517 |
| PD Patient Urine | Unused Dialysate | 1.00 |
| PD Patient Urine | Healthy Urine | <0.001 |
| PD Patient Urine | Surine ™ | 0.346 |
| Unused Dialysate | Healthy Urine | 0.905 |
| Unused Dialysate | Surine ™ | 0.689 |
| Healthy Urine | Surine ™ | 0.874 |

Figure 20B:
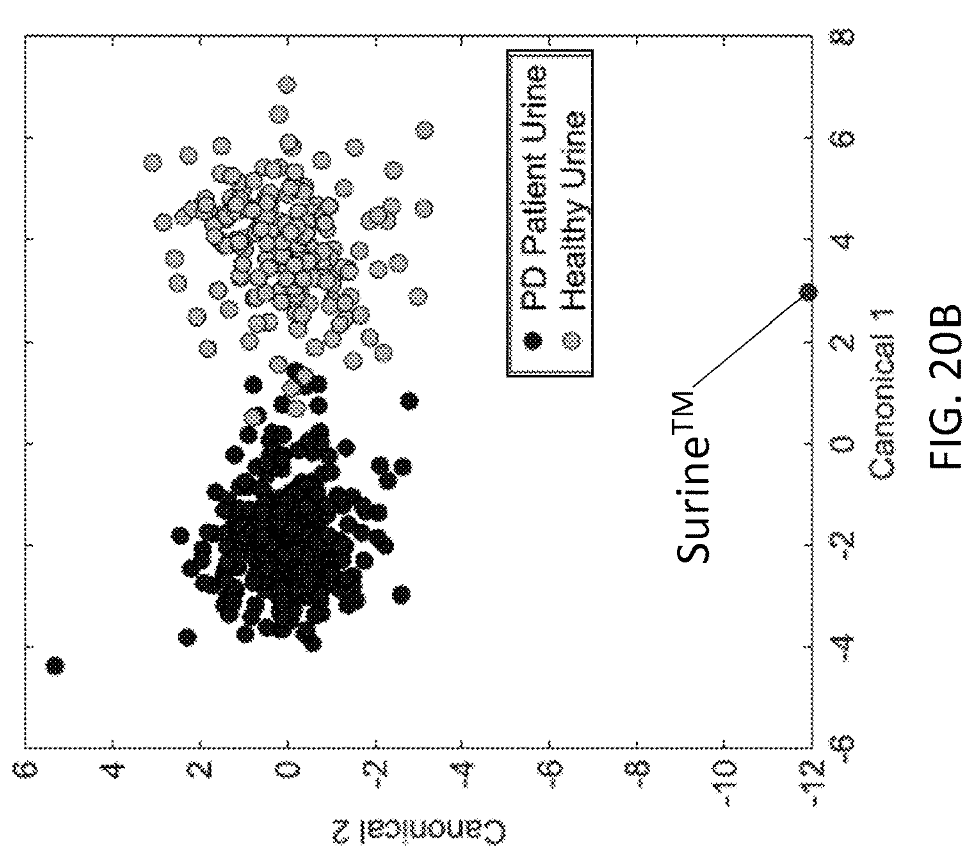
FIGS. 20A-B are graphs showing DAPC of A) 362 urine specimens obtained from patients receiving PD therapy for ESKD and 395 spent dialysate specimens and B) 362 urine specimens obtained from patients receiving PD therapy for ESKD and 235 urine specimens from healthy individuals.
Figure 20A:
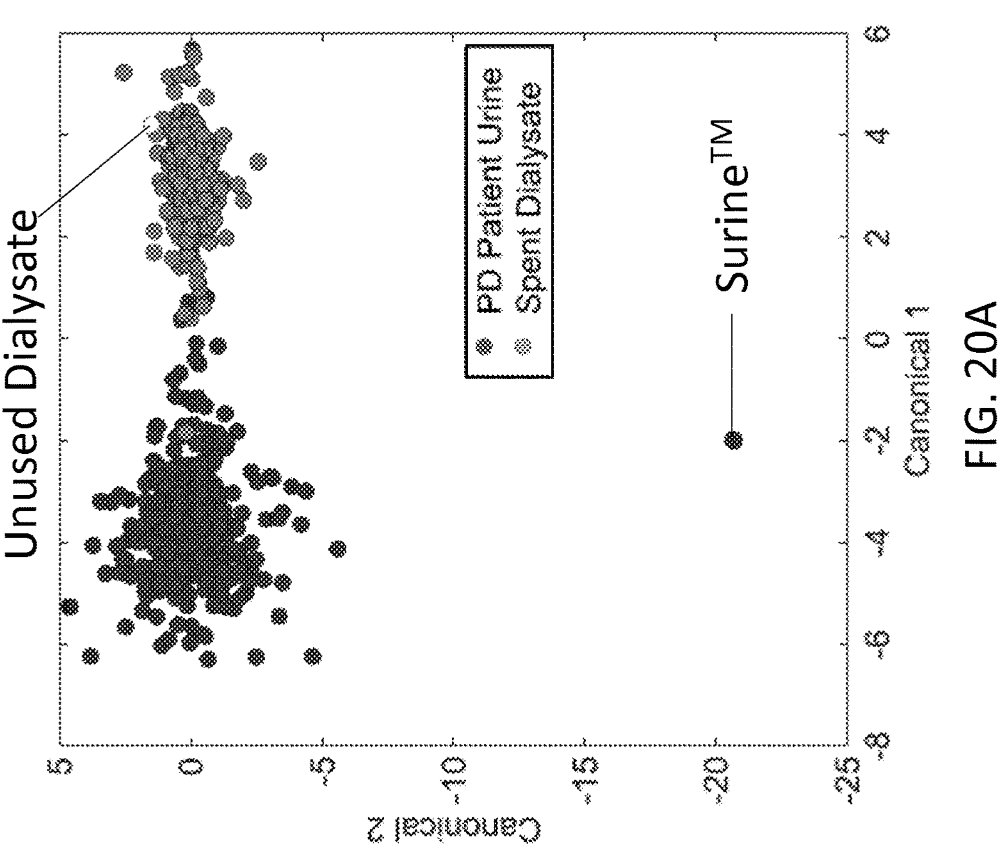

Discriminant analysis of principal components models. The Rametrix™ LITE Toolbox was used to generate DAPC models for datasets consisting of Raman scans of: (i) PD patient urine and spent dialysate and (ii) PD patient urine and urine from healthy human volunteers. Surine™ was included as a control in both models, and unused dialysate was used as an additional control for the model containing PD patient spent dialysate. The Rametrix™ PRO Toolbox was then used to evaluate the predictive capabilities of these models using a leave-one-out build/test validation routine. DAPC model clustering is shown in FIGS. 20A-B for both models when 50 principal components were used in model construction. Good separation of clusters (with some overlap) was observed in both cases. Surine™ was separated from all clusters in both models, and the unused dialysate standard clustered with the PD patient spent dialysate specimens.

The prediction capabilities (from "leave-one-out" build/test routines) of the DAPC models are shown in Tables 13 and 14. The DAPC models were built with different numbers of principal components to ensure enough dataset variance was included in the models and to test for model overfitting. DAPC models were evaluated in terms of prediction accuracy (the percentage of data points predicted correctly), sensitivity (the true positive percentage), and specificity (the true negative percentage). Results in Table 13 convey Rametrix™ can determine the identity of an "unknown" specimen from a PD patient as being either urine or spent dialysate with very high confidence.

TABLE 13

Rametrix ™ PRO results showing the ability to predict whether an unknown specimen from a PD patient is urine or spent dialysate.

| Percent Variability Explained by Principal Components | Number of Principal Components used in DAPC Model | Accuracy* | Sensitivity* | Specificity* |
|---|---|---|---|---|
| 90% | 4 | 97.8% | 98.6% | 97.0% |
| 95% | 5 | 97.2% | 98.1% | 96.5% |
| 99% | 10 | 98.7% | 98.9% | 98.5% |
| 99.9% | 50 | 98.2% | 98.9% | 97.5% |

*Predictions were from a leave-one-out training/testing routine.

Greater than 98% accuracy, sensitivity, and specificity were obtained for a DAPC model consisting of 10 principal components. For all DAPC models tested, the accuracy, sensitivity, and specificity values exceeded 97%. This high level of confidence in identifying the type of sample (i.e., urine or spent dialysate) is unsurprising given the clear differences in Raman spectra shown in FIGS. 17A-B. For determining whether a urine specimen originated from a PD patient or healthy human volunteer, Rametrix™ prediction results are given in Table 14.

TABLE 14

Rametrix ™ PRO results showing the ability to predict whether an unknown urine specimen came from a PD patient or healthy human volunteer.

| Percent Variability Explained by Principal Components | Number of Principal Components used in DAPC Model | Accuracy* | Sensitivity* | Specificity* |
|---|---|---|---|---|
| 90% | 3 | 94.0% | 95.6% | 90.8% |
| 95% | 5 | 93.1% | 92.8% | 93.6% |
| 99% | 11 | 96.1% | 97.0% | 94.2% |
| 99.9% | 50 | 97.4% | 99.7% | 92.5% |

*Predictions were from a leave-one-out training/testing routine.

Better than 96% prediction accuracy (with better than 97% sensitivity and 94% specificity) was obtained for the DAPC model constructed with 11 principal components. Using 50 principal components led to increased accuracy and sensitivity with decreased specificity, which is characteristic of model over-fitting.

Rametrix™ has demonstrated the ability to discern effectively among (i) urine from PD patients (ESKD), (ii) spent dialysate from their PD therapies, and (iii) urine from healthy human volunteers. Cluster separations (according to specimen type) were readily apparent in PCA and DAPC model plots, and the conversion of spectral data to TPD values for statistical analyses also confirmed these differences were statistically significant. The inventors have begun the process of identifying molecules responsible for these differences and belive this may result in a new set of biomarkers for ESKD and earlier stages of chronic kidney disease. However, the inventors were able to show that the entire Raman spectrum of a specimen can be used (i.e., chemometrics) to determine its type (i.e., urine or dialysate) or the state of the donor (i.e., healthy human or PD patient). The leave-one-out build/test validations of Tables 13 and 14 are particularly important because they describe how well Rametrix™ can perform with "unknown" specimens. Of course, the long-term vision with Rametrix™ is not to be able to discern whether an unknown specimen is urine or dialysate but to be able to screen for the presence of incipient disease and patient-specific PD responses. For example, Rametrix™ could be used to determine whether PD therapies are patient-specific and if there are variations among successive treatments. If so, how do these affect long-term patient outcomes? Comparing urine from PD patients to that of healthy human volunteers is a first crucial step in this process. The PD patients used in this study have ESKD; thus, the differences between urine from these patients and healthy human volunteers should be significant and easily detectable by Rametrix™, as was confirmed by this study. The next steps in Rametrix™ development are to be able to detect earlier stages (i.e., G1-4) and track patient progress over longer periods of time.

Section V

Raman Chemometric Urinalysis as a Screen for Bladder Cancer

Bladder cancer (BCA) is relatively common and potentially recurrent/progressive disease. It is also costly to detect, treat, and control. Definitive diagnosis is made by examination of urine sediment, imaging, direct visualization (cystoscopy), and invasive biopsy of suspect bladder lesions. There are currently no widely-used BCA-specific biomarker urine screening tests for early BCA or for following patients during/after therapy. Urine metabolomic screening for biomarkers is costly and generally unavailable for clinical use. In response, the inventors developed Raman spectroscopy-based chemometric urinalysis (Rametrix™) as a direct liquid urine screening method for detecting complex molecular signatures in urine associated with BCA and other genitourinary tract pathologies. (See Huttanus, H, Vu, T, Guruli, G, Tracey, A, Carswell, W, Said, N, Du, P, Parkinson, B, Orlando, G, Robertson, J, Senger, R, "Raman Chemometric Urinalysis (Rametrix™) as a screen for bladder cancer," PLOS One. 2020; 15 (8): e0237070. Published online 2020 Aug. 21. doi: 10.1371/journal.pone.0237070 ("Huttanus, H, et. al. (2020)")). In particular, the Rametrix™ screen used principal components (PCs) of urine Raman spectra to build discriminant analysis models that indicate the presence/absence of disease. The number of PCs included was varied, and all models were cross-validated by leave-one-out analysis. In Study 1 reported here, the Rametrix™ screen was tested using urine specimens from 56 consented patients from a urology clinic. This proof-of-concept study contained 17 urine specimens with active BCA (BCA-positive), 32 urine specimens from patients with other genitourinary tract pathologies, seven specimens from healthy patients, and the urinalysis control Surine™. Using a model built with 22 PCs, BCA was detected with 80.4% accuracy, 82.4% sensitivity, 79.5% specificity, 63.6% positive predictive value (PPV), and 91.2% negative predictive value (NPV). Based on the number of PCs included, it was found that the Rametrix™ screen could be fine-tuned for either high sensitivity or specificity. In other studies reported here, Rametrix™ was also able to differentiate between urine specimens from patients with BCA and other genitourinary pathologies and those obtained from patients with end-stage kidney disease (ESKD). This study demonstrates the ability of the Rametrix™ screen to differentiate urine of BCA-positive patients. Molecular signature variances in the urine metabolome of BCA patients included changes in: phosphatidylinositol, nucleic acids, protein (particularly collagen), aromatic amino acids, and carotenoids.

Bladder cancer (BCA) is common and the most costly type of cancer to treat. More than 80,000 new cases were expected to be diagnosed in 2019 (4.6% of all newly-diagnosed cancer cases), and almost 18,000 patients would die due to tumor progression and treatment failure. There are currently over 577,400 patients under treatment. The five-year survival rate for BCA is 77.4%, and early-stage disease is correlated with better five-year survival (Stage 0-98%, Stage 1-88%, Stage 2-63%). Five-year survival is worse for more advanced stages (Stage 3-46%, Stage 4-15%). Approximately 30% of all new muscle-invasive cases are first diagnosed in Stages 2-4.

Early detection of asymptomatic BCA is problematic. The onset of clinical symptoms (e.g., hematuria, dysuria, urgency, lower back pain) usually triggers further clinical and diagnostic investigation. Routine urinalysis is not useful for early BCA detection, and the significance of minimal hematuria in specimens is debatable. Definitive diagnosis of BCA in symptomatic patients is accomplished with a combination of imaging studies, urine cytology, direct bladder examination (i.e., cystoscopy) and tests for BCA biomarkers. None of the current urine-based biomarker tests have gained wide acceptance or become a standard-of-care for screening or patient follow-up.

All current diagnostic procedures, including testing for urine-based biomarkers, are either (i) costly, (ii) require some degree of expertise to achieve valid results, (iii) invasive, (iv) not reliably sensitive or specific, (v) highly dependent on sample quality and stage of tumor growth, (vi) analytical resource intensive (e.g., requiring mass spectroscopy), and/or (vii) not scalable for mass screening. A simple, non-invasive and reliable screening technology for detection of BCA could reduce the use of invasive and costly evaluation tests for the patients unlikely to have cancer, and expedite the diagnosis and treatment for those who do. For BCA surveillance, such a test could improve the identification of the disease recurrence/progression, and reduce cystoscopy in patients with low risk.

Unlike some other tumors (e.g., prostate cancer), no case of BCA can be left untreated, since it will predictably become symptomatic and will progress without treatment. The earlier a tumor is diagnosed, the greater the chances are that BCA will be curable or controllable, or that less aggressive treatment can be used (i.e., bladder-sparing therapies). Thus, an accurate, non-invasive screening technology could be used clinically for annual urinalysis of the population at increased risk for developing BCA (e.g., users of tobacco products; >27 million people in the US), for monitoring the efficacy of therapy in patients who have BCA (over 577,000 people), and monitoring patients for tumor recurrence/progression.

The inventors have developed a novel screening technology, Raman chemometric urinalysis (Rametrix™), for use in detecting BCA markers (Raman multi-molecular spectral fingerprints, or spectral fingerprints) in urine.

Urine contains hundreds of individual molecules that reflect metabolism and health, as well as the important physiologic activities of the urinary system. The composition is highly variable among individuals and, in fact, varies substantially in every individual, every day, depending on activity, diet, metabolism, ingestion of exogenous drugs and chemicals, state of hydration, and renal function. In a single Raman spectral scan (obtained in <5 minutes), many of these molecules can be identified easily and reliably as spectral bands that can be correlated to analytical standards in Raman reference libraries. For example, small molecules (e.g., urea, creatinine, uric acid, glucose) and macromolecules commonly used to assess health and renal function all produce Raman intensity bands at specific wave numbers. These collectively create a unique "Raman spectral fingerprint" of a urine specimen's molecular composition. Understandably, the presence of BCA and other bladder pathologies has a profound effect on urine composition. These compositional changes are present in the spectral fingerprints, and they can be resolved by multivariate statistical models.

Others have recognized the value of using Raman spectroscopy for studying urinary tract disease, including BCA. DeJong and coworkers were able to distinguish a unique Raman signature associated with BCA cells in surgical (excisional) biopsy touch preparations. Bird and co-workers used IR Raman microscopy for detection of BCA in cytology preparations. Canetta and co-workers used modulated Raman spectroscopy to differentiate unique Raman spectral signatures in preparations of urothelial and bladder cancer cells derived from tissue cultures. Shapiro and co-workers used Raman micro-spectroscopy to evaluate bladder cancer lesions and found a unique spectral band at wavelength 1,584 $cm^{-1}$ that distinguished tumor vs. non-tumor tissue and low-grade vs. high-grade BCA. Kerr and co-workers used Raman micro-spectroscopy to differentiate bladder cancer cells from other urine sediments. Yang et al. created a surface enhanced Raman scattering (SERS) assay for specific receptors on cancer cells. The signal amplification properties of SERS allow these molecules to be illuminated in liquid urine specimens. Further, Raman spectroscopy-based screens with Fe304 functionalized surfaces have been developed for detecting urine crystals, which may go on to form stones. (See de Jong BW, Schut TC, Maquelin K, van der Kwast T, Bangma CH, Kok D J, et al. Discrimination between nontumor bladder tissue and tumor by Raman spectroscopy. Anal Chem. 2006; 78:7761-9. Doi: 10.1021/ac061417b; Bird B, Romeo MJ, Diem M, Bedrossian K, layer N, Naber S. Cytology by Infrared Micro-Spectroscopy: Automatic Distinction of Cell Types in Urinary Cytology. Vib Spectrosc. 2008; 48:101-106. Doi: 10.1016/j.vibspec.2008.03.006; Canetta E, Mazilu M, De Luca AC, Carruthers AE, Dholakia K, Neilson S, et al. Modulated Raman spectroscopy for enhanced identification of bladder tumor cells in urine samples. J Biomed Opt. 2011; 16:037002. Doi: 10.1117/1.3556722; Shapiro A, Gofrit ON, Pizov G, Cohen JK, Maier J. Raman molecular imaging: a novel spectroscopic technique for diagnosis of bladder cancer in urine specimens. Eur Urol. 2011; 59:106-12. Doi: 10.1016/j.eururo.2010.10.027; Kerr, al. L T et. Methodologies for bladder cancer detection with Raman based urine cytology. Anal Methods-Uk. 2016; 8:4991-5000. Yang YT, Hus IL, Cheng TY, Wu WJ, Lee CW, Li TJ, Cheung CI, Chin YC, Chen HC, Chiu YC, Huang CC, Liao MY. Off-Resonance SERS Nanoprobe-Targeted Screen of Biomarkers for Antigens Recognition of Bladder Normal and Aggressive Cancer Cells. Analytical Chemistry 2019; 91 (13): 8213-8220. DOI: 10.1021/acs.analchem.9b00775; Lo PA, Huang YH, Chiu YC, Huang LC, Bai JL, Wu SH, Huang CC, Chaing CC. Automatic Raman spectroscopic urine crystal identification system using fluorescent image-guided 2D scanning platform with Fe304 crystal violet nanoclusters. J Raman Spectrosc 2018; 50 (1) 34-50, doi: 10.1002/jrs.5495;

Chiu YC, Chen PA, Chang PY, Cheng YH, Tao CW, Huang C, Chiang HK. Enhanced Raman sensitivity and magnetic separation for urolithiasis detection using phosphonic acid-terminated Fe304 nanoclusters. J. Mater. Chem. B 2015 (3): 4282-4290.doi: 10.1039/C5TB00419E.

As can be seen, a large percentage of the published literature on the use of Raman spectroscopy for detection of BCA is centered on the evaluation of cytologic preparations, with a small fraction focused on evaluation of the urine metabolome. The inventors, however, are the first to use liquid-phase Raman analysis for the detection of conditions and diseases. The Rametrix™ technology, uniquely, relies on discerning molecular changes in liquid urine, making it significantly more practical and suitable for mass screening of specimens. Here, the inventors report the results of a preliminary clinical study where Raman spectroscopy was used with the Rametrix™ LITE and Rametrix™ PRO spectral processing methods to analyze urine specimens from BCA patients and from patients with other genitourinary diseases. The inventors performed the study to test the hypothesis that "unique Raman spectral patterns (i.e., spectral fingerprints) are associated with BCA and can be detected in liquid urine by Rametrix™." The inventors compared the results of these Raman spectroscopic analyses with those obtained from Rametrix™ analysis of urine from healthy volunteers, those with end-stage kidney disease (ESKD), and a synthetic urinalysis analytical standard (Surine™). The inventors also evaluated Rametrix™ as a screen for BCA by calculating its sensitivity, specificity, positive predictive value (PPV), and negative predictive value (NPV) metrics. These metrics are critical to assessing the potential usefulness of the screening test, as high sensitivity (true-positive screen result) leads to a higher percentage of BCA cases being identified, and high specificity (true-negative screen result) minimizes false-positive screen results that can lead to unnecessary (and invasive) tests and examinations.

Urine Specimen Preparation. Urine specimens were collected following IRB approval and obtaining patient written consent; specifics are provided below for each group of patients. Specimens were stored at −35° C. for no more than four weeks prior to analysis; such conditions preserve the veracity of the Raman signature (see below Specimen Stability Validation). Stored specimens were thawed for approximately 25 minutes in an incubator at 37° C. in preparation for analysis. A total of 1.5 mL of each urine specimen was then aliquoted into glass vials, which were then sealed. Specimens exhibiting precipitates were vortexed briefly to re-suspend and dissolve these prior to Raman scanning. Surine™ (Dyna-Tek Industries, Lenexa, KS), a synthetic analytical standard, was used as the urinalysis control and was also prepared in a similar manner.

Raman Spectroscopy. Urine specimens were analyzed as bulk liquids using a PeakSeeker™ dispersive Raman spectrometer (Agiltron; Woburn, MA). Specimens were each scanned 10 times using 785 nm 100 mW laser intensity, with 15 second exposure time and a 15 second delay between each scan. Specimens were scanned in a random order, and Surine™ was scanned with each batch of urine specimens analyzed.

Urology Clinic Patients Dataset. Urine specimens were obtained from 56 subjects (patients and volunteers) presenting at a urology clinic, as described above. The sample size of this study was determined by the collection period duration. The characteristics of the study population are presented in Table 15. Mid-stream free-catch urine specimens were acquired in sterile sample cups from the study subjects. Specimen integrity was preserved prior to Raman scanning using methods described above. Patient diagnosis was noted during collection so that results could be correlated with analytical data.

A definitive diagnosis for each patient presenting with clinical signs indicative of BCA was made using a combination of patient history, standard clinical pathology laboratory studies, imaging, direct visualization (cystoscopy) and a confirmatory biopsy. The definitive diagnosis was used to classify urine specimens for subsequent Rametrix™ analysis. Clinical diagnoses for other patients were made using a combination of patient history, standard clinical pathology laboratory studies, imaging, direct visualization (cystoscopy) and confirmatory biopsy, as needed. The definitive diagnosis is referred to as the "Gold Standard" test when describing metrics to evaluate Rametrix™ as a screening test. These metrics are defined later.

TABLE 15

Characteristics of study populations and categories of genitourinary tract pathology studied.

| Dataset | Total Number of Specimens | Number of Males | Number of Females | Median Age (Years) |
|---|---|---|---|---|
| Urology Clinic Patients Dataset | 56 | 35 | 21 | 62 |
| BCA patients (active) | 17 | 8 | 9 | 70 |
| BCA patients (inactive a/o under treatment) | 8 | 7 | 1 | 62 |
| Genitourinary cancer (Renal, prostate) | 8 | 7 | 1 | 60.5 |
| Other non-neoplastic genitourinary (GU) disease | 16 | 11 | 5 | 59 |
| Urology clinic healthy volunteers | 7 | 2 | 5 | 40 |
| Healthy Volunteers Dataset | 56 | 13 | 43 | 22 |
| Nephrology Clinic Patients Dataset | 56 | N/A | N/A | N/A |

Healthy Volunteers Dataset. For the study reference population, a subset of a previous dataset of consented healthy female and male volunteers, ranging in age from 19-69 years old (median age 22 years old) was used (Table 15). The state of "healthy" was defined as free of infectious or degenerative disease at the time of sample collection, and with no history/evidence of renal disease (based on laboratory measurements). Samples from healthy volunteers were handled in an identical manner to those described above.

Nephrology Clinic Patient Dataset. In previous research, urine specimens were collected from patients undergoing peritoneal dialysis therapy for ESKD. A subset of this larger patient database was used for this study (Table 15), and the data derived from many of these specimens have also been used with Rametrix™ in other studies.

Specimen Stability Validation. In prior research, the effects of storage conditions on urine specimens and Surine™ molecular composition were studied in detail. Here, is presented a subset of this data to validate storage at −35° C. for four weeks. Surine™ and two of the urine specimens used in this study were transferred to glass vials and were analyzed by Raman spectroscopy initially (t=0), after an initial freeze/thaw, and then once every seven days for 12 weeks. All vials were thawed and vortexed briefly before analysis. Data were analyzed by Rametrix™ LITE and statistical models as described below.

Rametrix™ Analysis. Urine sample spectra were processed and analyzed using the Rametrix™ LITE v1.1 and PRO v1.0 Toolboxes and the Statistics and Machine Learning Toolboxes in MATLAB r2017b (The MathWorks, Inc.;

Natick, MA). The Rametrix™ LITE Toolbox was used for spectral processing and for building Principal Component Analysis (PCA) and Discriminant Analysis of Principal Components (DAPC) models. The Rametrix™ PRO Toolbox was used to test the ability of DAPC models to classify "unknown" urine specimens by leave-one-out analysis. Statistical analyses including one-way Analysis of Variance (ANOVA) and pairwise comparisons, using Tukey's Honestly Significant Difference (HSD), were performed in MATLAB.

Rametrix™ LITE

Figure 21:
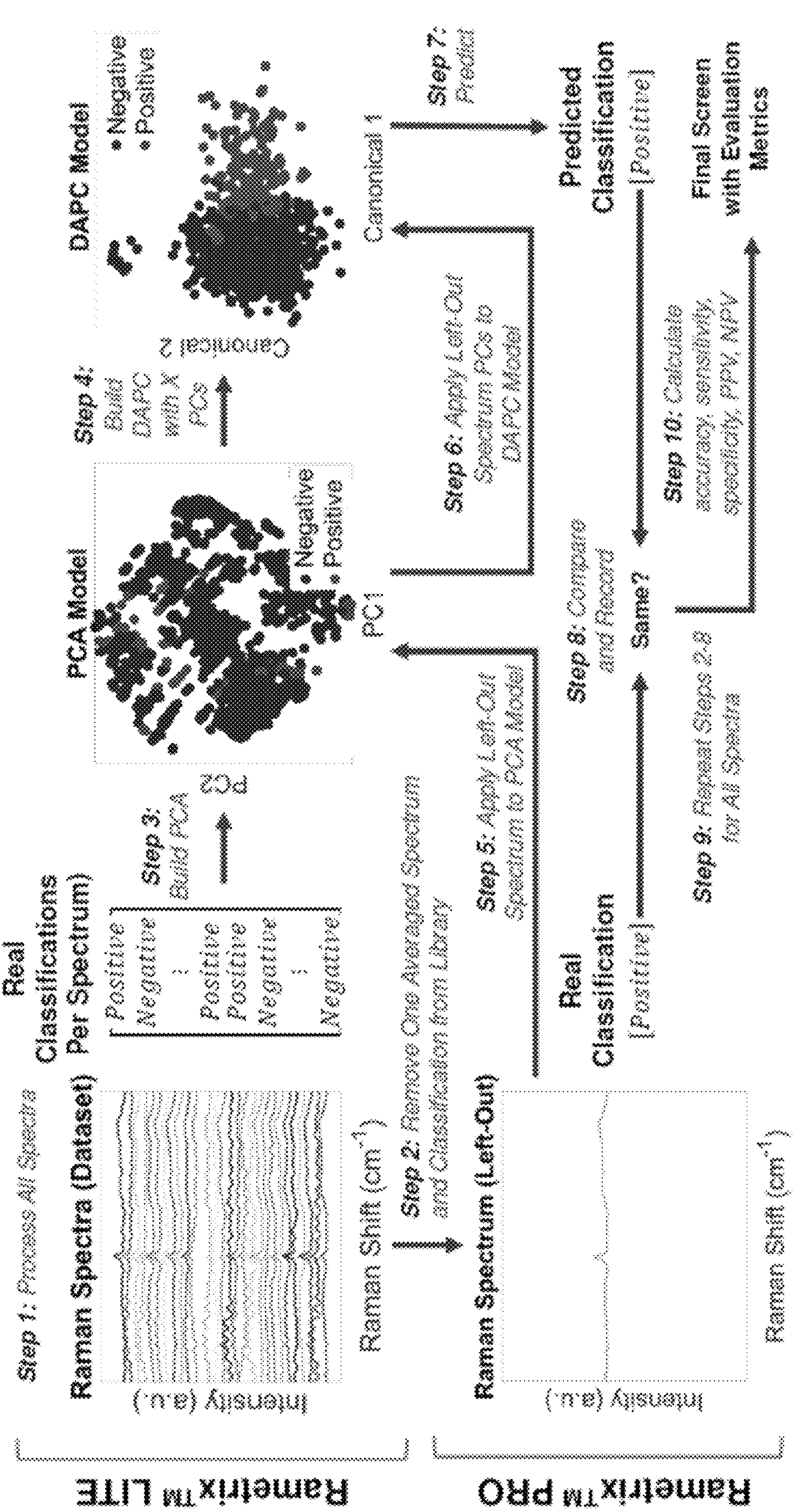
FIG. 21 is a flow diagram of Rametrix™ calculations and the leave-one-out routine. Rametrix™ LITE comprises steps 1, 3, and 4. Rametrix™ PRO comprises steps 2, 5-10.

For the PCA and DAPC model-building process with Rametrix™ LITE, each Raman spectrum was assigned a classification based on the patient diagnosis (e.g., BCA-positive or BCA-negative). Each Raman spectrum was truncated to 400-1,800 $cm^{-1}$, followed by baseline correction using the Goldindec algorithm with the parameters: baseline polynomial order=3; estimated peak ratio=0.5; smoothing window size=5. All spectra from each urine specimen were then vector normalized and averaged. Next, PCA was applied with the Rametrix™ LITE Toolbox, and a specified number of PCs was used to create DAPC model(s). The Rametrix™ LITE Toolbox also automated calculation of Raman shift contributions to PCA and DAPC models. In this procedure, the contribution of each Raman shift to the separation of classification groups (e.g., BCA-positive vs. BCA-negative) was determined. Those Raman shifts with significantly large contributions were investigated further through the use of Raman spectral libraries. This enabled conversion of spectral signatures into inferences about the metabolome of BCA-Rametrix™-based urine screen for BCA involves obtaining a Raman spectrum of urine, processing the spectrum as described above, reducing the spectrum to its PCs, and using those with the DAPC model to generate a prediction (e.g., BCA-positive or BCA-negative). To do this, Rametrix™ PRO routines tested DAPC models for their predictive capabilities following their construction with Rametrix™ LITE. Specifically, Rametrix™ PRO performed a leave-one-out analysis over all models and datasets. This procedure is shown as a flow-diagram in FIG. 21. Leave-one-out analysis is a subset of K-fold analysis and ensures every urine specimen in the dataset is evaluated as an "unknown" at some point in the routine (FIG. 21). In particular, the leave-one-out analysis removed one spectrum from the dataset (or spectral library) and treated it as an unknown. PCA and DAPC models were constructed using the remaining spectra, and the classification of the unknown was predicted by the model (e.g., "BCA-positive" or "BCA-negative"). This process was repeated for each spectrum in the dataset. With correct/incorrect predictions for every spectrum in the dataset, the urine screen evaluation metrics were calculated as described below. This process was repeated for every study.

Evaluation metrics. Urine screen accuracy (i.e., adequacy) for BCA was calculated as the percentage of spectra classifications predicted correctly in the leave-one-out routines. Sensitivity, specificity, PPV, and NPV evaluation metrics were calculated as described in the literature. Briefly, sensitivity is the true-positive rate (reported as percentage) of the Rametrix™ screen. This is the proportion of BCA cases confirmed via Gold Standard test (i.e., the definitive diagnosis described earlier) which also test positive according to the screen. The specificity is the true-negative rate and is the proportion of negative cases confirmed via Gold Standard which also test negative by the screening test. The PPV indicates the proportion of positive screening tests that then test positive via Gold Standard. The NPV indicates the proportion of negative screening tests that then test negative via Gold Standard.

These metrics (i.e., accuracy, sensitivity, specificity, PPV, and NPV) were compared to their random chance rates. For example, for the BCA-positive or BCA-negative classification, the random chance rates of all metrics were all 50%. DAPC models for high sensitivity and specificity. Different numbers of PCs were used to construct DAPC models. This frequently impacted model performance and resulted in different metric values. Thus, results from multiple models are reported for each scenario tested in this study. In all cases, at least one high-sensitivity and one high-specificity model are reported with associated values of all other metrics (i.e., accuracy, PPV, and NPV).

ANOVA and pairwise comparisons. The classification groups (e.g., BCA-positive and BCA-negative) were also tested for statistically significant differences among their spectra using ANOVA and pairwise comparisons using Tukey's HSD (Honestly Significant Difference) procedure of Total Principal Component Distance (TPD). To do this, each spectrum was reduced from several hundred of Raman intensity values (one at each wavenumber) into a single numerical value. This was done by calculating the distance between the top four PCs of each spectrum and a reference spectrum, as shown in Eq. 5. In this research, the spectrum for Surine™ served as the reference. The TPD calculation has been used in other analyses with Rametrix™. In Eq. 5, is the value of the PC of urine spectrum, and is the value of the PC of the reference (i.e., Surine™) spectrum. In contrast to Rametrix™ PRO analysis of DAPC models, Rametrix™ LITE and statistical analyses were performed without averaging replicate spectra for each urine specimen.

$$TPD = \sum_{i=1}^{4} \sqrt{(P_{u,i} - P_{ref,i})^2} \quad \text{Eq. 5}$$

Defining the Studies and Goals. Two preliminary studies were conducted followed by five larger studies involving patient datasets described in Table 15. In the first preliminary study, the storage conditions of the urine specimens and Surine™ were validated. In the second preliminary study, the Raman spectra were inspected visually to determine if chemometric methods by Rametrix™ were needed in this study. The larger patient studies are listed in Table 16. In Study 1, the 56 urine specimens of the urology clinic dataset were used. Those (17) with active BCA were classified as "BCA-positive." The remaining specimens were classified as "BCA-negative." This study was designed to determine if urine from patients with active BCA could be distinguished from urine of patients (39) from the same urology clinic who did not (classified as "BCA-negative"). In Study 2, the 56 urine specimens from the Healthy Volunteers dataset were added as additional "BCA-negative" specimens to the dataset described for Study 1. Here, the goal was to determine if adding urine spectra from healthy volunteers (median age of 22 years) would skew the results obtained in Study 1 (median age of 62 years). In Study 3, the Nephrology Clinic dataset, composed of urine from ESKD patients, was added to the "BCA-negative" classification. ESKD is known to affect urine molecular composition and Raman spectral characteristics. The inventors then cross-referenced these spectral differences with a Raman band database to identify potential molecules significantly altered in BCA-positive urine. The inventors refer to this as the "Raman spectral fingerprint" of BCA based on the Rametrix™ urine screen. In Study 4, it was sought to determine whether the urine specimens could be distinguished by clinic type. The goal was to identify specific urine spectral signatures of patients visiting urology and nephrology clinics, independent of patient health status, and whether these signatures can be distinguished from urine of healthy volunteers. Finally, in Study 5, the Urology Clinic dataset was used, and specimens were re-classified as "Genitourinary (GU) Cancer," "Other GU Disease," and "Healthy." The goal was to differentiate among all of these to determine if a disease type could be identified among urology clinic patients.

TABLE 16

Definition of studies and urine specimen classifications.

| Study | Datasets | Classifications |
|---|---|---|
| Study 1 | Urology Clinic Patients + Surine ™ | BCA-Positive, BCA-Negative, Surine ™ |
| Study 2 | Urology Clinic Patients + Healthy Volunteers + Surine ™ | BCA-Positive, BCA-Negative, Surine ™ |
| Study 3 | Urology Clinic Patients + Healthy Volunteers + Nephrology Clinic Patients + Surine ™ | BCA-Positive, BCA-Negative, Surine ™ |
| Study 4 | Urology Clinic Patients + Healthy Volunteers + Nephrology Clinic Patients + Surine ™ | Urology Clinic Patients, Nephrology Clinic Patients, Healthy Volunteers, Surine ™ |
| Study 5 | Urology Clinic Patients + 9 Healthy Volunteers + Surine ™ | GU Cancer, Other GU Disease, Healthy, Surine ™ |

Stability Validation

Surine™ and two urine specimens used in this study were stored in triplicate vials at −35° C. and analyzed weekly for 12 weeks. The purpose of the study was to justify storage of all urine specimens used in the study for up to four weeks at −35° C. The spectra were analyzed, first, with Rametrix™ LITE by averaging the 10 Raman scans per analysis for each vial, and truncating, baselining, and vector normalizing. PCA, with respect to storage time, was applied with Rametrix™ LITE, followed by calculation of TPD (Eq. 5). Here, the initial time point (time=0) served as the reference ($P_{ref}$) in Eq. 5, and the TPD values were analyzed by ANOVA and pairwise comparisons. ANOVA results revealed no statistical significance of storage time (p=0.29). Pairwise comparisons allowed each time point to be compared with the initial time point. Here, all p-values were greater than 0.54, and those of the first four weeks of storage were all greater than 0.91. These results coordinate well with the inventors' larger study, suggesting urine specimens can be stored at −35° C. for at least four weeks while awaiting analysis.

Identifying BCA through Direct Comparisons of Raman Spectra.

Figure 22:
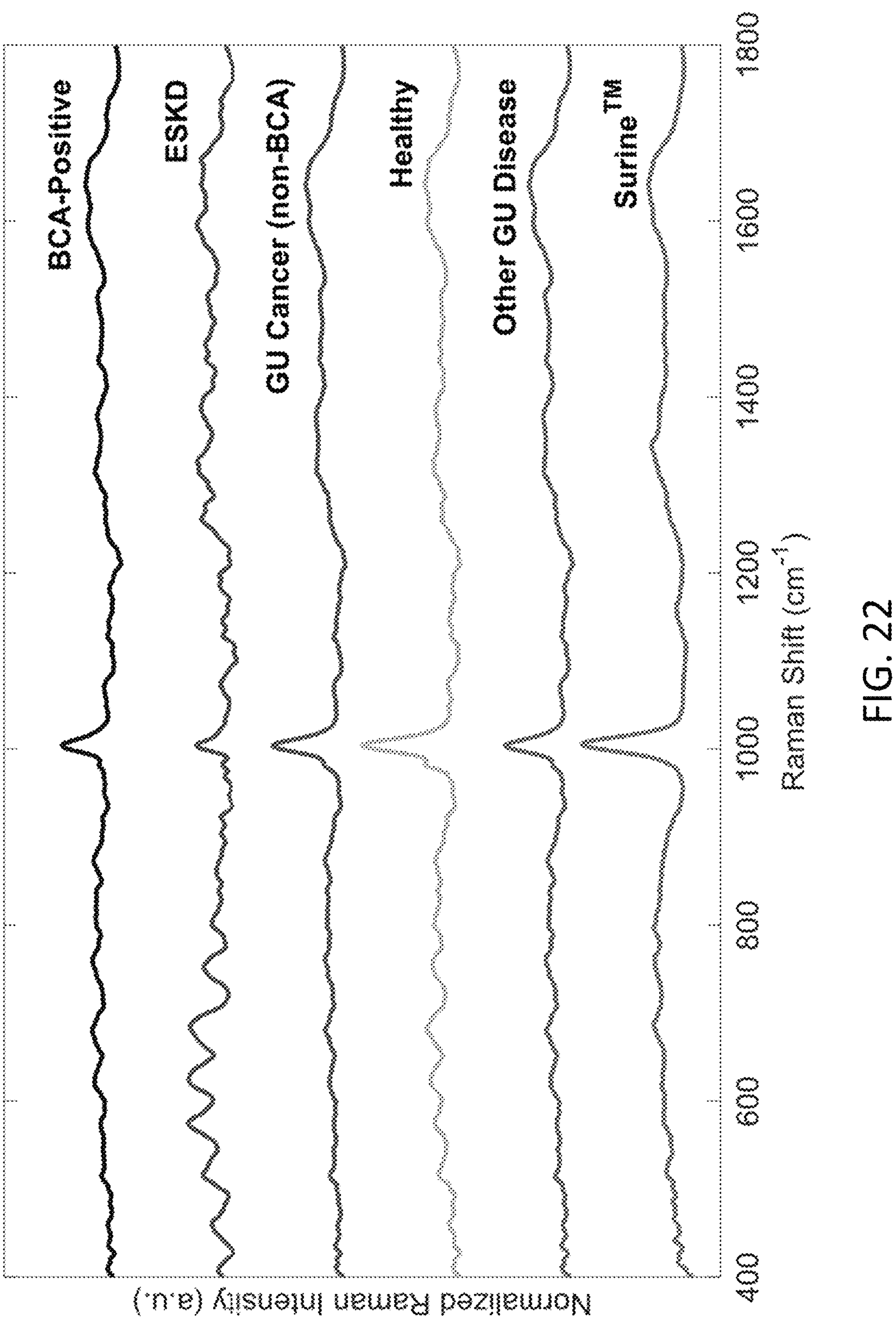
FIG. 22 is a graph showing representative baselined and vector normalized urine spectra. BCA-positive is representative of patients with active BCA. GU Cancer (non-BCA) includes genitourinary cancers (Renal, prostate). Other GU Disease includes those patients with non-neoplastic diseases.
Figures 23A, 23B:
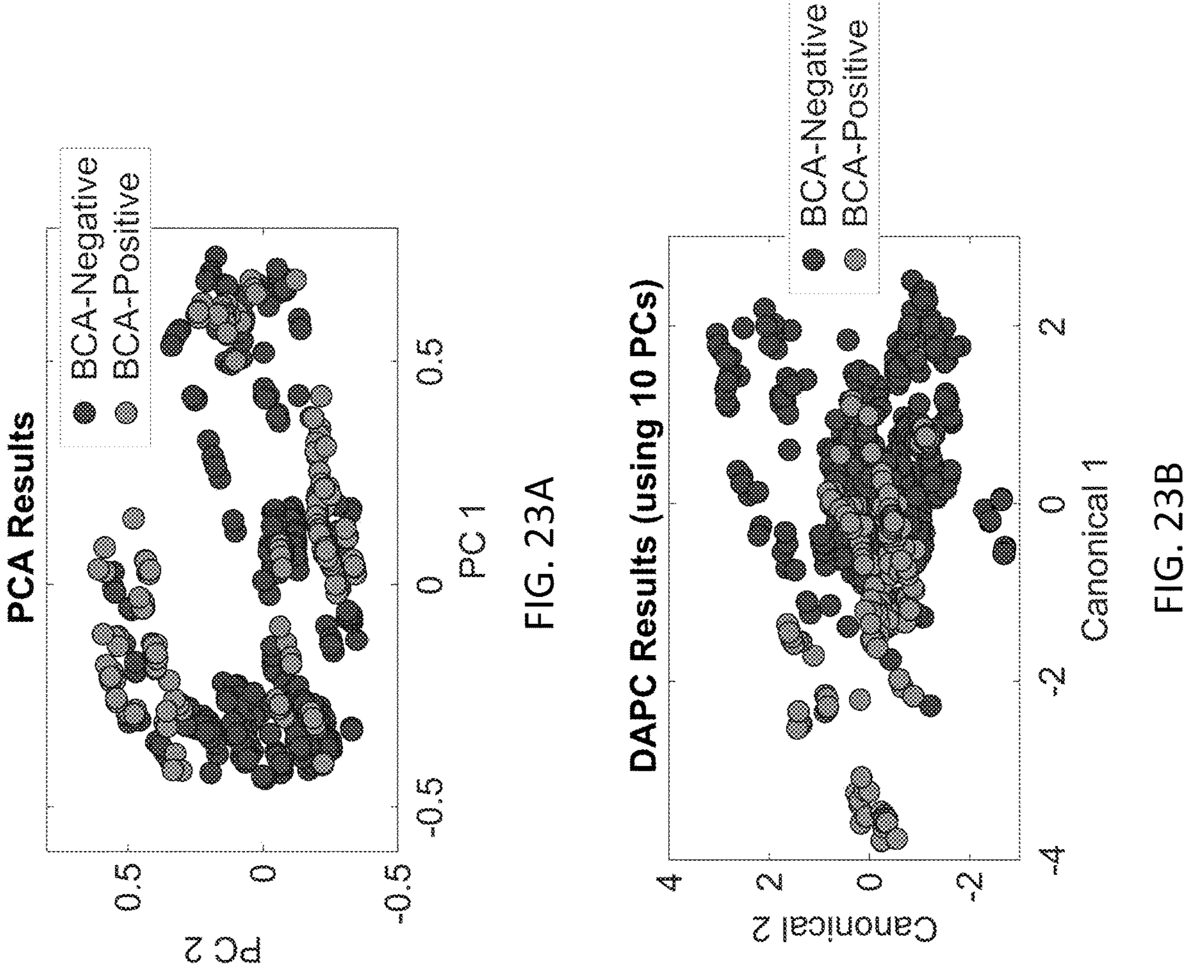
FIGS. 23A-D are graphs showing Rametrix™ LITE results for BCA-positive and BCA-negative spectra. A) PCA results, B) DAPC results (model built with 10 PCs), C) DAPC results (model built with 22 PCs), D) DAPC results (model built with 40 PCs).
Figures 23C, 23D:
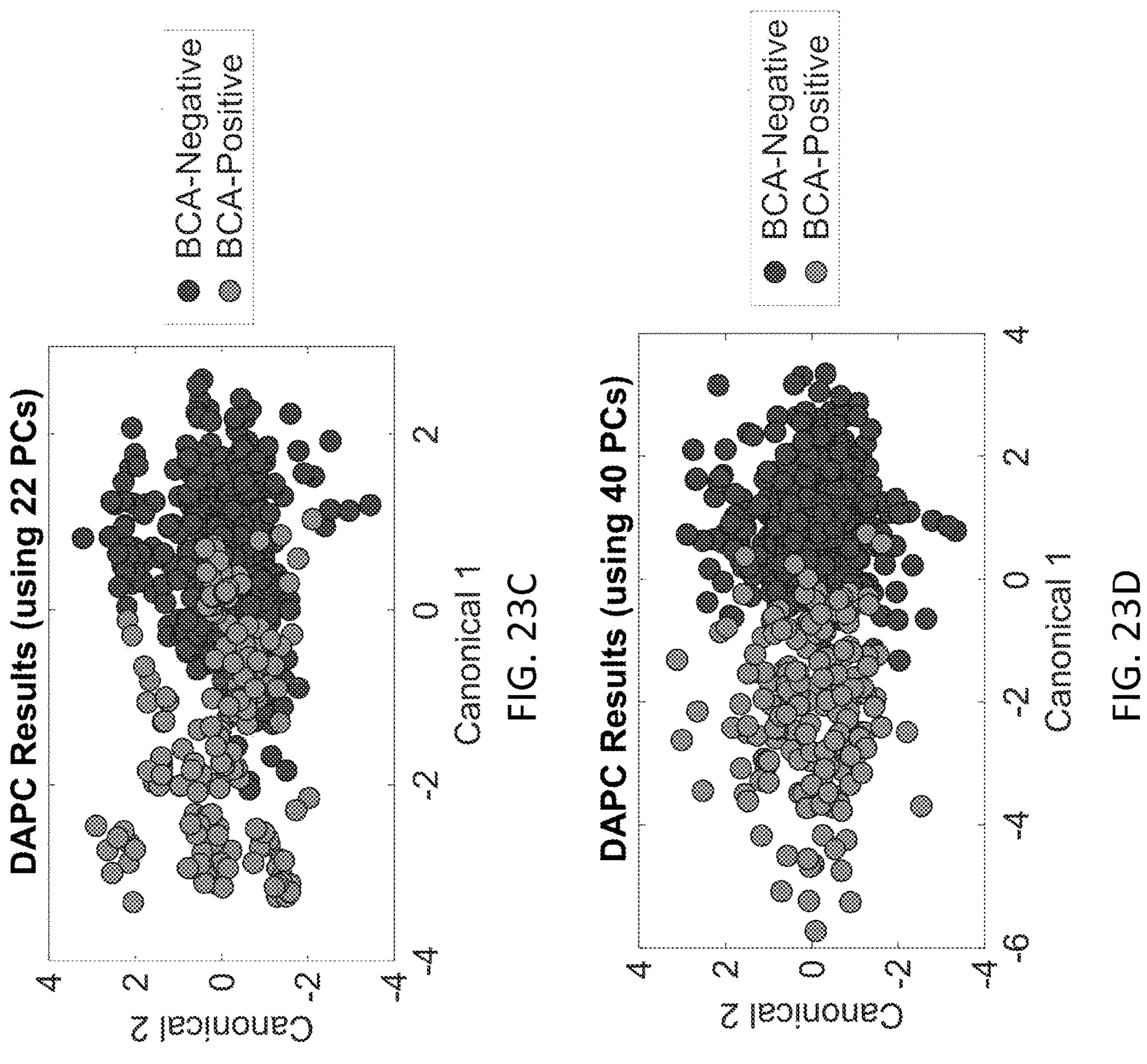

Raman spectral data from the Urology Clinic Patients dataset were processed and vector normalized using the Rametrix™ LITE Toolbox for MATLAB. Representative spectra are shown in FIG. 22 collected from analysis of urine from patients with a BCA diagnosis, ESKD, non-BCA GU cancer (e.g., renal and prostate), healthy volunteers and patients, other non-cancer GU diseases, and Surine™. There are differences between each of the spectra, with some, especially for ESKD, appearing pronounced. Urine spectra obtained from urology clinic patients, which included BCA-positive, healthy patients, non-BCA GU cancer, and non-cancer GU diseases revealed no large defining spectral characteristics of BCA upon visual inspection, which is consistent with the current lack of urine biomarkers. This indicates computational analyses are needed to detect and quantify differences, so PCA, DAPC, and multivariate statistical analyses, including ANOVA and pairwise comparisons, were performed.

With these methods, it was determined whether defining characteristics of BCA existed in the Raman spectra. The non-BCA GU Cancer, healthy patients, and non-cancer GU diseases spectra were combined to form a "BCA-negative" classification and were compared against the BCA-positive spectra. The TPD of each sample, relative to a Surine™ control, was calculated as described above (Eq. 5); the urine specimens from BCA-positive patients were found to be significantly different from BCA-negative patients in the dataset by both ANOVA and pairwise comparisons (p<0.001). This prompted further analyses to develop a Rametrix™-based urine screen for BCA and discover the urine metabolome differences of BCA-positive patients.

Study 1:

Identifying Active BCA in the Urology Clinic Patients Dataset

Rametrix™ LITE Results. In the initial analysis, differences between urine from BCA-positive and BCA-negative patients from the Urology Clinic dataset (Table 15) were explored. To build a predictive DAPC model, spectra from the Urology Clinic patient dataset were classified simply as "BCA-positive" (urine from a patient with active BCA) and "BCA-negative" (urine from a urology clinic patient without active BCA), as shown in Table 16. PCA and DAPC analyses were performed with Rametrix™ LITE. Plots shown in FIGS. 23A-D provide a visual representation of the statistical similarities/differences represented by clustering. Here, each data point of FIGS. 23A-D represents one Raman spectrum. Each PC represents a direction of variation among the different spectra, with the first PC being the direction of greatest variation, the second PC being the direction of next greatest variation, and so forth. A total of n minus 1 PCs were used, with n being the total number of spectra. The PCA plot (FIG. 23A) does not have outliers or data points indicative of system errors, but the data do not cluster according by spectrum classification. Thus, DAPC was needed to find spectral differences according to classification and build a model capable of identifying an unknown specimen correctly.

DAPC results (FIGS. 23B-D) show specific clustering of the data classes after variance between groups is factored into the analysis. Unlike PCA, DAPC requires samples to be grouped prior to analysis and uses that classification information to generate canonicals, with each canonical representing (e.g., defined as) an axis of variation between the different classes. The DAPC plots (FIGS. 23B-D) show each Raman spectrum condensed into a single data point on the plot, with the first two (of several) canonicals represented on the x- and y-axes. By accounting for the variation between dataset classes, DAPC plots tend to show more distinct clustering than PCA. Thus, the role of PCA in Rametrix™ is to reduce a Raman spectrum from 1,400 data points (intensity values over the 400-1,800 $cm^{-1}$ Raman shift) to a smaller number of PCs that can be used in DAPC. In this case (FIGS. 23B-D), the specimens from BCA-positive patients clustered away from specimens from BCA-negative individuals along canonical 1, and clustering improved as more PCs were included in the DAPC model. Thus, these models were built using the top 10, 22, and 40 of the 552 PCs generated by PCA. These represented up to 99.6% of the dataset variance. While using a large number of PCs can lead to effective clustering in DAPC plots (FIG. 23D), using too many PCs can result in "over-fitting" the data. This results in poor performance when classifying unknown specimens. This was evaluated with leave-one-out predictions using Rametrix™ PRO.

Figure 24:
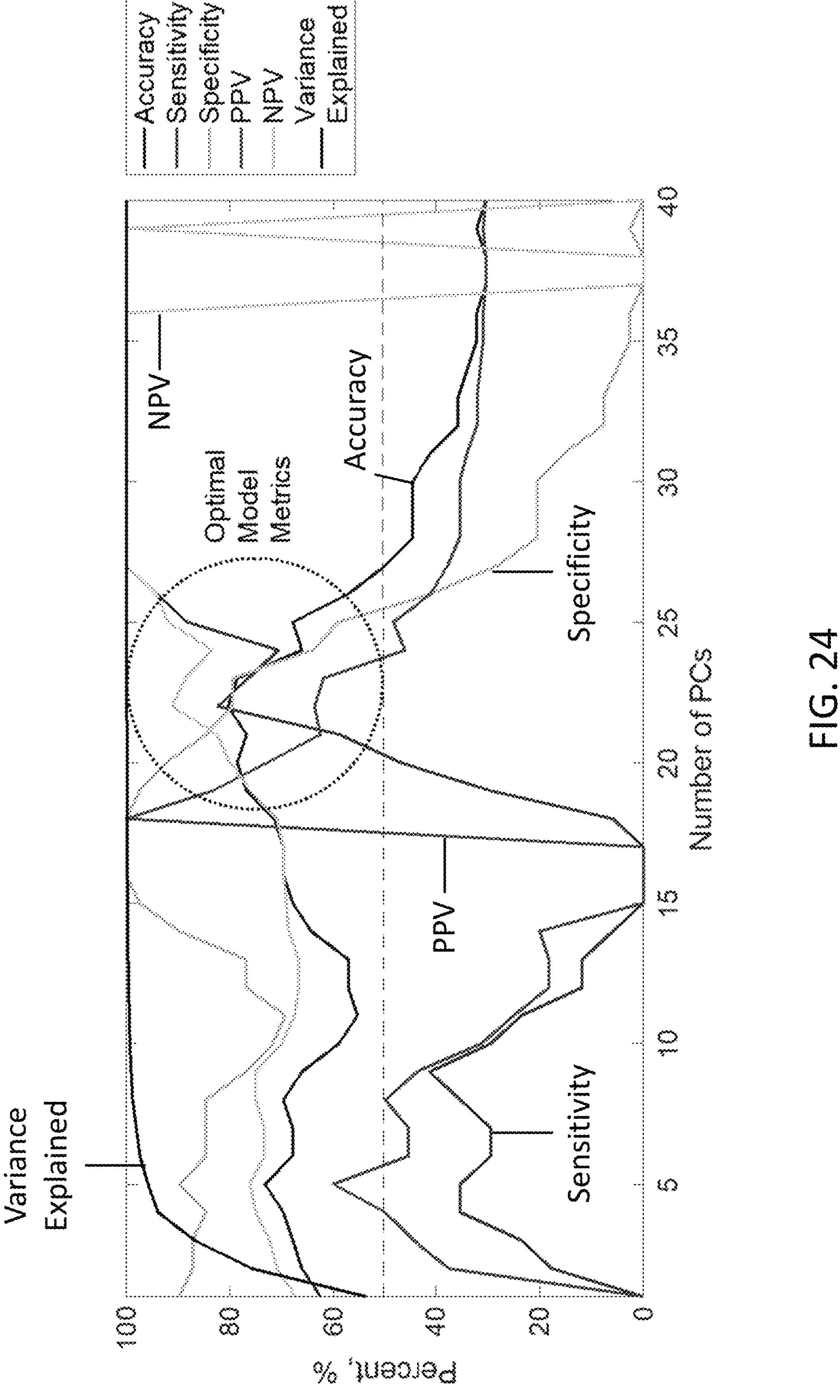
FIG. 24 is a graph showing Rametrix™ PRO results for BCA-positive and BCA-negative spectra. Accuracy, sensitivity, specificity, PPV, and NPV results are given for leave-one-out analyses.

Evaluating the DAPC Model with Rametrix™ PRO. The leave-one-out analysis was carried out using Rametrix™ PRO on DAPC models built with up to 40 PCs. The output includes the evaluation metrics (accuracy, sensitivity, specificity, PPV, and NPV), the number of PCs used to build the DAPC model, and the percent of dataset variance explained by those PCs. Results are presented graphically as FIG. 24, highlighted metric values are given in Table 17. For the Urology Clinic Patients dataset, models constructed with a low number (<20) of PCs exhibited low sensitivity (<50%) and PPV (<60%) metrics but specificity values that approached 90% and NPVs above 75%. As the number of PCs increased, sensitivity and PPV increased non-linearly while specificity and NPV decreased. Between 19 and 23 PCs (region circled on FIG. 24 and metric values given in Table 17), accuracy was maximized at about 80%, but different values of sensitivity, specificity, PPV, and NPV were observed. This suggests Rametrix™ could be operated at high accuracy but be fine-tuned to favor any one (or multiple) metric(s). For example, the sensitivity range was 29.4 to 82.4% over the five models highlighted. Specificity showed an inverse relationship, relative to sensitivity, with the maximum being 97.4%. The model built with 22 PCs showed the highest accuracy (80.4%) with relatively high values of the other metrics, and all metrics were above the 50% random chance value.

TABLE 17

DAPC model metrics for BCA-positive and BCA-negative spectra of the Urology Clinic patients dataset*.

| PCs | Accuracy | Sensitivity | Specificity | PPV | NPV |
|---|---|---|---|---|---|
| 19 | 77.7% | 29.4% | 97.4% | 83.3% | 76.0% |
| 20 | 78.6% | 47.1% | 92.3% | 72.7% | 80.0% |
| 21 | 76.8% | 58.8% | 84.6% | 62.5% | 82.5% |
| 22 | 80.4% | 82.4% | 79.5% | 63.6% | 91.2% |
| 23 | 78.6% | 76.5% | 79.5% | 61.9% | 88.6% |

*The BCA-positive/BCA-negative ratio of the Urology Clinic Patients dataset was approximately 30/70%.

Studies 2 and 3: Adding Spectra from Healthy Volunteers and ESKD Patients to the Dataset.

Figures 25A, 25B:
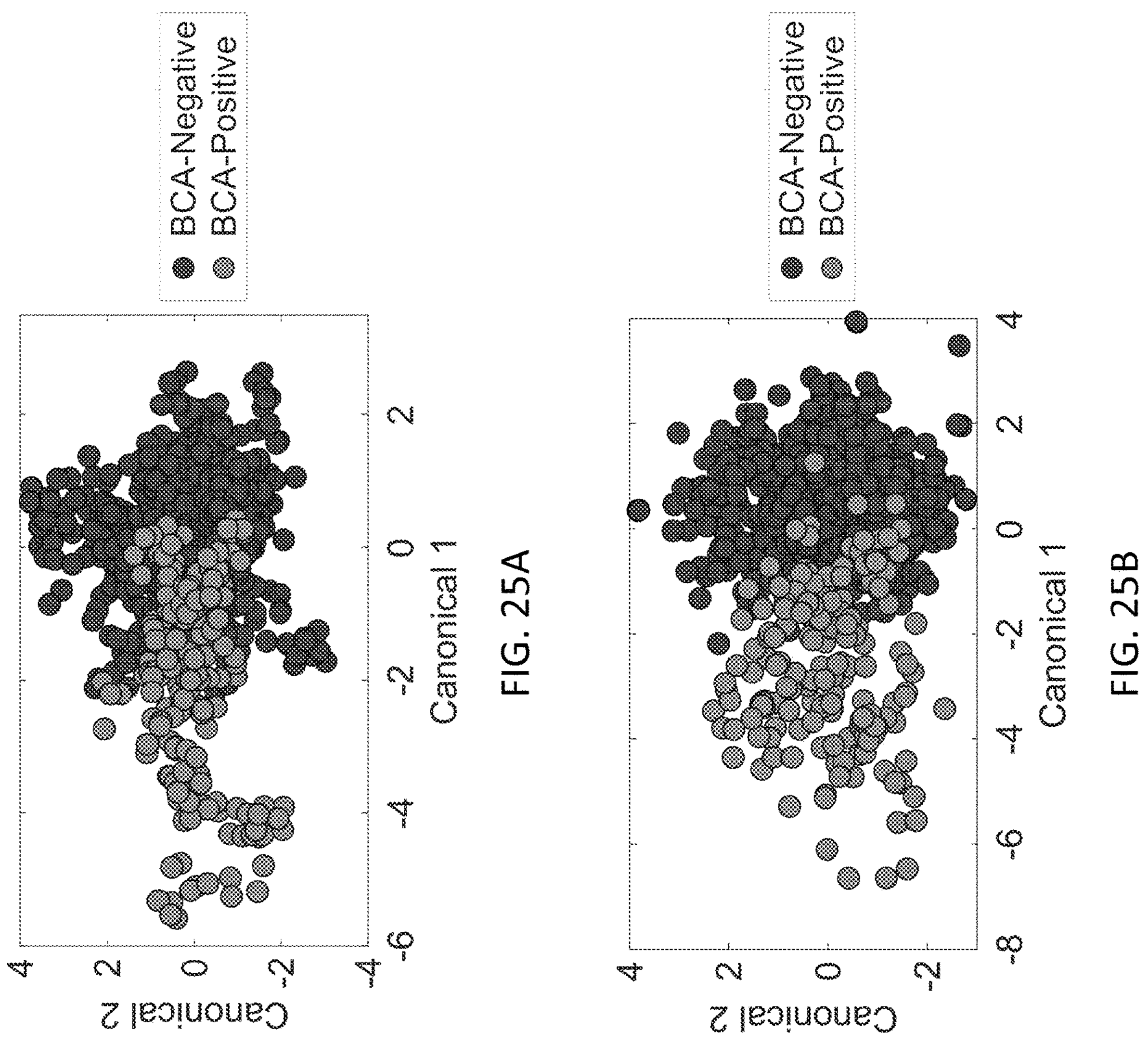
FIGS. 25A-D are graphs showing DAPC model results for BCA-positive and BCA-negative spectra when including healthy volunteers and ESKD patients. A) Urology clinic patients and healthy volunteers (26 PCs), B) Urology clinic patients and healthy volunteers (50 PCs), C) Urology clinic patients, healthy volunteers, and nephrology clinic patients (ESKD) (22 PCs), D) Urology clinic patients, healthy volunteers, and nephrology clinic patients (ESKD) (50 PCs). DAPC models were built with the number of PCs listed.
Figures 25C, 25D:
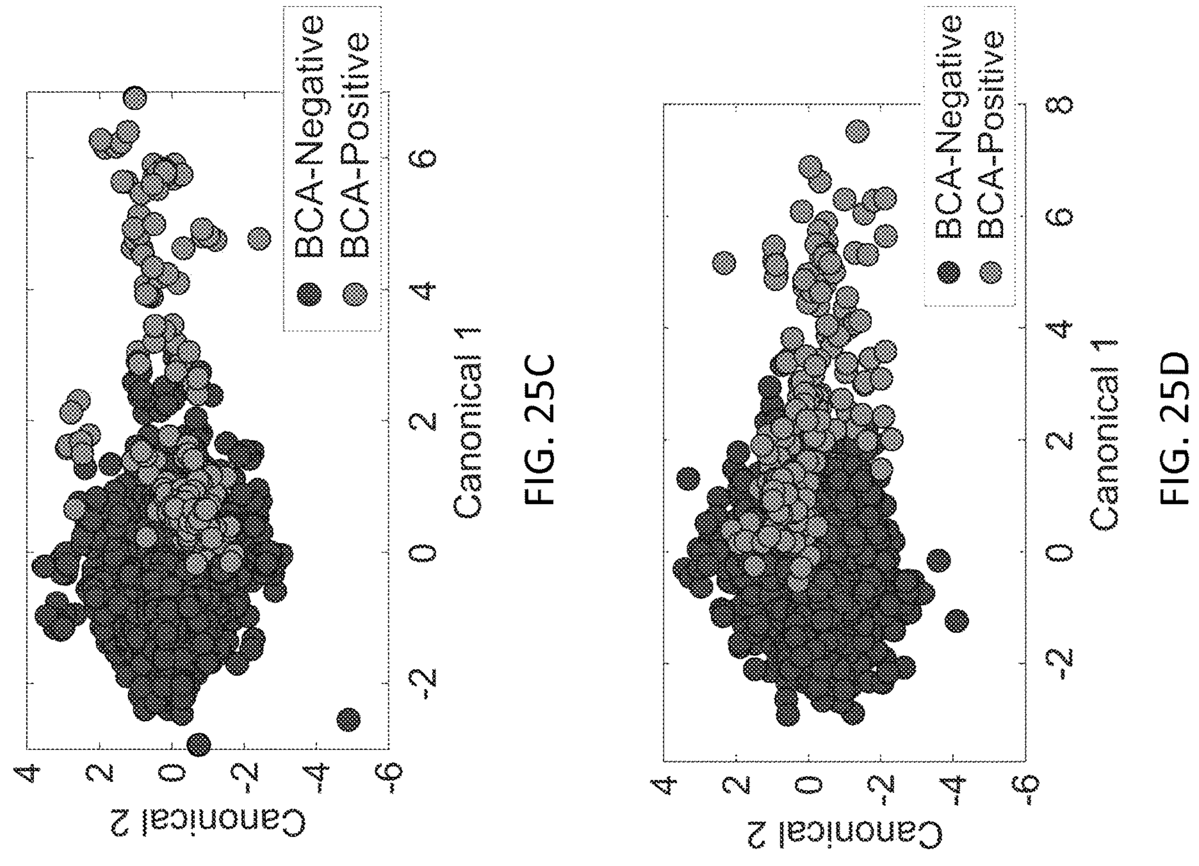

The BCA prediction model was re-built using an expanded dataset containing more BCA-negative samples. By adding 56 healthy volunteers from the VT dataset, pairwise comparisons of TPD data continued to show significant differences between BCA-positive and BCA-negative spectra (p<0.001). DAPC results from models built from this expanded dataset with 26 and 50 PCs are shown in FIGS. 25A-B. Then, urine spectra from 56 late-stage ESKD patients (selected randomly from the inventors' larger dataset) were added to the dataset to generate the DAPC plots using 22 and 50 PCs, respectively, in FIGS. 25C-D. Despite having a condition known to alter their urine Raman spectra, the spectra from ESKD patient specimens were clearly different from spectra of BCA-positive patients and clustered with other BCA-negative individuals. The spectra were still distinguishable between BCA-positive and BCA-negative by TPD calculations and pairwise comparisons (p<0.001).

Highlighted Rametrix™ PRO results from analysis of these datasets are given in Table 18. When the Healthy Volunteers dataset was added to the Urology Clinic Patients database, the percentage of BCA-positive patients dropped from 30% of the total spectra to 15%. This influenced model metrics, as seen by comparing Tables 17 and 18. Highly specific models were generated (i.e., specificity reaching 100%), but this came at the expense of sensitivity and PPV. For example, the model in Table 18 built with 19 PCs had one of the higher PPV metrics (66.7%) for a comparatively high value of overall accuracy (86.6%). This means that for every positive screen, two out of three patients would test positive with Gold Standard testing. In addition, only 23.5% of positive cases (according to the Gold Standard) would test positive with the screening test, which is a measure of the screening test sensitivity. In addition, a model was found with 26 PCs that yielded high accuracy (83.9%), sensitivity (58.8%), and specificity (88.4%), but the PPV showed that, of those testing positive with the screen, only one of two would test positive by the Gold Standard. This study shows the value of maintaining a relatively balanced dataset between the number of BCA-positive and BCA-negative cases.

TABLE 18

DAPC model metrics for BCA-positive and BCA-negative spectra of Urology Clinic Patients, healthy volunteers, and nephrology clinic patients.

| Datasets* | PCs | Accuracy | Sensitivity | Specificity | PPV | NPV |
|---|---|---|---|---|---|---|
| Urology Clinic | 19 | 86.6% | 23.5% | 97.9% | 66.7% | 87.7% |
| Patients + Healthy | 26 | 83.9% | 58.8% | 88.4% | 47.6% | 92.3% |
| Volunteers | 35 | 58.0% | 88.2% | 52.6% | 25.0% | 96.2% |
| Urology Clinic | 19 | 90.5% | 11.8% | 99.3% | 66.7% | 90.9% |
| Patients + Healthy | 22 | 89.9% | 23.5% | 97.4% | 50.0% | 91.9% |
| Volunteers + Nephrology | 30 | 81.0% | 58.8% | 83.4% | 28.6% | 94.7% |
| Clinic Patients | | | | | | |

*The values for the Urology Clinic Patients only are given in Table 16.

Figures 26A, 26B:
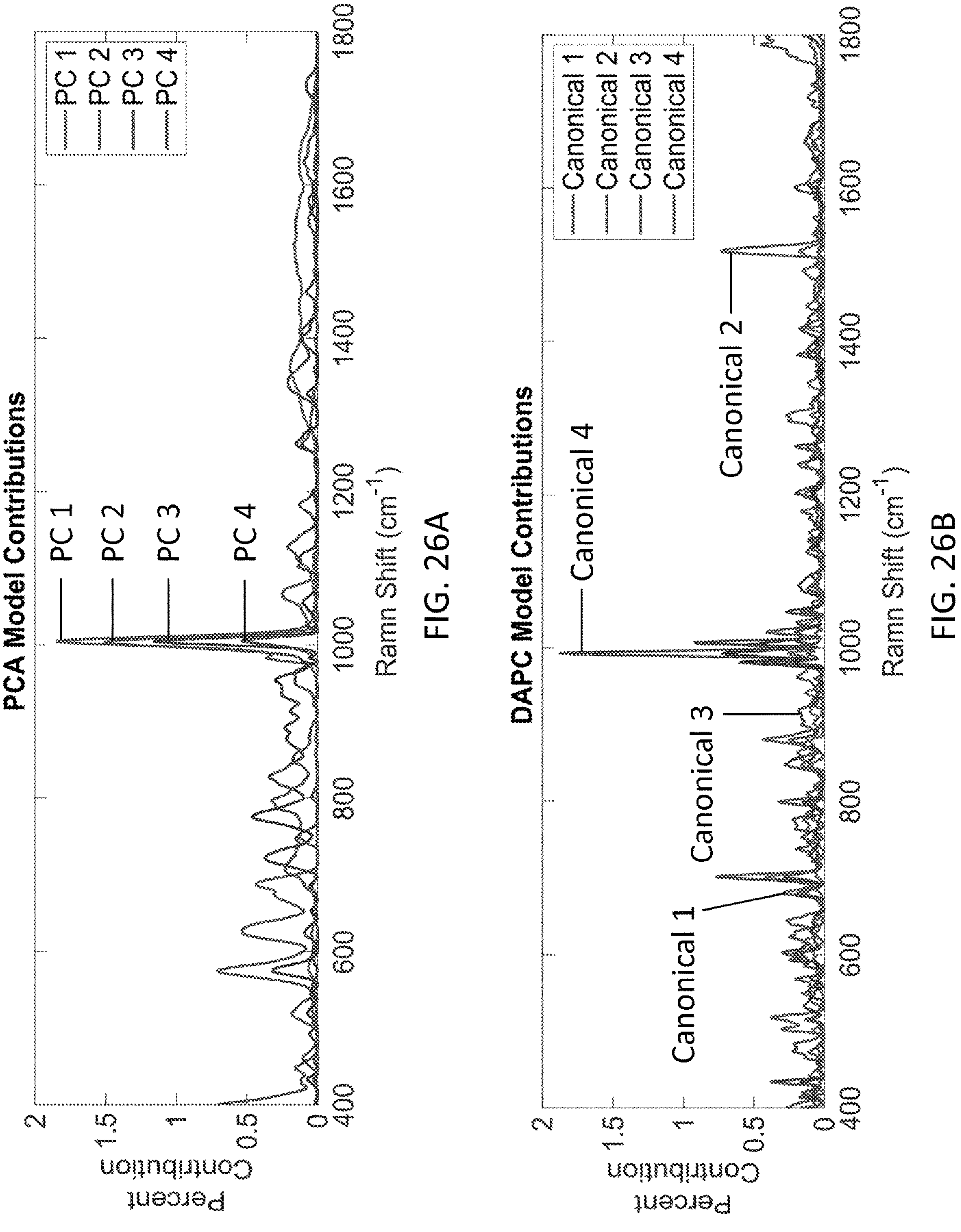
FIGS. 26A-B are graphs showing Raman shift contributions to cluster separations in A) PCA and B) DAPC.

Raman Molecular Signature of BCA. The Rametrix™ LITE Toolbox was used to extract the Raman shift contributions to separation of the BCA-positive and BCA-negative spectra in the study involving all three datasets (Urology Clinic Patients, Healthy Volunteers, and Nephrology Clinic Patients). The DAPC model constructed with 30 PCs (Table 18) was used here. Several Raman shift contributions were observed for each model, and plots of these are given in the supplementary information. The major Raman shift contributions in the top four PCs of PCA and the first four canonicals of DAPC were defined as those surpassing 0.3% contribution in FIGS. 26A-B.

The molecular assignment of these bands was extracted from a reference Raman band database for biological molecules. For PCA, these molecular assignments included: phosphatidylinositol (576 $cm^{-1}$), nucleic acids (721, 827, and 1340 $cm^{-1}$), protein (particularly collagen) (817, 981, 1065, 1127, and 1340 $cm^{-1}$), and aromatic amino acids (827 and $10^{04}$ $cm^{-1}$). For DAPC, all of these molecules were in agreement; although some Raman shifts differed. Additional assignments for DAPC included: cholesterol and fatty acids (702 and 1297 $cm^{-1}$), monosaccharides (846 $cm^{-1}$), glycogen ($10^{48}$ $cm^{-1}$), and carotenoids (1417 and 1518 $cm^{-1}$). These are identified as the major components of the molecular signature for BCA; although, the direction (increase/decrease) and levels indicative of disease have not been established. The inventors also note that several minor, still unidentified, components are present in this molecular signature for BCA (see FIGS. 26A-B).

Study 4: Detecting Differences by Clinic Type

Figure 27:
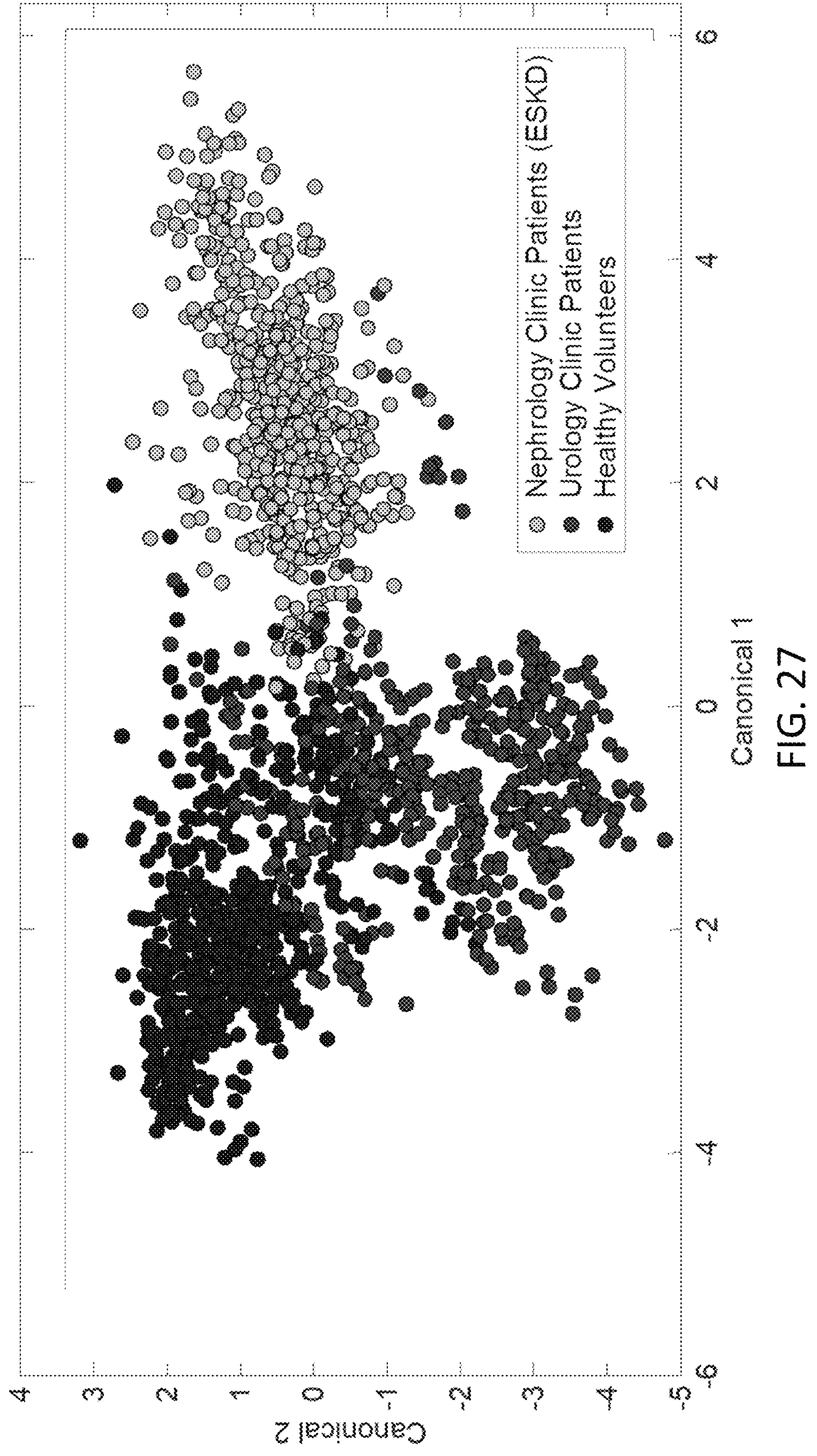
FIG. 27 is a graph showing DAPC model results in clustering spectra by clinic type. Spectra were classified as Urology Clinic Patients, Healthy Volunteers, or Nephrology Clinic Patients. The DAPC model shown was built using 28 PCs.

DAPC models were constructed to classify specimens as belonging to the classifications "Urology Clinic Patients," "Healthy Volunteers," or "Nephrology Clinic Patients." The healthy controls from the Urology Clinic Patient dataset were re-classified with the Healthy Volunteers. The Urology Clinic Patients classification included BCA-positive patients and those specified in Table 15. The Nephrology Clinic Patients were all being treated for ESKD with peritoneal dialysis at the time of urine specimen collection and analysis. DAPC results for a model built with 28 PCs are shown in FIG. 27 and exhibited separation and clustering of these classes. Pairwise comparisons of TPD data showed both the Urology Clinic Patients and the Nephrology Clinic Patients were statistically different from the Healthy Volunteers classification and Surine™ ($p<0.001$), but they were not statistically different from one other ($p=0.92$). It is expected that BCA, ESKD, and other GU pathologies all deviate from Surine™ in different ways. In addition, it is possible that several of the Urology Clinic Patients may also have undiagnosed or underlying kidney disease, leading these to be identified as not statistically different according to TPD data. However, the clustering in FIG. 27 suggests DAPC models may be able to discern among these patient types. Leave-one-out analysis was performed with Rametrix™ PRO for each classification identified above, with the other two categories being considered negative results. Results of highlighted DAPC models are given in Table 19. Here, high-sensitivity and high-specificity model results (relative to all results) are given for each classification type.

TABLE 19

DAPC model metrics for patient-type classifications.

| Clinic Type | PCs | Accuracy | Sensitivity | Specificity | PPV | NPV |
|---|---|---|---|---|---|---|
| Urology Clinic | 10 | 84.5% | 61.2% | 94.1% | 81.1% | 85.5% |
| Patients | 20 | 85.7% | 59.2% | 96.6% | 87.9% | 85.2% |
| Nephrology Clinic | 15 | 92.9% | 94.6% | 92.0% | 85.5% | 15 |
| Patients | 28 | 97.0% | 91.1% | 100.0% | 100.0% | 95.7% |
| Healthy | 21 | 90.5% | 84.1% | 94.3% | 89.8% | 90.8% |
| Volunteers | 35 | 88.1% | 73.0% | 97.1% | 93.9% | 85.7% |

Study 5: Detecting Other Cancer Types and GU Conditions

The ability of Rametrix™ to detect BCA was broadened to detecting GU cancers (e.g., kidney or prostate) and other conditions identified in the Urology Clinic Patients dataset. It was also tested to see if differences could be detected between cancerous and non-cancerous GU pathologies. Towards this aim, the inventors sorted the Urology Clinic Patients dataset into three new classifications: "GU Cancer," "Other GU Disease," and "Healthy." To balance the relative sample abundance for each category, nine samples from the Healthy Volunteers dataset were added to the "Healthy" class of the Urology Clinic Patients dataset. Pairwise comparisons of TPD data showed GU Cancer spectra were statistically different from all others (i.e., Other GU Disease, Healthy, and Surine™) (all $p<0.001$). Interestingly, the only classifications with TPD values not statistically different from one another were Healthy and Other GU Disease ($p=0.99$). This may point to limitations of Rametrix™ to detect other forms of disease, or it may indicate a limitation of the current dataset, perhaps associated with the number of samples of each type that were analyzed.

Leave-one-out analysis was performed for each class individually. Highlighted leave-one-out results are given in Table 20. Multiple model results are given for each classification in Table 20, and these represent relatively high-sensitivity and high-specificity models for each classification. Model metrics showed to be lower than those of the other studies, pointing to additional challenges of resolving different pathologies from specimens represented in the Urology Patients Clinic dataset.

TABLE 20

DAPC model metrics for detecting GU pathologies.

| GU Pathology | PCs | Accuracy | Sensitivity | Specificity | PPV | NPV |
|---|---|---|---|---|---|---|
| GU Cancer | 30 | 66.15% | 56.00% | 72.50% | 56.00% | 72.50% |
| | 33 | 58.46% | 84.00% | 42.50% | 47.73% | 80.95% |
| Other GU | 19 | 73.85% | 18.75% | 91.84% | 42.86% | 77.59% |
| Disease | 23 | 66.15% | 62.50% | 67.35% | 38.46% | 84.62% |
| Healthy | 27 | 72.31% | 45.83% | 87.80% | 68.75% | 73.47% |
| | 29 | 67.69% | 66.67% | 68.29% | 55.17% | 77.78% |

The molecular composition of urine from BCA-positive patients differs from that of normal urine, and this is detectable by Raman spectroscopy and Rametrix™. Additionally, the Raman spectra of BCA urine was found to also be different from urine of patients with ESKD and other GU conditions. The inventors were able to use Raman data and Rametrix™ calculations to identify spectral characteristics unique to BCA-positive urine and the metabolome of those specimens. While the inventors were able to make molecular assignments for the dominant spectral differences (e.g., collagen, DNA, phosphatidylinositol, and others mentioned in the Results), it is noted that several more minor contributors exist and likely are significant as well. Examples of these might include biomarkers such as NMP-22 and bladder tumor associated antigens present in bladder cancer urine. However, since Rametrix™ relies on chemometrics (i.e., extracting information from Raman spectra representing many molecules), individual biomarkers do not need to be identified specifically in a specimen to build an effective urine screen for BCA. The analysis specifically detects broad metabolomic signatures of disease. Thus, it is a combination of many molecular factors (some unknown at this point) that cause BCA-positive urine to be distinctly different. Nonetheless, the inventors have begun the process of relating these spectral differences to specific metabolites and patterns using Raman spectral reference libraries, and the inventors believe this may result in a new set of metabolomic biomarkers (i.e., Raman spectral fingerprint of a molecular fingerprint—from the molecular composition of urine) for BCA. However, more research is needed to validate these initial spectral findings with more patient samples, use of several analytical standards, and exploration of the minor components contributing to the molecular signature variances. The inventors anticipate that no particular molecule, or small subset, will be indicative of BCA alone. It is likely that the entire molecular signature, analyzed using Rametrix™, will be necessary to relate the urine metabolome to the presence of BCA. The leave-one-out analysis with Rametrix™ PRO determines how well DAPC models will perform in characterizing new urine specimens. The results of the Rametrix™ model to identify BCA-positive and BCA-negative patients of the Urology Clinic Dataset (Table 17 with 22 PCs) are used here to further illustrate the concepts of sensitivity, specificity, PPV, and NPV. Of those in a patient population, all who test BCA-positive by the Gold Standard (i.e., diagnostic tests and physical exam), 82.4% of these would test positive with the Rametrix™ screening test (sensitivity). In this population, of those who test negative by the Gold Standard, 79.5% of these people would test negative with the Rametrix™ screen (specificity). Of all who test positive with the Rametrix™ screen, 63.6% of these would test positive with the Gold Standard (PPV). Finally, of all to test negative with the Rametrix™ screen, 91.2% of these would also test negative with the Gold Standard (NPV). With the sensitivity, specificity, PPV, and NPV all exceeding the random chance value (50%) for a BCA-positive or BCA-negative designation, larger clinical studies of BCA patients and those with other GU pathologies could improve these metrics.

The inventors also recognize that the DAPC model architecture can be altered by including different numbers of PCs, and that better-performing models were chosen in this study based on performance. Once used clinically, the model architecture will remain static. In this study, the inventors showed that by tuning the number of PCs used to build the model, higher sensitivity or specificity of the Rametrix™ screening test could be achieved. High sensitivity would ensure more true-positive BCA cases are identified and recommended for further Gold Standard (i.e., definitive diagnostic) testing. Likewise, maximizing PPV may be useful in that those who screen positive have a higher likelihood of also testing positive by the Gold Standard. Given the invasive nature and resources required for Gold Standard testing for BCA, high PPV is a desirable attribute for the screening test. This also favors maximizing specificity (i.e., the true-negative rate) to minimize the false-positive rate. Those falsely identified by the screen as BCA-positive would, of necessity, undergo Gold Standard testing (which would occur if the Rametrix™ screen did not exist) and be re-classified as BCA-negative with the results of those tests and exams. Extended clinical testing and thorough analysis of the costs/benefits will enable proper tuning of Rametrix™ models and metrics to better align with clinical goals. Of course, the option exists to build multiple Rametrix™ models with each tuned to favor different metrics. Further Gold Standard testing could be designed in response to which, or how many, of the Rametrix™ models return a BCA-positive result. In addition, further developments could include "At Risk" predictions in addition to "BCA-positive" and "BCA-negative." This new "At Risk" classification would arise from the region(s) of overlap in DAPC plots of the training datasets. These are apparent in FIGS. 23B-D, 25A-D, and 27.

In addition to these observations, the inventors have noted the predictive power of DAPC models is influenced by the size of the spectral dataset used to build the model. Including more spectra generally improves predictive performance, but the number of positive and negative samples should be kept relatively balanced. Care should also be taken to ensure that even the negative samples are representative of the setting in which the predictions will be performed. Using negative samples that include many potentially obfuscating factors (e.g., hematuria and pyuria associated with infectious cystitis) will reduce estimated sensitivity, but more accurately portrays the true predictive power under worst case scenarios. If, however, Rametrix™ is used in combination with other techniques or known patient history, the range of applicable negative training data could be reduced, resulting in improved screen metrics.

In this study, for example, the Healthy Volunteers dataset was largely composed of healthy college student volunteers (median age=22); whereas, the Urology Clinic Patients dataset had a much higher median age (62 years) and included a significant portion of individuals with other GU conditions. If one were to design a screening strategy for cancer recurrence, the youthful healthy individuals may not be a representative source of training data. A recurrence screen scenario was tested in this study with the BCA-positive spectra compared to patients with BCA in remission, but predictions did not exceed random chance, largely due to the low sample size of patients with remission.

With large enough datasets, Rametrix™ showed the technology was capable of distinguishing between different kinds of diseases in this study. Not only can it distinguish BCA and ESKD, but it revealed the capability to distinguish among different GU conditions, including prostatic and renal disease. However, these distinctions had lower predictive power, owing largely, again, to the limited population size and wide variety of conditions aggregated in the category. This was also true of establishing separate screens based on sex in this study, where the low population size was the limiting factor. In a clinical setting, however, these factors will be important and should be incorporated into a single urine screen or require the use of separate screens and also repetitive/replicate sampling, based on specific patient identifiers. It will be imperative in extended clinical trials to expand upon these observations and consider the population size and composition carefully to include conditions that may influence urine composition.

With sufficiently-sized spectral datasets, Rametrix™ provides an attractive method for BCA screening. More definitive diagnosis always relies on urine cytology and cystoscopy, but Rametrix™ boasts several advantages as a screening method. Urinalysis by Rametrix™ is significantly less invasive than cystoscopy, does not require a trained pathologist, requires relatively inexpensive equipment and supplies, and results can be obtained remotely by technicians. Rametrix™ can also be used for early and routine screening of individuals at high risk for developing BCA such as heavy smokers or plastics factory workers and can be used for screening treated BCA patients for signs of recurrence.

Raman Spectroscopic Detection and Quantification of Macro- and Microhematuria in Human Urine Section VI The presence of blood in urine samples ("hematuria") is abnormal. Blood, even in small amounts, may be indicative of disease, ranging from urinary tract infection to cancer. Here, Raman spectroscopy was used to detect and quantify macro- and microhematuria in human urine samples. (See Carswell, W, Guruli, G, Tracy, A, Xu, Y, Du, P, Senger, R, Robertson, J, "Raman Spectroscopy as a non-cytological detection and quantification urinalysis method for microhematuria in human urine" (submitted, Dec. 31, 2020, Applied Spectroscopy ("Carswell, W, et. al. (2020)")). Anticoagulated whole blood was mixed with freshly-collected urine to achieve concentrations of 0%, 0.25%, 0.5%, 1%, 2%, 5%, 10%, and 20% blood/urine (v/v). Raman spectra were obtained at 785 nm and data analyzed using the Raman Chemometric Urinalysis (Rametrix™) LITE/PRO toolboxes for MATLAB and other statistical techniques. Goldindec and ISREA baselining methods were used for initial spectral normalization and nodal assignments. Rametrix™ was used to process spectra, develop Principal Component Analysis (PCA) and Discriminate Analysis of Principal Component (DAPC) models, and to validate these models using Leave-One-Out Cross-Validation (LOOCV). DAPC models were able to detect various levels of microhematuria in unknown urine samples, with prediction accuracies of 91% (using Goldindec spectral baselining) and 94% (using ISREA baselining). Partial Least-Squares Regression (PLSR) was then used to estimate/quantify the amount of blood (v/v) in a urine specimen, based on the Raman spectrum of various samples. Comparing actual and predicted (from Raman spectral computations) hematuria levels, a coefficient of determination (R2) of 0.91 was obtained over all hematuria levels, and an R2 of 0.92 was obtained for microhematuria (0-1% v/v) specifically. Overall, the results of this preliminary study demonstrated that Raman spectroscopy and chemometric analyses can be used to detect and quantify macro- and microhematuria in unprocessed, clinically-relevant urine specimens.

The presence of blood in urine is abnormal and is frequently associated with disease in the genitourinary tract (kidneys, bladder, male/female reproductive organs). The presence of blood in urine ("hematuria") may be suspected by obvious red-brown discoloration of urine (macrohematuria). Small amounts of blood (microhematuria) may not discolor urine or be detected visually, but discovered with urinalysis in patients displaying clinical signs of genitourinary disease. Detection or suspicion of hematuria is invariably confirmed with other medical tests, including urine sediment examination, biochemical (dry chemistry-"dipstick") assays, and multimodality imaging (Kavuru, 2020).

Hematuria can be caused by a large variety of diseases (ranging, for example, from bladder infections and acute renal disease, to cancer), injuries, or even exposure to toxicants (such as the chemotherapeutic agent cyclophosphamide). Testing for macrohematuria and early intervention has been shown to be cost effective, but early, aggressive testing for microhematuria has not been shown to produce an increased health benefit (i.e., early detection of disease) compared to the cost of screening "at-risk" populations. Laboratory costs and technician time associated with testing for hematuria make generalized population screening logistically and economically impractical. Here, the inventors present a low cost, low impact screening method for detecting both macro- and microhematuria, that relies evaluation of urine using Raman spectroscopy and Rametrix™ Chemometric Urinalysis of spectra.

Raman spectroscopy is a well-documented spectrographic method of examining the molecular composition of both solids and solutions. When examining even complex aqueous solutions (such as urine), Raman spectroscopy may take as little as 5 seconds to generate spectral data, and there is minimal spectral interference from water. Analysis of aqueous solution spectra involves data transformation in the form of baseline correction, truncation, normalization, and statistical processing. These transformations help to eliminate various spectral artifacts such as autofluorescence, photobleaching, cosmic spikes, and background signals. Two baselining methods used in this study were the Goldindec (Liu J., et al. (2015) Goldindec: A novel algorithm for Raman spectrum baseline correction. *Appl Spectrosc* 69 (7): 834-42 ("Liu, 2015)) and ISREA methods (Xu Y (2020) Statistical methods for in-session hemodialysis monitoring. *Personal communication* ("Xu, 2020a"); Xu Y (2020) et al. ISREA: An efficient peak-preserving baseline correction algorithm for Raman spectra. *Appl Spectrosc*doi: 10.1177/0003702820955245 ("Xu, 2020b")). The Goldindec algorithm provides an adaptable means to subtract background signals and baseline Raman spectra. The recently-developed ISREA method has been optimized for full baseline fitting, even at the ends of spectra (Xu, 2020b). The ISREA method uses cubic splines to create and distribute customized wavenumber range nodes, placed throughout a spectrum, as a means to optimize data analysis for presumed target molecules. This type of spectral filtering may provide modeling advantages and avoid the negative impact of trends in other, unrelated spectral data.

Principal Component Analysis (PCA) and Discriminant Analysis of Principal Components (DAPC) are multivariate statistical analysis methods for complex data sets. As noted above, these methods, used in conjunction with the Rametrix™ platform (MATLAB Toolbox), are useful in assessing the qualitative similarity and difference between spectra. In particular, PCA is a method that serves to reduce data-rich spectra from hundreds of intensity values into a small number (e.g., 5-30) of Principal Components (PCs). DAPC, on the other hand, uses PCs in a structured algorithm that can then be mapped other data, such as medical observations (e.g., levels of hematuria). This procedure is subject to validation, and leave-one-out cross-validation (LOOCV) has been used in several studies. With these results, metrics such as overall accuracy, sensitivity, specificity, positive predictive value (PPV), and negative predictive value are calculated. From there, PCA and DAPC loadings represent Raman shifts that distinguish groups of spectra from one another. These are traced to individual molecules (using Raman shift databases) that are involved in the disease pathology (e.g., heme associated with hematuria).

In addition to these chemometric methods, more direct comparisons of spectra have been used to determine if statistically significant differences exist. One approach is to calculate the Total Principal Component Distance (TPD) between two Raman spectra. Here, the total distance across all PCs of a sample and an analytical standard spectrum is calculated. Once TPD values are determined, statistical tests, including ANOVA and pairwise comparisons, are applied to these values to determine if/where statistically significant differences exist between groups of spectra. In the context of analyzing urine specimens, this approach has been used to determine if Raman spectra of urine from healthy volunteers are statistically different from those of patients with chronic kidney disease.

Evaluating hematuria quantitatively is an important goal of urinalysis, as the amount of blood in urine can be an important diagnostic metric when determining cause, severity, and etiology of the hematuria. It is believed that generating a calibration curve is critical when using Raman spectroscopy to define quantitative values, but in cases where the molecular signature of the molecule or solution is complex, creating meaningful calibration curves and standards can be complex, misleading, or ineffective. To address this complexity, Partial Least-Squares Regression (PLSR) can be useful in evaluating complex data sets and correlating those data sets to quantitative classifications (Chung SH and Park KS (2004) A study on the factor number determination methods in the partial least squares model for the urinalysis using Raman spectroscopy. *Conf Proc IEEE Eng Med Biol Soc* 2006:490-493 ("Chung, 2004"). This approach was used here, in place of a calibration curve, and used to generate a model which can predict the amount of blood in a urine sample given its Raman spectrum.

For this study, it was hypothesized that both macro- and microhematuria could be detected and quantified from Raman spectral analysis of human urine and chemometric analyses. Specifically, the inventors sought to determine: (i) are Raman spectra of urine with 'spiked' with whole blood (i.e., a model of hematuria) statistically different from those without the addition of blood (i.e., no hematuria) (ii) can the presence of large amounts of 'spiked' blood (i.e., a model of macrohematuria) be distinguished from small amounts of 'spiked' blood (i.e., a model of microhematuria) and (iii) can the quantity of 'spiked' blood (i.e., the degree of hematuria) be quantified?

Raman Spectroscopy. Raman spectroscopy data was acquired using a PeakSeeker™ dispersive Raman spectrometer (Agiltron; Woburn, MA). Urine specimens were analyzed as bulk liquid stored in 1.5 mL glass vials (ThermoFisher Scientific). Raman scans were acquired at 785 nm, 100 mW laser intensity, 15 second exposure time, and with a 15 second delay between scans. Ten replicate scans were obtained for each sample. The urinalysis standard Surine™ (Dyna-Tek Industries, Lenexa, KS) was also scanned and used in data analysis.

Specimens and creation of the "hematuria" dataset. Informed written consent for the collection of specimens was obtained from healthy volunteers affiliated with Virginia Tech, under an IRB-approved protocol (VT-IRB 15-703). The hematuria dataset was composed of urine specimens generated to simulate macro- and microhematuria of varying levels of severity. In particular, urine and blood were collected the same day from an informed, healthy volunteer. "Macrohematuria" samples were generated by mixing a 20% v/v solution (4 mL urine with 1 mL of blood), then a second and third sample in 50% dilutions, producing 10%, and 5% volume of blood samples. "Microhematuria" samples were generated by initially mixing a 2% v/v solution (49 mL of urine with 1 mL of blood). Then, 1%, 0.5%, and 0.25% mixtures were obtained through 50% dilutions of the initial mixture with addition of pure urine. All samples were analyzed by Raman spectroscopy, as described above. The resulting hematuria dataset contained urine samples with: no blood (0% v/v), microhematuria (0.25%, 0.5%, and 1%), and macrohematuria (2%, 6%, 10%, 20%). Ten replicates were prepared for each sample.

Raman spectra processing and baselining. All spectral processing and statistical methods were performed in MATLAB R2018a and made use of the Rametrix™ LITE (Fisher, 2018) and PRO (Senger, 2020a) Toolboxes (available through GitHub with license agreement). Acquired Raman spectra were first averaged (among replicates) and truncated between Raman shifts of 600-1,800 $cm^{-1}$. Next, the scans were baselined and vector normalized. The recently-developed ISREA method (Xu, 2020a, b) was used for baselining, as was the established Goldindec algorithm (Liu, 2015). These different baselining algorithms were applied separately to the same data set to assess the impact each would have on the statistical analysis. The Goldindec algorithm was used with the following options: polynomial order of 3, estimated peak ratio of 0.5, and smoothing window size of 5. ISREA involves the placement of baselining "nodes," or Raman shifts that anchor the cubic spline baseline along the spectral data. Multiple sets of nodes were tested to observe the effect changing baselining strategies had on data output from the analysis and modeling. The first node set (called the "ISREA Node Set 1") was developed based on the objective of selecting spectral regions with low signal and variability throughout the dataset. The ISREA Node Set 2 was constructed to subtract the Raman signal of Surine™, the urinalysis control. The ISREA Node Set 3 was a control strategy that included 13 evenly spaced nodes from Raman shifts 600 to 1,800 $cm^{-1}$. Statistical analysis was performed given spectral baselining with each set of ISREA nodes, as well as with the Goldindec algorithm.

Analysis of Variance (ANOVA) and Pairwise Comparison Tests. Statistical comparisons among spectra were performed by first calculating the Total Principal Component Distance (TPD), as previously described. With these data, ANOVA and pairwise comparisons were performed, using Tukey's Honestly Significant Difference (HSD) method. ANOVA was used to determine if the differences in Raman spectra between those specimens with added blood and those without were statistically significant. Further, the pairwise comparisons were used to establish if the data provided significant differences between different amounts of blood. The primary determination between the samples was to differentiate between macrohematuria, microhematuria, and no blood (i.e., normal urine). Then, differences among the amounts of blood in the microhematuria samples were determined by pairwise tests between each combination of comparisons (0% vs. 0.25%, 0% vs. 0.5%, 0.25% vs. 1%, etc.) to show the significance or lack thereof. Statistical significance was defined as $p<0.05$ in all cases.

Principal Component Analysis (PCA) and Discriminate Analysis of Principal Component (DAPC) Models. PCA was performed to reduce the complex data of the spectra, identify outlier spectra, and identify the Raman shifts with strong contributions (i.e., dominant molecules/bond energies). The selected PCs were then used in DAPC, and several models were built for each dataset, where the number of PCs included was varied. Specifically, DAPC models accommodating between two and 35 PCs were constructed for each dataset. These PCs represented between approximately 65% to 99.95% of the dataset variance, respectively. All models were then validated by LOOCV as described below.

Partial Least-Squares Regression (PLSR). PLSR provides a measure of correlation between complex data inputs and a quantitative output. PCs of processed spectra served as inputs and the sample percent blood (% v/v) served as the output. Calculations were performed in MATLAB, and the output included the PLS response (training data), the PLS prediction (testing data), the percent variance explained, and the estimated mean-squared prediction error for the dataset. Like DAPC models, the PLSR procedure was also subjected to LOOCV (discussed below) to assess predictive capabilities given spectra not used to build the model. Goodness-of-fit results for training and testing data were returned as coefficient of determination (R2) values.

Leave-One-Out Cross-Validation (LOOCV). LOOCV was performed for PCA/DAPC models with the Rametrix™ PRO Toolbox and with custom scripts for PLSR. DAPC models built with different numbers of PCs were assessed individually. Predictions were tabulated at the end of the routine to calculate metrics of overall prediction accuracy, sensitivity, specificity, PPV, and NPV. The LOOCV was also applied to PLSR predictions. One sample was systematically left-out of the PLSR model building and was used as the testing dataset. The procedure was performed over the entire dataset, and the coefficient of determination (R2) was calculated between all PLSR-predicted and actual percent blood values for each sample.

Figures 28A, 28B:
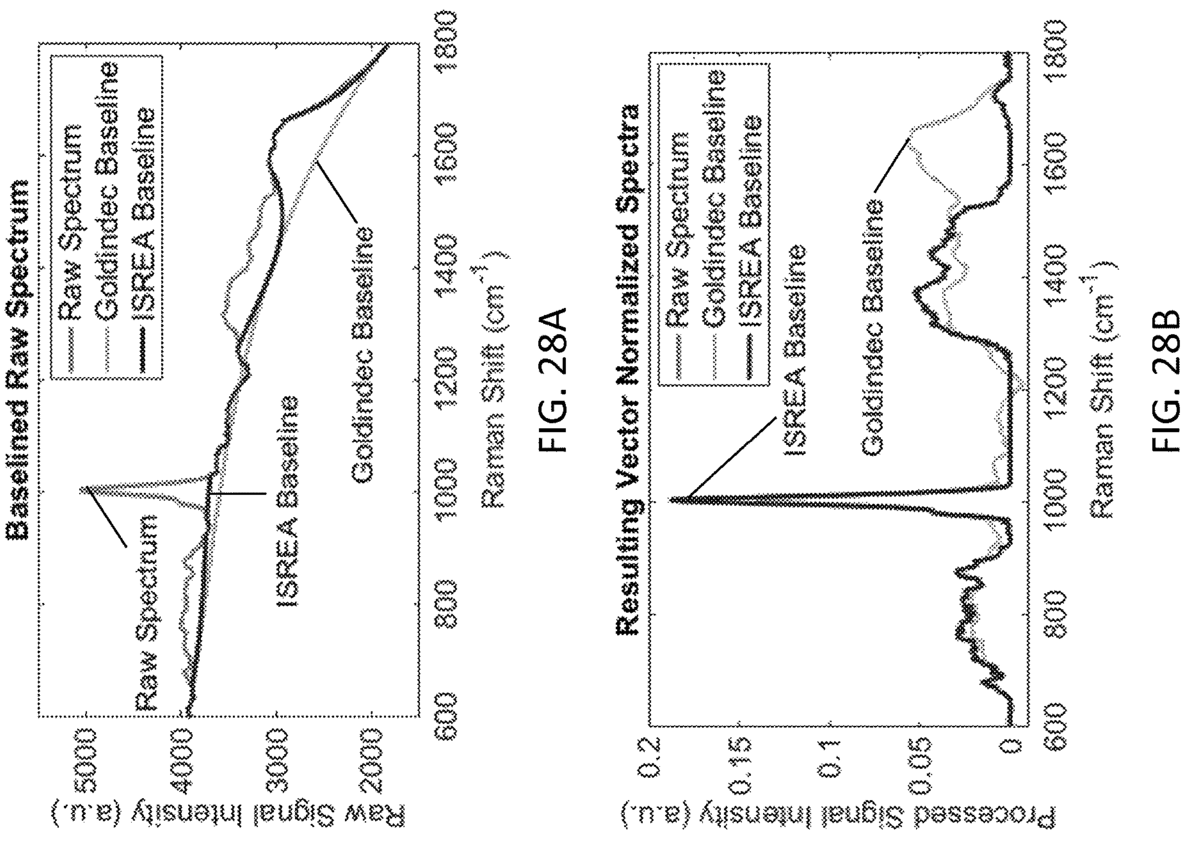
FIGS. 28A-D are graphs showing a Raman spectrum of urine with hematuria. A) The raw spectrum with Goldindec and ISREA (Node Set 3) baselining; B) Resulting vector normalized transformed spectra; C) transformed spectra to emphasize the 669 $cm^{-1}$ region; and D) transformed spectra to emphasize the Raman shift region containing 1,543 and 1,579 $cm^{-1}$.
Figures 28C, 28D:
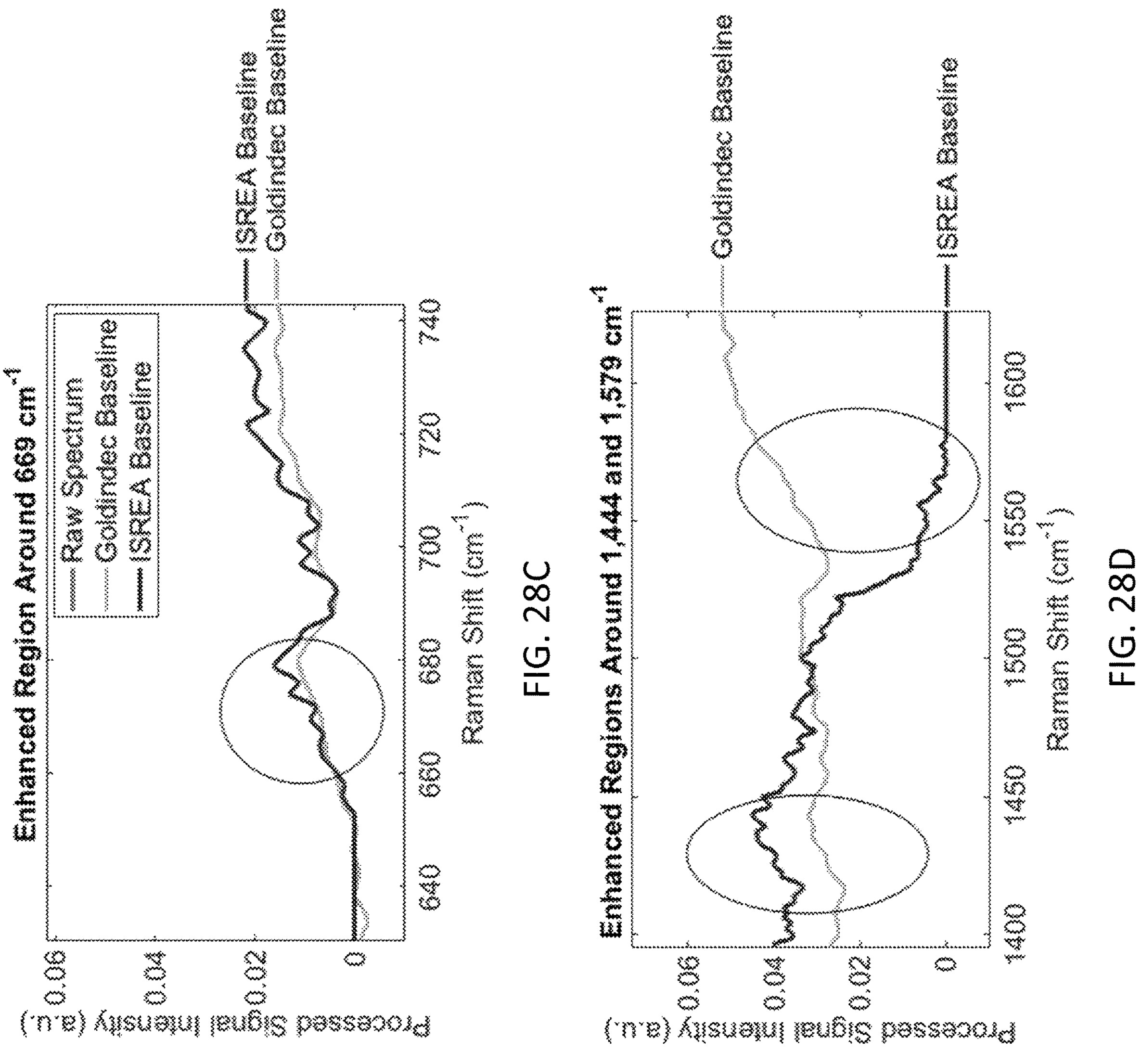
Figures 29A, 29B, 29C, 29D:
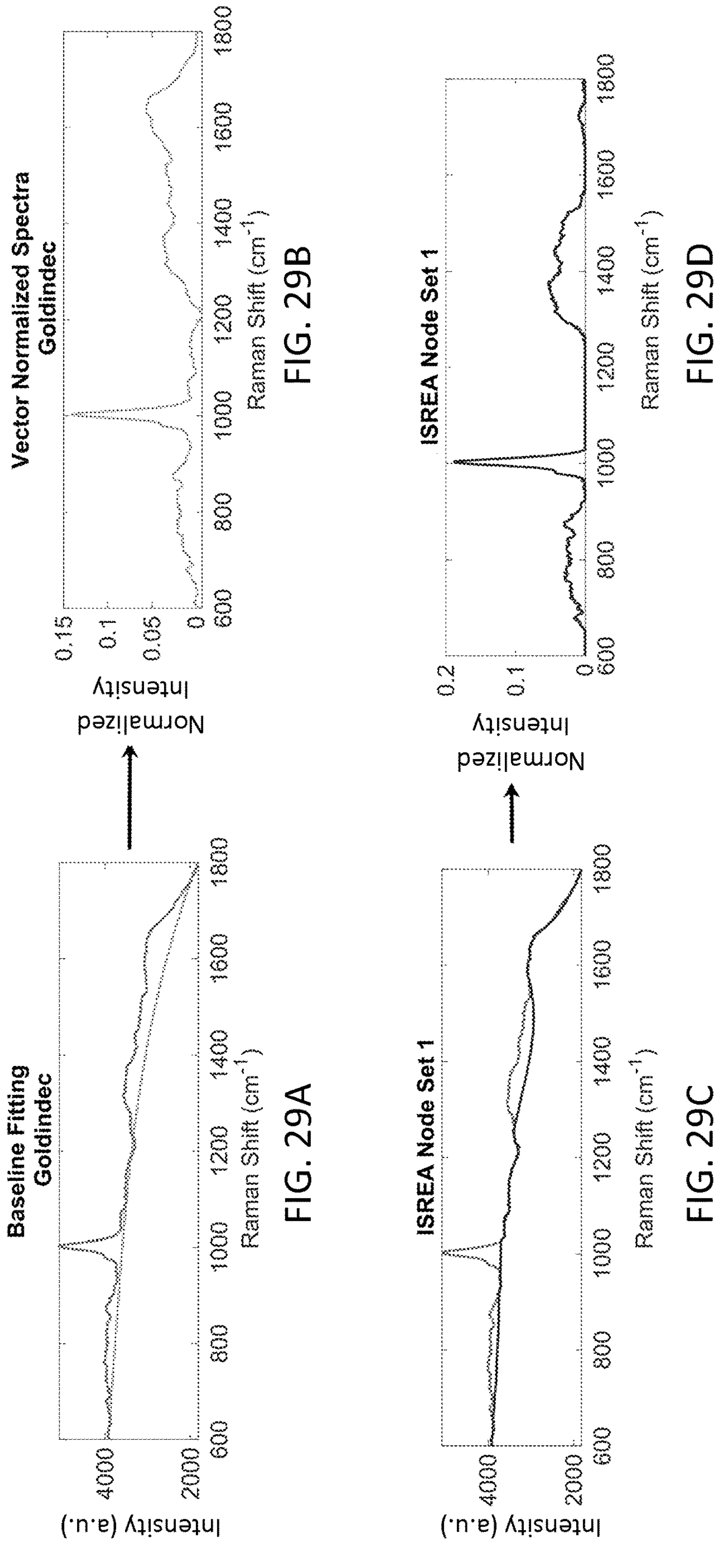
FIGS. 29A-H are graphs showing baseline fitting to a representative spectrum using the Goldindec algorithm (A, B), ISREA Node Set 1 (C, D), ISREA Node Set 2 (E, F), ISREA Node Set 3 (G, H). The graphs show the representative spectrum with baselines (A, C, E, G) and resulting vector normalized spectra (B, D, F, H).
Figures 29E, 29F, 29G, 29H:
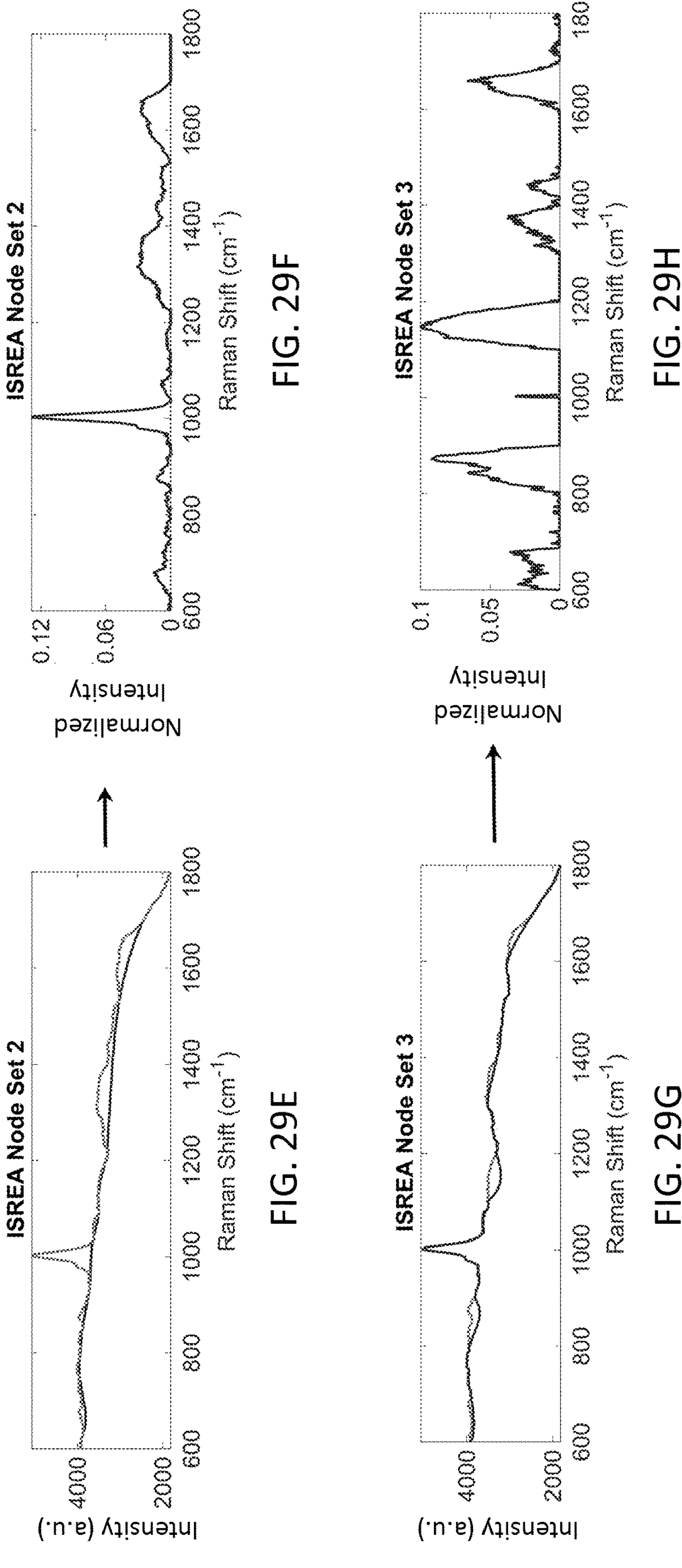

Raman Spectra and Baselining Methods. Raw Raman spectra were processed by averaging (among replicates), Raman shift truncation (600-1,800 $cm^{-1}$), baselining, and vector normalization. The Goldindec and ISREA baselining algorithms were applied to all spectra, and three ISREA node sets were used (see Materials and Methods for descriptions). A representative (chosen randomly) averaged and truncated spectrum is shown in FIGS. 28A-D. Baseline fitting with the Goldindec algorithm and ISREA method with Node Set 1 is shown in FIG. 28A. The resulting vector normalized (i.e., transformed) spectra are shown in FIG. 28B. The Goldindec algorithm leveled the spectrum endpoints as well as the lowest mid points. The ISREA algorithm with Node Set 1 resulted in significantly different normalized signal intensities (compared to Goldindec) in the Raman shift regions of 1,050-1,250 $cm^{-1}$ and 1,590-1,750 $cm^{-1}$ Raman shifts (FIG. 28B). The 1,050-1,250 $cm^{-1}$ region is dominated by Raman shift assignments to lipids, carbohydrates, phosphate stretching, and some C—N stretching of amides and proteins (among others). The 1,590-1,750 $cm^{-1}$ region is dominated by protein assignments, namely to aromatic amino acids. However, as shown later, removing these regions provided an advantage to resolving hematuria concentrations. In addition, heme and red blood cell bands have been identified in the literature at Raman shifts at 669; 750; 752; 999; 1,122; 1,210; 1,444; 1,543; 1,579; and 1,617 $cm^{-1}$. The ability of ISREA to resolve specific bands in the region of 669 $cm^{-1}$ is shown in FIG. 28C and for the region of 1,543 and 1,579 $cm^{-1}$ in FIG. 28D. Also noted, the ISREA method removed the spectral regions containing 1,210 and 1,617 $cm^{-1}$, which have been attributed to the human red blood cell. Two other Node Sets were tried with the ISREA method. The baselining results are shown in FIGS. 29A-H.

The inventors first applied the Goldindec algorithm to all analyses due to prior success with this algorithm and the popularity of polynomial-based baselining algorithms (Senger RS and Scherr D (2020), "Resolving complex phenotypes with Raman spectroscopy and chemometrics." Current Opinion in Biotechnology. 66:277-282 ("Senger and Scherr, 2020"). This was done in the section, "Analysis of All Hematuria Samples," which included the no blood (0% v/v), microhematuria (0.25-1%), and macrohematuria (2-20%) samples for the initial analysis of all hematuria samples. The ISREA method was implemented to further resolve the no blood and microhematuria samples in "Analysis of No Blood and Microhematuria.".

Analysis of All Hematuria Samples

Statistical Analyses. TPD data were generated (see Senger, 2019) from processed spectra baselined with the Goldindec algorithm. First, ANOVA was performed these TPD data given sample classifications of macrohematuria, microhematuria, and no blood. Statistical significance ($p<0.05$) was observed for differences among these classes of spectra. Next, statistical significance was also observed when the analysis was performed based on the volume of blood added to the urine samples (i.e., 0%, 0.25%, 0.5%, 1%, 2%, 6%, 10%, and 20% v/v).

From here, pairwise comparisons were performed. For comparison of microhematuria, macrohematuria, and no blood classifications, all pairwise comparisons returned statistical significance (Supplementary Appendix Table 21).

TABLE 21

Pairwise comparisons of TPD data based on percent blood volume classification.

| Pairwise Comparison | p |
|---|---|
| Microhematuria vs. Macrohematuria | 0.0239 |
| Microhematuria vs. No Blood | <0.001 |
| Macrohematuria vs. No Blood | <0.001 |

For the blood volume classifications, 16/28 (57%) of the comparisons showed statistical significance (Table 22).

TABLE 22

Pairwise comparisons of TPD data based on percent blood volume.

| Pairwise Comparison | p |
|---|---|
| 0% vs 0.25% | 0.680 |
| 0% vs 0.5% | 0.00190 |
| 0% vs 1% | 0.195 |
| 0% vs 2% | 0.908 |
| 0% vs 6% | <0.001 |
| 0% vs 10% | <0.001 |
| 0% vs 20% | <0.001 |
| 0.25% vs 0.5% | 0.386 |
| 0.25% vs 1% | 0.999 |
| 0.25% vs 2% | 0.226 |
| 0.25% vs 6% | 0.0208 |
| 0.25% vs 10% | <0.001 |
| 0.25% vs 20% | <0.001 |
| 0.5% vs 1% | 0.538 |
| 0.5% vs 2% | <0.001 |
| 0.5% vs 6% | 0.989 |
| 0.5% vs 10% | 0.201 |
| 0.5% vs 20% | <0.001 |
| 1% vs 2% | 0.0509 |
| 1% vs 6% | 0.0307 |
| 1% vs 10% | <0.001 |
| 1% vs 20% | <0.001 |
| 2% vs 6% | <0.001 |
| 2% vs 10% | <0.001 |
| 2% vs 20% | <0.001 |
| 10% vs 6% | 0.552 |
| 10% vs 20% | 0.122 |
| 20% vs 6% | <0.001 |

This number suggested that distinguishing among blood volume classifications (e.g., 0%, 0.25%, 1%, etc.) in further modeling may be limited. In addition, the number of statistically significant pairwise comparisons was likely limited by the sample size of this initial proof-of-concept study.

Figure 30B:
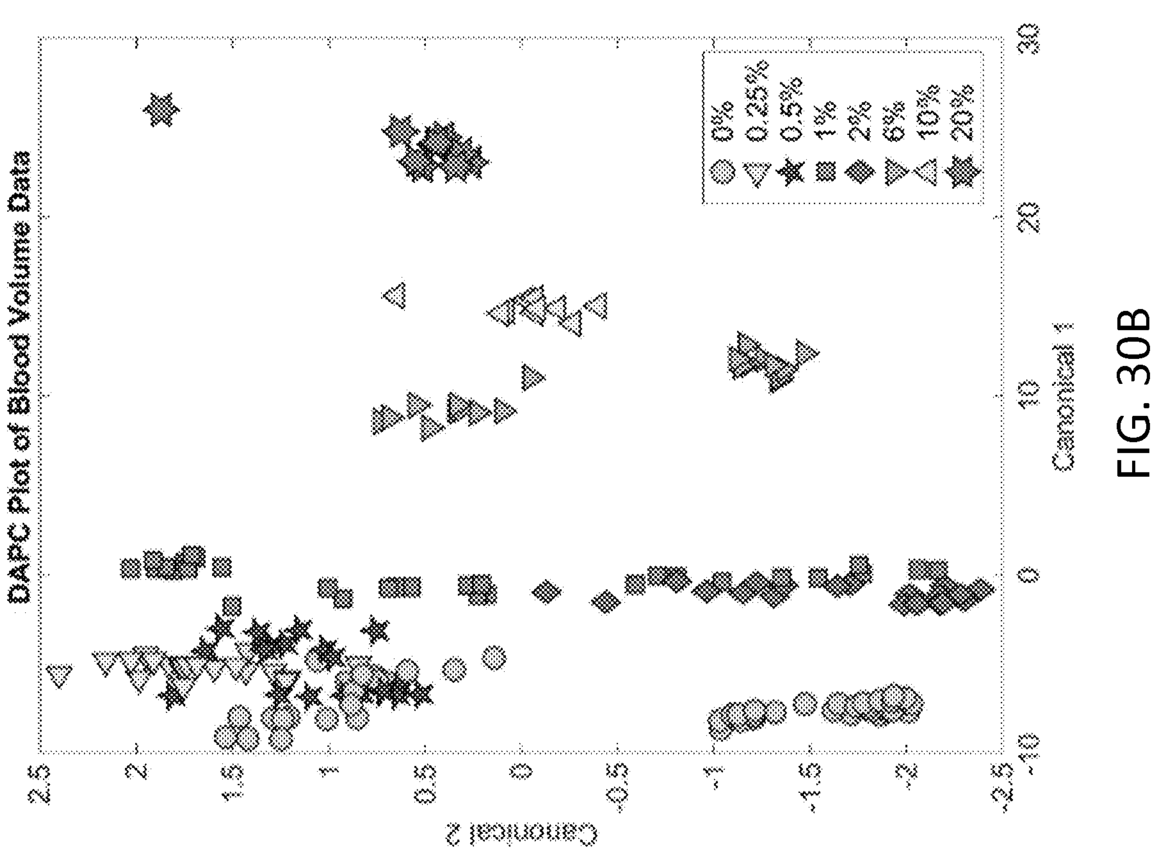
FIGS. 30A-B are graphs showing DAPC plots of hematuria classifications including: A) Macrohematuria, microhematuria, and no blood and B) percent blood (v/v) of each urine sample. DAPC was performed with 19 PCs, representing 99% of spectral dataset variance.
Figure 30A:
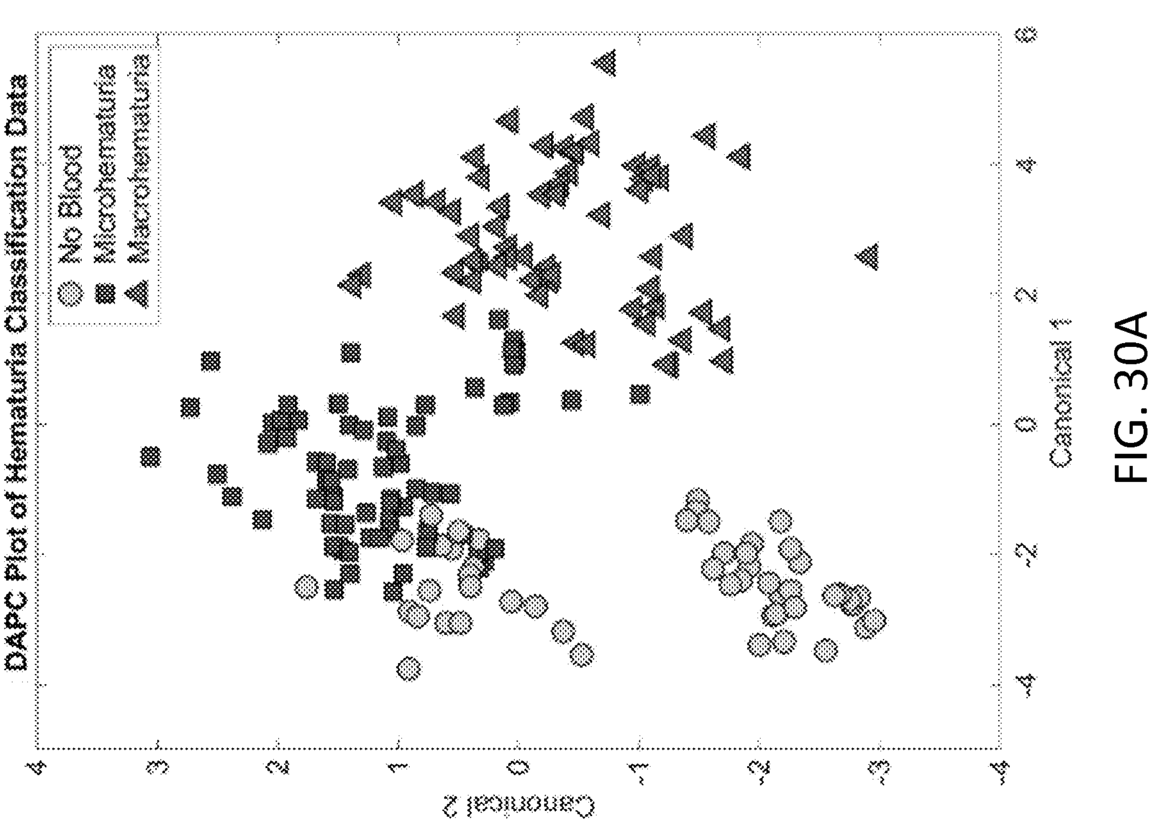

Classifications with PCA and DAPC. PCA and DAPC were performed with Rametrix™ LITE on the spectral data using both classifications mentioned above. The DAPC results for both classifications are given as cluster plots in FIGS. 30A-B. Here, DAPC results were produced using 19 PCs (representing 99% variance) of the spectral data. With 19 PCs, 19 canonical dimensions are created by the DAPC analysis. Only the first two are shown in FIGS. 30A-B to demonstrate clustering, where clusters are indicative of similar processed Raman spectra. Cluster separation with some overlap was achieved between macrohematuria, microhematuria, and no blood in FIG. 30A, with the microhematuria cluster appearing between those of macrohematuria and no blood along the first canonical. For the analysis by blood volume, in FIG. 30B, the samples clustered from left-to-right along canonical 1 according to increasing blood volume concentrations.

Next, Rametrix™ PRO was used to perform LOOCV on both DAPC models and determine prediction metrics for unknown urine samples. Results are shown in Table 23 for each classification. Prediction accuracy exceeded 90% for classifying an unknown urine sample as macrohematuria, microhematuria, or no blood (Table 23). However, some metrics (e.g., sensitivity for classifying a sample as no blood) failed to reach 90%.

TABLE 23

DAPC LOOCV results for hematuria status classification.

| Classification[1] | Accuracy | Sensitivity | Specificity | PPV | NPV |
|---|---|---|---|---|---|
| No Blood | 94% | 80% | 100% | 100% | 93% |
| Microhematuria | 91% | 97% | 86% | 82% | 98% |
| Macrohematuria | 96% | 93% | 97% | 93% | 97% |

[1]The results shown are for a DAPC model built with 19 PCs representing 99% of the spectral dataset variance.

Figures 31A, 31B:
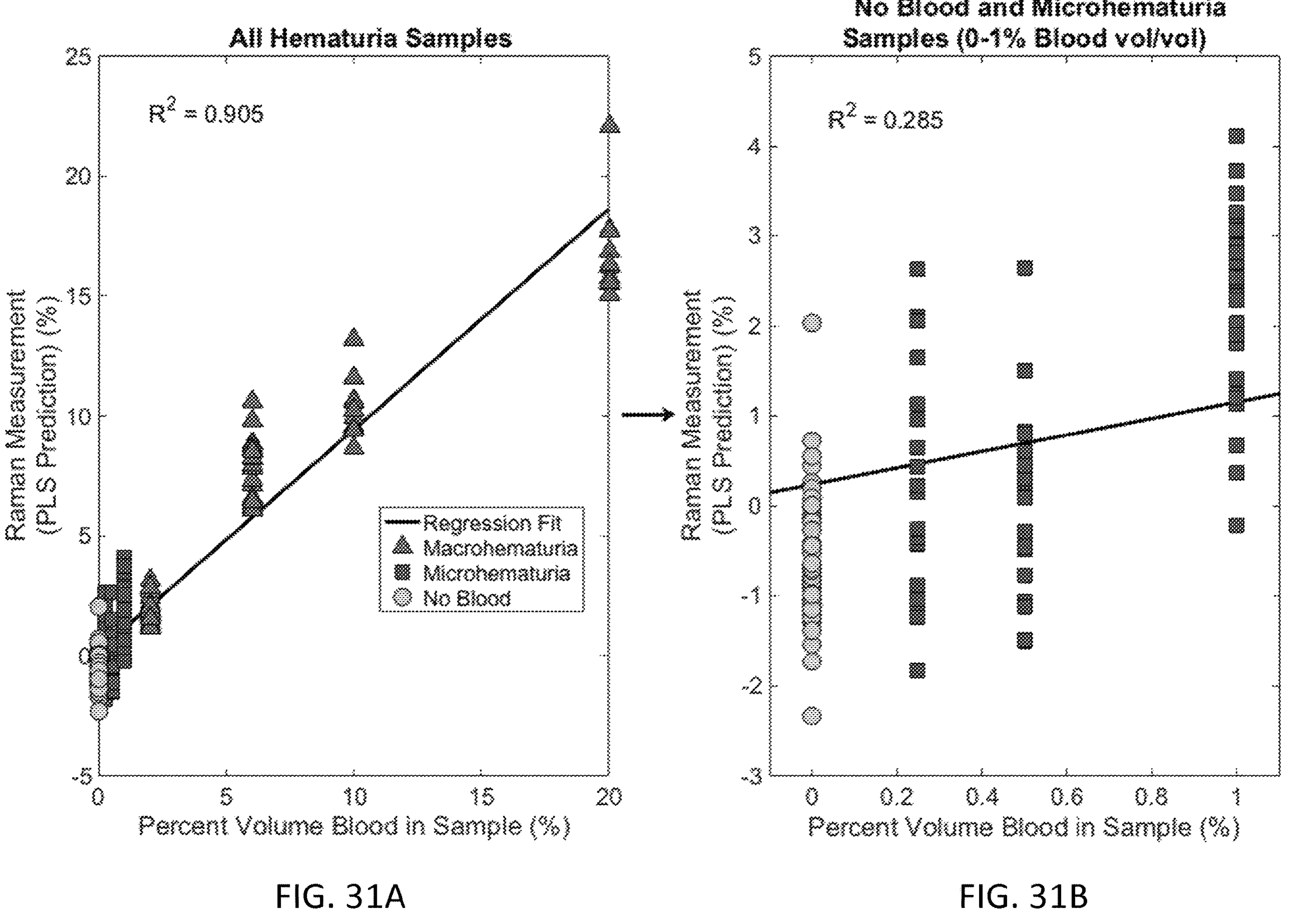
FIGS. 31A-B are graphs showing the Raman measurement PLSR LOOCV predictions vs. actual percent blood in urine samples (v/v) over A) all hematuria samples and B) for no blood and microhematuria (0-1% blood volume).
Figures 32A, 32B:
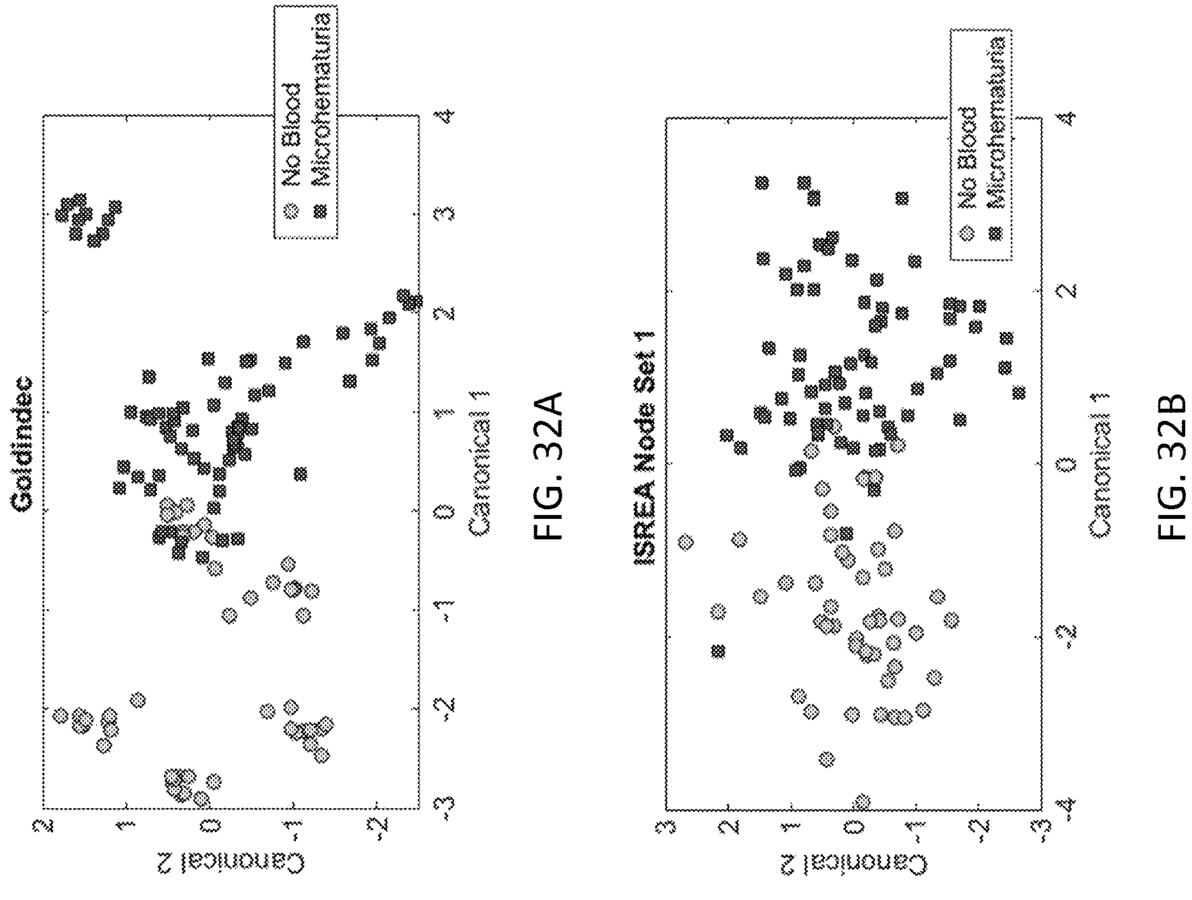
FIGS. 32A-D are graphs showing DAPC plots to distinguish between no blood and microhematuria given different spectral baselining: A) Goldindec algorithm, B) ISREA Node Set 1, C) ISREA Node Set 2, and D) ISREA Node Set 3.
Figures 32C, 32D:
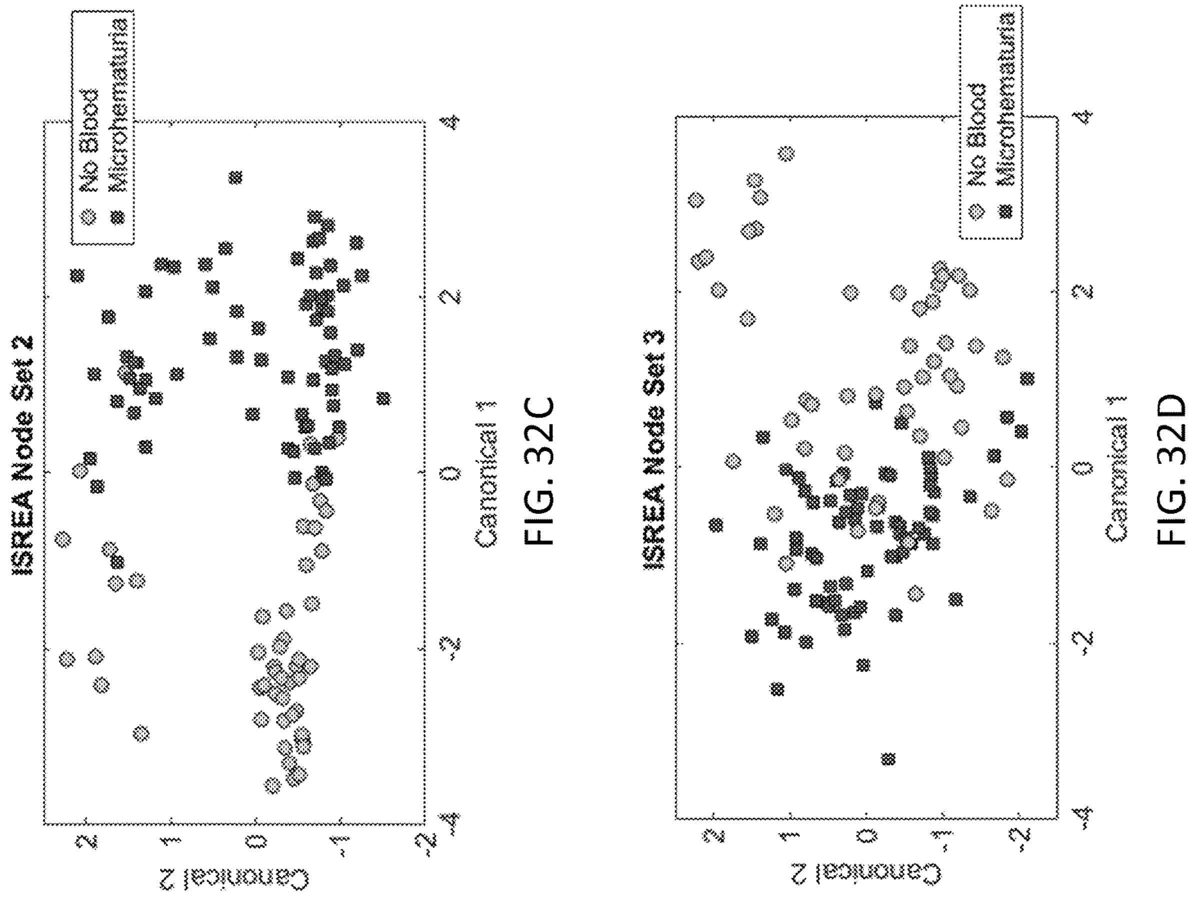

PLSR. To return a quantitative value of hematuria based on the Raman spectrum for a sample, PLSR with LOOCV was implemented. Results are shown in FIGS. 31A-B, with the line of regression fit showing the correlation between the Raman measurement predicted values (from PLSR and LOOCV) and the actual blood percent volume in urine samples. The coefficient of determination (R2) was greater than 0.9 when considering all samples (i.e., no blood, microhematuria, and macrohematuria), as shown in FIG. 31A. However, the correlation for no blood and microhematuria samples only (i.e., 0-1% blood v/v) was much less (R2=0.285), as shown in FIG. 31B. This R2 value suggests this PLSR model performs better for macrohematuria than for blood volumes below 1%. The microhematuria region is important for accurate measurements by Raman spectroscopy as blood may not be visible by visual inspection at these levels. Thus, additional data analysis techniques were explored for better quantifying Raman spectra of no blood and microhematuria samples.

Analysis of No Blood and Microhematuria Samples. To improve the determination of percent blood in urine, in the 0-1% v/v range, by Raman measurements, the inventors employed ISREA baselining with Node Sets 1-3 in addition to the Goldindec algorithm. The baseline fits and resulting vector normalized spectra for all baselining algorithms used are shown in FIGS. 28A-D and 29A-H. The overall goal of the following approach was to improve the correlation between Raman measurements and actual percent blood in urine specimens (R2=0.285). As apparent in FIGS. 28A-D and 29A-H, the choice of Node Set for ISREA can transform Raman spectra significantly. Regions of the spectra can be emphasized/minimized, and the inventors sought to determine whether this could be used to resolve the no blood and microhematuria region of the dataset.

Statistical Analyses. The ANOVA results for the comparison of no blood vs. microhematuria samples (i.e., with macrohematuria samples excluded) showed statistical significance (p<0.001) for each ISREA Node Set. Pairwise comparisons, however, differed given the different baselining methods, and results are given in Table 24.

TABLE 24

Pairwise comparisons of TPD data based on no blood and microhematuria classifications.

| Baselining Method | Pairwise Comparison | p |
|---|---|---|
| Goldindec | 0% vs 0.25% | 0.457 |
| | 0% vs 0.5% | <0.001 |
| | 0% vs 1% | 0.142 |
| | 0.25% vs 0.5% | 0.257 |
| | 0.25% vs 1% | 0.982 |
| | 0.5% vs 1% | 0.353 |
| ISREA Node Set 1 | 0% vs 0.25% | <0.001 |
| | 0% vs 0.5% | <0.001 |
| | 0% vs 1% | <0.001 |
| | 0.25% vs 0.5% | 0.9011 |
| | 0.25% vs 1% | <0.001 |
| | 0.5% vs 1% | <0.001 |
| ISREA Node Set 2 | 0% vs 0.25% | 0.0932 |
| | 0% vs 0.5% | 0.0122 |
| | 0% vs 1% | 0.978 |
| | 0.25% vs 0.5% | 0.999 |
| | 0.25% vs 1% | 0.263 |
| | 0.5% vs 1% | 0.317 |
| ISREA Node Set 3 | 0% vs 0.25% | 0.0685 |
| | 0% vs 0.5% | 0.0905 |
| | 0% vs 1% | 0.993 |
| | 0.25% vs 0.5% | 0.999 |
| | 0.25% vs 1% | 0.173 |
| | 0.5% vs 1% | 0.213 |

In summary, the Goldindec and ISREA Node Set 2 algorithms each returned 1/6 (<17%) pairwise comparisons with statistical significance (p<0.05). ISREA with Node Set 3 did not return any with statistical significance, and ISREA with Node Set 1 returned 5/6 (>83%) with statistical significance. This provided strong evidence that the choice of baselining method could influence the detection of microhematuria. The inventors have interpreted the results to suggest that ISREA Node Set 1 removes or reduces spectral data which otherwise conflates other data points. While all baseline methods led to statistical separation between no blood and microhematuria samples, only ISREA Node Set 1 showed the ability to differentiate between different blood volumes at the microhematuria level.

Classifications with PCA and DAPC. Again, PCA and DAPC models were built but only included the no blood and microhematuria samples. DAPC clustering results are shown in FIGS. 32A-D for the Goldindec and all ISREA baselining methods. Differences in cluster separations were apparent, especially with ISREA Node Set 3, which showed considerable overlap. Each DAPC model in FIGS. 32A-D was built with the number of PCs required to represent 99% of the dataset variance. Next, LOOCV was applied to determine prediction metrics for distinguishing whether an unknown urine sample belonged to the no blood or microhematuria classification. These results are shown in Table 25. Both the Goldindec algorithm and ISREA Node Set 1 exceeded 90% prediction accuracy and showed 100% sensitivity and NPV. The ISREA Node Set 1 showed improved specificity and PPV metrics. The ISREA Node Set 2 method showed 90% overall accuracy with 100% specificity, and ISREA Node Set 3 showed the least accurate predictions.

TABLE 25

DAPC LOOCV results identification of microhematuria.

| Baselining Method | PCs | Accuracy | Sensitivity | Specificity | PPV | NPV |
|---|---|---|---|---|---|---|
| Goldindec | 8 | 91% | 100% | 78% | 86% | 100% |
| ISREA Node Set 1 | 12 | 94% | 100% | 86% | 91% | 100% |
| ISREA Node Set 2 | 9 | 90% | 76% | 100% | 100% | 85% |
| ISREA Node Set 3 | 20 | 86% | 97% | 70% | 82% | 95% |

*The number of PCs included represented 99% of the dataset variance.

PLSR. The PLSR correlations (R2) between Raman measurements, no blood, and microhematuria percent blood concentrations are given in Table 26. These were generated from LOOCV of the PLSR model. Noted is that the Goldindec algorithm improved from an $R^2$ of 0.285 to 0.876 when including all hematuria samples (FIG. 31A) or only no blood and microhematuria (FIG. 31B, Table 26).

TABLE 26

PLSR LOOCV correlations (R2) for Raman measurements and microhematuria percent blood volumes (0-1%)

| Baselining Method | R2 |
|---|---|
| Goldindec | 0.876 |
| ISREA Node Set 1 | 0.920 |
| ISREA Node Set 2 | 0.691 |
| ISREA Node Set 3 | 0.547 |

Figure 33A:
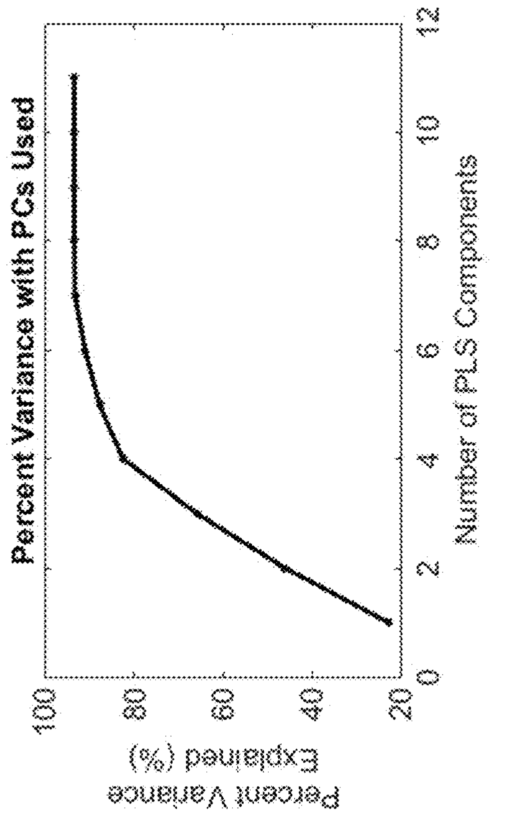
FIGS. 33A-D are graphs showing PLSR modeling results for no blood and microhematuria. A) Percent variance as a function of PCs used; B) Estimated mean squared prediction error (MSE) as a function of PCs used; C) PLSR model training; and (D) PLSR LOOCV model testing results.
Figure 33B:
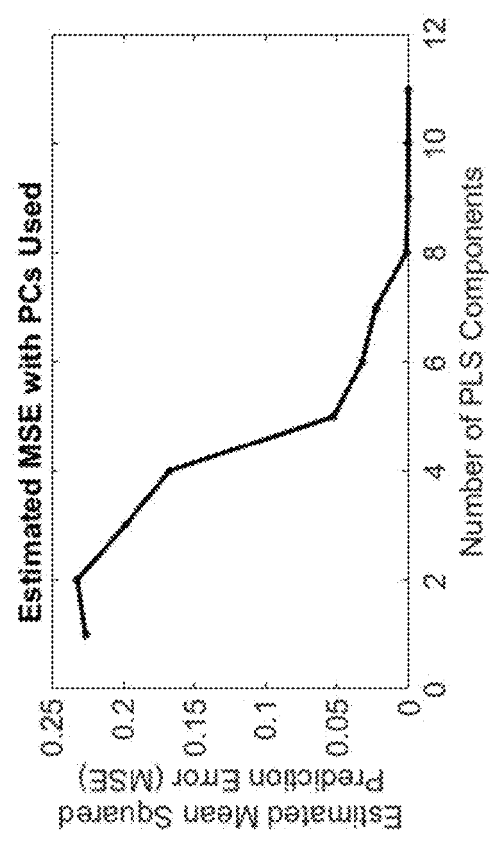
Figure 33C:
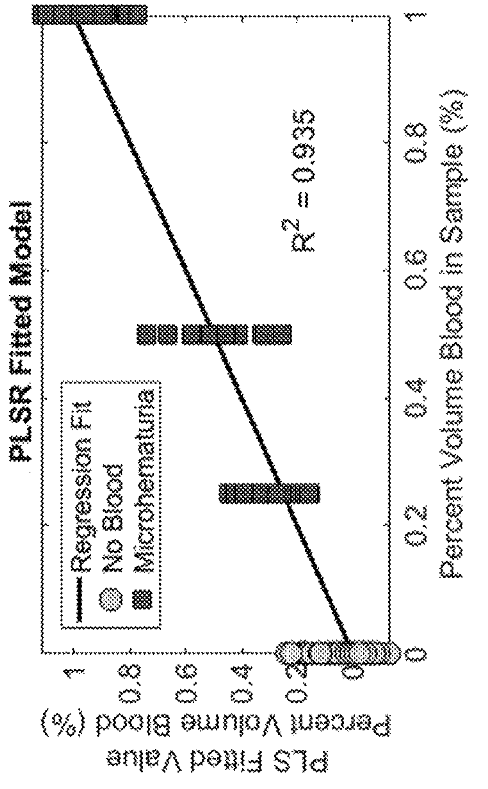
Figure 33D:
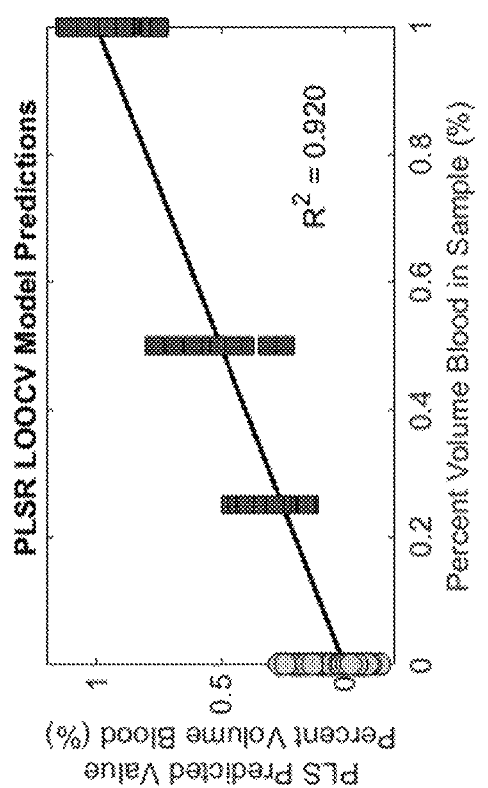

This demonstrates how an initial DAPC classification of hematuria (FIG. 30A) may be useful in determining which PLSR model to apply. The ISREA Node Set 1 outperformed the Goldindec algorithm slightly in Table 26. The specific PLSR results for ISREA Node Set 1 are shown in FIGS. 33A-D. The effect from number of PLS components used is shown in FIG. 33A. For the purposes of this analysis, 11 components were chosen. The PLSR model training is shown in FIG. 33C ($R^2$=0.935), and the PLSR model testing results with LOOCV is given in FIG. 33D ($R^2$=0.920). While the ISREA Node Set 1 generated the highest $R^2$ value among the baselining methods tested, it is clear that the choice of node set weighs heavily on the predictive capability of a PLSR model given Raman spectra inputs.

The use of Raman spectroscopy for detection and quantification of hematuria with high accuracy and low cost has important implications, including near-real time testing at points of patient care, low cost/test, and accuracy to guide clinical decisions.

This proof-of-concept study successfully demonstrated the capacity to detect and quantify macro- and microhematuria with Raman spectroscopy and chemometric analyses. The inventors focused here on the impact of the predictive capabilities of PCA with DAPC and PLSR. These statistical assessment methods used here form the key moving parts of the proposed computational data pipeline. PCA and DAPC, in short, help to reduce the complexity of the spectra and group the data points by similarities inherent in the spectra. The PCA and DAPC models thus can serve as predictive classifiers (e.g., no blood, microhematuria, macrohematuria). The PLSR analysis provides quantitative predictions within each class and improves quantitative results for low ends of a measurement spectrum, where the overall PLSR prediction accuracy ($R^2$) may not represent the strength of correlation for all sections of the data. The impact of baselining algorithm, on the predictive capabilities of a DAPC or PLSR model, was demonstrated. Choosing a reliable, application agnostic method of baselining, such as Goldindec, has its advantages, but choosing a method that has more customization options, such as ISREA, can improve the outcome.

The idea of customization introduces the question of what is happening between the two methodologies to produce the difference. One of the main differences is data removal, in the form of zeroing out data which falls below the baseline. This type of data transformation is similar to analyzing only sections of the spectra, but avoids making specific assumptions about which 'windows' of information to include or exclude. One benefit of using a customizable baselining method is the ability to perform semi-recursive learning processes on the modeling data in order to generate higher classification fidelity. That is to say, by using a customizable baseline, the inventors are able to determine the most efficient background signal to eliminate through baselining in order to distinguish between the classifications at hand. Similar attention could instead be given to quantitative output such as PLSR, maximizing the $R^2$ value achieved.

The inventors were able to distinguish between macro- and microhematuria with 96% overall accuracy, and found that determination of microhematuria was inaccurate for micro-levels of blood ($R^2$=0.28). By refining computational modeling to only microhematuria levels of blood (<1% v/v) and incorporating ISREA baselining, a high level of correlation ($R^2$=0.92) was achieved, leading to high predictive accuracy. Overall, this shows that Raman spectroscopy, baselining, PCA, DAPC, ANOVA, pairwise comparisons, PLSR, and LOOCV can be utilized to perform screening or rapid testing for the presence of blood in urine, as well as identify the level of blood with high accuracy. This rapid screening technology could be automated, improving the availability of early detection and monitoring urine specimens for hematuria.

Section VII

Disease-Associated Multimolecular Signature in the Urine of Patients with Lyme Disease, Detected Using Raman Spectroscopy and Chemometrics (Rametrix™)

A urine-based screening technique for Lyme disease was developed in this research. Senger, R, Sayed Issa, A, Agnor, B, Talty, J, Hollis, A, Robertson, J L, "Disease-associated multimolecular signature in the urine of patients with Lyme disease, detected using Raman spectroscopy and chemometrics (Rametrix™)" (submitted, 12 14 2020, Applied Spectroscopy ("Senger, R, Sayed Issa, A, et. al. (2020)")). The screen is based on Raman spectroscopy and chemometric analysis (Rametrix™). Raman spectra of urine from 30 patients with positive serologic tests (including the CDC two-tier standard) were compared against the database of urine spectra from 235 healthy human volunteers, 362 end-stage kidney disease (ESKD) patients, and 17 patients with active or remissive bladder cancer (BCA). The inventors found statistical differences (p<0.001) between urine scans of healthy volunteers and LD-positive patients. The inventors also found a unique LD molecular signature in urine involving 33 Raman bands with significant differences from urine from healthy individuals. This signature also contained several minor Raman band contributors, and the inventors were able to distinguish the LD molecular signature as statistically different (p<0.001) from the molecular signatures of ESKD and BCA. When comparing LD-positive patients against healthy volunteers, the Rametrix™-based urine screen performed with 94.9% overall accuracy, 86.7% sensitivity, 96.2% specificity, 78.8% positive predictive value (PPV), and 97.8% negative predictive value (NPV). When considering patients with ESKD and BCA in the LD-negative group, these values were 83.7% (accuracy), 70.0% (sensitivity), 90.3% (specificity), 77.8% (PPV), and 86.2% (NPV), respectively. Additional advantages to the Rametrix™-based urine screen include it is rapid (minutes per analysis), is minimally invasive, requires no chemical labeling, uses a low-profile, off-the-shelf spectrometer, and is inexpensive relative to other available LD tests.

Lyme disease (LD) in North America is caused by infection with the spirochete, *Borrelia burgdorferi* sensu lato-a pathogen transmitted through bites from ixodid ticks. A second pathogen, *B. mayonii*, has also been associated with some LD cases in North America. Other species of *Borrelia* are associated with LD in Europe and Asia. Ixodid tick vectors, capable of transmitting *B burgdorferi* and several other diseases (TBRF-tick-borne relapsing fever [*B. miyamotoi* or *B. hermsii*], for example), are present worldwide. Wildlife hosts, such as deer and mice, play an important role in disease transmission. Domesticated animals (horses, cattle, dogs, cats) may show serologic reactivity to *B burgdorferi* antigens and may also develop clinical signs of acute and chronic LD, although most infections may be inapparent. The role of domesticated animals in supporting/fostering transmission of LD is unknown.

Some physicians, faced with deciding whether or not to treat a patient for LD solely on the basis of clinical signs, but without serologic confirmation, opt for treatment with antibiotics. Some patients believe they may be suffering from "chronic LD"-a clinical syndrome for which there is no precise definition, diagnostic test, or definitive immediate response to appropriate antibiotic therapy.

In 2017, the Centers for Disease Control and Prevention reported nearly 43,000 LD cases, based on laboratory confirmation or clinical diagnosis by physicians. Researchers estimate that the number of actual cases is significantly higher (>300,000 per year) when extrapolating from laboratory submissions and clinical reports. This estimate was based on more than 3.4 million tests for LD infection performed annually (on approximately 2.4 million specimens), with positive results from two-tiered serologic testing (see below), showing infection in approximately 10-18% of patients.

Laboratory confirmation of LD infection is commonly done with two-stage serology (enzyme immunoassay, followed by Western immunoblot assay) in which antibody titers against *B. burgdorferi* antigens are compared from acute and convalescent sera. This is widely considered the definitive procedure for LD diagnosis. The accuracy of the recommended serologic assays is dependent on timely elaboration of antibodies-specifically to the *B burgdorferi* pathogen. The development of antibodies, however, may take several weeks in patients with clinical signs, and reliance on serology alone may delay disease recognition or treatment. In some patients with a slow or minimal serologic response, those with persistence of antibodies from distant exposure/past infection, or potential cross-reactivity with other antigens/tick-borne diseases, the confirmation of LD infection through serology alone may be problematic.

Other tests for LD have been developed and used, but the relevance, accuracy and value of such tests has been questioned and considered unsupported by objective, robust, and correlative (clinical symptoms/laboratory data) studies. Correlations of chronic LD with decreased CD57 lymphocyte levels have been noted. Advances in serodiagnostic methods, combined with state-or-the-art molecular technologies, hold the promise of more accurate and timely LD diagnosis. However, no current test has been widely accepted as a suitable replacement for the recommended two-stage serologic assay on acute and convalescent sera.

Recently, Pegalajar-Jurado and co-workers (2018) (Pegalajar-Jurado A, Fitzgerald BL, Islam MN, Belisle JT, Wormser GP, Waller KS, Ashton LV, Webb KJ, Delorey MJ, Clark RJ, Molins CR (2018) "Identification of urine metabolites as biomarkers of early Lyme Disease," Nature Scientific Reports 8:12204| DOI: 10.1038/s41598-018-29713-y), building on both positive and negative results from previous urinalysis studies (Hyde F W, et al., "Detection of antigens in urine of mice and humans infected with *Borrelia burgdorferi*, etiologic agent of Lyme disease," J Clin Microbiol 27, 58-61 (1989); Rauter C, et al., "Critical evaluation of urine-based PCR assay for diagnosis of Lyme borreliosis," Clin Diagn Lab Immunol 12:910-917, doi: 10.1128/CDLI.12.8.910-917 PMCID: PMC1182183 (2005); Magni R, et al., "Application of Nanotrap technology for high sensitivity measurement of urinary outer surface protein A carboxyl terminus domain in early stage Lyme borreliosis," J Transl Med 13:346 Published online 2015 Nov. 4. doi: 10.1186/s12967-015-0701-z PMCID: PMC4634744 (2015) ("Magni, R (2015)"), described detection of urinary metabolites/biomarkers associated with early LD infection, in specimens of fourteen (14) early LD patients, using liquid chromatography-mass spectroscopy (LC-MS)-based methods. Comparing the urine metabolome of fourteen (14) patients with infectious mononucleosis and that of fourteen (14) healthy human volunteers, they found dysregulation of multiple metabolic pathways (including the tryptophan pathway) that they considered signatory (71-100% accurate, depending on the pathway and comparison population) for early LD. With additional studies and verification, these proof-of-concept studies suggest strongly that a urine-based test for LD is entirely possible.

It Is clear that there is a pressing need, given the increased incidence of LD, to evolve diagnostic tests that are rapid, inexpensive, relevant, and potentially non-invasive (most current methods require blood/serum). Such tests must be supported by objective evidence of high positive and negative predictive value, specifically for LD, while excluding myriad other causes of chronic LD.

Here, the inventors describe the results of analyzing urine specimens using Raman spectroscopy and chemometrics ("Rametrix™"), from patients testing positive for LD with a host of serologic tests. These patients are referred to as "LD-positive" throughout the description. LD-positive patient urine spectra (n=30) were compared with a subset of the urine spectra database containing 235 spectra of healthy human volunteers, 362 patients with end-stage kidney disease (ESKD), and 56 patients with active or remissive bladder cancer (BCA).

The inventors discovered that LD-positive patients have a distinctive multimolecular signature in urine that can be detected with Raman spectroscopy and Rametrix™. The inventors further explored the accuracy, including sensitivity, specificity, positive predictive value (PPV), and negative predictive value (NPV) of the Rametrix™-based urine screen for the presence of LD. This urine screen was then applied to the urine spectra of patients displaying LD symptoms who either had not taken a two-tiered serologic test or had a negative two-tier serologic test result, even though some of these patients had exhibited a low CD57 NK count (<60) (not considered by many to indicate LD).

Eighty-five (85) patients were seen by two primary care specialists (JT, AH) for evaluation of chronic fatigue/related issues, potentially indicative of infection with *B. burgdorferi* or exposure to environmental contaminants such as molds. The patient population consisted of 59 female and 26 male patients. The age range of female patients was 2-74 years and of male patients 17-74 years. As would be expected, the clinical presentation of patients was highly variable, as was the duration and severity of clinical symptoms. Many patients had pursued multiple avenues of diagnosis and variable courses and types of therapies (including antibiotics) prior to evaluation.

Of these patients, 30 tested positive for LD with serologic tests. Of this group, 14 tested positive with the CDC serologic test. No patients evaluated had erythema migrans at the time of presentation. A majority of patients were also evaluated with other types of testing for LD (not CDC serologic testing) or to screen for the presence of other disease entities, including LD tests from IGeneX, iGene, iSPOT, LabCorp, and/or Quest. As noted previously (see above), the value and acceptance of results of these tests is debatable.

Fifteen (15)-30 ml of voided, mid-stream urine was collected in sterile specimen containers and frozen (−35° C.) until retrieved for analysis, at which point specimens were warmed to 25° C. and analyzed (see below).

Controls: Healthy volunteers: A full analysis of the healthy human volunteer urine dataset is available above. (Senger, R, Kavuru, V, et. al. (2019)). Briefly, 235 urine specimens were collected from 48 (39 females, 9 males) healthy human volunteers with no history or evidence of renal disease. Volunteers were also free of infectious or degenerative disease at the time of sample collection. The age range of the healthy volunteer population was 18-70 years; 87.5% of volunteers were of ages 19-22 years, and the median age was 21 years. From this dataset, 185 urine spectra were selected randomly and a subset of 30 were used in this study for computations.

Controls: End-Stage kidney disease (ESKD) patients: A full analysis of the ESKD patient urine dataset is provided above. (Senger, R, Sullivan, M, et. al. (2020)). In total, 362 urine specimens were collected from 96 patients. Patients had advanced ESKD were undergoing treatment with ambulatory peritoneal dialysis (PD). Patients ranged in age from 24-90 years old. The mean age was 60 years, and the median age was 63.5 years. Multiple urine specimen collections (4-8 separate collections) were available from multiple patients, allowing repetitive measurements and correlations over a protracted course of PD therapy (18 months). From this dataset, 30 urine spectra were selected randomly and used.

Controls: Bladder cancer (BCA) patients. (See Huttanus, H, et. al. (2020)). In total, 56 urine specimens (one per patient) were collected. The patients ranged in age from 31-91 years old. The mean and median age of 62 years. Of this dataset, 17 specimens were from patients with active bladder cancer. The median age of this population was 70 years. In addition, 17 of these specimens were selected randomly, among the patients with active BCA at time of collection, and used.

Specimen collection and storage: Voided, mid-stream urine specimens were collected and transferred into sterile specimen cups and then immediately frozen to −15° C. and then stored at −35° C. until analyzed.

Analytical standards: Surine™ Urine Negative Control (Dyna-Tek Industries, Lenexa, KS) was used as a control standard for urinalysis.

Raman methodology and measurements: Briefly, an Agiltron PeakSeeker™ dispersive Raman spectrometer (Woburn, MA) was used. All specimens were Raman scanned as "bulk" liquid samples in 1.5 mL glass vials at 25° C. using 785 nm (100 mW) laser excitation for 15 s with spectral resolution of 8 $cm^{-1}$. A minimum of 10 scans were collected per specimen and averaged.

Computational methodology: Spectral processing and analyses were performed with the Rametrix™ LITE v1.1 (Fisher et al., 2018), Rametrix™ PRO v1.0 (Senger, R, Robertson, J, "The Rametrix PRO™ Toolbox V1.0 for MATLAB®," Peer J, 3:35799:2:0, 2019, Jan. 6, 2020 ("Senger and Robertson, 2020)"), and the Statistics and Machine Learning Toolboxes with MATLAB r2018A (Math Works, Inc.; Natick, MA). In Rametrix™ LITE, Raman spectra were truncated to Raman shifts of 400-1,800 $cm^{-1}$, baseline corrected using the Goldindec algorithm (Liu J, Sun J, Huang X, Li G, Liu B. Goldindec: A Novel Algorithm for Raman Spectrum Baseline Correction. Appl Spectrosc. 2015; 69:834-42. doi: 10.1366/14-07798), and vector normalized. Principal component analysis (PCA) and discriminant analysis of principal components (DAPC) models were also constructed with the Rametrix™ LITE Toolbox. The DAPC models were tested by leave-one-out analysis with the Rametrix™ PRO Toolbox, as has been described and demonstrated (above). In short, a leave-one-out analysis works by (i) removing all spectra for one urine specimen from the dataset, (ii) using the remaining dataset to build a DAPC model, (iii) use the model to predict the grouping (e.g., LD-positive or healthy) of the left-out urine specimen, (iv) compare this prediction to the known grouping, and (v) repeat this procedure for all urine specimens in the dataset. This procedure allowed calculation of the test accuracy, sensitivity, specificity, PPV, and NPV. The CDC serologic test is treated as the "Gold-Standard" test when comparing to the Rametrix™ urine screen. The urine screen accuracy is the percentage of spectra that were assigned to the correct group when treated as the "unknown" in the leave-one-out analysis. The sensitivity describes the percentage of patients that test positive by the Gold-Standard test that then go on to test positive by the urine screen. The specificity is the percentage of patients that test negative by the Gold-Standard test that then go on to test negative by the urine screen. The Positive Predictive Value (PPV) is the percentage of patients that screen positive by the urine screen that then go on to test positive by the Gold-Standard test. Finally, the Negative Predictive Value (NPV) is the percentage of patients that screen negative by the urine screen that then go on to test negative by the Gold-Standard test.

Statistical comparisons of spectra were performed with 1-Way Analysis-of-Variance (ANOVA) and pairwise comparisons using Tukey's honestly significant difference (HSD) procedure in MATLAB. Data-rich spectra contained intensity values for Raman shifts between 600-1,800 $cm^{-1}$.

These were reduced to single-value entities by calculation of the total spectral distance (TSD) and total principal component distance (TPD) by comparison with the urine analytical standard Surine™. The calculation of TSD and TPD for statistical analyses has been described in the literature (Senger et al., 2019 a, b), and the calculations are herein described briefly. For the calculation of TSD, the distance between a patient urine spectrum (e.g., an LD-positive patient or healthy volunteer) and an analytical reference standard (i.e., Surine™) was calculated at every Raman shift and summed over all Raman shifts (i.e., 600-1,800 cm$^{-1}$). For the TPD, the distance between the top four principal components was calculated between a patient urine spectrum and a reference spectrum. ANOVA and pairwise comparisons were then performed on these TSD and TPD calculated values.

Raman spectra of individual patient groups. A summary of the patients, urine specimens collected and used, and dataset groupings used in this study are given in Table 27.

TABLE 27

A summary of patients, urine specimens, and group assignments used in this study.

| Description | Number of urine specimens collected and used in this study | Assigned group name in this study | Reference for those specimens in this study or used previously |
|---|---|---|---|
| Patients with symptoms resembling LD and no serologic test results | 41 | No-Test | This study |
| Patients with symptoms resembling LD and a negative serologic test | 13 | Neg-Test | This study |
| Patients with positive serologic test (CDC, IGeneX, iGene, iSPOT, LabCorp, and/or Quest) | 30 | LD-Positive | This study |
| Patients with positive CDC serologic test[1] | 14 | CDC-LD-Positive[1] | This study |
| Patients with positive IGeneX test only | 11 | Other-LD-Positive | This study |
| Patients with positive iGene or iSPOT test only | 2 | Other-LD-Positive | This study |
| Patients with positive LabCorp or Quest test only | 3 | Other-LD-Positive | This study |
| Patients with CD57 NK count only (value <60) and no other positive test[2] | 11 | CD57[2] | This study |
| Healthy volunteers | 30 (of 235 total) | Healthy | Senger, R, Kavuru, V, et.al. (2019) |
| Patients with ESKD | 30 (of 362 total) | ESKD | Senger, R, Sullivan, M, et.al. (2020) |
| Patients with active BCA | 17 | BCA | Huttanus, H, et. al. (2020) |
| Healthy volunteers, patients with ESKD; patients with active BCA | 77 | LD-Negative | This study |
| Surine ™ urine analytical standard | 1 | Surine | Senger, R, Kavuru, V, et.al. (2019); Senger, R, Sullivan, M, et.al. (2020); Huttanus, H, et. al. (2020) |

Figure 34:
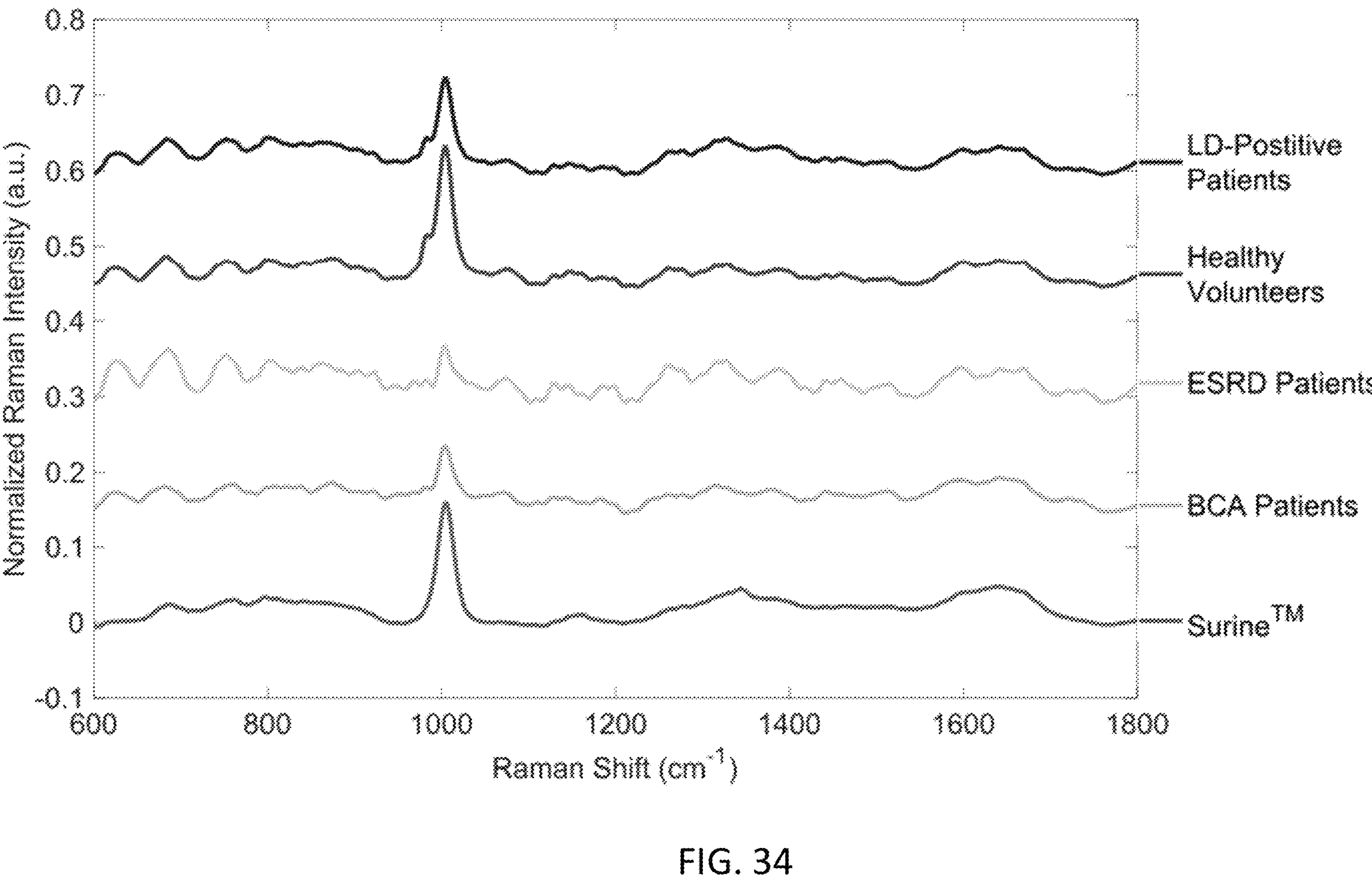
FIG. 34 is a graph showing representative baselined and normalized spectra prepared by Rametrix™ LITE.

[1]Patients testing positive with the CDC serologic test and one or more other tests were grouped with the "CDC-LD-Positive" dataset.
[2]One patient presenting with symptoms resembling LD was found to have a CD57 NK count of 68. This patient was included in the group.

ization in Rametrix™ LITE. These processed representative spectra are shown in FIG. 34.

Apparent from visual inspection of representative spectra is that the urine spectrum of LD-positive patients more closely resembles the spectrum of healthy human volunteers than the urine spectra of either ESKD or BCA patients. Subtle differences between the LD-positive representative spectrum and that of healthy volunteers were observed in the 1,002 cm$^{-1}$ band (representative of urea), around 900 cm$^{-1}$, and from 1,200-1,400 cm$^{-1}$ (all commonly associated with tryptophan and protein signal shifts, including collagen) (Movasaghi, Z., Rehman, S., Rehman, I.U. (2007) "Raman spectroscopy of biological tissues," Applied Spectroscopy Reviews 42 (5): 493-541). However, these subtle differences were both subjective and insufficient to identity the presence of LD in urine through simple visual inspection alone. Thus, Rametrix™ computational tools were needed to perform a chemometric analysis of the spectra to discover defining characteristics (i.e., the "molecular signature") of LD in urine.

Raman spectra from all patient groups and the urinalysis standard Surine™ were processed with the Rametrix™ LITE Toolbox v1.1 for MATLAB, as described previously. The urine spectra were averaged for each group following truncation (600-1,800 cm$^{-1}$), baselining, and vector normal- Statistical comparisons among groups of urine Raman spectra To determine whether the groups (as defined in Table 27) of urine spectra (i.e., LD-positive vs. Healthy) were statistically different, 1-way ANOVA and pairwise comparisons with Tukey's HSD procedure were applied in MATLAB. To do this, the entire Raman spectrum of each sample, consisting of band intensities between 600-1,800 $cm^{-1}$, was reduced to a single value with TSD and TPD calculations, as described earlier. A statistically significant difference was found between urine spectra of LD-positive patients and healthy volunteers by ANOVA and pairwise comparison ($p<0.001$) when using both TSD and TPD calculated values. This suggests that real molecular differences exist between the two groups that can be elucidated by chemometric analysis with Rametrix™.

The same procedure above was applied to the CDC-LD-Positive and Other-LD-Positive groups, defined in Table 27, to test if there was any significant difference in the urine spectra of patients who tested LD-positive by different tests. Results of comparing TSD and TPD values of these groups with 1-way ANOVA and pairwise comparisons revealed no statistically significant difference (p=0.38 and 0.41 for TSD and TPD, respectively). This confirmed that the CDC-LD-Positive and Other-LD-Positive groups could be grouped together as LD-Positive and used in further calculations.

Again, the same TSD and TPD calculations and statistical procedures were applied to the LD-Positive and Neg-Test groups of Table 27. Results showed these groups were not statistically different (p=0.30 and 0.31 for TSD and TPD, respectively). This suggests that some urine specimens of the Neg-Test group could have the LD molecular signature. Individual specimens were analyzed for this using the Rametrix™-based screen, and results are reported in a later section.

The same analysis was applied to the LD-Positive and CD57 groups of Table 27. Again, these groups were found to not be statistically different (p=0.38 and 0.36 for TSD and TPD, respectively). This also suggests that some urine specimens of the CD57 group could have the LD molecular signature. It is noted that several specimens are contained in both the Neg-Test and CD57 groups, so this is logical. Again, the individual specimens were analyzed with the Rametrix™-based screen, and results are given later.

Building a Rametrix™-Based Urine Screen for LD

First, the differences between the urine spectra of the LD-Positive group were compared further against those of the Healthy group using Rametrix™ LITE. Results of PCA and several DAPC models are shown in FIGS. 35A-D.

Figures 35A, 35B:
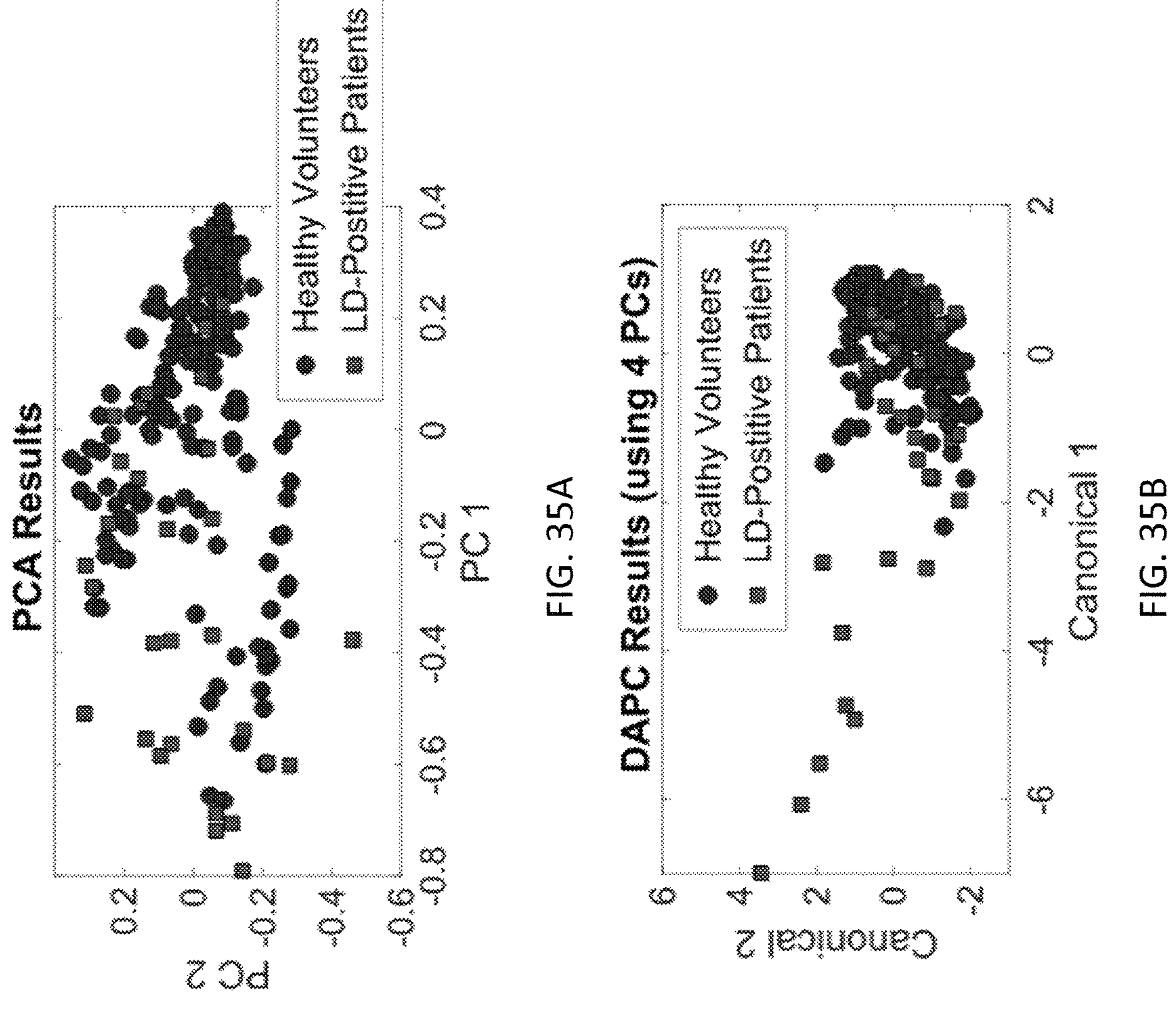
FIGS. 35A-D are graphs showing Rametrix™ LITE results for spectra from LD-positive patients and healthy volunteers: A) PCA results, B) DAPC results for a model built with 4 PCs (95% of dataset variance), C) DAPC results for a model built with 9 PCs (99% of dataset variance), and D) DAPC results for a model built with 45 PCs (99.9% of dataset variance).
Figures 35C, 35D:
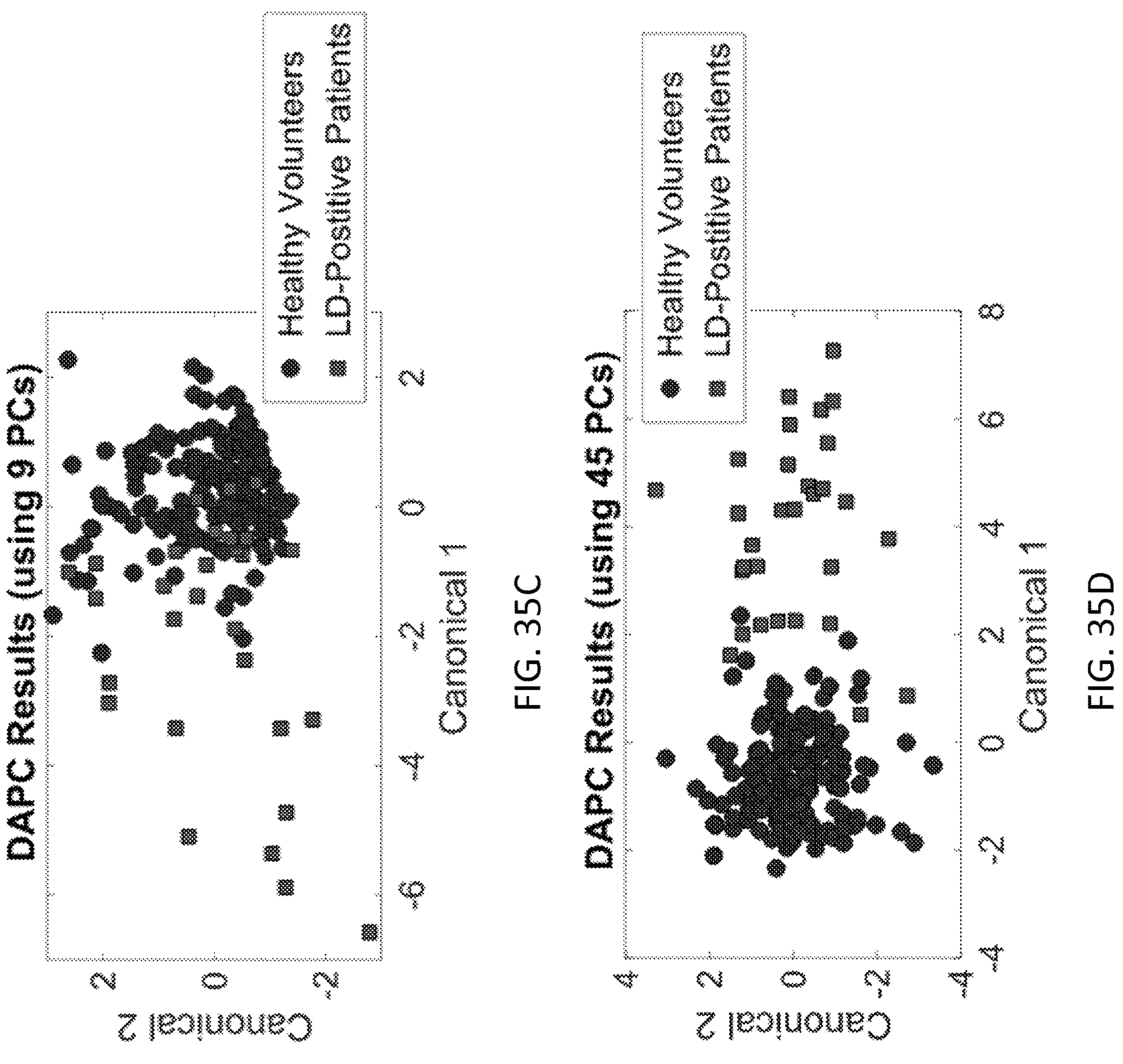

The PCA results (FIG. 35A) showed little separation between the urine spectra of LD-positive patients and those of healthy volunteers, so DAPC models were applied. For a DAPC model built with four principal components (PCs) (FIG. 35B), 95% of the dataset variance was represented. This led to separation of about one-third of the LD-Positive urine spectra from those of the Healthy group along the first two canonical axes. For reference, in DAPC plots, data point clustering represents spectral (and molecular) similarities. Distance between data points arises from dissimilarities among groups (defined in Table 27) of spectra (i.e., LD-Positive vs. Healthy). As the DAPC model complexity was increased to include 9 PCs (representing 99% of the dataset variance) (FIG. 35C), the separation of the two clusters improved, and this was improved further by including 45 PCs (99.9% of the dataset variance) (FIG. 35D). However, this visual representation only demonstrates that the two groups of spectra can be separated by increasingly complex DAPC models. Importantly, this analysis, alone, shows that spectral differences can be found between these two groups of urine spectra and that a unique LD molecular signature may exist. How well this DAPC model performs in assigning a group (i.e., LD-Positive or Healthy) to an "unknown" urine specimen is addressed in the following sections. At this point, it is also unclear, but of interest, whether those spectra that become distinct from the healthy volunteers' cluster in simpler DAPC models (e.g., with 4 PCs) represent more 'severe' LD-positive cases.

The Rametrix™ PRO computational tool was then applied for further analysis of spectral data. This was done to assess how well the Raman-based analysis would serve as a urine screen to detect a unique spectral signature associated with LD. In short, Rametrix™ PRO implements a leave-one-out analysis in building DAPC models. In this leave-one-out analysis, the urine spectrum "left-out" of the model building process was treated as the "unknown" and then assigned to a group (i.e., LD-Positive or Healthy) using the model. The prediction was then compared to its real grouping. This procedure was repeated for all spectra in the dataset. From this, overall model accuracy, sensitivity, PPV, and NPV were calculated. Several DAPC models were then constructed with different numbers of PCs, and the leave-one-out analysis was performed for each one with Rametrix™ PRO. Performance metrics are given in Table 2. With this dataset, the DAPC model with 45 PCs led to a urine screen for LD with almost 95% accuracy, 87% sensitivity, 96% specificity, 79% PPV, and 98% NPV. When examining correlations with serologic tests as the "Gold-Standard" test for LD, the Rametrix™-based urine screen performed well. With a positive urine screen result, 79% of those patients tested positive by the Gold-Standard test (example of PPV). Additionally, of those screening negative, 98% tested negative by the Gold-Standard test (example of NPV). This high value of NPV helps ensure false-positives are minimized and treatment is not administered to heathy individuals.

Elucidating the molecular signature of LD in Raman spectra of urine specimens

TABLE 28

Rametrix ™ PRO results for LD-positive patients and heathy human volunteers.

| PCs | Accuracy | Sensitivity | Specificity | PPV | NPV |
|---|---|---|---|---|---|
| 5 | 89.3% | 43.3% | 96.7% | 68.4% | 91.3% |
| 15 | 88.8% | 53.3% | 94.6% | 61.5% | 92.6% |
| 25 | 89.3% | 30.0% | 98.9% | 81.8% | 89.7% |
| 35 | 90.2% | 33.3% | 99.5% | 90.9% | 90.2% |
| 45* | 94.9% | 86.7% | 96.2% | 78.8% | 97.8% |
| 50 | 86.5% | 86.7% | 86.5% | 51.0% | 97.6% |

*The DAPC model with 45 PCs was found to be the best performer.

Figures 36A, 36B:
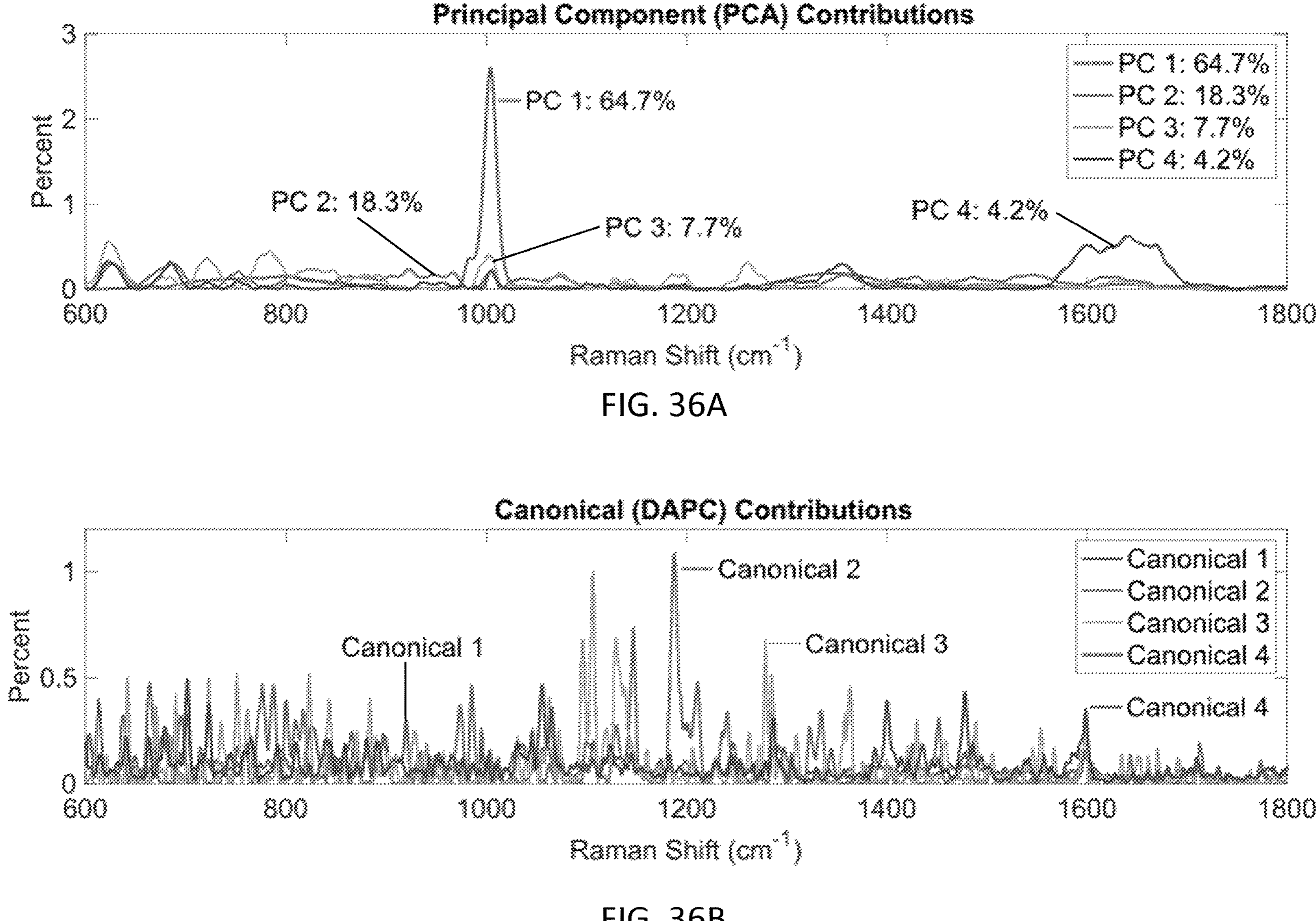
FIGS. 36A-B are graphs showing Raman shifts leading to cluster separations in A) PCA and B) DAPC (model built with 45 PCs). Percentages in (A) indicate the percent of dataset variance represented by each principal component.

A useful feature of the Rametrix™ LITE Toolbox is the identification of spectral contributions (i.e., molecular constituents) leading to separations of clusters in PCA and DAPC. In other words, Rametrix™ reveals what Raman shifts have band intensities that are significantly different among groups of spectra (i.e., LD-Positive vs Healthy), due to differences in the molecular composition of urine between the two classes. The difference that is unique to LD is referred to as its molecular signature. FIGS. 36A-B shows the contribution of each Raman shift to the separations between LD-Positive and Healthy (shown in FIGS. 35A-D).

The most prominent contributions (i.e., greater than 0.4% in FIGS. 36A-B) were compiled, and biological molecules giving rise to these Raman shifts were identified in a popular database (Movasaghi, Z, et. al. (2007)). Analysis of these results and correlations is shown in Table 29.

TABLE 29

Prominent[1] Raman shifts arising from PCA and DAPC comparisons of urine spectra from LD-positive patients and healthy volunteers.

| Raman Shift ($cm^{-1}$) | Band Assignment | PCA, DAPC, or Both |
|---|---|---|
| 615 | Cholesterol ester | DAPC |
| 620 | Related to aromatics | PCA |
| 642 | Tyrosine | DAPC |
| 665 | Tyrosine | DAPC |
| 700 | Methionine | DAPC |
| 720 | Phospholipids/DNA | Both |
| 752 | Heme | Both |
| 775 | phosphatidylinositol | Both |
| 785 | DNA/RNA | Both |
| 820-840 | Proteins, including collagen | PCA |
| 825 | Phosphodiester | DAPC |
| 843 | Glucose | DAPC |
| 880 | Tryptophan | Both |
| 890 | Structural protein modes of tumors | PCA |
| 920 | C-C stretch of proline/glucose/lactic acid/collagen | PCA |
| 1,002 | Urea (dominant in urine) | PCA |
| 1,056 | Lipids | DAPC |
| 1,064 | Lipids | DAPC |
| 1,074 | Triglycerides | PCA |
| 1,096 | Phosphodioxy $PO_2$- groups | DAPC |
| 1,106 | Carbohydrates | DAPC |
| 1,130 | Phospholipids and fatty acids | Both |
| 1,185 | DNA | PCA |
| 1,211 | Tyrosine and phenylalanine | DAPC |
| 1,279 | Amide III | DAPC |
| 1,260 | Amides and protein | PCA |
| 1,275 | Amide III | PCA |
| 1,360 | Tryptophan | PCA |
| 1,364 | Tryptophan | DAPC |
| 1,488 | Collagen | DAPC |
| 1,600 | Amide I band of proteins | Both |
| 1,640 | Amide I | PCA |
| 1,665 | Collagen | PCA |

[1]Prominent is defined as band (i.e., peak) height of more than 0.4% in FIGS. 36A-B.

A recent metabolomic analysis of urine, using liquid chromatography-mass spectroscopy for the detection of LD, highlighted the presence of tryptophan and tryptophan metabolites, among others, in the urine of LD-positive patients (Pegalajar-Jurado A, Fitzgerald BL, Islam MN, Belisle JT, Wormser GP, Waller KS, Ashton LV, Webb KJ, Delorey MJ, Clark RJ, Molins CR (2018) "Identification of urine metabolites as biomarkers of early Lyme Disease," Nature Scientific Reports 8:12204| DOI: 10.1038/s41598-018-29713-y). Tryptophan was also present as a prominent contributor in the analysis. In PCA, intensities at the following Raman shifts ($cm^{-1}$) were found as major contributors to the differences between LD-positive patients and healthy volunteers: 620 $cm^{-1}$ (related to aromatics), 880 $cm^{-1}$ (tryptophan), and 1,360 $cm^{-1}$ (tryptophan). In the DAPC analysis, the following Raman shift contributors ($cm^{-1}$) were noted: 642 $cm^{-1}$ and 665 $cm^{-1}$ (related to tyrosine), 880 $cm^{-1}$ (tryptophan), 1,211 $cm^{-1}$ (tyrosine and phenylalanine), and 1,364 $cm^{-1}$ (tryptophan). These and other significant contributors are given in Table 29, and it is specified whether the Raman shift contributor was found in PCA results, DAPC results, or both (band assignments listed are given in Movasaghi, Z, et. al. (2007)). These are the major bands of the Raman molecular signature for LD. However, this molecular signature contains several other minor bands that are not listed here but are recognized in the Rametrix™ analysis.

Testing the Rametrix™-based LD urine screen against other patient groups. ESKD (end-stage kidney disease) and BCA (bladder cancer) are two other disease conditions that significantly impact the molecular composition of urine. Previously, the inventors have shown these can both be resolved using Rametrix™-based computational analysis (Senger et al., 2019 b; Huttanus et al., 2020). Here, the inventors sought to determine whether urine from ESKD and BCA patients could be resolved from those of the LD-positive patients. The results of the Rametrix™ LITE DAPC model with 45 PCs are shown in FIG. 37.

Figure 37:
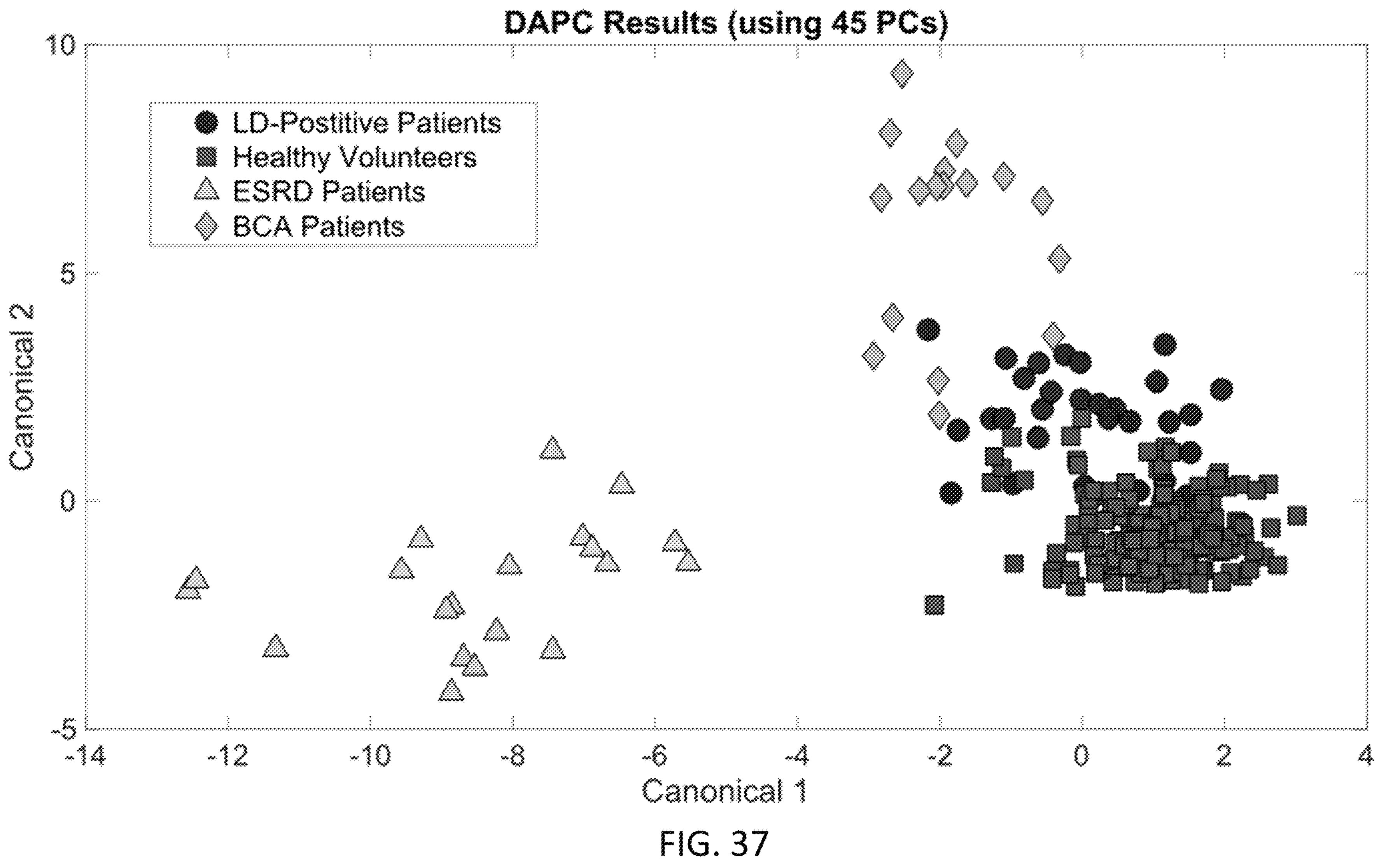
FIG. 37 is a graph showing a Rametrix™ LITE DAPC model built with 45 PCs (99.9% of the dataset variance) with urine spectra from LD-positive patients, CKD patients, BCA patients, and healthy human volunteers.

Apparent in FIG. 37 is the degree of separation among the different classes of spectra, with the urine spectra of LD-positive patients most resembling that of the healthy volunteers. This was also observable in FIG. 34, as ESRD (end-stage renal disease, also referred to as end-stage kidney disease, ESKD) and BCA produced significantly altered urine spectra (i.e., Raman molecular signatures) compared to the healthy volunteers. However, and importantly, the LD-Positive group clustered differently from the ESKD and BCA groups, suggesting Rametrix™ can detect the presence of LD differentially from ESKD and BCA.

Next, the inventors determined whether urine spectra from LD-positive patients could be distinguished from those with ESKD and BCA. Using TSD and TPD values with 1-way ANOVA and pairwise comparisons, the LD-Positive group was found significantly different from the ESKD and BCA groups ($p<0.001$ in both cases). Rametrix™ PRO was then used to determine the effectiveness of identifying a urine spectrum as belonging to the LD-Positive group versus the ESKD and BCA groups. These results are shown in Table 30 for models built with 45 PCs (identical to optimal DAPC model in FIGS. 35A-D and Table 28).

TABLE 30

Rametrix ™ PRO results for identifying LD-positive urine spectra against those of ESKD and BCA patients.

| Comparison | Accuracy | Sensitivity | Specificity | PPV | NPV |
|---|---|---|---|---|---|
| LD-positive vs. ESKD | 96.0% | 96.7% | 95.0% | 96.7% | 95.0% |
| LD-positive vs. BCA | 87.2% | 90.0% | 82.4% | 90.0% | 82.4% |

Identification of LD-positive urine specimens from urine specimens of ESKD patients was robust with accuracy, sensitivity, specificity, PPV, and NPV all exceeding 95%. This is evident in FIG. 37, as the ESKD group cluster separated from the LD-Positive group cluster. For identifying LD-positive urine spectra against those from BCA patients, the screen exceeded 80% for all metrics, with overall accuracy of 87%, sensitivity of 90%, and PPV of 90%.

Finally, the inventors constructed a Rametrix™-based urine screen that differentiates the LD-Positive group from the LD-Negative group (Table 27), containing healthy volunteers, patients with ESKD, and patients with active bladder cancer. Here, the goal was to produce a urine screen where the LD-Negative designation could be a condition other than healthy. Results of the urine screen are given in Table 31 below and demonstrate that a molecular signature for LD can be found and is unique from molecular signatures of ESKD and BCA.

Table 5. RametrixTM PRO results for LD-positive patients against the LD-Negative group, containing healthy human volunteers, ESKD patients, and BCA patients.

TABLE 31

Rametrix ™ PRO results for LD-positive patients against the LD-Negative group, containing heathy human volunteers, ESKD patients, and BCA patients.

| PCs | Accuracy | Sensitivity | Specificity | PPV | NPV |
|---|---|---|---|---|---|
| 42 | 83.7% | 70.0% | 90.3% | 77.8% | 86.2% |

The inventors applied the Rametrix™-based screens of Table 28 (LD-Positive vs. Healthy groups; called "Simple Screen") and Table 31 (LD-Positive vs. LD-Negative groups; termed here "Comprehensive Screen") to the patients of Table 27 who had no serological test (No-Test group) and those who had tested negative previously but still presented with LD-like symptoms (Neg-Test group). The percentage of urine specimens that screened positive for LD with each test are given below in Table 32.

TABLE 32

Percentage of the No-Test and Neg-Test groups screening positive for LD with the Simple and Comprehensive Rametrix ™-based urine screens.

| | Simple Screen (LD-Positive vs. Healthy groups) | Comprehensive Screen (LD-Positive vs. LD-Negative groups) |
|---|---|---|
| No-Test group | 100% | 80% |
| Neg-Test group | 100% | 65% |

As shown, the Rametrix™-based screens can be used to identify additional patients with a LD molecular signature in urine. The Simple Screen showed that all patients presenting with symptoms resembling LD had urine that more resembled the LD-Positive group than the Healthy group. However, some of these patients then screened LD-negative when the negative group also contained urine specimens from patients with other diseases.

The major findings from this study are summarized as follows:

- Patients who were seropositive by the two-tier CDC standard diagnostic test for LD had statistically significant changes in the molecular composition of their urine that differentiated them from normal, healthy individuals, as determined by Raman spectroscopy and Rametrix™ analyses of urine specimens;
- The molecular signature of LD in urine is complex, comprising more than 33 Raman bands with major changes and several more with minor changes;
- Urine specimens from patients who were considered to be LD-positive with other laboratory tests (not the two-tier CDC standard diagnostic test) were statistically similar to specimens of urine from patients who tested positive with the CDC standard two-tier test;
- Several patients who were LD-negative (with two-tier or other LD diagnostic tests) had urine spectral changes similar to those who were LD-positive, but it is possible they had been previously infected but were not reactive at the time of assay (i.e., presented for long-term chronic fatigue);
- The molecular changes seen in the urine of LD-positive patients were not only statistically different from the urine of normal, healthy individuals, but also from the urine of patients with other genitourinary tract pathologies, including ESKD and BCA, suggesting the LD-associated urine molecular signature appears to be unique.

As noted above, current serodiagnostic methods for diagnosis of LD fall short of needs (rapid and early detection), may have unsatisfactory sensitivity/specificity/predictive value, can be costly, and require multiple invasive blood collections over a period of several weeks.

There have been a number of studies, over the past 30 years, that have reported changes in the composition of urine that may have reflected the presence of LD. Early studies looked for pathogen-related proteins in urine; these studies were not sufficiently definitive to result in laboratory use, but did encourage continued investigation that could lead (eventually) to clinical application of these methods. Magni and co-workers (Magni, 2015) showed that a molecular marker-outer surface protein A C-terminus peptide (OspA)—of the pathogen could be detected in the urine of patients with early, active infections with nanotrap technology. Levels of OspA declined with clinical recovery, suggesting that this testing procedure could have value in detection and management of early infections (i.e., use or non-use of antibiotics). This test has been commercialized (Nanotrap™, Ceres Nanoscience, Manassas, VA); the extent of clinical use is difficult to discern from the literature. The recent study by Pegalajar-Jurado (2018) showed that LD urine could be differentiated from non-LD urine using advanced metabolomic analysis, using liquid chromatography/mass spectroscopy. In the Pegalaiar-Jurado study, changes in metabolism, related to infection, were shown by alterations in urine metabolites (including alterations in tryptophan metabolism).

Thus, access to a simple, rapid, economical, non-invasive, and accurate test would be a significant and meaningful step in detection and management of LD. The inventors believe the Rametrix™-based urine screening procedure, described here, fulfills these needs. The data show that a molecular signature, associated with serologically-confirmed LD, can be detected, and this molecular signature differentiates LD from urine specimens of healthy individuals and from specimens of patients with genitourinary pathologies, such as ESKD or BCA. Sample collection (free catch) simply requires urinating into a cup. Samples can be stored at room temperature for up to twelve hours before analysis. No processing (i.e., addition of chemical preservatives or centrifugation) of the urine specimen is needed and total time required to scan the sample repetitively (10-15 repeat scans/sample) and generate a spectrum for computational analysis is <15 minutes, including sample handling time (transfer from urine collection cup to 1.5 ml sample vial). A miniscule (<2 ml) volume of urine is required for analysis and scanning is non-destructive. Samples can be stored at low temperatures (<−30° C. for >30 days), thawed and then scanned/re-scanned, as needed (Senger, et. al., 2020). Technical personnel can be trained in a few hours to analyze specimens. The Raman spectrometers used for these analyses are inexpensive (<$25,000) and are commercially available. Clearly, the capital and personnel costs of running Raman-based assays in laboratory settings are modest (approximately $50/sample), in comparison to urine metabolomic screening (ca. $400/sample), and serodiagnostic testing (>$200/sample).

The results are based on robust computational/statistical analysis of Raman spectra and capitalize on the ability to compare the characteristics of these spectra (at hundreds of different Raman shifts) with extensive libraries of Raman chemical reference spectra (El Mendili, et. al., 2019), urine metabolomics (Bouatra, et. al., 2013), and the inventors' own Raman databases (235 normal [healthy adult], 455 ESKD, and 74 BCA urine Raman spectra). Access to this database of specimens was a key to detecting statistically meaningful results reported here.

The inventors are currently collecting data from more LD-positive and LD-negative patients and conducting studies to further identify major molecular contributors to the LD "Raman urine signature" and to enroll more LD-positive and LD-negative patients. The inventors acknowledge the ongoing controversies surrounding the contribution of LD infection to persons experiencing chronic fatigue. The inventors believe the results of the current study are indicative of a currently undefined systemic reaction to LD infection, but fully expect this systemic reaction could be seen with other pathologies (Myalgic Encephalomyelitis/Chronic Fatigue Syndrome, post-acute COVID-19 Long Haul Syndrome). The inventors believe that the methods may be used to help identify patients who would benefit from various therapies directed at LD management, but also other infectious or environmental diseases (e.g., other tick-borne diseases, mold exposure, COVID-19, etc.). Ongoing work is also directed at determining if co-morbidities may affect the LD molecular signature and results returned by the Rametrix™-based analysis.

Here the inventors present results of studies conducted to determine if Raman spectroscopy and Rametrix™ analysis of urine would serve as a suitable screen for LD. The results indicate there are statistically significant changes in the urine of patients who test positive for LD when their urine molecular composition is compared to that of normal, healthy volunteers or patients with genitourinary tract pathology. As such, the methods could be easily applied as an accurate, rapid, and inexpensive urine screen for LD.

Section VIII

Detection of unique multimolecular signatures in the urine of patients with myalgic encephalomyelitis/chronic fatigue syndrome, using Raman spectroscopy and chemometrics (Rametrix™).

A urine-based screen for myalgic encephalomyelitis/chronic fatigue syndrome (ME/CFS) was developed in this research. (See Senger, R, Issa, A, Gouldin, A, Talty, J, Hollis, A, Robertson, J, "Detection of unique multimolecular signatures in the urine of patients with myalgic encephalomyelitis/chronic fatigue syndrome, using Raman spectroscopy and chemometrics (Rametrix™)", unpublished) The screen is based on Raman spectroscopy and chemometric analysis (Rametrix™). Raman spectra of urine from 85 patients diagnosed with ME/CFS were compared against the database of urine spectra from 235 healthy human volunteers, 362 end-stage kidney disease (ESKD) patients, and 17 patients with active or remissive bladder cancer (BCA). The inventors found statistical differences ($p<0.001$) between urine scans of healthy volunteers and ME/CFS-positive patients. The inventors also found a unique ME/CFS molecular signature in urine involving 40 Raman bands with significant differences from urine from healthy individuals. This signature also contained several minor Raman band contributors, and the inventors were able to distinguish this molecular signature as statistically different ($p<0.001$) from those of ESKD and BCA. When comparing ME/CFS-positive patients against healthy volunteers, the optimum Rametrix™-based urine screen performed with 91.4% overall accuracy, 78.6% sensitivity, 97.3% specificity, 93.0% positive predictive value (PPV), and 90.9% negative predictive value (NPV). Subsets of the ME/CFS patient group included patients with histories of Lyme disease (LD), mold exposure (MD), Hemobartonella infection (BT), and *babesia* infection (BA). A unique molecular signature involving 33 Raman bands was found for LD, and urine screens were developed and tested. Overall prediction accuracies above 90% and specificities above 95% were found for all cases. Additional advantages to the Rametrix™-based urine screen include it (i) is rapid (minutes per analysis), (ii) is minimally invasive (iii) requires no chemical labeling, (iv) uses a low-profile, off-the-shelf spectrometer, and (iv) is inexpensive relative to other available tests.

Myalgic encephalomyelitis/chronic fatigue syndrome (ME/CFS) (known commonly as "Chronic Fatigue Syndrome") is a well-recognized, debilitating disease entity. Between 1.7-3.38 million Americans are estimated to suffer from this debilitating illness. The toll that ME/CFS takes on patients and their families is immense, as are the economic consequences. Individuals with ME/CFS may be unable to work, and the loss of their productivity is estimated to cost the US economy between $17-24 billion per year. Here, the inventors introduce a new urine-based screen for ME/CFS that is based on Raman spectroscopy and chemometric analysis (Rametrix™).

First recognized in the 1930s, ME/CFS is a challenge to define clinically and diagnostically. Many patients suffer for years, and frequently need to be evaluated by multiple physicians before ME/CFS is diagnosed and treatment attempted. Fukuda and co-workers identified eight common symptoms, including altered mentation (cognitive impairment, short-term memory loss, loss of concentration), sore throat, lymph node pain/swelling, muscle pain (myalia), joint pain, episodic headache, unrefreshing sleep and sleep disorders, and persistent fatigue lasting >24 hours after exertion. Not all patients have all symptoms, but the presence of at least 4/8 symptoms is considered clinically diagnostic of ME/CFS. Following Fukuda's work, more than a dozen other clinical symptoms have been added to the diagnostic classification algorithm. Unfortunately, the wide range and severity of individual patient symptoms and chronicity of disease (months to many years), makes diagnosis elusive and effective treatment difficult. Some patients have been stigmatized as having 'a psychological condition' rather than a serious, frequently untreatable, systemic disease process.

The etiology of ME/CFS is unknown, but it is likely there are a number of causes, expressed through common pathophysiologic pathways involving the central nervous, immune/inflammatory, and endocrine systems. Infectious agents (e.g., Epstein-Barr virus, influenza virus, Lyme pathogen [*Borrelia burgdorferi*], other tick-borne pathogens) have long been implicated in initiation and/or progression. In fact, a primary focus of current diagnostic testing for ME/CFS is determining if patients have been exposed to infectious agents. Interactions between genetic predispositions and possible etiologic factors (see above) have been suggested. Many patients are routinely tested for reactivity to environmental molds or other allergens, many others for evaluation of immune dysfunction, and many/most patients for all of the above.

This "shotgun" diagnostic approach, aimed at exclusion of potential causes, is problematic. There is currently no widely-accepted laboratory testing protocol, based on published research, for the diagnosis of ME/CFS. The inventors discuss (see Discussion) the rationale, design, and results of the most common serologic/blood tests (Lyme disease [ID], immune dysregulation [CD57], Hemobartonella, mold exposure) to which ME/CFS patients are subjected and then contrast those test results with the Raman spectroscopy-based methods for screening ME/CFS patients. The inventors particularly focus on similarities and differences in results of the testing with results of serologic testing for "chronic LD", a condition for which there is no precise medical definition or diagnostic code and no accepted diagnostic test.

It Is clear that there is a pressing need, given the incidence and burden of ME/CFS, to evolve diagnostic tests that are rapid, inexpensive, relevant, and potentially non-invasive (most current methods require blood/serum). Such tests must be supported by objective evidence of high positive and negative predictive value, specifically for ME/CFS. Other urine-based screening tests have been developed with Rametrix™ (see above) and include (i) establishing a range of normal human urine, (il) end-stage kidney disease (ESKD), and (iii) bladder cancer (BCA).

Here, the inventors describe the results of Rametrix™ analysis of urine specimens from 85 patients presenting for clinical and diagnostic evaluation of ME/CFS. A significant number of these patients tested positive for LD with one or more types of serologic test. Some patients had evidence of exposure to Hemobartonella, environmental molds, and/or had assays indicative of immune dysfunction (CD57 assay). The urine Raman spectra of these ME/CFS patients were compared with a subset of the urine spectra database containing 235 spectra of healthy human volunteers, 362 patients with end-stage kidney disease (ESKD), and 56 patients with active or remissive bladder cancer (BCA). The inventors hypothesized that ME/CFS patients would have a distinctive multimolecular signature in urine that could be detected with Raman spectroscopy and Rametrix™. Once proven true, the inventors explored the accuracy, including sensitivity, specificity, positive predictive value (PPV), and negative predictive value (NPV), of a Rametrix™-based urine screen for the presence of ME/CFS. This was then extended to determine if urine screens could also be developed for LD, mold exposure (MD), Hemobartonella exposure (BT), and *babesia* exposure (BA).

Patients: Eighty-five (85) patients were seen by two primary care specialists (JT, AH) for evaluation of chronic fatigue/related issues, potentially indicative of infection with *B. burgdorferi* (LD), *bartonella, babesia*, or exposure to environmental contaminants such as molds. The patient population consisted of 59 female, 18 male, and 8 unspecified patients. The age range of female patients was 2-74 years and of male patients 17-74 years. As would be expected, the clinical presentation of patients was highly variable, as was the duration and severity of clinical symptoms. Many patients had pursued multiple avenues of diagnosis and variable courses and types of therapies (including antibiotics) prior to evaluation. These patients were all classified as ME/CFS-positive, based on evaluation by physicians specializing in diagnosis and treatment of ME/CFS.

Of these patients, 30 tested positive for LD with serologic tests. Of this group, 14 tested positive with the CDC serologic test. No patients evaluated had erythema migrans at the time of presentation. A majority of patients were also evaluated with other types of testing for LD (not CDC serologic testing) or to screen for the presence of other disease entities, including LD tests from IGeneX, iGene, iSPOT, LabCorp, and/or Quest. It is acknowledged the value and acceptance of results of these tests is debatable.

Also, of the ME/CFS-positive patients, 51 had a history or current signs of mold exposure, 17 had a history of *bartonella*, and 6 had a history of *babesia* infection. These were classified as MD-positive, BT-positive, and BA-positive, respectively. All patients complained of fatigue, and 16 patients were identified in physician notes to suffer from profound or significant fatigue.

15-30 mL of voided, mid-stream urine was collected in sterile specimen containers and frozen (−35° C.) until retrieved for analysis, at which point specimens were warmed to 25° C. and analyzed (see below).

Healthy volunteers (controls): A full analysis of the healthy human volunteer urine dataset is provided above. Briefly, 235 urine specimens were collected from 48 (39 females, 9 males) healthy human volunteers with no history or evidence of renal disease. Volunteers were also free of infectious or degenerative disease at the time of sample collection. The age range of the healthy volunteer population was 18-70 years; 87.5% of volunteers were of ages 19-22 years, and the median age was 21 years. 185 urine spectra were selected randomly and used in this study.

End-stage kidney disease (ESKD) patients (controls): In total, 362 urine specimens were collected from 96 patients. Patients had advanced ESKD and were undergoing treatment with ambulatory peritoneal dialysis (PD). Patients ranged in age from 24-90 years old. The mean age was 60 years, and the median age was 63.5 years. Multiple collections (4-8 separate collections) were available from multiple patients, allowing repetitive measurements and correlations over a protracted course of PD therapy (18 months). From this dataset, 30 urine spectra were selected randomly and used in this study.

Bladder cancer (BCA) patients (controls): In total, 56 urine specimens (one per patient) were collected. The patients ranged in age from 31-91 years old. The mean and median age of 62 years. Of this dataset, 17 specimens were from patients with active bladder cancer. The median age of this population was 70 years. In addition, 17 of these specimens were selected randomly, among the patients with active BCA at time of collection, and used in this study.

Specimen collection and storage: Voided, mid-stream urine specimens were collected and transferred into sterile specimen cups and then immediately frozen to −15° C. and then stored at −35° C. until analyzed.

The inventors previously determined the suitability of collection and storage conditions in separate studies of urine stability and adhered to the guidelines set forth in that study. Unused portions of urine and spent dialysate specimens were stored at −35° C. for the duration of the study and re-analyzed, as needed.

Analytical standards: Surine™ Urine Negative Control (Dyna-Tek Industries, Lenexa, KS) was used as a control standard for urinalysis.

Raman methodology and measurements: Briefly, an Agiltron PeakSeeker™ dispersive Raman spectrometer (Woburn, MA) was used. All specimens were Raman scanned as "bulk" liquid samples in 1.5 mL glass vials at 25° C. using 785 nm (100 mW) laser excitation for 15 s with spectral resolution of 8 $cm^{-1}$. A minimum of 10 scans were collected per specimen and averaged.

Computational methodology: Spectral processing and analyses were performed with the Rametrix™ LITE v1.1, Rametrix™ PRO v1.0, and the Statistics and Machine Learning Toolboxes with MATLAB r2018A (MathWorks, Inc.; Natick, MA). In Rametrix™ LITE, Raman spectra were truncated to Raman shifts of 400-1,800 $cm^{-1}$, baseline corrected using the Goldindec algorithm (Liu, et. al., 2015), and vector normalized. Principal component analysis (PCA) and discriminant analysis of principal components (DAPC) models were also constructed with the Rametrix™ LITE Toolbox. The DAPC models were tested by leave-one-out cross-validation (LOOCV) analysis with the Rametrix™ PRO Toolbox (above). In short, LOOCV works by (i) removing all spectra for one urine specimen from the dataset, (ii) using the remaining dataset to build a DAPC model, (iii) use the model to predict the grouping (e.g., ME/CFS-Positive or Healthy, i.e., ME/CFS-Negative) of the left-out urine specimen, (iv) compare this prediction to the known grouping, and (v) repeat this procedure for all urine specimens in the dataset. This procedure allowed calculation of the test accuracy, sensitivity, specificity, PPV, and NPV.

Here, the physician diagnosis of ME/CFS (from a variety of clinical tests and exams) was treated as the "Gold-Standard" test, and the CDC serologic test was treated as the "Gold-Standard" test for LD when comparing to the Rametrix™ urine screen. The urine screen accuracy is the percentage of spectra that were assigned to the correct group when treated as the "unknown" in the LOOCV. The sensitivity describes the percentage of patients that test positive by the Gold-Standard test that then go on to test positive by the urine screen. The specificity is the percentage of patients that test negative by the Gold-Standard test that then go on to test negative by the urine screen. The PPV is the percentage of patients that screen positive by the urine screen that then go on to test positive by the Gold-Standard test. Finally, the NPV is the percentage of patients that screen negative by the urine screen that then go on to test negative by the Gold-Standard test.

Statistical comparisons of spectra were performed with 1-Way Analysis-of-Variance (ANOVA) and pairwise comparisons using Tukey's Honestly Significant Difference (HSD) procedure in MATLAB. Data-rich spectra contained intensity values for Raman shifts between 600-1,800 $cm^{-1}$. These were reduced to single-value entities by calculation of the total spectral distance (TSD) and total principal component distance (TPD) by comparison with the urine analytical standard Surine™. The calculation of TSD and TPD for statistical analyses has been described in the literature (Senger et al., 2019 a, b), and the calculations are herein described briefly. For the calculation of TSD, the distance between a patient urine spectrum (e.g., an LD-positive patient or healthy volunteer) and an analytical reference standard (i.e., Surine™) was calculated at every Raman shift and summed over all Raman shifts (i.e., 600-1,800 $cm^{-1}$). For the TPD, the distance between the top four principal components was calculated between a patient urine spectrum and a reference spectrum. ANOVA and pairwise comparisons were then performed on these TSD and TPD calculated values.

Computational targets: The inventors performed multiple analyses to test the hypothesis, "Patients with ME/CFS have a distinctive multimolecular signature in urine that can be detected with Raman spectroscopy and Rametrix™." Following this, the inventors explored how Rametrix™ would perform as a urine screen for ME/CFS, LD, MD, BT, and BA. The inventors have structured the Results section to address the following questions:

A summary of the patients, urine specimens collected, and dataset groupings used in this study are given in Table 33.

TABLE 33

A summary of patients, urine specimens, and group assignments used in this study.

| Description | Number of urine specimens collected and used in this study | Assigned group name in this study | Reference for those specimens in this study or used previously |
|---|---|---|---|
| Patients with ME/CFS diagnosis | 85 | ME/CFS-Positive | This study |
| Patients with symptoms resembling LD and no serologic test results | 41 | No-LD-Test | This study |
| Patients with symptoms resembling LD and a negative serologic test | 13 | Neg-LD-Test | This study |
| Patients with positive serologic test (CDC, IGeneX, iGene, iSPOT, LabCorp, and/or Quest) | 30 | LD-Positive | This study |
| Patients with positive CDC serologic test[1] for LD | 14 | CDC-LD-Positive[1] | This study |
| Patients with positive IGeneX, iGene, iSPOT, LabCorp, or Quest test for LD | 16 | Other-LD-Positive | This study |
| Patients with CD57 NK count only (value <60) and no other positive LD test[2] | 11 | CD572 | This study |
| Patients with current or prior environmental mold exposure | 51 | MD-Positive | This study |
| Patients testing positive or exhibiting symptoms of bartonella | 17 | BT-Positive | This study |
| Patients testing positive or exhibiting symptoms of babesia | 6 | BA-Positive | This study |
| Healthy volunteers | 185 (of 235 total) | Healthy | Senger, R, Kavuru, V, et.al. (2019) |
| Patients with ESKD | 30 (of 362 total) | ESKD | Senger, R, Sullivan, M, et.al. (2020) |
| Patients with active BCA | 17 | BCA | Huttanus, H, et. al. (2020) |
| Surine ™ | 1 | Surine | Senger, R, Kavuru, V, et.al. (2019); Senger, R, Sullivan, M, et.al. (2020); Huttanus, H, et. al. (2020) |

TABLE 33-continued

A summary of patients, urine specimens, and group assignments used in this study.

| Description | Number of urine specimens collected and used in this study | Assigned group name in this study | Reference for those specimens in this study or used previously |
|---|---|---|---|
| Healthy volunteers, Patients with ESKD; Patients with active BCA; Surine ™ | 233 | ME/CFS-Neg-Full | Senger, R, Kavuru, V, et.al. (2019); Senger, R, Sullivan, M, et.al. (2020); Huttanus, H, et. al. (2020) |
| Healthy volunteers, Patients with ESKD; Patients with active BCA; Surine ™ | 85 | ME/CFS-Neg-Reduced | Senger, R, Kavuru, V, et.al. (2019); Senger, R, Sullivan, M, et.al. (2020); Huttanus, H, et. al. (2020) |

[1]Patients testing LD-positive with the CDC serologic test and one or more other tests were grouped with the "CDC-LD-Positive" dataset.
[2]One patient presenting with symptoms resembling LD was found to have a CD57 NK count of 68. This patient was included in the group.

Figure 38:
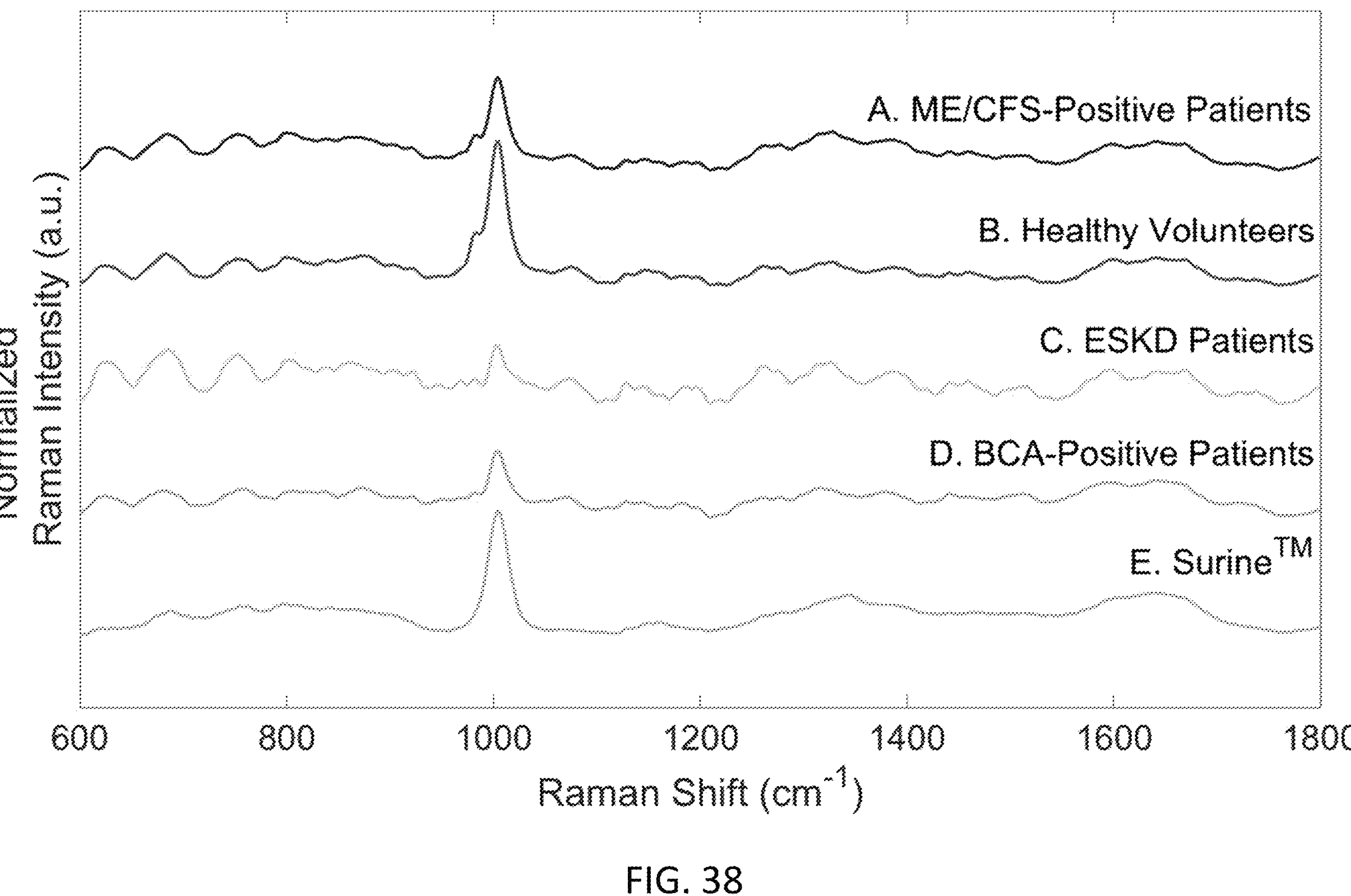
FIG. 38 is a graph showing representative baselined and normalized spectra prepared by Rametrix™ LITE for A) ME/CFS-positive patients, B) healthy volunteers, C) ESKD patients, D) BCA-positive patients, and E) Surine™.

Raman spectra from all patient groups and the urinalysis standard Surine™ were processed with the Rametrix™ LITE Toolbox v1.1 for MATLAB, as described previously. The urine spectra were averaged for each group following truncation (600-1,800 $cm^{-1}$), baselining, and vector normalization in Rametrix™ LITE. These processed representative spectra are shown in FIG. 38.

Apparent from visual inspection of representative spectra is that the averaged urine spectrum of ME/CFS-positive patients more closely resembles that of healthy human volunteers than the urine spectra of either ESKD or BCA patients. Subtle differences between the ME/CFS-positive representative spectrum and that of healthy volunteers were observed in the 1,002 $cm^{-1}$ band (representative of urea), around 900 $cm^{-1}$, and from 1,200-1,400 $cm^{-1}$ (all commonly associated with tryptophan and protein, including collagen) (Movasaghi, Z, et. al. (2007)). However, these subtle differences were both subjective and insufficient to identify the presence of ME/CFS in urine through simple visual inspection of spectra alone. Thus, Rametrix™ computational tools were used to perform a chemometric analysis of the spectra to discover defining characteristics (i.e., the "molecular signature") of ME/CFS in urine.

Statistical comparisons among groups of urine Raman spectra.

To determine whether the ME/CFS patient groups (ME/CFS-positive,

LD-positive, MD-positive, BT-positive, and BA-positive, as defined in Table 33) of urine spectra were statistically different from those of the healthy volunteers, 1-way ANOVA and pairwise comparisons with Tukey's HSD procedure were applied in MATLAB. To do this, the entire Raman spectrum of each sample, consisting of band intensities between 600-1,800 $cm^{-1}$, was reduced to a single value with TSD and TPD calculations, as described earlier. Statistical significance was found for most tests, suggesting real molecular differences exist between the two groups that can be elucidated by chemometric analysis with Rametrix™. For cases where statistical significance was not observed, it is suspected this may be due to relatively small sample populations in those cases. Specific results are given below.

ME/CFS-positive patient urine spectra were statistically different from those of healthy volunteers ($p<0.001$ for both TSD and TPD).

LD-positive patient urine spectra were statistically different from those of healthy volunteers ($p<0.001$ for both TSD and TPD).

LD-positive patient urine spectra were statistically different from other ME/CFS-positive urine spectra ($p<0.001$ for both TSD and TPD).

MD-positive patient urine spectra were statistically different from those of healthy volunteers ($p<0.001$ for both TSD and TPD).

MD-positive patient urine spectra were statistically different from other ME/CFS-positive urine spectra ($p<0.001$ for both TSD and TPD).

BT-positive patient urine spectra were statistically different from those of healthy volunteers ($p<0.001$ for both TSD and TPD).

BT-positive patient urine spectra were not statistically different from other ME/CFS-positive urine spectra ($p=0.59$ for TSD and $p=0.67$ for TPD).

BA-positive patient urine spectra were not statistically different from those of healthy volunteers ($p=0.27$ for TSD and $p=0.32$ for TPD).

BA-positive patient urine spectra were not statistically different from other ME/CFS-positive urine spectra ($p=0.38$ for TSD and $p=0.35$ for TPD).

The same procedure above was applied to the CDC-LD-Positive and Other-LD-Positive groups, defined in Table 33, to test if there was any significant difference in the urine spectra of patients who tested LD-positive by different tests. Results of comparing TSD and TPD values of these groups with 1-way ANOVA and pairwise comparisons revealed no statistically significant difference ($p=0.38$ and 0.41 for TSD and TPD, respectively). This confirmed that the CDC-LD-Positive and Other-LD-Positive groups could be grouped together as LD-Positive, as was done above and in other analyses.

Again, the same TSD and TPD calculations and statistical procedures were applied to the LD-Positive and Neg-LD-Test groups of Table 33. Results showed these groups were not statistically different ($p=0.30$ and 0.31 for TSD and TPD, respectively). This suggests that some urine specimens of the Neg-LD-Test group could have the LD molecular signature. Individual specimens were analyzed for this using the Rametrix™-based screen, and results are reported in a later section The same analysis was applied to the LD-Positive and CD57 groups of Table 33. Again, these groups were found to not be statistically different (p=0.38 and 0.36 for TSD and TPD, respectively). This also suggests that some urine specimens of the CD57 group could have the LD molecular signature. It is noted that several specimens are contained in both the Neg-LD-Test and CD57 groups, so this is logical. Again, the individual specimens were analyzed with the Rametrix™-based screen, and results are given later.

Building Rametrix™-based urine screens. First, the differences between the urine spectra of the ME/CFS-Positive group were compared further against those of the Healthy group using Rametrix™ LITE. Results of PCA and several DAPC models are shown in FIGS. 39A-D.

Figures 39A, 39B:
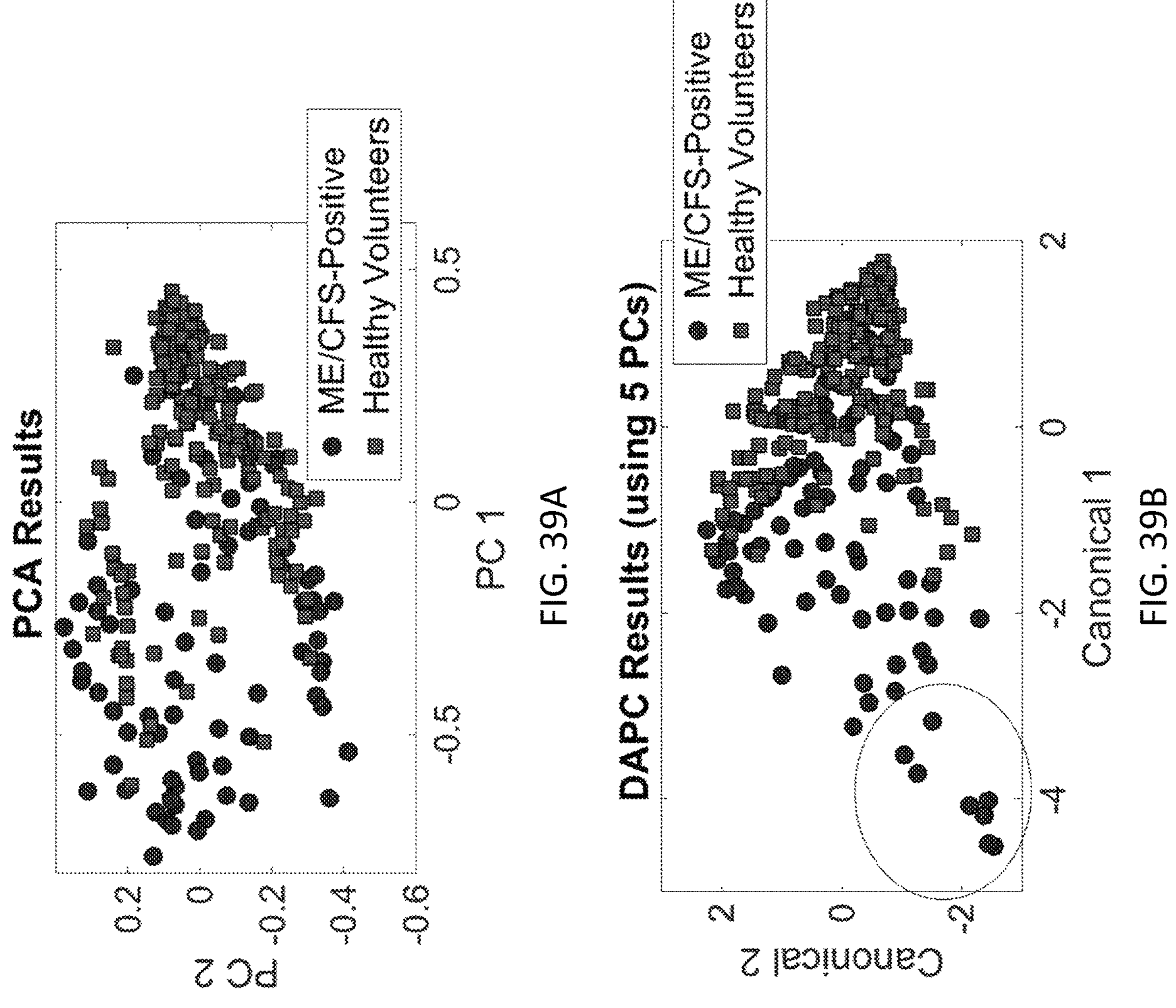
FIGS. 39A-D are graphs showing Rametrix™ LITE results for spectra from ME/CFS-positive patients and healthy volunteers: A) PCA results, B) DAPC results for a model built with 5 PCs (95% of dataset variance), C) DAPC results for a model built with 10 PCs (99% of dataset variance), and D) DAPC results for a model built with 47 PCs (99.9% of dataset variance).
Figures 39C, 39D:
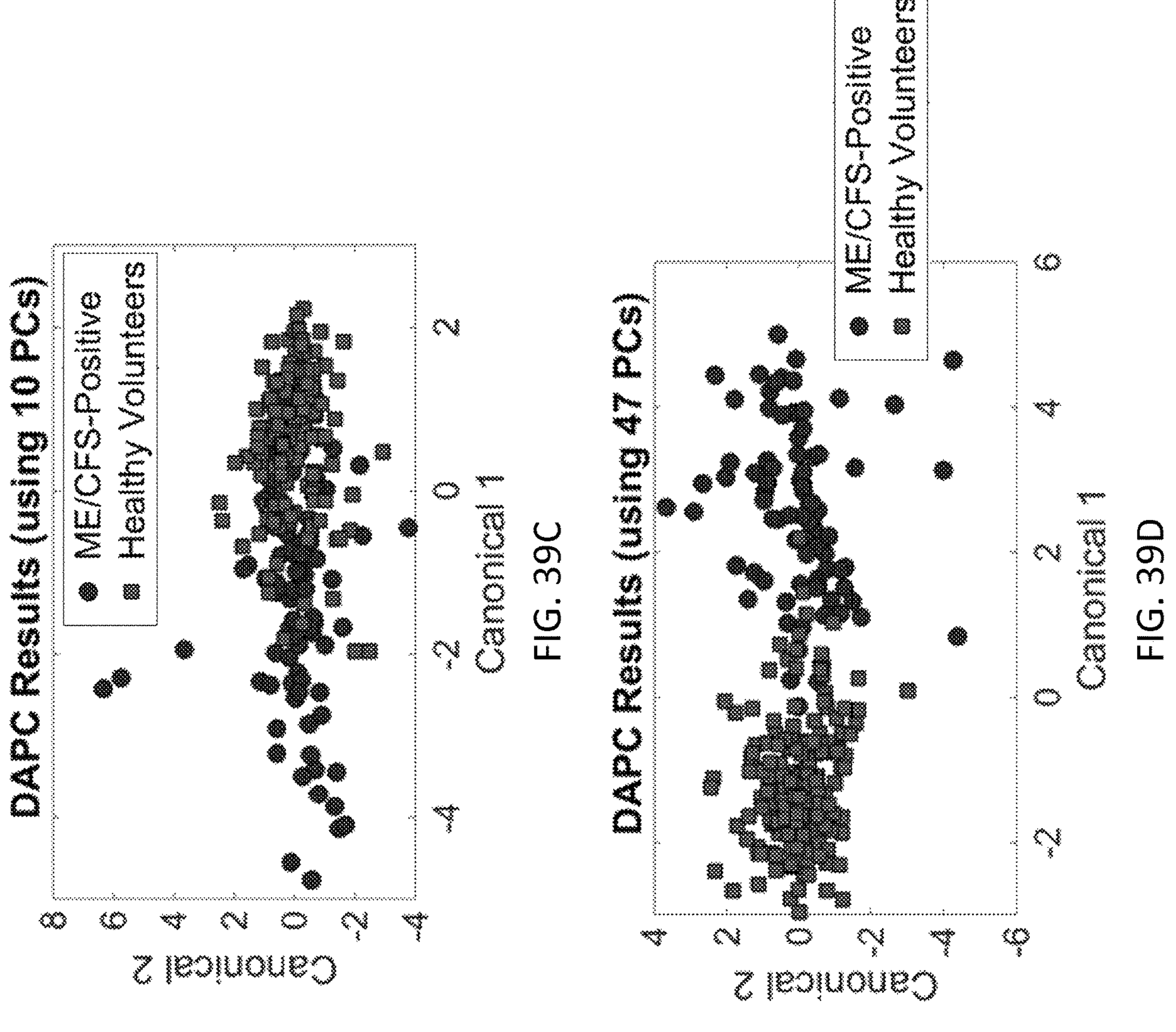

The PCA results (FIG. 39A) showed little separation between the urine spectra of LD-positive patients and those of healthy volunteers, so DAPC models were implemented. For a DAPC model built with five principal components (PCs) (FIG. 39B), 95% of the dataset variance was represented. This led to separation of about one-half of the ME/CFS-Positive urine spectra from those of the Healthy group along the first two canonical axes. For reference, in DAPC plots, data point clustering represents spectral (and molecular) similarities. Distance between data points arises from dissimilarities among groups (defined in Table 33) of spectra (i.e., ME/CFS-Positive vs. Healthy). As the DAPC model complexity was increased to include 10 PCs (representing 99% of the dataset variance) (FIG. 39C), the separation of the two clusters improved, and this was improved further by including 47 PCs (99.9% of the dataset variance) (FIG. 39D). However, this visual representation only demonstrates that the two groups of spectra can be separated by increasingly complex DAPC models. Importantly, this analysis shows that spectral differences can be found between these two groups of urine spectra and that a unique ME/CFS molecular signature may exist. How well this DAPC model performs in assigning a group (i.e., ME/CFS-Positive or Healthy) to an "unknown" urine specimen is addressed in the following sections. It was also unclear, but of interest, whether those spectra that become distinct from the healthy volunteers' cluster in simpler DAPC models represent more 'severe' ME/CFS-positive cases. Thus, the physician notes for the circled ME/CFS-Positive patients in FIG. 39B were investigated. While no striking similarities were found among these patients, the physician notes contained the following for these patients: fatigue, insomnia, joint pain, anxiety, gastro-intestinal issues, shortness of breath, syncope, peripheral neuropathy, Wolff-Parkinson-White syndrome, obsessive compulsive disorder, somatic pain, significant weight gain/loss, and hormonal dysregulation.

The Rametrix™ PRO computational tool was then applied for further analysis of spectral data. This was done to assess how well the Raman-based analysis would serve as a urine screen to detect a unique spectral signature associated with ME/CFS. The details of Rametrix™ PRO are provided above. In short, Rametrix™ PRO implements a LOOCV for validating DAPC models. In this analysis, the urine spectrum "left-out" of the model building process was treated as the "unknown" and then assigned to a group (i.e., ME/CFS-Positive or Healthy) using the model. The prediction was then compared to its real grouping. This procedure was repeated for all spectra in the dataset. From this, overall model prediction accuracy, sensitivity, PPV, and NPV were calculated. Several DAPC models were then constructed with different numbers of PCs, and the leave-one-out analysis was performed for each one with Rametrix™ PRO. Performance metrics are given in Table 34, and models with maximized accuracy, sensitivity, specificity, PPV, and NPV are given.

TABLE 34

Rametrix ™ PRO results for ME/CFS-positive patients and healthy human volunteers.

| PCs* | Accuracy | Sensitivity | Specificity | PPV | NPV |
|---|---|---|---|---|---|
| 32 | 88.5% | 83.3% | 90.8% | 80.5% | 92.3% |
| 46 | 91.1% | 76.2% | 97.8% | 94.1% | 90.0% |
| 47** | 91.4% | 78.6% | 97.3% | 93.0% | 90.9% |
| 55 | 88.5% | 65.5% | 98.9% | 96.5% | 86.3% |

*Models are shown that maximize accuracy, sensitivity, specificity, PPV, and NPV (bold values).
*The DAPC model with 47 PCs was found to be the best overall performer.

With this dataset, the DAPC model with 47 PCs (also shown in FIG. 39D) was considered an optimum performer and led to a urine screen for ME/CFS with 91% accuracy, 79% sensitivity, 97% specificity, 93% PPV, and 91% NPV. When examining correlations with a barrage of clinical tests and expert physician diagnosis as the Gold-Standard test for ME/CFS, the Rametrix™-based urine screen performed well. With a positive urine screen result, 93% of those patients tested positive by the Gold-Standard test (example of PPV). Additionally, of those screening negative, 91% tested negative by the Gold-Standard test (example of NPV). A high value of NPV helps ensure false-positives are minimized and treatment is not administered to healthy individuals.

The Rametrix™ LITE and PRO analyses described above for the ME/CFS-Positive and Healthy groups were repeated to determine if the method could serve as useful urine screens for LD, MD, BT, and BA individually. Screen metrics, given the optimum number of PCs, are given in Table 35. Total accuracy in all screens exceeded 90%, specificities exceeded 95%, and NPV values exceeded 90%. However, sensitivities of 41% and 33% were obtained for screens for BT and BA, respectively, and the PPV of the BA screen was 40%. It is noted that BA-Positive and Healthy group urine spectra were found not statistically different when comparing TSD and TPD values (described earlier). It is also noted that the screen metrics for LD exceed those of most commercial antibody tests.

TABLE 35

Rametrix ™ PRO results for LD-Positive, MD-Positive, BT-Positive, and BA-Positive patients and healthy human volunteers.

| Condition | Optimum PCs | Accuracy | Sensitivity | Specificity | PPV | NPV |
|---|---|---|---|---|---|---|
| ME/CFS-Positive* | 47* | 91.4% | 78.6% | 97.3% | 93.0% | 90.9% |
| LD-Positive | 46 | 94.0% | 86.7% | 95.1% | 74.3% | 97.8% |
| MD-Positive | 22 | 91.1% | 72.5% | 96.2% | 84.1% | 92.7% |
| BT-Positive | 21 | 95.0% | 41.2% | 100.0% | 100.0% | 94.9% |
| BA-Positive | 6 | 96.3% | 33.3% | 98.4% | 40.0% | 97.8% |

*This result was presented in Table 34. It is being shown here for comparison.

Elucidating the molecular signature of ME/CFS and LD in Raman spectra of urine specimens. A useful feature of the Rametrix™ LITE Toolbox is the identification of spectral contributions (i.e., molecular constituents) leading to separations of clusters in PCA and DAPC. These are also referred to as PCA and DAPC loadings. In other words, Rametrix™ reveals which Raman shifts have band intensities that are significantly different among groups of spectra (i.e., ME/CFS-Positive vs Healthy), due to differences in the molecular composition of urine between the two classes. The difference that is unique to ME/CFS is referred to as its molecular signature. The most prominent Raman shift contributors were compiled based on cutoffs in the contributions/loading data generated by Rametrix™ LITE. The biological molecules giving rise to these Raman shifts were identified in a published database (Movasaghi, Z, et. al. (2007)). Results are given in Table 36 comparing the ME/CFS-Positive and LD-Positive datasets to the Healthy dataset (Table 33). Results are given for both PCA and DAPC data.

Analysis of Table 36 revealed that the molecular signatures for ME/CFS-positive and LD-positive patients are somewhat different.

TABLE 36

Prominent[1] Raman shifts arising from PCA and DAPC comparisons of urine spectra from ME/CFS-positive and LD-positive patients with healthy volunteers.

| Raman Shift ($cm^{-1}$) | Band Assignment | ME/CFS-Positive | LD-Positive |
|---|---|---|---|
| 615 | Cholesterol ester | N/A[2] | DAPC |
| 620 | Related to aromatics | PCA | PCA |
| 642 | Tyrosine | DAPC | DAPC |
| 665 | Tyrosine | N/A | DAPC |
| 678 | DNA | Both | N/A |
| 700 | Methionine | DAPC | DAPC |
| 720 | Phospholipids/DNA | PCA | Both |
| 752 | Heme | PCA | Both |
| 775 | phosphatidylinositol | PCA | Both |
| 785 | DNA/RNA | PCA | Both |
| 810 | Phosphodiester | DAPC | N/A |
| 820-840 | Proteins, including collagen | PCA | PCA |
| 825 | Phosphodiester | DAPC | DAPC |
| 843 | Glucose | Both | DAPC |
| 853 | Tyrosine/proline | DAPC | N/A |
| 859 | Tyrosine/collagen | PCA | N/A |
| 880 | Tryptophan | PCA | Both |
| 890 | Structural protein modes of tumors | N/A | PCA |
| 920 | C-C stretch of proline/glucose/lactic acid/collagen | PCA | PCA |
| 956 | Carotenoids | PCA | N/A |
| 968 | Lipids | PCA | N/A |
| 974 | Ribose (RNA) | DAPC | N/A |
| 1,002 | Urea (dominant in urine) | N/A | PCA |
| 1,004 | Phenylalanine of collagen | PCA | N/A |
| 1,030 | Phenylalanine of collagen | DAPC | N/A |
| 1,035 | Collagen | DAPC | N/A |
| 1,048 | Glycogen | DAPC | N/A |
| 1,056 | Lipids | N/A | DAPC |
| 1,064 | Lipids | N/A | DAPC |
| 1,074 | Triglycerides | Both | PCA |
| 1,096 | Phosphodioxy $PO_2$- groups | DAPC | DAPC |
| 1,106 | Carbohydrates | PCA | DAPC |
| 1,117 | Glucose | PCA | N/A |
| 1,130 | Phospholipids and fatty acids | PCA | Both |
| 1,185 | DNA | PCA | PCA |
| 1,211 | Tyrosine and phenylalanine | N/A | DAPC |
| 1,224 | β-Sheet structure of Amide III | DAPC | N/A |
| 1,260 | Amides and protein | PCA | PCA |
| 1,275 | Amide III | N/A | PCA |
| 1,279 | Amide III | N/A | DAPC |
| 1,304 | Collagen | DAPC | N/A |
| 1,315 | Guanine | PCA | N/A |
| 1,327 | Nucleic acids | PCA | N/A |
| 1,360 | Tryptophan | N/A | PCA |
| 1,364 | Tryptophan | N/A | DAPC |
| 1,450 | Collagen and proteins | PCA | N/A |
| 1,460 | Lipids and collagen | PCA | N/A |
| 1,488 | Collagen | Both | DAPC |
| 1,600 | Amide I band of proteins | PCA | Both |
| 1,640 | Amide I | PCA | PCA |
| 1,665 | Collagen | PCA | PCA |

[1]Prominent is defined as a band (i.e., peak) contribution (loading) of more than 0.1% for PCA and 0.4% for DAPC.
[2]N/A indicates the band was not prominent as defined above.

In particular, the molecular signature for ME/CFS is characterized by multiple bands related to collagen and nucleic acids; whereas, that for LD is more weighted for aromatic amino acids, including tryptophan. This is the first characterization of ME/CFS-positive urine, to the inventors' knowledge. A recent metabolomic analysis of urine, using liquid chromatography-mass spectroscopy for the detection of LD, highlighted the presence of tryptophan and tryptophan metabolites, among others, in the urine of LD-positive patients (Pegalajar-Jurado et al., 2018). Tryptophan was also present as a prominent contributor in this ME/CFS analysis. In PCA, intensities at the following Raman shifts ($cm^{-1}$) were found as major contributors to the differences between LD-positive patients and healthy volunteers: 620 $cm^{-1}$ (related to aromatics), 880 $cm^{-1}$ (tryptophan), and 1,360 $cm^{-1}$ (tryptophan). In the DAPC analysis, the following Raman shift contributors ($cm^{-1}$) were noted: 642 $cm^{-1}$ and 665 $cm^{-1}$ (related to tyrosine), 880 $cm^{-1}$ (tryptophan), 1,211 $cm^{-1}$ (tyrosine and phenylalanine), and 1,364 $cm^{-1}$ (tryptophan). These and other significant contributors are given in Table 36, and it is specified whether the Raman shift contributor was found in PCA results, DAPC results, or both (band assignments listed are given in Movasaghi, Z, et. al. (2007)). These are the major bands of the Raman molecular signatures for ME/CFS and LD. However, this molecular signature contains several other minor bands that are not listed here but are recognized in the Rametrix™ analysis.

Figure 40:
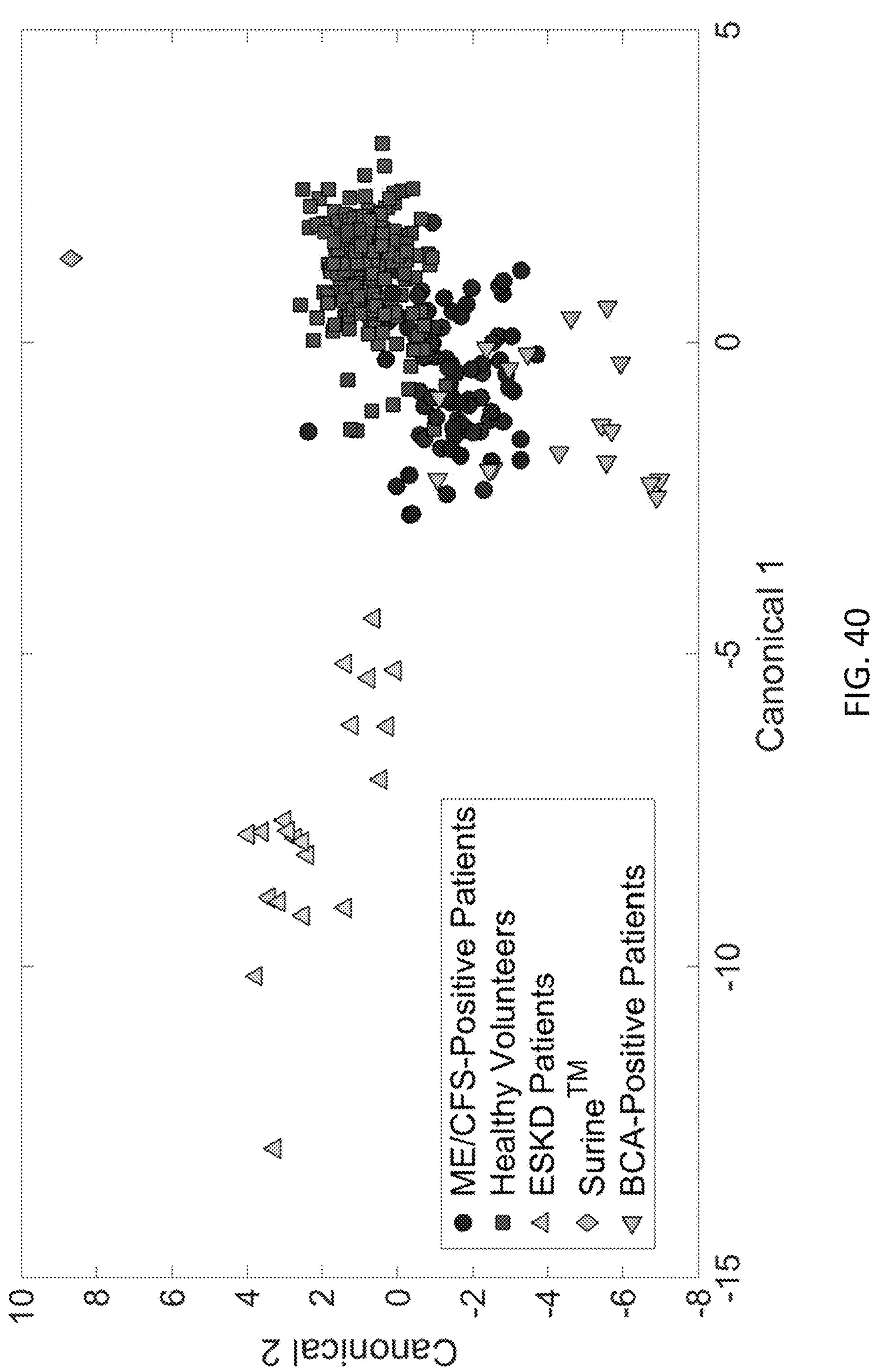
FIG. 40 is a graph showing a Rametrix™ LITE DAPC model built with 46 PCs (99.9% of the dataset variance) with urine spectra from ME/CFS-positive patients, ESKD patients, BCA-positive patients, healthy human volunteers, and Surine™.

Testing the Rametrix™-based LD urine screen against other patient groups. ESKD (end-stage kidney disease) and BCA (bladder cancer) are two other disease conditions that significantly impact the molecular composition of urine. Previously, the inventors have shown these can both be resolved using Rametrix™ based computational analysis (above). Here, the inventors sought to determine whether urine from ESKD and BCA patients could be resolved from those of the ME/CFS-positive patients. The results of the Rametrix™ LITE DAPC model with 46 PCs are in FIG. 40.

Apparent is the degree of separation among the different classes of spectra, with the urine spectra of ME/CFS-positive patients somewhat resembling that of the BCA-positive patients and healthy volunteers. The ESKD urine spectra cluster separated from the others entirely. This was also observable in FIG. 38, as ESKD produced significantly altered urine spectra (i.e., Raman molecular signatures). However, and importantly, the ME/CFS-Positive group clustered differently (with some acknowledged overlaps) from the other groups, suggesting Rametrix™ can detect the presence of ME/CFS when confronted with multiple disorders known to affect urine molecular composition.

Next, the inventors determined whether urine spectra from ME/CFS-positive patients could be distinguished from those with ESKD and BCA with statistical significance. Using TSD and TPD values with 1-way ANOVA and pairwise comparisons, the LD-Positive group was found significantly different from the ESKD and BCA groups (p<0.001 in both cases). Rametrix™ PRO was then used to determine the effectiveness of identifying a urine spectrum as belonging to the ME/CFS-Positive group versus the ESKD, BCA, Healthy, and Surine™ ME/CFS-negative groups (i.e., the ME/CFS-Neg-Full dataset in Table 33). Results are shown in Table 37 for multiple models. Optimized numbers of PCs that maximized accuracy (86.6%), sensitivity (72.6%), specificity (99.1%), PPV (94.9%), and NPV (88.9%) are given. As shown in Table 33, the ME/CFS-Neg-Full dataset contained 233 spectra, and the ME/CFS-Positive dataset contained 85 spectra. Also tested whether an equal number of ME/CFS-positive and ME/CFS-negative spectra in the analysis would impact results. The inventors included only 85 ME/CFS-negative urine spectra in the ME/CFS-Neg-Reduced dataset (Table 33), and repeated the analysis. Results are in Table 37.

TABLE 37

Rametrix ™ PRO results for ME/CFS-positive patients against the ME/CFS-Negative group, containing healthy human volunteers, ESKD patients, BCA-positive patients, and Surine ™

| Dataset | PCs* | Accuracy | Sensitivity | Specificity | PPV | NPV |
|---|---|---|---|---|---|---|
| ME/CFS-Neg-Full | 46 | 86.6% | 60.7% | 96.4% | 86.4% | 86.7% |
| | 30 | 85.7% | 72.6% | 90.6% | 74.4% | 89.8% |
| | 54 | 84.0% | 44.0% | 99.1% | 94.9% | 82.5% |
| | 28 | 84.4% | 70.2% | 89.7% | 72.0% | 88.9% |
| ME/CFS-Neg-Reduced | 61 | 81.7% | 70.2% | 92.9% | 90.8% | 76.0% |
| | 35 | 76.9% | 79.8% | 74.1% | 75.3% | 78.8% |

*Models shown maximize accuracy, sensitivity, specificity, PPV, and NPV (bold values).

The only screen metric to show improvement was sensitivity (maximum of 79.8% with 35 PCs). Thus, balancing the dataset with ME/CFS-positive and ME/CFS-negative urine spectra did not improve predictive performance in this case.

These studies were conducted to determine if Raman spectroscopy and Rametrix™ analysis of urine would serve as a suitable screen for ME/CFS and related conditions, including LD, MD, BT, and BA. The results indicate there are statistically significant changes in the urine of patients who are diagnosed with ME/CFS and/or test positive for LD when their urine molecular composition is compared to that of normal, healthy volunteers or patients with genitourinary tract pathology. As such, the inventors believe the methods could be easily applied as an accurate, rapid, and inexpensive urine screen for ME/CFS, LD, MD, and possibly BT and BA.

Section IX

Figure 41A:
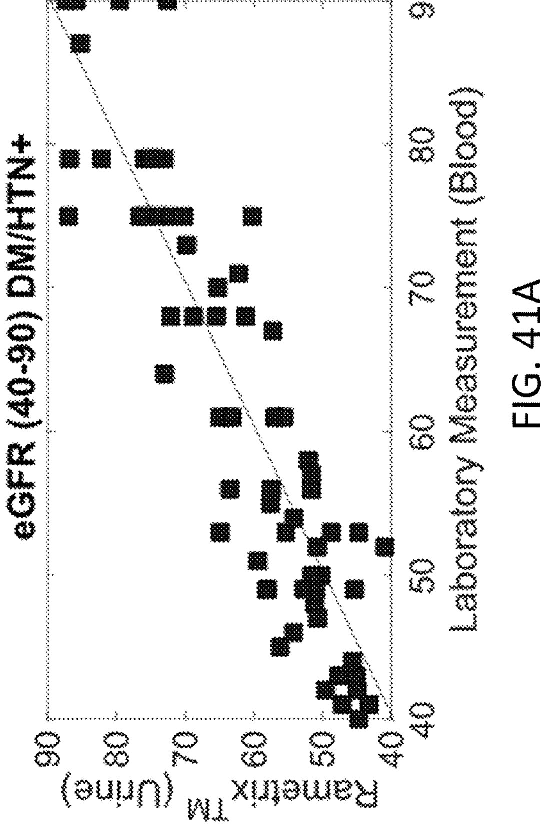
FIGS. 41A-D are graphs showing how Rametrix can be used to measure eGFR (and GFR) (glomerular filtration rate), for example, as a measure of the stage or extent of glomerulonephritis (A-B) as well as proteinuria (C-D) in patients positive for hypertension and diabetes (HT/DM+, A and C) and negative for hypertension and diabetes (HT/DM−, B and D).
Figure 41B:
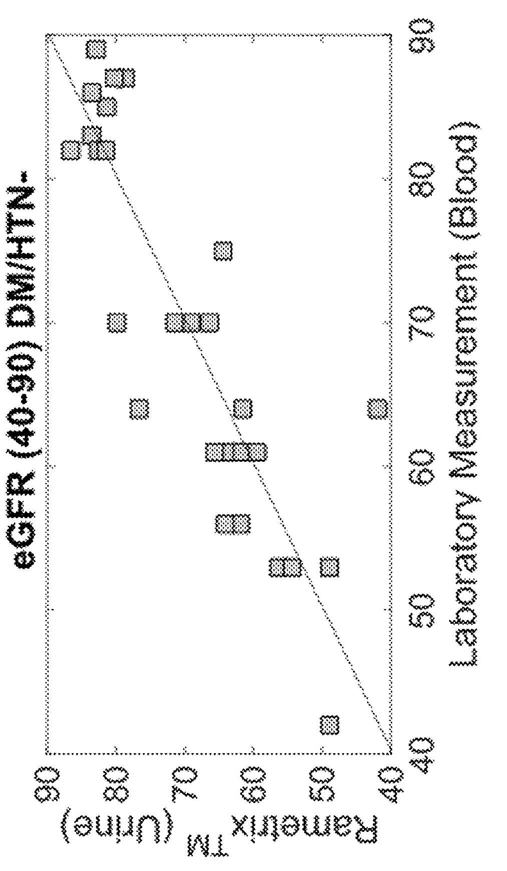
Figures 41C, 41D:
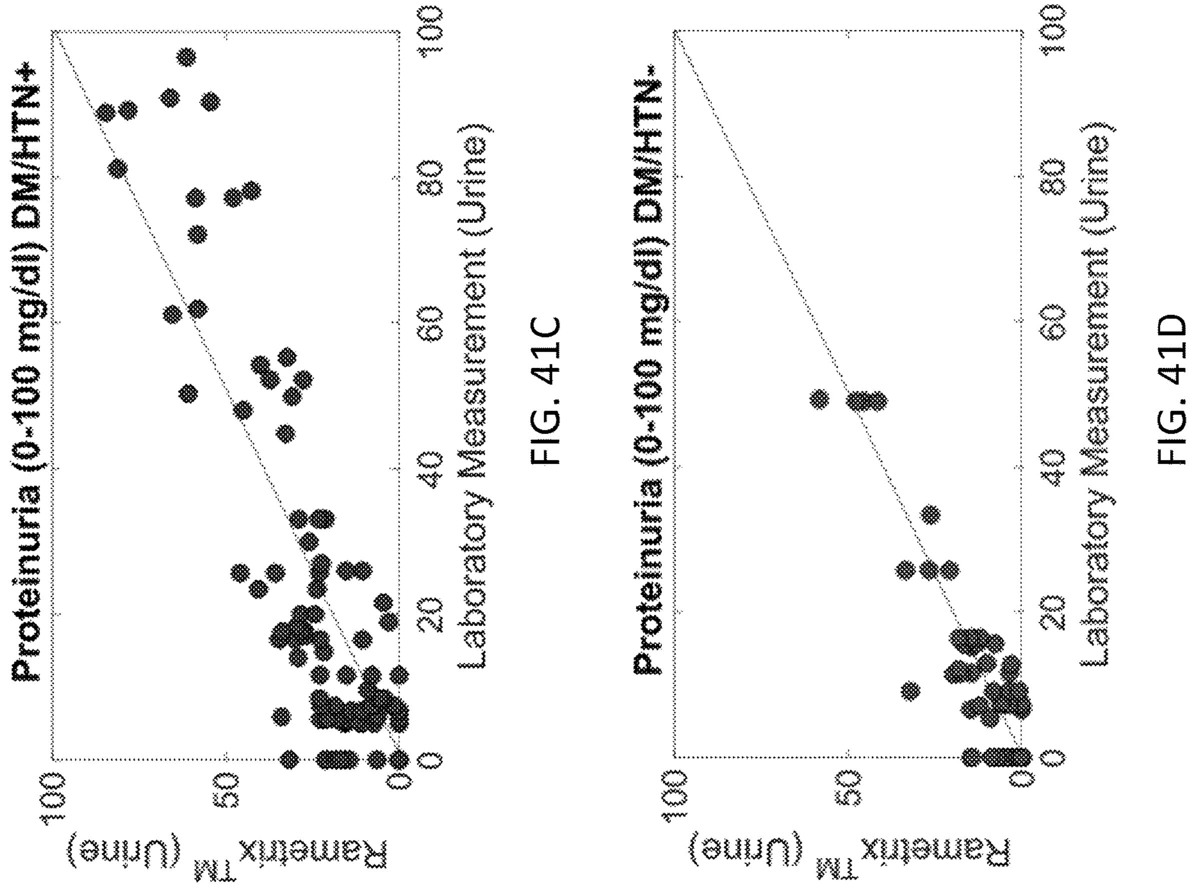

Assessing Renal Function Using Raman Spectroscopic of Urine and Computation of GFR FIGS. 41A-D shows Rametrix can be used to measure eGFR (and GFR) (glomerular filtration rate), for example, as a measure of the stage or extent of glomerulonephritis (FIGS. 41A-B), as well as proteinuria (amount of protein in the urine) (FIGS. 41C-D). One method is used if a patient is positive for hypertension and diabetes (HT/DM+, FIGS. 41A and 41C) and another if the patient is negative (HT/DM−, FIGS. 41B and 41D).

Section X

Figures 42A, 42B, 42C, 42D:
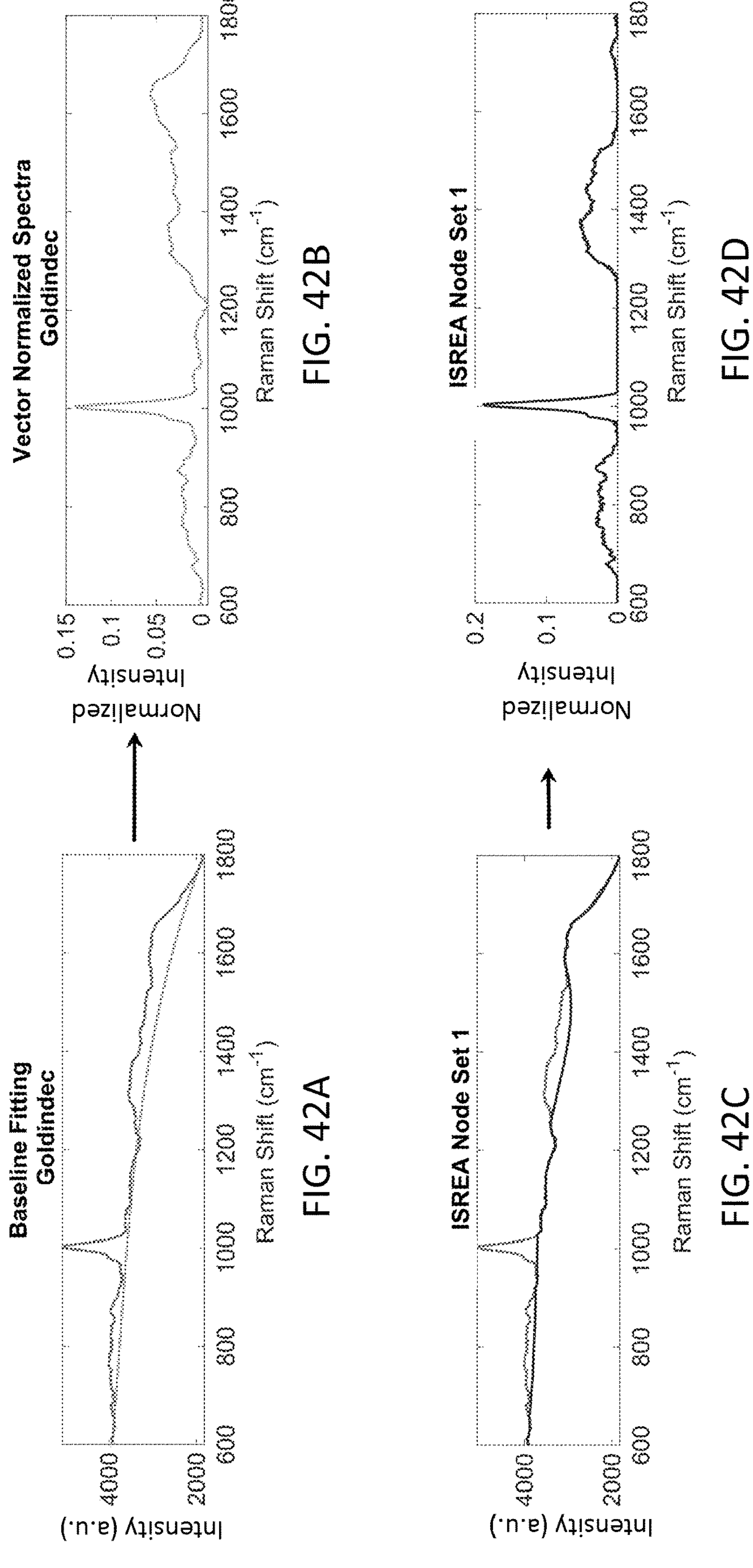
FIGS. 42A-H are graphs showing Goldindec and ISREA (with StaBAL) baselining of a Raman spectrum.
Figures 42E, 42F, 42G, 42H:
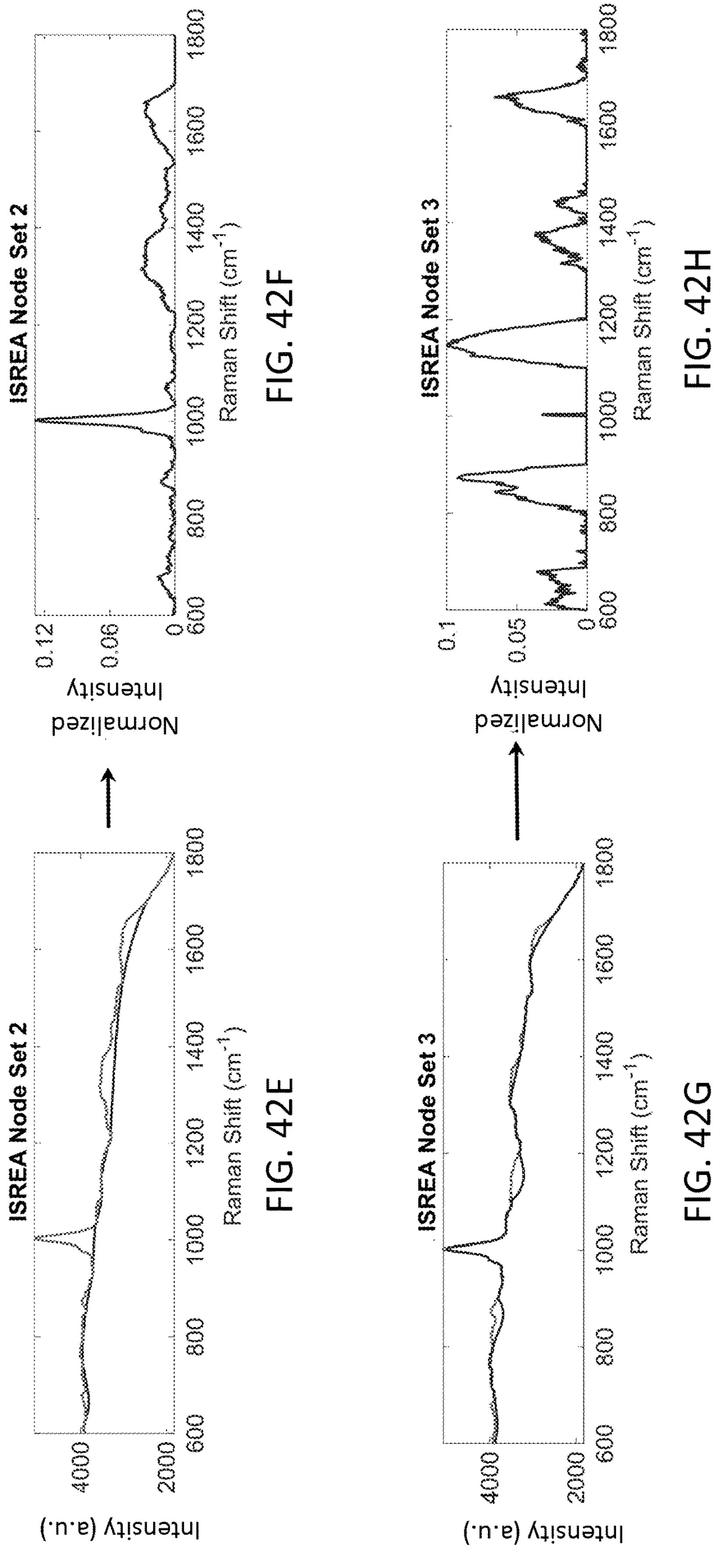

Assessing Renal Function Using Raman Spectroscopic of Urine and Computation of Proteinuria Rametrix™ brings a new method for analyzing Raman spectra. From this, the inventors have been able to detect the presence of several diseases and pathologies from routine Raman analysis of liquid urine. A typical Raman spectrum is shown in FIG. 42A. Raman spectra are typically baselined to remove background fluorescence from the Raman signal. One previously patented method for doing this is by the Goldindec algorithm. This is shown as the dotted line in FIG. 42A. When this background is subtracted, the resulting spectrum is used for analysis (FIG. 42B). Rametrix™ originally used the Goldindec algorithm for this purpose. Rametrix™ has since been updated to remove the Goldindec algorithm and replace it with ISREA and StaBAL.

ISREA fits several cubic splines through a Raman spectrum. See Xu, Y, et. al. (2020): Xu, Y, Du, P, Senger, R, Robertson, J, Pirkle, J "ISREA: An efficient peak-preserving baseline correction algorithm for Raman spectra," First Published Oct. 8, 2020/doi: 10.1177/0003702820955245. This method has been published in Applied Spectroscopy in 2020. The cubic splines attach to nodes placed in the Raman spectrum. In the original version of ISREA, these nodes were static in number and placement in a spectrum. StaBAL expands this by instructing ISREA how many nodes to place in a spectrum and where to place them. The result is a baselined and transformed spectrum. A provisional patent application has been filed on this method, U.S. 62/983,045, filed Feb. 28, 2020. The combination of ISREA and StaBAL allow certain regions of a Raman spectrum to be emphasized and other areas to be minimized or disregarded altogether. After node placement, baselined and transformed spectra are analyzed by principal component analysis (PCA), discriminant analysis of principal components (DAPC), partial least squares (PLS), and artificial neural networks (NN) to detect the presence of disease. StaBAL optimizes nodes so a particular disease becomes visible in transformed spectra. This is unique and a new advancement in Raman spectroscopy data analysis.

FIGS. 42C-D provides further examples of spectrum transformation with ISREA and StaBAL. FIG. 42C shows ISREA fitting of the same Raman spectrum using an optimized set of StaBAL nodes to detect hematuria (i.e., blood) in human urine. The resulting baselined spectrum is shown in FIG. 42D.

This transformed spectrum eliminates superfluous Raman data present in FIG. 42B and has shown to greatly improve the detection of hematuria. Other node sets designed by StaBAL, and combined with ISREA, are shown in FIGS. 42E-H. While these do not improve hematuria detection, they demonstrate how different node placements can transform a Raman spectrum differently. The inventors have found that specific node sets exist for each disease detected. Thus, the combination of ISREA and StaBAL baselining and spectrum transformation are unique aspects of Rametrix™ that enable the detection of disease in human urine. The technique is also applicable to other fluids, tissues, gasses, and solids. It can enable identifying environmental toxins, physiology changes, other pathologies, specific chemicals such as explosives, and biomolecular/chemical changes in general.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

REFERENCES (INCORPORATED HEREIN BY REFERENCE IN THEIR ENTIRETIES)

Carswell, W, et. al. (2020): Carswell, W, Guruli, G, Tracy, A, Xu, Y, Du, P, Senger, R, Robertson, J, "Raman Spectroscopy as a non-cytological detection and quantification urinalysis method for microhematuria in human urine" (submitted, 12 31 2020, Applied Spectroscopy);

Fisher, A, et. al. (2018): Fisher, AK, Carswell, WF, Athamaneh, AIM,

Sullivan, MC, Robertson, J L, Bevan, DR, Senger, R S, "The Rametrix™ LITE Toolbox v1.0 for MATLAB®," J Raman Spectro 49 (5): 885-896, 2018;

Huttanus, H, et. al. (2020): Huttanus, H, Vu, T, Guruli, G, Tracey, A, Carswell, W, Said, N, Du, P, Parkinson, B, Orlando, G, Robertson, J, Senger, R, "Raman Chemometric Urinalysis (Rametrix™) as a screen for bladder cancer," PLOS One. 2020; 15 (8): e0237070. Published online 2020 Aug. 21. doi: 10.1371/journal.pone.0237070;

International Patent Application, US2017/0045455, published Feb. 16, 2017, "SYSTEM AND METHOD FOR MONITORING THE HEALTH OF DIALYSIS PATIENTS";

Kavuru, V, et. al. (2019): Kavuru, V, Vu, T, Karageorge, L, Choudhury, D, Senger, R, Robertson, J, "Dipstick analysis of urine chemistry: benefits and limitations of dry chemistry-based assays," Postgrad Med Published on-line Oct. 19 2019 doi: 10.1080/00325481.2019.1679540;

Senger, R, Robertson, J (2019): Senger, R, Robertson, J, "The Rametrix PRO™ Toolbox V1.0 for MATLAB®," Peer J, 3:35799:2:0, 2019;

Senger, R, Kavuru, V, et. al. (2019): Senger, R, Kavuru, V, Sullivan, M, Gouldin, A, Lundgren, S, Merrifield, K, Steen, C, Baker, E, Vu, T, Agnor, B, Martinez, G, Coogan, H, Carswell, W, Karageorge, L, Dev, D, Du, P, Sklar, A, Pirkle, J, Orlando, G, Lianos, E, Robertson, J L (2019a) "Spectral characteristics of urine specimens from healthy human volunteers analyzed using Raman Chemometric Urinalysis (Rametrix™)," PLOS One 2019, doi: 10.1371/journal.pone.0222115;

Senger, R, Robertson, J (2019): Senger, R, Robertson, J, "The Rametrix PRO™ Toolbox V1.0 for MATLAB®," Peer J, 3:35799:2:0, 2019 https://peerj.com/articles/8179;

Senger, R, Kavuru, V, et.al. (2019): Senger, R, Kavuru, V, Sullivan, M, Gouldin, A, Lundgren, S, Merrifield, K, Steen, C, Baker, E, Vu, T, Agnor, B, Martinez, G, Coogan, H, Carswell, W, Karageorge, L, Dev, D, Du, P, Sklar, A, Pirkle, J, Orlando, G, Lianos, E, Robertson, J L (2019a) "Spectral characteristics of urine specimens from healthy human volunteers analyzed using Raman Chemometric Urinalysis (Rametrix™)," PLOS One 2019, https://doi.org/10.1371/journal.pone.0222115;

Senger, R, Sullivan, M, et.al. (2020): Senger, R, Sullivan, M, Gouldin, A, Lundgren, S, Merrifield, K, Steen, C, Baker, E, Vu, T, Agnor, B, Martinez, G, Coogan, H, Carswell, W, Kavuru, V, Karageorge, L, Dev, D, Du, P, Sklar, A, Pirkle, J, Gulich, S, Lianos, E, Orlando, G, Robertson, J L, "Spectral characteristics of urine from patients with end-stage kidney disease, analyzed using Raman Chemometric Urinalysis (Rametrix™)," PLOS One 2020, Published: Jan. 10, 2020; pone.0227281;

Senger, R, Sayed Issa, A, et. al. (2020): Senger, R, Sayed Issa, A, Agnor, B, Talty, J, Hollis, A, Robertson, J L, "Disease-associated multimolecular signature in the urine of patients with Lyme disease, detected using Raman spectroscopy and chemometrics (Rametrix™)" (submitted, 12 14 2020, Applied Spectroscopy);

Senger, R, Kavuru, V, Dev, D, et. al. (in preparation): Senger, R, Kavuru, V, Dev, D, Agnor, B, Karageorge, L, Lianos, E, Pirkle, J, Robertson, J "Screening eGFR and proteinuria levels in chronic kidney disease patients with Raman Chemometric Urinalysis (Rametrix™)" (in preparation).

Xu, Y, et. al. (2020): Xu, Y, Du, P, Senger, R, Robertson, J, Pirkle, J "ISREA: An efficient peak-preserving baseline correction algorithm for Raman spectra," First Published Oct. 8, 2020 doi: 10.1177/0003702820955245;

Supporting References on methods, diseases, and comparators:

Shinzawa H, Awa K, Kanematsu W, Ozaki Y. 2009. Multivariate data analysis for Raman spectroscopic imaging. Journal of Raman Spectroscopy 40:1720-1725. DOI: 10.1002/jrs.2525;

Gautam R, Vanga S, Ariese F, Umapathy S. 2015. Review of multidimensional data processing approaches for Raman and infrared spectroscopy. EPJ Techniques and Instrumentation 2:1-38. DOI: 10.1140/epjti/s40485-015-0018-6;

Liu, J, et. al. (2015): Liu J, Sun J, Huang X, Li G, Liu B. 2015. Goldindec: A Novel Algorithm for Raman Spectrum Baseline Correction. Applied Spectroscopy 69:834-842. DOI: 10.1366/14-07798;

Bouatra, S, et. al. (2013): Bouatra S, Aziat F, Mandal R, Guo AC, Wilson MR, Knox C, et al. The Human Urine Metabolome. PLOS ONE. 2013; 8: e73076. doi: 10.1371/journal.pone.0073076;

Senger, R, DeLaTorre, D, et. al. (unpublished): Senger R, Du P, DeLaTorre Campos D, Carswell W, Webster K, Sullivan M, et al. Assessment of Urine Specimen Storage Conditions using Raman Chemometric Urinalysis (Rametrix™). Submitted to PeerJ. 2019;

Movasaghi, Z, et. al. (2007): Movasaghi Z, Rehman S, Rehman DIU. Raman Spectroscopy of Biological Tissues. Appl Spectrosc Rev. 2007; 42:493-541. doi: 10.1080/05704920701551530;

Athamneh AIM, Senger RS. Peptide-Guided Surface-Enhanced Raman Scattering Probes for Localized Cell Composition Analysis. Appl Env Microbiol. 2012; 78:7805-7808. doi: 10.1128/AEM.02000;

Athamneh AIM, Alajlouni RA, Wallace RS, Seleem MN, Senger RS. Phenotypic Profiling of Antibiotic Response Signatures in *Escherichia coli* Using Raman Spectroscopy. Antimicrob Agents Chemother. 2014; 58:1302-1314. doi: 10.1128/AAC.02098;

Zu TNK, Athamneh AIM, Collakova E, Robertson J, Hawken T, Aardema C, et al. Assessment of ex vivo Perfused Liver Health by Raman Spectroscopy. J Raman Spectrosc. 2015; 46:551-558. doi: 10.1002/jrs.4688;

Zu TNK, Athamneh AIM, Wallace RS, Collakova E, Senger RS. Near-Real-Time Analysis of the Phenotypic Responses of *Escherichia coli* to 1-Butanol Exposure Using Raman Spectroscopy. J Bacteriol. 2014; 196:3983-3991. doi: 10.1128/JB.01590-14;

Pegalajar-Jurado A, Fitzgerald BL, Islam MN, Belisle JT, Wormser GP, Waller KS, Ashton LV, Webb KJ, Delorey MJ, Clark RJ, Molins CR (2018) "Identification of urine metabolites as biomarkers of early Lyme Disease," Nature Scientific Reports 8:12204| DOI: 10.1038/s41598-018-29713-y;

Hyde F W, et al., "Detection of antigens in urine of mice and humans infected with *Borrelia burgdorferi*, etiologic agent of Lyme disease," J Clin Microbiol 27, 58-61 (1989);

Rauter C, et al., "Critical evaluation of urine-based PCR assay for diagnosis of Lyme borreliosis," Clin Diagn Lab Immunol 12:910-917, doi: 10.1128/CDLI.12.8.910-917 PMCID: PMC1182183 (2005);

Magni, R (2015): Magni R, et al., "Application of Nanotrap technology for high sensitivity measurement of urinary outer surface protein A carboxyl terminus domain in early stage Lyme borreliosis," J Transl Med 13:346 Published online 2015 Nov. 4. doi: 10.1186/s12967-015-0701-z PMCID: PMC4634744 (2015);

Senger, R, Issa, A, Gouldin, A, Talty, J, Hollis, A, Robertson, J, "Detection of unique multimolecular signatures in the urine of patients with myalgic encephalomyelitis/chronic fatigue syndrome, using Raman spectroscopy and chemometrics (Rametrix™)" (in preparation);

de Jong BW, Schut TC, Maquelin K, van der Kwast T, Bangma CH, Kok D J, et al. Discrimination between nontumor bladder tissue and tumor by Raman spectroscopy. Anal Chem. 2006; 78:7761-9. doi: 10.1021/ac061417b;

Bird B, Romeo MJ, Diem M, Bedrossian K, layer N, Naber S. Cytology by Infrared Micro-Spectroscopy: Automatic Distinction of Cell Types in Urinary Cytology. Vib Spectrosc. 2008; 48:101-106. doi: 10.1016/j.vibspec.2008.03.006;

Canetta E, Mazilu M, De Luca AC, Carruthers AE, Dholakia K, Neilson S, et al. Modulated Raman spectroscopy for enhanced identification of bladder tumor cells in urine samples. J Biomed Opt. 2011; 16:037002. doi: 10.1117/1.3556722;

Shapiro A, Gofrit ON, Pizov G, Cohen JK, Maier J. Raman molecular imaging: a novel spectroscopic technique for diagnosis of bladder cancer in urine specimens. Eur Urol. 2011; 59:106-12. doi: 10.1016/j.eururo.2010.10.027;

Kerr, al. L T et. Methodologies for bladder cancer detection with Raman based urine cytology. Anal Methods-Uk. 2016; 8:4991-5000.Yang YT, Hus IL, Cheng TY, Wu WJ, Lee CW, Li TJ, Cheung CI, Chin YC, Chen HC, Chiu YC, Huang CC, Liao MY. Off-Resonance SERS Nanoprobe-Targeted Screen of Biomarkers for Antigens Recognition of Bladder Normal and Aggressive Cancer Cells. Analytical Chemistry 2019; 91 (13): 8213-8220. DOI: 10.1021/acs.analchem.9b00775;

Lo PA, Huang YH, Chiu YC, Huang LC, Bai JL, Wu SH, Huang CC, Chaing CC. Automatic Raman spectroscopic urine crystal identification system using fluorescent image-guided 2D scanning platform with Fe304 crystal violet nanoclusters. J Raman Spectrosc 2018; 50 (1) 34-50. doi: 10.1002/jrs.5495;

Chiu YC, Chen PA, Chang PY, Cheng YH, Tao CW, Huang C, Chiang HK. Enhanced Raman sensitivity and magnetic separation for urolithiasis detection using phosphonic acid-terminated Fe304 nanoclusters. J. Mater. Chem. B 2015 (3): 4282-4290.doi: 10.1039/C5TB00419E.

The invention claimed is:

1. A method comprising:

obtaining a urine sample from a subject;

obtaining Raman spectra from the urine sample;

comparing the Raman spectra of the urine sample to a selected model;

wherein the selected model is constructed from various Raman spectra of urine from:

one or more individuals having bladder cancer;

one or more individuals not having bladder cancer; and one or more individuals having kidney disease, renal cancer, prostate cancer, and/or a non-neoplastic disease, and by:

(a) applying baseline correction to a range of wavenumbers of the various Raman spectra to obtain baseline corrected Raman spectra;

(b) performing normalization of the baseline corrected Raman spectra to obtain normalized Raman spectra;

(c) performing principal component analysis (PCA) of the normalized Raman spectra to identify principal components (PCs) of the urine;

(d) performing discriminant analysis of principal components (DAPC) to obtain one or more chemometric models based on one or more of the PCs, the one or more chemometric models comprising canonicals equal in number to the PCs;

(e) for the DAPC analysis, determining a fractional contribution of at least four selected wavenumbers of the range of wavenumbers to each of the canonicals of the one or more chemometric models to determine which of the selected wavenumbers give rise to separations seen in a plot of two or more of the canonicals, wherein the selected wavenumbers correspond with at least nucleic acids, proteins, blood cells, and inflammatory cells; and (f) testing one or more of the chemometric models, using a leave-one-out or multi-fold cross-validation technique to select one of the chemometric models as the selected model having a desired level of accuracy, sensitivity, specificity, positive predictive value, and/or negative predictive value;

wherein the selected model is one where the chemometric model is one comprising an accuracy of 100%, a sensitivity of 100% and/or a specificity of 100%;

wherein the comparing of the Raman spectra of the urine sample to the selected model comprises classifying the urine sample according to the selected model as being urine from a subject who has bladder cancer, and the stage thereof; and administering cystoscopy to the subject whose urine sample has been classified according to the selected model as being urine from a subject who has bladder cancer and confirming the severity or stage thereof.

2. The method of claim 1, further comprising:

identifying statistically significant spectral differences between the urine from the individuals having bladder cancer and the urine from the individuals not having bladder cancer by performing one or more of total canonical distance (TCD), total principal component distance (TPD), or total spectral distance (TSD).

3. The method of claim 1, wherein the selected model is one where:

the testing is based on the leave-one-out analysis, and the leave-one-out analysis provides leave-one-out accuracy, sensitivity and/or specificity that exceeds random chance accuracy, sensitivity, and/or specificity; and/or the testing is based on multi-fold cross-validation, and the testing reveals a favorable positive predictive value and/or negative predictive value, and/or the testing provides a positive predictive value (PPV) and/or negative predictive value (NPV) that exceed(s) random chance PPV and/or NPV, and/or the testing provides an accuracy, sensitivity and/or specificity that exceeds random chance accuracy, sensitivity, and/or specificity.

4. The method of claim 2, wherein the TSD is calculated and:

the TSD is calculated for one or more or every Raman shift of the range of wavenumbers;

the TSD is a sum of a distance between a spectrum of a first urine and a corresponding spectrum of a reference standard;

wherein the first urine is the urine from the individuals having bladder cancer or from the individuals not having bladder cancer; and the sum is performed over selected Raman shifts, or all Raman shifts, or all Raman shifts within 600-1,800 $cm^{-1.}$ 5. The method of claim 2, wherein four principal components (PCs) are selected as the top four PCs, and the TPD is calculated as a sum of a distance between the top four PCs of urine, from the individuals having bladder cancer or from the individuals not having bladder cancer, and a reference standard.

6. The method of claim 5, wherein the top four PCs are selected such that together the top four PCs represent over 85%, over 90%, over 91%, over 92%, over 93%, over 94%, over 95%, over 96%, over 97%, over 98%, over 99%, over 99.5%, or over 99.9% of the dataset variance.

7. The method of claim 1, wherein the leave-one-out technique is performed in a manner such that:

(a) one spectrum is left out and treated as an unknown;

(b) the PCA and DAPC analyses are performed using the remaining spectra;

(c) classification by positive or negative, and/or disease or no disease, and/or condition or no condition is predicted by one or more of the chemometric models;

(d) parts (a)-(c) are repeated for other or each spectrum in a dataset; and (e) the predictions are evaluated as correct or incorrect and evaluation metrics are calculated based thereon.

8. The method of claim 1, wherein a cross-validation technique, or the leave-one-out technique, is performed such that every specimen in the dataset is evaluated as an unknown.

9. The method of claim 1, wherein the classifying of the urine sample as being from a subject who has bladder cancer is performed in a manner such that it is determined that the spectra of the urine sample of the subject who has bladder cancer fits closer mathematically to the spectra of the urine samples of the individuals who have bladder cancer rather than to the spectra of the urine samples of the individuals who do not have bladder cancer.

10. The method of claim 1, wherein the baseline correction is applied to a truncated range of wavenumbers in the range of 400-1800 $cm^{-1}$ or in the range of 600-1800 $cm^{-1.}$ 11. The method of claim 1, wherein the performing of the PCA comprises transforming intensity values of the normalized Raman spectra intensities into principal component scores and using the principal component scores to calculate a fractional contribution of each wavenumber to each principal component to obtain a % contribution.

12. The method of claim 1, wherein the DAPC is performed to obtain one or more chemometric models based on a number of PCs that is up to one less than a total number of PCs calculated and/or using 90% to less than 100% of the PCs calculated, and/or where one or more of the chemometric models represents from 90% to 99.9% of the dataset variance.

13. The method of claim 1, wherein:

the Raman spectra are collected using a 785 nm laser; and distinguishing features of variability in Raman spectra of urine and the wavenumbers that give rise to the separations indicating a difference between having and not having bladder cancer occur at one or more wavenumbers representing nucleic acids (721, 827, and/or 1340 $cm^{-1}$), protein (or collagen) (817, 981, 1065, 1127, and/or 1340 $cm^{-1}$), aromatic amino acids (827 and/or 1004 $cm^{-1}$), C—N stretching of amides and proteins (1,050-1,250 cm “1), aromatic amino acids (1,590-1,750 $cm^{-1}$), and/or heme or red blood cells (669; 750; 752; 999; 1,122; 1,210; 1,444; 1,543; 1,579; and/or 1,617 $cm^{-1}$).

14. The method of claim 1, wherein the selected model is constructed from various Raman spectra of urine from:

one or more individuals having bladder cancer;

one or more individuals not having bladder cancer;

one or more individuals having kidney disease;

one or more individuals having renal cancer;

one or more individuals having prostate cancer; and one or more individuals having a non-neoplastic disease.

* * * * *